United States Patent
LaBaer et al.

(10) Patent No.: US 10,787,710 B2
(45) Date of Patent: Sep. 29, 2020

(54) RADIATION BIODOSIMETRY SYSTEMS

(71) Applicant: ARIZONA BOARD OF REGENTS ON BEHALF OF ARIZONA STATE UNIVERSITY, Scottsdale, AZ (US)

(72) Inventors: Joshua LaBaer, Chandler, AZ (US); Kristin Gillis, Mesa, AZ (US); Garrick Wallstrom, Mesa, AZ (US); Jin Park, Phoenix, AZ (US); Vel Murugan, Chandler, AZ (US); Mitch Magee, Chandler, AZ (US)

(73) Assignee: Arizona Board of Regents on behalf of Arizona State University, Scottsdale, AZ (US)

( * ) Notice: Subject to any disclaimer, the term of this patent is extended or adjusted under 35 U.S.C. 154(b) by 0 days.

(21) Appl. No.: 16/532,138

(22) Filed: Aug. 5, 2019

(65) Prior Publication Data

US 2020/0010899 A1 Jan. 9, 2020

Related U.S. Application Data

(62) Division of application No. 14/823,433, filed on Aug. 11, 2015, now Pat. No. 10,435,747.

(60) Provisional application No. 62/038,969, filed on Aug. 19, 2014.

(51) Int. Cl.
*C12Q 1/6883* (2018.01)
*C12Q 1/6827* (2018.01)

(52) U.S. Cl.
CPC ........ *C12Q 1/6883* (2013.01); *C12Q 1/6827* (2013.01); *C12Q 2600/156* (2013.01)

(58) Field of Classification Search
None
See application file for complete search history.

(56) References Cited

U.S. PATENT DOCUMENTS

| | | | |
|---|---|---|---|
| 6,228,575 B1 | 5/2001 | Gingeras | |
| 9,442,111 B2 | 9/2016 | Lindsay | |
| 9,535,070 B2 | 1/2017 | Saul | |
| 9,719,144 B2 | 8/2017 | Krajmalnik-Brown | |
| 9,857,374 B2 | 1/2018 | Labaer | |
| 9,938,523 B2 | 4/2018 | Labaer | |
| 10,045,990 B2 | 8/2018 | Festa | |
| 10,351,842 B2 | 7/2019 | Labaer | |
| 10,435,747 B2* | 10/2019 | LaBaer | C12Q 1/6827 |
| 2003/0175761 A1 | 9/2003 | Sabath | |
| 2006/0286558 A1 | 12/2006 | Novoradovskaya | |
| 2007/0122815 A1 | 5/2007 | Horvais | |
| 2008/0076122 A1 | 3/2008 | Wyrobek | |
| 2008/0294403 A1* | 11/2008 | Zhu | G16B 5/00 703/11 |
| 2009/0023149 A1 | 1/2009 | Knudsen | |
| 2010/0196880 A1 | 8/2010 | Satyaraj | |
| 2010/0255004 A1 | 10/2010 | DePinho | |
| 2010/0304995 A1 | 12/2010 | Shen | |
| 2011/0152115 A1 | 6/2011 | Staudt | |
| 2013/0136722 A1 | 5/2013 | Mahmud | |
| 2014/0128277 A1 | 5/2014 | Moller | |
| 2014/0162902 A1 | 6/2014 | Labaer | |
| 2014/0371091 A1 | 12/2014 | Wiktor | |
| 2015/0362497 A1 | 12/2015 | Anderson | |
| 2016/0041159 A1 | 2/2016 | Labaer | |
| 2016/0083793 A1* | 3/2016 | LaBaer | C12Q 1/6883 424/93.7 |
| 2016/0195546 A1 | 7/2016 | Labaer | |
| 2017/0045515 A1 | 2/2017 | Anderson | |
| 2017/0115299 A1 | 4/2017 | Saul | |
| 2017/0176423 A1 | 6/2017 | Anderson | |
| 2017/0356029 A1 | 12/2017 | Krajmalnik-Brown | |
| 2017/0363631 A1 | 12/2017 | Labaer | |
| 2018/0067117 A1 | 3/2018 | Labaer | |
| 2018/0201923 A1 | 7/2018 | Labaer | |
| 2018/0224448 A1 | 8/2018 | Wang | |
| 2018/0267029 A1 | 9/2018 | Wiktor | |
| 2018/0320230 A1 | 11/2018 | Labaer | |
| 2019/0004051 A1 | 1/2019 | Labaer | |
| 2019/0062728 A1 | 2/2019 | Labaer | |
| 2019/0127778 A1 | 5/2019 | Labaer | |
| 2019/0144923 A1 | 5/2019 | Krajmalnik-Brown | |
| 2019/0162725 A1 | 5/2019 | Magee | |
| 2019/0302122 A1 | 10/2019 | Katchman | |
| 2019/0366237 A1 | 12/2019 | Labaer | |

FOREIGN PATENT DOCUMENTS

| | | |
|---|---|---|
| WO | 2012021887 A2 | 2/2012 |
| WO | 2012120026 | 9/2012 |
| WO | 2013019680 A1 | 2/2013 |
| WO | 2013063126 A2 | 5/2013 |
| WO | 2013090364 A1 | 6/2013 |
| WO | 2013176774 A1 | 11/2013 |

(Continued)

OTHER PUBLICATIONS

Dressman et al, PLoS Medicine, vol. 4, pp. 0690-0701 (2007).*
Ahmed et al, Free Radical Biology and Medicine vol. 44, pp. 1-13 (2008).
Amundson, S.A., et al., Differential responses of stress genes to low dose-rate gamma irradiation. Mol Cancer Res, 2003. 1(6): p. 445-52.
Amundson, S.A., et al., Identification of potential mRNA biomarkers in peripheral blood lymphocytes for human exposure to ionizing radiation. Radiat Res, 2000. 154(3): p. 342-6.
Anno GH, Young RW, Bloom RM, Mercier JR. Dose response relationships for acute ionizing-radiation lethality. Health Phys. 2003;84:565-575.

(Continued)

*Primary Examiner* — Robert T. Crow
(74) *Attorney, Agent, or Firm* — Quarles & Brady LLP; Jessica L. Lewis

(57) ABSTRACT

Disclosed herein are compositions and methods for accurately estimating the absorbed dose of radiation indicated by a subject based on the expression pattern of a panel of radiation-modulated (RM) genes at various time points following exposure of the subject to ionizing radiation.

6 Claims, 14 Drawing Sheets

Specification includes a Sequence Listing.

(56) References Cited

FOREIGN PATENT DOCUMENTS

| WO | 2013176774 A9 | 11/2013 |
| WO | 2014120902 A1 | 8/2014 |
| WO | 2014143954 A2 | 9/2014 |
| WO | 2014145458 A1 | 9/2014 |
| WO | 2015148202 A1 | 10/2015 |
| WO | 2015167678 A1 | 11/2015 |
| WO | 2015167678 A8 | 11/2015 |
| WO | 2015175755 A1 | 11/2015 |
| WO | 2016094558 A1 | 6/2016 |
| WO | 2016141044 A1 | 9/2016 |
| WO | 2017048709 A1 | 3/2017 |
| WO | 2017075141 A1 | 5/2017 |
| WO | 2017075141 A8 | 5/2017 |
| WO | 2017123648 A1 | 7/2017 |
| WO | 2017218677 A2 | 12/2017 |
| WO | 2018013531 A1 | 1/2018 |
| WO | 2018013531 A8 | 1/2018 |
| WO | 2018156553 A1 | 8/2018 |
| WO | 2019136169 A1 | 7/2019 |
| WO | 2019241361 A1 | 12/2019 |

OTHER PUBLICATIONS

Boldrick, J.C., AA. Alizadeh, M. Diehn, S. Dudoit, C.L. Liu, C.E. Belcher, D. Botstein, L.M. Staudt, P.O. Brown, and D. A. Reiman, Stereotyped and specific gene expression programs in humane innate immune responses to bacteria. Proc Natl Acad Sci U S A, 2002. 99(2):p. 972-7.

Braga-Neto, U.M. and E.R. Dougherty, Is cross-validation valid for small-sample microarray classification? Bioinformatics, 2004. 20(3): p. 374-80.

Brengues, M., et al., Biodosimetry on small blood volume using gene expression assay. Health Physics, 2010. 98(2): p. 179-85.

Brun, M., Q. Xu, and E.R. Dougherty, Which is better: holdout or full-sample classifier design? EURASIP J Bioinform Syst Biol, 2008: p. 297945.

Coleman N.C., et al, Medical response to a radiologic/nuclear event: integrated plan from the office of the Asisstant Secretary for preparedness and response, DHHS, Annals of Emergency Medicine, vol. 53(2), Feb. 2009: p. 223-225.

Copeland S, Warren HS, lowry SF, Calvano SE, Remick D. Acute inflammatory response to endotoxin in mice and humans. Clin Diagn Lab Immunol. 2005;12:60-67.

Dieffenbach et al, Genome Research, vol. 3, pp. 30-37 (1993).

Feldschuh J. and Enson Y. Prediction of the normal blood volume. Relation of blood volume to body habitus. Circulation. 1977. 56(4 Pt 1):605-12.

Fornace, A.J., Jr., et al., Stress-gene induction by low-dose gamma irradiation. Mil Med, 2002. 167(2 Suppl): p. 13-5.

Fornace, A.J., Jr., et al., The complexity of radiation stress responses: analysis by informatics and functional genomics approaches. Gene Expr, 1999. 7(4-6): p. 387-400.

Ganguly, D., K Paul, J. Bagchi, S. Rakshit, L. Mandal, G. Bandyopadhyay, and S. Bandyopadhyay, Granulocyte-macrophage colony-stimulating factor drives monocytes to CD14low CD83+ DCSIGNinterleukin-10-producing myeloid cells with differential effects on T-cell subsets. Immunology, 2007.121(4):p. 499-507.

Golde WT, Gollobin P, Rodriguez LL. A rapid, simple, and humane method for submandibular bleeding of mice using a lancet. Lab Anim (NY). 2005;34:39-43.

Hanczar, B. and E.R. Dougherty, Classification with reject option in gene expression data Bioinformatics, 2008. 24(17): p. 1889-95.

Hanczar, B., J. Hua, and E.R. Dougherty, Decorrelation of the true and estimated classifier errors in high-dimensional settings. EURASIP J Bioinform Syst Biol, 2007: p. 38473.

Hua, J., et al., Optimal number of features as a function of sample size for various classification rules. Bioinformatics, 2005. 21(8): p. 1509-15.

Kallman RF. The effect of dose rate on mode of acute radiation death of C57BL and BALB/c mice. Radiat Res. 1962;16:796-810.

Kim, S., et al., Strong feature sets from small samples. J Comput Biol, 2002. 9(1): p. 127-46.

Kuo, W.P., et al., A sequence-oriented comparison of gene expression measurements across different hybridization-based technologies. Nat Biotechnol, 2006. 24(7): p. 832-40.

Lee ML, Whitmore GA. Power and sample size for DNA microarray studies. Stat Med. 2002;21:3543-3570.

Lowry SF. Human endotoxemia: a model for mechanistic insight and therapeutic targeting. Shock. 2005; 24 Suppl 1:94-100.

Morgan, T.M., et al., Nonvalidation of reported genetic risk factors for acute coronary syndrome in a large-scale replication study. JAMA, 2007. 297(14): p. 1551-61.

Nifontova IN, Svinareva DA, Chertkov IL, Drize NI, Savchenko VG. Delayed effects of long-term administration of granulocyte colony-stimulating factor to mice. Bull Exp Biol Med. 2008;145:629-633.

Paul, S. and S.A. Amundson, Development of gene expression signatures for practical radiation biodosimetry. Int J Radiat Oncol Biol Phys, 2008. 71(4): p. 1236-1244.

Planning Guidance for Response to a Nuclear Detonation, First Edition, Jan. 16, 2009, developed by Homeland Sceurity Council Interagency Policy Coordination Subcommittee for Preparedness & Response to Radiological and Nuclear Threats.

Roux, Genome Research, vol. 4, pp. 185-194 (1994).

Schwab G, Hecht T. Recombinant methionyl granulocyte colony-stimulating factor (filgrastim): a new dimension in immunotherapy. Ann Hematol. 1994;69:1-9.

Sima, C. and E.R. Dougherty, What should be expected from feature selection in small-sample settings. Bioinformatics, 2006.22(19): p. 2430-6.

Sima, C., U. Braga-Neto, and E.R. Dougherty, Superior feature-set ranking for small samples using bolstered error estimation. Bioinformatics, 2005. 21(7): p. 1046-54.

Simon R, Lam A, Li M-C, Ngan M, Menenzes S, Zhao Y. Analysis of gene expression data using BRBArray Tools. Cancer Informatics. 2007;2:11-17.

Warren HS. Editorial: Mouse models to study sepsis syndrome in humans. J Leukoc Biol. 2009;86:199-201.

Waselenko JK, MacVittie TJ, Blakely WF et al. Medical management of acute radiation syndrome: recommendations of the Strategic National Stockpile Radiation Working Group. Ann Intern Med. 2004;140:1037-1051.

Xiao, Y., J. Hua, and E.R. Dougherty, Quantification of the impact of feature selection on the variance of cross-validation error estimation. EURASIP J Bioinform Syst Biol, 2007: p. 16354.

Xu, Q., et al., Confidence intervals for the true classification error conditioned on the estimated error. Technol Cancer Res Treat, 2006. 5(6): p. 579-89.

Zhu H, Melder RJ., Baxter LT. and Jain RK. Physiologically based kinetic model of effector cell biodistribution in mammals: implication for adoptive immunotherapy. Cancer Res. 1996. 56(16):3771-81.

U.S. Appl. No. 16/743,906, filed Jan. 15, 2020, Labaer et al.
U.S. Appl. No. 16/791,640, filed Feb. 14, 2020, Labaer et al.
U.S. Appl. No. 16/097,791, filed Oct. 30, 2018, Labaer et al.

\* cited by examiner

FIG. 1A

| Gene | Regulated | Function | Day 1 | Day 2 | Day 3 | Day 5 | Day 7 |
|---|---|---|---|---|---|---|---|
| CR2 | Down | Immune Response | | | | | |
| DHRS4L1 | Down | Metabolism | | | | | |
| HCK | Up | Cell Signaling | | | | | |
| IL1RAP | Up | Immune response | | | | | |
| LYRM4 | Down | Mitochondrial Fe-S Syn | | | | | |
| MYC | Down | DNA Damage/Apoptosis | | | | | |
| TMEM63B | Down | Membrane transport | | | | | |
| ALOX5 | Up | Immune Response | | | | | |
| CAMK4 | Down | Cell Signaling | | | | | |
| CDKN1A | Up | DNA Damage/Apoptosis | | | | | |
| COCH | Down | Cell shape | | | | | |
| DHRS4 | Down | Metabolism | | | | | |
| MICAL1 | Up | Metabolism | | | | | |
| MOB3B | Down | Regulates kinases | | | | | |
| NUSAP1 | Down | DNA Damage/Apoptosis | | | | | |
| IL27RA | Down | Immune Response | | | | | |

FIG. 1B

| Gene | Regulated | Function | Day 1 | Day 2 | Day 3 | Day 5 | Day 7 |
|---|---|---|---|---|---|---|---|
| HBA2 | Down | Hemoglobin | | | | | |
| PPM1F | Up | Cell Signaling | | | | | |
| PPP2R1A | Down | Cell Signaling | | | | | |
| CFLAR | Up | DNA Damage/Apoptosis | | | | | |
| DHRS13 | Up | Metabolism | | | | | |
| ACAA1 | Up | Metabolism | | | | | |
| INPP5J | Up | Cell Signaling | | | | | |
| OAZ1 | Down | Metabolism | | | | | |
| PNOC | Down | Cell Signaling | | | | | |
| PDE4B | Up | Metabolism | | | | | |
| SCARB1 | Down | Immune Response | | | | | |
| TMEM98 | Down | Membrane Signaling | | | | | |
| PPP6R3 | Reference | Immune Tolerance | | | | | |
| Number of Biomarkers Used Post-Event Start Day # | | | 29 | | 24 | | 22 |

FIG. 6

| Test Model Sample Set | Sample Set Number | Performance Rate | |
|---|---|---|---|
| | | Sensitivity True Positive (+) | Specificity True Negative (-) |
| NHP Fractionated (2 Gy Fractions) | 6 Control | - | 100% |
| | 42 Irradiated | 100% | - |
| Human TBI Model (2 Gy Fractions) | 5 Control | - | 100% |
| | 26 Irradiated | 100% | - |
| Normal Human (not Irradiated) | 23 Control | - | 100% |

*No False (-) or False (+) observations for Human TBI and Normal samples.*

FIGS. 10A-B
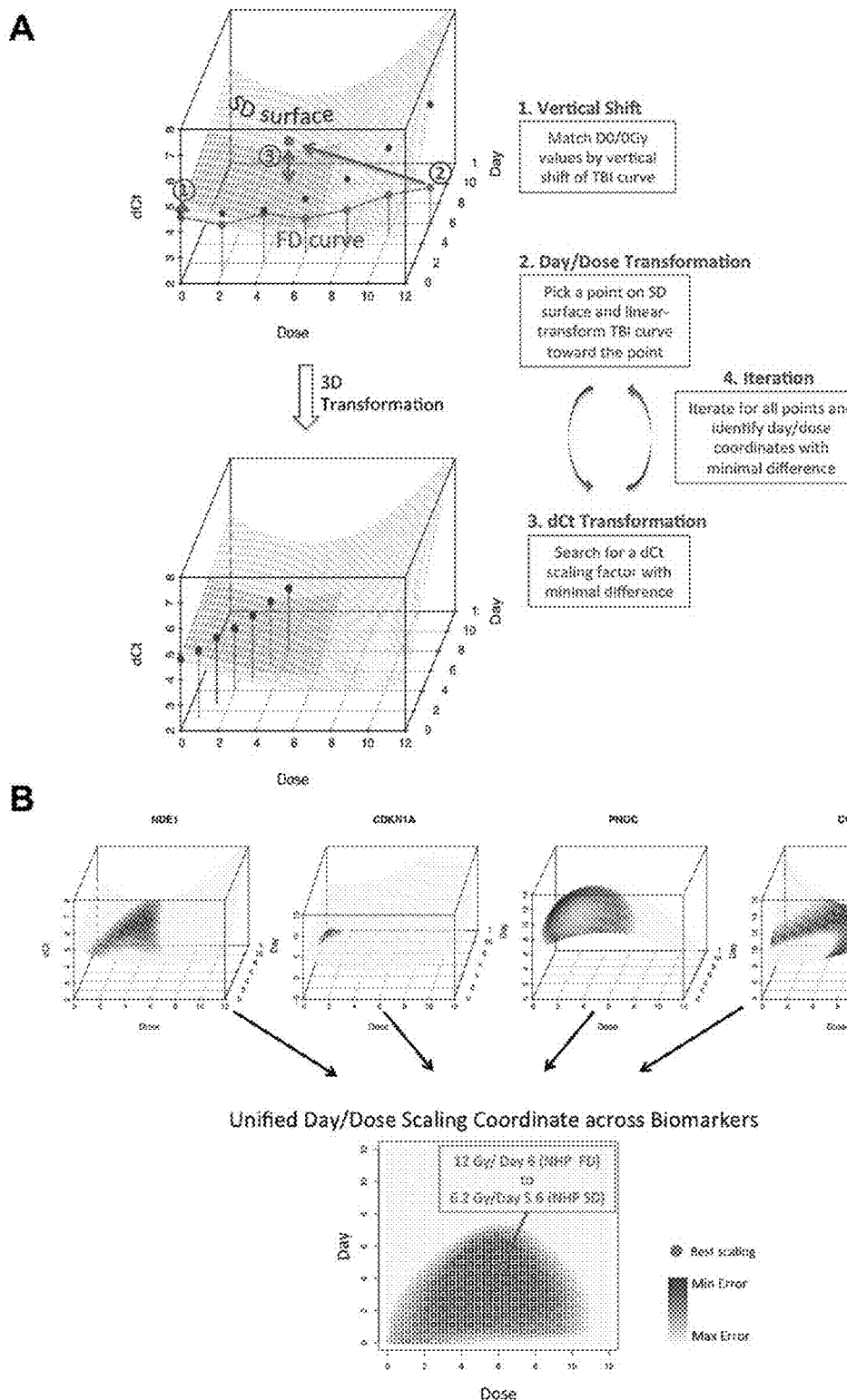

FIGS. 11A-B
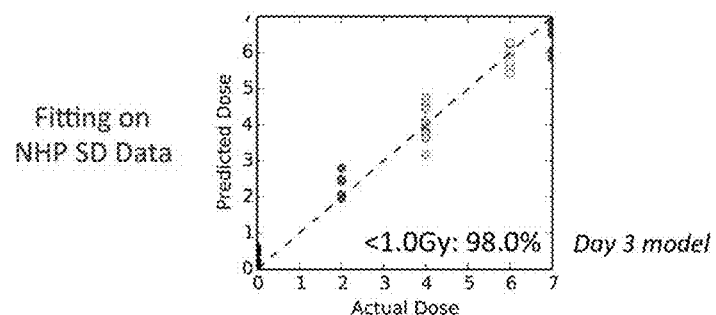
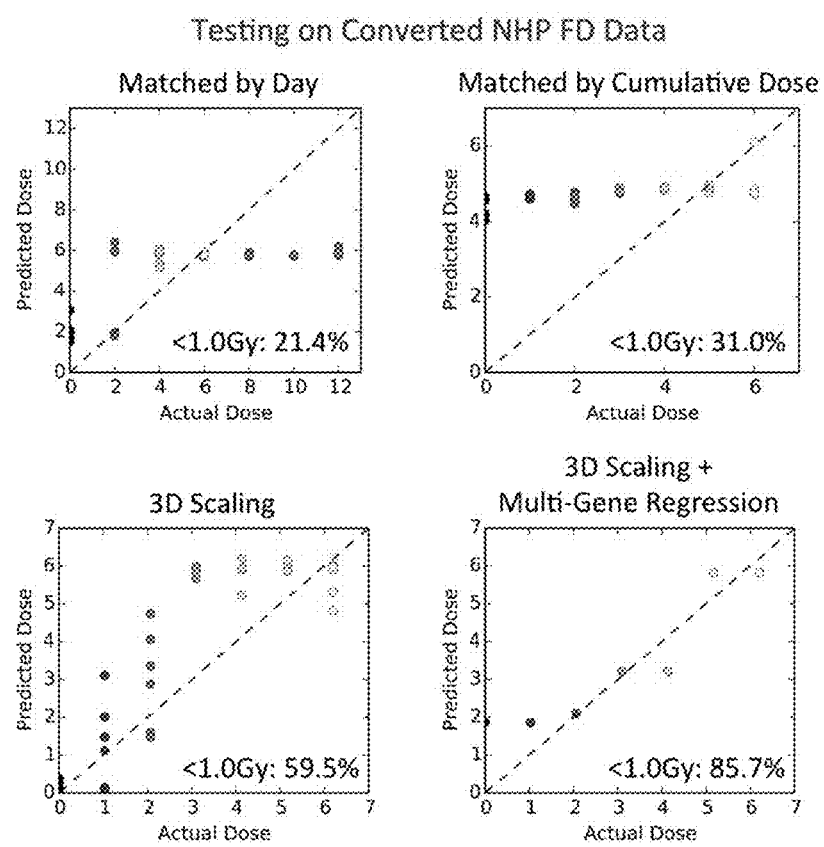

FIGS. 12A-B
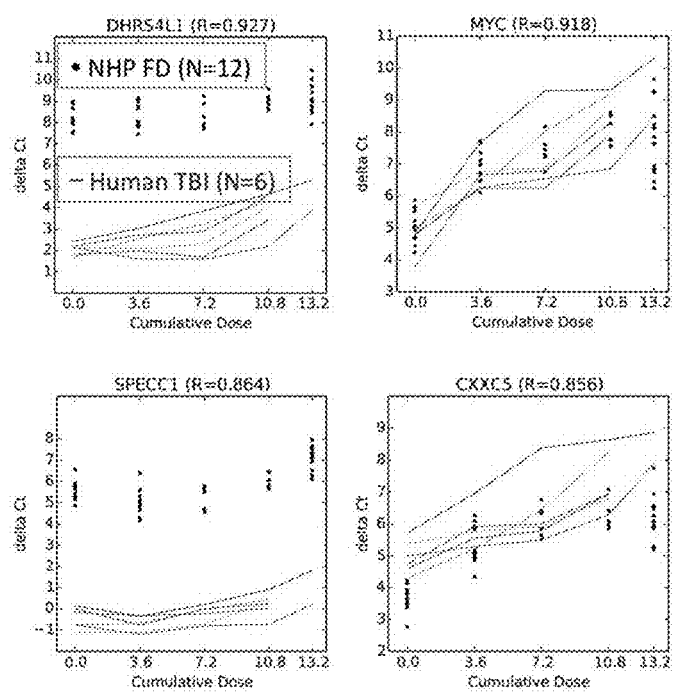

FIGS. 13A-B
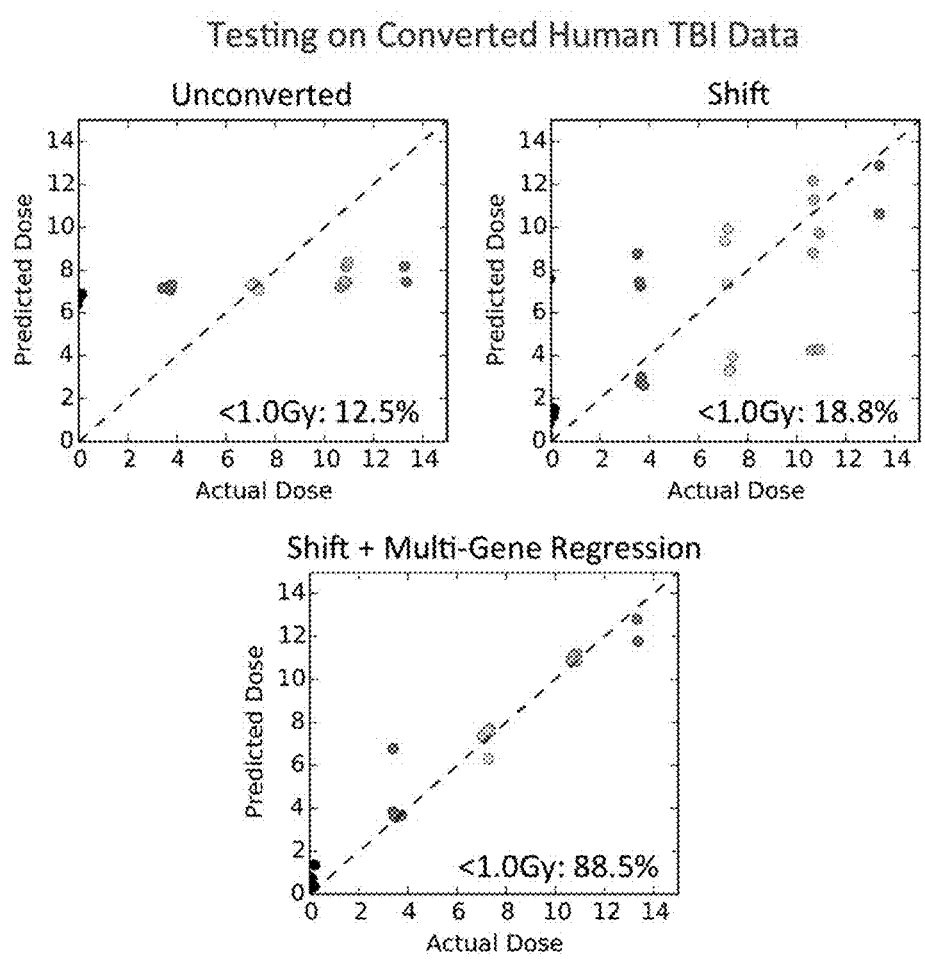

RADIATION BIOSIMETRY SYSTEMS

CROSS-REFERENCE TO RELATED APPLICATIONS

This application is a divisional of U.S. patent application Ser. No. 14/823,433, filed on Aug. 11, 2015, and claims the benefit of U.S. Provisional Application No. 62/038,969, filed Aug. 19, 2014, the disclosures of which are hereby incorporated by reference in their entirety for all purposes.

STATEMENT REGARDING FEDERALLY SPONSORED RESEARCH OR DEVELOPMENT

This invention was made with government support under HHSO100201000008C awarded by Biomedical Advanced Research and Development Authority. The government has certain rights in the invention.

BACKGROUND

Radiation exposure is one of the most serious hazards of the modern era. The health consequences to individuals and populations exposed to radiological incidents, accidental or otherwise, can range from negligible to fatal depending on the amount of radiation that is absorbed by an individual. Yet, it is often difficult or impossible to quickly determine the absorbed dose of radiation for an individual or population after a radiological event and thereby determine an appropriate course of treatment. This is particularly critical when large numbers of individuals are potentially affected by radiation exposure and must be quickly "triaged" to prioritize treatment strategies. Thus, there is a great need for systems that quickly estimate, post-hoc, the absorbed dose of radiation by an individual resulting from an ionizing radiation exposure incident.

BRIEF SUMMARY OF THE INVENTION

Disclosed herein are compositions and methods for accurately estimating the absorbed dose of radiation suffered by a subject based on the expression pattern in RNA obtained from peripheral blood of a panel of radiation-modulated (RM) genes at various time points following exposure of the subject to ionizing radiation.

Accordingly in one aspect provided herein is a radiation biosimetry assay system, comprising a plurality of nucleic acid amplification reactions comprising (i) mRNA or cDNA from a human subject suspected of (but not necessarily) suffering from radiation exposure; (ii) primer pairs capable of hybridizing under stringent conditions to mRNAs or cDNAs comprising the nucleotide sequences referred to in Table 4 or the complementary sequences thereof, wherein each primer pair hybridizes to a different one of the mRNAs or cDNAs; and (iii) a thermostable enzyme suitable for amplification of target amplicon sequences from the mRNAs or cDNAs. A mathematical algorithm that converts gene expression results to estimated absorbed dose of radiation.

In some embodiments the one or more nucleic acid amplification reactions further comprise detectably labeled TAQMAN® probes capable of hybridizing under stringent conditions to the mRNAs or cDNAs. In some embodiments the thermostable enzyme is a thermostable polymerase.

In some embodiments the mRNA is from a subject that was exposed to radiation about 4-hours to about seven days prior to the time at which a biological sample comprising the mRNA was obtained.

In another aspect provided herein is a radiation biomarker assay kit, comprising a nucleic acid probe set consisting essentially of nucleic acid probes that hybridize specifically with nucleic acid targets comprising at least one of the nucleotide sequences referred to in SEQ ID NOs: 1-29 or the complementary sequences thereof. In some embodiments the probe set comprises no more than 100 probes. In some embodiments the probe set consists of the nucleic acid probes that hybridize specifically with the nucleic acid targets.

In some embodiments the nucleic acid probe set comprises primer pairs and TAQMAN® probes suitable for qPCR analysis of mRNAs or cDNAs comprising at least one of the nucleotide sequences referred to in SEQ ID NOS: 1-29 or the complementary sequences thereof. In some embodiments the nucleic acid probes are provided in a multi-well plate. In some embodiments, where the nucleic acid probes are provided in a multi-well plate, at least two nucleic acid probes that hybridize to at least two different nucleic acid targets are in the same wells of the multi-well plate.

In some embodiments the kit also includes radiation exposure positive and negative control mRNA samples or cDNAs thereof. In another aspect provided herein is a method for assessing a dose of ionizing radiation absorbed by a subject, comprising (i) determining the mRNA expression levels of mRNAs comprising at least one of the nucleotide sequences referred to in SEQ ID NOs: 1-29 in a biological sample, comprising mRNA from the subject, to obtain an expression profile; and (ii) transforming the gene expression profile and when available, the duration of time from exposure to sample collection, into a measure of absorbed dose of radiation for the subject based on a mathematical algorithm. In one embodiment, the algorithm utilizes multiple random forest regression trees to estimate absorbed dose and confidence limits and then a top-level logic layer to combine outputs into a single estimated absorbed dose with confidence limits.

In some embodiments the method further includes treating the subject based on the estimated absorbed dose of radiation determined in step (ii).

In some embodiments the absorbed dose of ionizing radiation is determined within about seven days of subject exposure to ionizing radiation.

In some embodiments the method also includes a step of obtaining the biological sample from the subject prior to step (i).

In a further aspect provided herein is a method for radiation treatment triage of a subject in need thereof comprising (i) determining the mRNA expression levels of mRNAs comprising the nucleotide sequences referred to in at least one of SEQ ID NOs: 1-29 (or any other sequence identifier included herein, in any combination) in a biological sample comprising leukocyte mRNA from the subject to obtain a gene expression profile; and (ii) providing a suitable treatment for radiation exposure to the subject based on the expression levels of the genes.

INCORPORATION BY REFERENCE

All publications, patents, and patent applications mentioned in this specification are herein incorporated by reference to the same extent as if each individual publication, patent, and patent application was specifically and individually indicated to be incorporated by reference.

BRIEF DESCRIPTION OF THE DRAWINGS

The present invention will be better understood and features, aspects and advantages other than those set forth above will become apparent when consideration is given to the following detailed description thereof. Such detailed description makes reference to the following drawings, wherein:

FIG. 1A show tables listing a set of 28 radiation modulated (RM) genes and their expression pattern at various time points following absorption of ionizing radiation.

FIG. 1B show tables listing a set of 28 radiation modulated (RM) genes and their expression pattern at various time points following absorption of ionizing radiation.

FIG. 6 shows a table describing the sensitivity and specificity of the biodosimetry algorithm in various NHP and human irradiation models.

FIG. 10A shows a schematic overview on the approach to convert NHP fractionated dose (FD) data to the corresponding values in NHP single-dose (SD) data by 3-dimensional linear scaling of day, dose, and expression values.

FIG. 10B shows the optimal range (in blue) of dose/day scaling factors for 12 Gy/day-6 data points of individual biomarkers (top panels) and a unified scaling factor (bottom panel) for 29 tested biomarkers.

FIG. 11A shows dose prediction performances of a random forests model based on 7 correlated biomarker genes on NHP SD data (for day 3, as an example).

FIG. 11B shows dose prediction performances of a random forests model based on 7 correlated biomarker genes on converted NHP FD values across all days by matching day/cumulative dose, 3D scaling, and 3D scaling followed by multi-gene regression. Prediction accuracies within 1.0 Gy are shown.

FIG. 12A shows correlation of individual biomarker expression values between NHP fractionated dose (FD) and human TBI, magnitude of expressional changes across dose, and mean absolute difference (MAD) between NHP FD and human TBI data points.

FIG. 12B shows dose response curves of the top 4 inter-species correlated genes in NHP FD and human TBI data.

FIG. 13A shows dose prediction performances of a random forests model based on 10 inter-species biomarker genes on NHP FD data.

FIG. 13B shows dose prediction performances of a random forests model based on 10 inter-species biomarker genes on unconverted and converted human TBI values by value shift, and value shift followed by multi-gene regression. Prediction accuracies within 1.0 Gy are shown.

DETAILED DESCRIPTION

Figure 2:
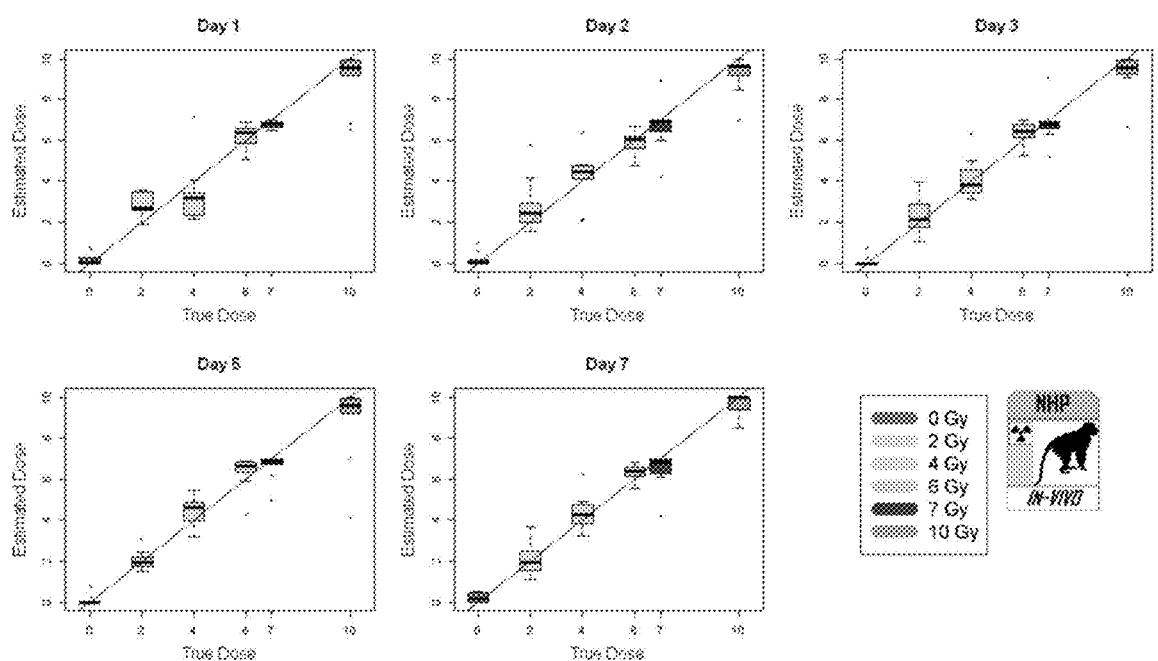
FIG. 2 shows a time series (days 1-7) of plots of actual delivered ionizing radiation dosage values (0 Gy to 10 Gy) versus estimated absorbed dose of radiation based on changes in RM gene expression in peripheral blood
Figure 3:
FIG. 3 shows a table providing the percentage accuracy (within 1 Gy) of the biodosimetry algorithm's absorbed radiation dose estimate based on expression of 29 RM genes in peripheral blood collected from rhesus macaque non-human primate (NHPs) at various time points (1-7 days) following exposure to irradiation doses ranging from 0 Gy to 10 Gy.
Figure 4:
FIG. 4 shows a table providing the percentage accuracy (within 0.5 Gy) of the biodosimetry algorithm's absorbed radiation dose estimate based on expression of 29 RM genes in peripheral blood from NHPs at various time points (1-7 days) following exposure to irradiation doses ranging from 0 Gy to 10 Gy.
Figure 5:
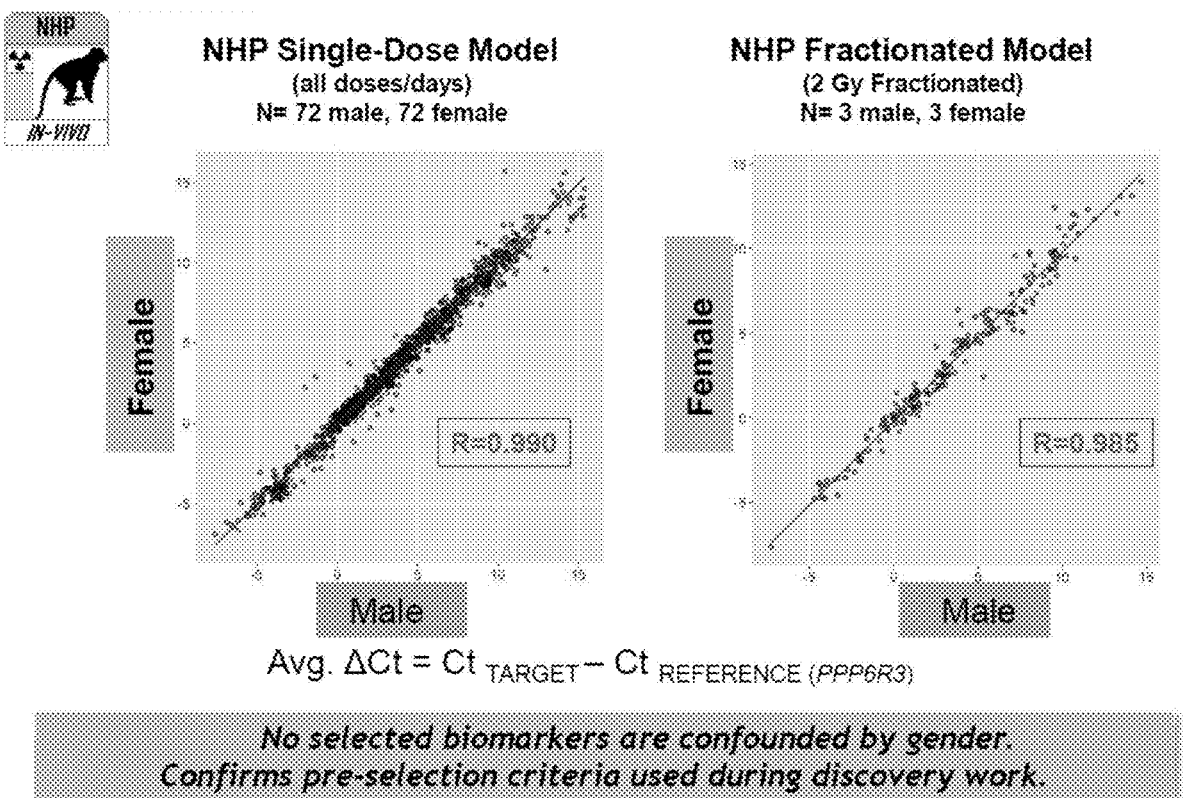
FIG. 5 shows scatter plots of changes in RM gene expression in male vs. female NHPs following radiation exposure of various doses and at different time points following radiation exposure. As shown, male and female RM gene expression responses were very closely correlated for the 29 RM genes.
Figure 7:
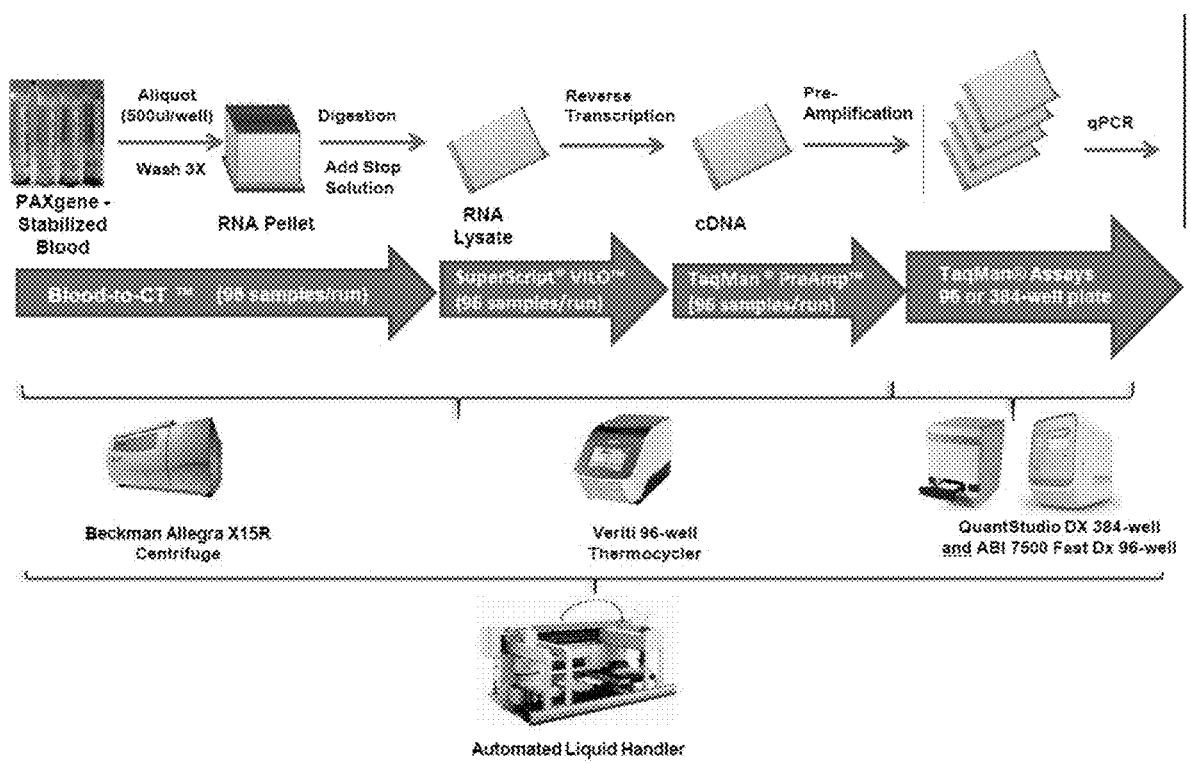
FIG. 7 shows an overview of an exemplary, non-limiting, embodiment of biodosimetry workflow illustrating the steps of: blood sample collection, RNA isolation, reverse transcription to obtain cDNA, pre-amplification of the cDNA, and qPCR assay of a RM biomarker and reference gene panel.

In General. Before the present materials and methods are described, it is understood that this invention is not limited to the particular methodology, protocols, materials, and reagents described, as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. As well, the terms "a" (or "an"), "one or more" and "at least one" can be used interchangeably herein. It is also to be noted that the terms "comprising", "including", and "having" can be used interchangeably.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods and materials are now described. All publications and patents specifically mentioned herein are incorporated by reference for all purposes including describing and disclosing the chemicals, cell lines, vectors, animals, instruments, statistical analysis and methodologies which are reported in the publications which might be used in connection with the invention. All references cited in this specification are to be taken as indicative of the level of skill in the art. Nothing herein is to be construed as an admission that the invention is not entitled to antedate such disclosure by virtue of prior invention.

The Invention

The present invention provides methods for estimating absorbed dose of ionizing radiation by a subject, which includes the steps of: (i) determining the mRNA expression levels of mRNAs comprising the nucleotide sequences referred to in SEQ ID NOs: 1-29 in a biological sample comprising peripheral blood mRNA collected from the subject to obtain an expression profile; and (ii) transforming the gene expression profile and when available, the duration of time from exposure to sample collection into an estimated absorbed dose of ionizing radiation and confidence limits for a subject based on a mathematical algorithm. For each of several durations for which training data were available, one primary random forest was developed to estimate absorbed dose of radiation. Additional secondary random forests were developed to provide more accurate dosimetry in narrow dosage intervals. The top-level logic layer uses the primary random forest to generate an initial estimate of absorbed dose of radiation, and based on that value, may select additional random forests to construct more refined estimates of absorbed dose, with confidence limits.

In some embodiments the method also includes treating the subject based on the absorbed dose of ionizing radiation determined in step (ii) above. In some embodiments the absorbed dose of ionizing radiation is determined within about seven days of exposure to the ionizing radiation, e.g., within about 30 minutes, 1 hour, 3 hours, 6 hours, 8 hours, 24 hours, 1 day, 2 days, 3 days, 4 days, 5 days, 6 days, or another time period within seven days following ionizing irradiation. In some embodiments, the absorbed dose of ionizing radiation is within the range of about 0.5 Grays (Gy) to about 10 Gy, e.g., about 1 Gy, 2 Gy, 3 Gy, 4 Gy, 6 Gy, 7 Gy, 8 Gy, 9 Gy, or another absorbed dose of ionizing radiation from about 0.5 Gy to about 10 Gy.

In some embodiments, the method also includes obtaining the biological sample from the irradiated subject prior to step (i) above.

In one embodiment, a whole blood sample, or other blood fraction containing lymphocytes, (including a finger stick or POC device) is collected from a subject known to be or suspected of being irradiated into a PAXGENE™ Blood RNA tube. The PAXGENE™ Blood RNA contains an additive that stabilizes in vitro gene expression and RNA degradation. Subsequently, RNA is extracted from the stabilized blood sample by using a Stabilized BLOOD-TO-CT™ Nucleic Acid Preparation Kit for qPCR (Life Technologies, Inc.). The RNA sample is then subjected to reverse transcription, e.g., using the INVITROGEN™ SUPERSCRIPT® VILO™ (Variable Input, Linear Output) cDNA synthesis kit (Life Technologies, Inc.) or equivalent kit. Afterwards, the resulting cDNA is pre-amplified using a TAQMAN® probe PreAmp Master Mix Kit (Life Technologies, Inc.) and the pre-amplified cDNA is then assayed by TAQMAN® probe-based qPCR in a 96-well or 384-well format using QUANTSTUDIO™ Dx or ABI7500 Fast Dx quantitative Real-Time PCR Instruments (Life Technologies, Inc.). Typically, expression levels of RM mRNAs will be expressed as a difference in $C_T$ between a test gene and a reference ("housekeeping") gene $C_T$.

In some embodiments the panel of RM mRNAs to be assayed include at least some combination of mRNAs for one or all of the following (human) genes: CR2 (SEQ ID NO: 1), DHRS4L1 (SEQ ID NO: 2), HCK (SEQ ID NO: 3), IL1RAP (SEQ ID NO: 4), LYRM4 (SEQ ID NO: 5), MYC (SEQ ID NO: 6), TMEM63B (SEQ ID NO: 7), ALOX5 (SEQ ID NO: 8), CAMK4 (SEQ ID NO: 9), CDKN1A (SEQ ID NO: 10), COCH (SEQ ID NO: 11), DHRS4 (SEQ ID NO: 12), MICAL1 (SEQ ID NO: 13), MOB3B (SEQ ID NO: 14), NUSAP1 (SEQ ID NO: 15), IL27RA (SEQ ID NO: 16), HBA2 (SEQ ID NO: 17), PPM1F (SEQ ID NO: 18), PPP2R1A (SEQ ID NO: 19), CFLAR (SEQ ID NO: 20), DHRS13 (SEQ ID NO: 21), ACAA1 (SEQ ID NO: 22), INPP5J (SEQ ID NO: 23), OAZ1 (SEQ ID NO: 24), PNOC (SEQ ID NO: 25), PDE4B (SEQ ID NO: 26), SCARB1 (SEQ ID NO: 27), TMEM9B (SEQ ID NO: 28), PPP6R3 (SEQ ID NO: 29), CXXC5, CD97, TEX10, SPECC1, ALAS2, ALPK1, ESD, GPR183, PPM1K, and SLC6A6 (collectively, SEQ ID NOs: 1-29).

In other embodiments RM mRNAs to be assayed can include at least some combination of one or all of the following genes: ADAM17, AKT1, ANK1, ANXA3, ARHGAP26, ARID4A, ATG2A, ATIC, BCL11A, BCL6, BID, CFLAR, CIT, CPVL, CYTH4, DDB2, DDX58, DTL, EHBPL1, FCGR2A, FGR, HPRT1, HSP90AB1, HTRA2, IDOL, IRF1, JMJD1C, KIAA0101, LARP4B, LRRC6, LYN, MAP3K11, MAPK3, MDM1, MKNK1, MXD1, NAIP, NFE2L2, NRG1, NUSAP, PCNA, PGK1, PMP22, RARA, RNASE6, RPL13A, RPL6, RPS14, SP110, SPOCK2, TAPBP, TBP, TCF3, TNFRSF1A, TNFRSF1B, TNFSF14, USP38, WDR48, XAFJ, ZAK, NPM1, CPSF1, COASY, DNAJC10, DYNLRB1, ELK4, GPRIN, NDE1, PGS1, PPM1K, and PTAFR. In some embodiments, the reference gene to be assayed is PPP6R3. In other embodiments the reference gene to be assayed may be USP38, WDR48 or LARP4B or some combination thereof.

In some embodiments, qPCR reactions are multiplexed such that multiple mRNAs (including a reference mRNA) are assayed in a single qPCR reaction.

Also disclosed herein is a method for radiation treatment triage of a subject in need thereof, which includes the steps of: (i) determining the mRNA expression levels of mRNAs comprising the nucleotide sequences referred to in any of SEQ ID NOS: 1-2949 (or any combination of any other SEQ ID NO provided herein) in a biological sample comprising mRNA from the subject to obtain an expression profile; and (ii) providing a suitable treatment for radiation exposure to the subject based on the expression levels of the genes. Exemplary treatments for radiation exposure based on radiation dosage are shown in Table 1 below:

TABLE 1

Exemplary treatments for radiation exposure based on radiation dosage.

| Symptoms and treatment strategy | | Mild (1-2 Gy) | Moderate (2-4 Gy) | Severe (4-6 Gy) | Very severe (6-8 Gy) | Lethal (a) (>8 Gy) |
|---|---|---|---|---|---|---|
| Vomiting | Onset | After 2 hr. | After 1-2 hrs. | Within 1 hr. | Within 30 min. | Within 10 min. |
| | Incidence | 10-50% | 70-90% | 100% | 100% | 100% |
| Diarrhea | Onset | None | None | Mild 3-8 hrs. | Heavy 1-3 hrs. | Heavy Within min.-1 hr. |
| | Incidence | | | <10% | >10% | almost 100% |
| Headache | Onset | Slight | Mild | Moderate 4-24 hrs. | Severe 3-4 hrs. | Severe 1-2 hrs. |
| | Incidence | | | 50% | 80% | 80-90% |

TABLE 1-continued

Exemplary treatments for radiation exposure based on radiation dosage.

| Symptoms and treatment strategy | | Mild (1-2 Gy) | Moderate (2-4 Gy) | Severe (4-6 Gy) | Very severe (6-8 Gy) | Lethal (a) (>8 Gy) |
|---|---|---|---|---|---|---|
| Consciousness | Onset Incidence | Alert | Alert | Alert | Possibility of impairment | Unconsciousness by order of seconds or minutes Seconds-minutes 100% (>50Gy) |
| Body Temperature | Onset Incidence | Normal | Increased 1-3 hrs. 10-80% | Fever 1-2 hrs. 80-100% | High fever <1 hrs. 100% | High fever <1 hrs. 100% |
| Treatment Strategy | | Outpatient observation | Observation at general hospital, treatment at specialized hospital if required | Treatment at specialized Hospital | Treatment at specialized hospital | Palliative treatment (a) (advanced medical care including stem cell transplantation) |

Also described herein is a radiation biodosimetry assay system that includes multiple nucleic acid amplification reactions containing the following: (i) mRNA or cDNA from a human subject suspected of suffering from radiation exposure; (ii) primer pairs capable of hybridizing under stringent conditions to mRNAs or cDNAs comprising the nucleotide sequences referred to in SEQ ID NOS: 1-29 (or any other SEQ ID NO provided herein), or the complementary sequences thereof, wherein each primer pair hybridizes to a different one of the mRNAs or cDNAs; and (iii) A mathematical algorithm the converts gene expression results to estimated absorbed dose of radiation.

In one embodiment, the mathematical algorithm of the present invention The Radiation Biodosimetry Absorbed Dose Estimation algorithm described herein takes as input sample qPCR data, sample barcode, and available information about the date and time of the exposure event and sample collection. The primary output of the algorithm is an absorbed dose report that contains an estimated absorbed dose and a dose interval that provides a range of dose values for the patient based on prediction intervals. The algorithm contains 6 basic steps, which are summarized in Table 2.

In Step 1, patient qPCR data are combined with the available information about the date and time of the event and sample collection using the patient barcode.

In Step 2, several quality control metrics are calculated for the qPCR data. Depending on the values of these metrics, the algorithm may determine that a sample requires re-testing. If the sample does not require re-testing, the quality control metrics will be utilized in the estimation of absorbed radiation dose, and in particular may affect the estimation interval.

In step 3, the qPCR data are checked against expected ranges for each biomarker.

In step 4, quality control metrics and the results of the biomarker range checks are used to determine whether specific biomarker values are invalid and whether sufficient biomarker values are valid for dose estimation.

Figure 8:
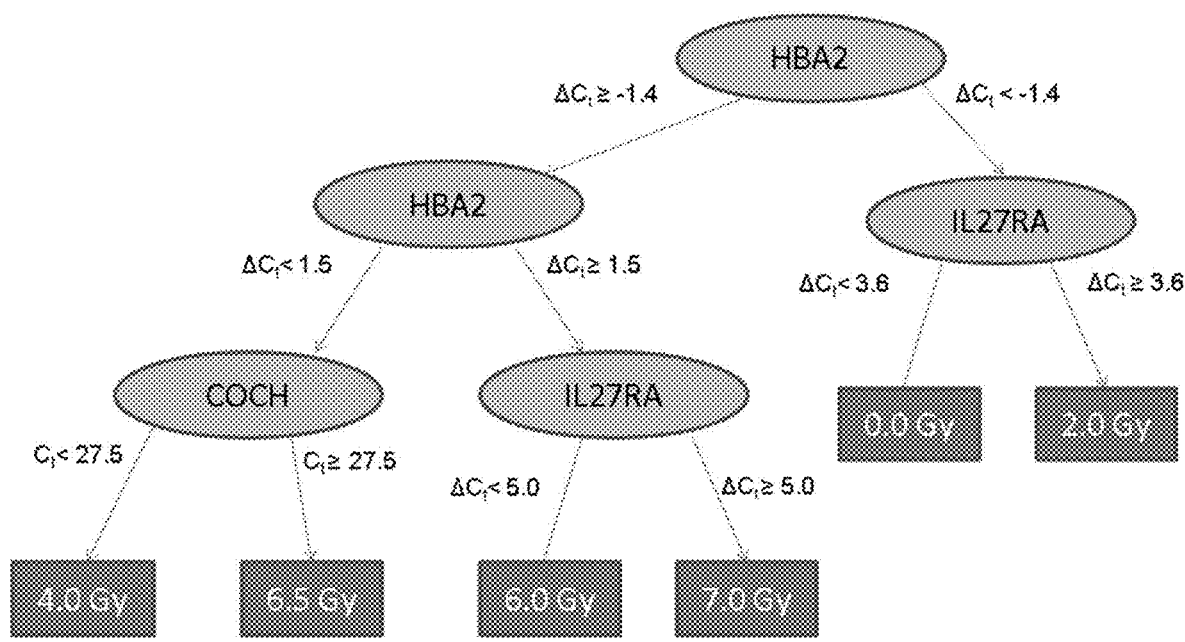
FIG. 8 shows a single regression tree in a random forest example. This tree generates an estimated absorbed dose using the relative expression levels of gene biomarkers, HBA2 and IL27RA, and the absolute expression level of gene biomarker, COCH.

In step 5, the qPCR data and the available temporal information for the event and sample collection are processed through a random forest-based mathematical algorithm that yields an estimated dose and a dose interval. The mathematical algorithm in Step 5 utilizes Random Forests™ method, introduced by Breiman (2001). Random forests is a popular machine-learning tool for prediction that combines large numbers of classification or regression trees to yield accurate and robust predictions. A random forest is a collection of classification or regression trees that we denote by $R=\{(T_1, \ldots, T_n\}$. The input to the forest is a vector X of relative and/or absolute expression levels of a set of genes. In a regression random forest, each tree $T_i$ takes X as input and outputs an estimate of absorbed dose, $T_i(X)$. For example, FIG. 8 depicts a single tree in a random forest that utilizes the relative expression levels for two gene biomarkers (HBA2 and IL27RA) and the absolute expression level for one gene biomarker (COCH). The estimate of absorbed dose from a regression random forest R is then the average of estimated absorbed doses from the trees within the forest. We write this estimate as:

$$AD = R(X) = \frac{1}{n} \times \sum_{i=1}^{n} T_i(X)$$

In a classification random forest, samples are partitioned into several non-intersecting groups. For example, samples may be partitioned based upon dose and each group then represents an interval for the absorbed dose. Each tree $T_i$ takes as input X and outputs the identity of a single group, $T_i(X)$. The output from the classification random forest is a probability distribution on the set of groups, where the probability assigned to each group is the proportion of trees that yield the group.

The inputs to the mathematical algorithm in Step 5 are a set of absolute and relative expression levels, X for a set of genes, and a probability distribution π that reflects the uncertainty in D, the duration of time from irradiation to sample collection. If the duration of time is known precisely, π will be a point mass distribution on that known duration of time. If the duration is only known to fall within an interval, then π may be any probability distribution on that interval such as a uniform distribution or a symmetric triangular distribution. If the duration is entirely unknown or not provided, then π may be calculated using a classification random forest that takes as input X and yields as output a probability distribution over a fixed set of duration values.

The outputs are an estimated absorbed dose, AD and a 95% prediction interval for the absorbed dose, ($AD_{low}$, $AD_{high}$). For NHP samples that were irradiated with a single acute dose (NHP SD), these outputs are computed in two steps. First, we compute an initial estimate of absorbed dose, AD$^I$. Secondly, we correct for bias in the estimate to yield the final estimate of absorbed dose, AD and generate the 95% prediction interval.

A novel aspect of our algorithm is the use of multiple random forests for each of several fixed durations, $D_1, \ldots, D_k$. For duration $D_i$, we use $n_i$ random forests, denoted by $RF_{i,1}, \ldots, RF_{i,n_i}$, to construct initial estimates of absorbed dose. A decision tree $T_i$ combines the outputs from $RF_{i,1}, \ldots, RF_{i,n_i}$ into a single initial estimate of absorbed dose. One additional random forest, denoted by $RF_i^E$, is a quantile regression random forest for error that uses the expression values X' and the output from $T_i$ for bias correction and construction of prediction intervals. These $n_i+1$ random forests utilize different, but possibly overlapping sets of genes, may be trained on different sets of samples and may include both regression forests and classification forests. Hence, if the duration is known to equal $D_i$, the initial estimate of absorbed dose, denoted by AD$^I$ ($D_i$), is computed as:

$$AD^I(D_i) = T_i(RF_{i,1}(X'), \ldots, RF_{i,n_i}(X'))$$

This estimate and the transformed expression levels X' are then passed to the random forest $RF_i^E$. The output from $RF_i^E$ is the conditional probability distribution for the error in the estimate AD$^I$($D_i$). We denote the cumulative distribution function for this conditional distribution by F(·|D=$D_i$). The bias corrected estimate of absorbed dose is then AD($D_i$)=AD$^I$($D_i$)−F$^{-1}$(0.5). If the duration is known to equal D* where $D_i$<D*<$D_{i+1}$, the estimated absorbed dose is computed as:

$$AD(D^*) = \frac{D_{i+1} - D^*}{D_{i+1} - D_i} \times AD(D_i) + \frac{D^* - D_i}{D_{i+1} - D_i} \times AD(D_{i+1})$$

The final estimate of absorbed dose is computed by averaging over the probability distribution π, that is, AD=∫AD(D)×π(D)dD.

Similarly, we define F(·|D=D*) by:

$$F(\cdot \mid D = D^*) = \frac{D_{i+1} - D^*}{D_{i+1} - D_i} \times F(\cdot \mid D = D_i) + \frac{D^* - D_i}{D_{i+1} - D_i} \times F(\cdot \mid D = D_{i+1})$$

The 95% prediction interval for the absorbed dose is then found by solving the equations:

$$\int F(e_1 \mid D) \times \pi(D) dD = 0.025, \text{ and}$$

$$\int F(e_2 \mid D) \times \pi(D) dD = 0.975$$

for $e_1$ and $e_2$, respectively, and setting AD$_{low}$=AD−$e_2$ and AD$_{high}$=AD−$e_1$.

In step 6, an absorbed dose estimation report is constructed utilizing the estimated dose and dose interval.

Figure 9:
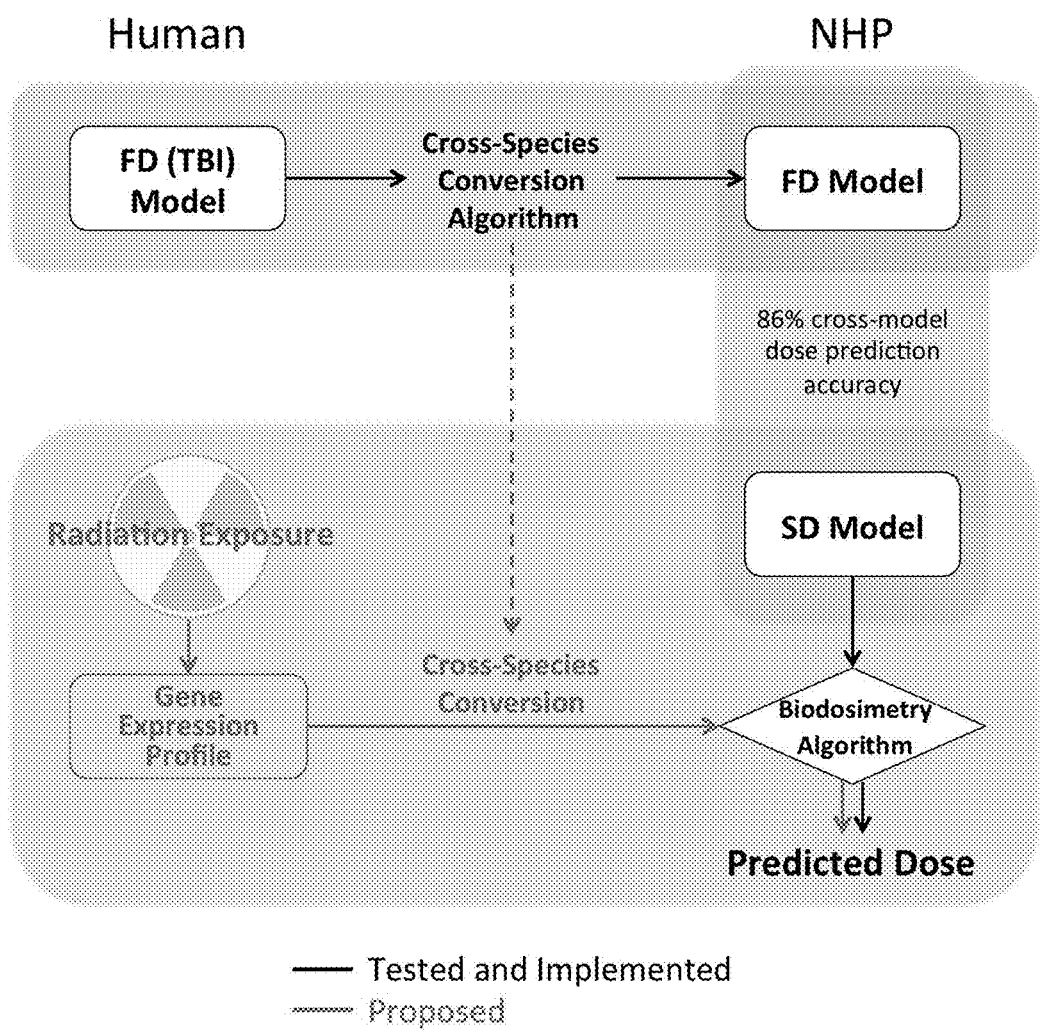
FIG. 9 shows a schematic overview on human and NHP data sets, cross-species conversion approaches to utilize the NHP single-dose (SD) biodosimetry algorithm to predict absorbed dose in human in case of acute radiation exposure. Cross-species conversion algorithms were developed with human and NHP fractionated-dose (FD) models that showed a good cross-model compatibility with NHP SD models.

In actual events of acute radiation exposure, to predict absorbed dose of human samples with the NHP-based biodosimetry algorithm, conceptually, gene expression measurements of each biomarker in a human sample need to be transformed by cross-species (i.e. human to NHP) algorithms. Ideal cross-conversion models could be built on two directly comparable single-dose (SD) data sets in human and NHP. However, due to practical difficulties in obtaining human blood samples with single acute irradiation, as an alternative, we obtain samples from human subjects who undergo total body irradiation (TBI). Unlike the acute single-dose (SD) irradiation that we used for development of a biodosimetry algorithm, these subjects under a fractionated dose (FD) schedule were irradiated three times (1.2 Gy each) a day for 6 days. Therefore, we obtained gene expression data from NHP-equivalents of human TBI subjects that underwent the identical fractionated irradiation, and developed novel gene-specific cross-species conversion algorithms. These algorithms will be used to transform human values prior to dose prediction (FIG. 9).

Unlike SD models that measure gene expression levels over the time after a single acute irradiation, data from a FD model has a linear relationship between cumulative dose and day. Therefore, prior to development of cross-species conversion algorithms based on human and NHP FD data sets, we first examined whether expression profiles of biomarker genes in NHP FD model were comparable to those in NHP SD model and thus could predict absorbed dose via the NHP SD model-based biodosimetry algorithm. For meta analyses of FD and SD data sets, we developed a three-dimensional (3D) curve fitting strategy to match the FD data to the SD data. Specifically, for each biomarker b we generate an FD curve of the mean expression level of NHP FD samples (2 Gy per day for 6 days) as a function of cumulative dose and day, $FD_b$ (dose, day), and a SD response surface of the mean expression level of NHP SD samples (0 to 6 days, 0 to 7 Gy) as a function of dose and day, $SD_b$(dose, day) (FIG. 10A). First, the entire FD curve for each biomarker is shifted to match the mean basal level (i.e. 0 Gy/Day 0) of SD values, which produces a scaling factor $\alpha_b$ for expression values for each biomarker. The shifted FD curve is denoted $FD_b'$ (dose, day)=$FD_b$ (dose, day)+$\alpha_b$, where $\alpha_b$=$SD_b$ (0, 0)−$FD_b$ (0, 0). Second, for each biomarker, optimal biomarker-specific dose and day scaling factors, $\beta_{b,dose}$ and $\beta_{b,day}$, are found that minimize the sum of absolute differences between the SD and scaled FD data.

Specifically, $\beta_{b,dose}$ and $\beta_{b,day}$ minimize the following expression, $$\sum_{d1,d2} \left| \frac{FD_b'(d1, d2)}{FD_b'(12, 6)} \times SD_b(\beta_{b,dose} \times d1, \beta_{b,day} \times d2) - SD_b(\beta_{b,dose} \times d1, \beta_{b,day} \times d2) \right|$$

By repeating this for all biomarkers and searching for common dose and day scaling factors that minimize the sum of absolute differences across biomarkers, doses and days, unified FD to SD scaling factors of $\beta_{dose}$=0.517 for dose (i.e. 12 Gy to 6.2 Gy) and $\beta_{day}$=0.933 for day (i.e. day 6 to day 5.6) (FIG. 10B) are obtained.

Mathematically, $\beta_{dose}$ and $\beta_{day}$ are defined to minimize $$\sum_b \sum_{d1,d2} \left| \frac{FD_b'(d1, d2)}{FD_b'(12, 6)} \times SD_b(\beta_{dose} \times d1, \beta_{day} \times d2) - SD_b(\beta_{dose} \times d1, \beta_{day} \times d2) \right|.$$

Third, linear transformation of FD curves by the scaling factors yields the converted expression values, $$FD_b''(d1, d2) = \frac{FD_b'(d1, d2)}{FD_b'(12, 6)} \times SD_b(\beta_{dose} \times d1, \beta_{day} \times d2). \quad \text{(FIG. 10A)}$$

To test the conversion strategy from NHP FD to NHP SD data, based on seven biomarkers (COCH, DHRS4L1, IL27RA, INPP5J, PNOC, SCARB1, and TEX10 in this example) with correlated dose responses between the data sets, random forests dose prediction models were generated on NHP SD data, which showed 84% to 98% dose prediction accuracy across days for the model fitting on NHP SD data (FIG. 11A). When expression values of NHP FD data were converted by matching days or doses and then applied to the NHP SD random forests model, dose prediction accuracies within 1.0 Gy were only 21% and 31%, respectively. After the FD values were transformed by the 3D scaling factors (i.e. for expression value, dose, and day), the accuracy was increased to 60% (FIG. 11B).

To increase performance of conversion algorithm, we explored a multi-gene regression approach that utilizes linear combinations of gene expression values rather than the expression values of individual biomarkers. This concept has been applied to predict missing values in large gene expression data sets. Since the biomarkers are functionally related within the key biological pathways related to radiation response, we hypothesized that expression profiles of other biomarkers could be informative in predicting expression values of a given gene. We employed Ridge regressions that provide robustness by constraining the size of coefficients by minimizing the summed squares of residuals and coefficients. By using converted NHP FD values by 3D scaling, a multi-gene regression model for each biomarker was generated with all seven genes that were used to build NHP SD biodosimetry algorithm. When the predicted values by the multi-gene regression models were applied to NHP SD algorithm, dose prediction accuracy was increased substantially to 86% (FIG. 11B).

Absolute gene expression values of biomarker genes are highly variable between NHP and human, and, thus, using an NHP biodosimetry algorithm to predict absorbed dose in human requires another step of cross-species expression value transformation from human to NHP. To explore the conversion strategies, we compared two data sets, for human and NHP, that were obtained from subjects treated with an identical irradiation schedule (3 times of irradiation at 1.2 Gy per day for 4 days), which is being used for total body irradiation (TBI) in clinical therapeutic setting. Among 29 biomarkers tested, although 17 genes had inter-species correlation coefficient above 0.6 between these two data sets (FIG. 12A), many genes showed substantial differences in absolute expression levels across doses (FIG. 12B). Therefore, we calculated the mean difference of expression for each biomarker and then applied the value to shift the entire expression values the gene across doses. This process decreased the mean absolute differences to less than 1.0 $\Delta Ct$ for the majority of 29 biomarkers (FIG. 12A, last two columns).

To test the conversion strategy from human TBI to NHP FD data, based on 10 biomarkers (DHRS4L1, MYC, SPECC1, CXXC5, ALAS2, HBA2, CDKN1A, GPR183, MOB3B, and PNOC in this example) with inter-species correlation above 0.75 (FIG. 12A), random forests dose prediction models were generated on NHP FD data, which showed a 98% dose prediction accuracy during the model fitting on NHP FD data (FIG. 13A). Appling the converted human TBI values to NHP FD random forests model, prediction accuracy within 1.0 Gy was 13%. When expression values of human TBI data were vertically shifted by the predetermined shift factors and then applied to the NHP FD random forests model, dose prediction accuracies within 1.0 Gy was increase marginally to 19%.

We then tested whether the multi-gene regression approaches could improve the cross-species conversion process. As previously done for NHP FD to NHP SD conversion, we also employed Ridge regressions. By using converted human TBI values by vertical shifting factors, a multi-gene regression model for each biomarker was generated with all 10 genes that were used to build the NHP FD biodosimetry algorithm in this example. When the predicted values by the multi-gene regression models were applied to NHP FD algorithm, dose prediction accuracy was increased substantially to 89%.

TABLE 2

| | | | | | | |
|---|---|---|---|---|---|---|
| | Algorithm Function. | | | | | |
| Step 1 | Combine Patient Barcode with Date/Time Event | Traceability | Barcode | Unique barcode | Adds all needed information to qPCR data | Flags data for operator intervention |
| Step 2 | Quality Control Check | Negative Control | 96-Well Prep Plate No Template Control (NTC) or Reagent Blank | Ct (Ref)(2) > 37 | Cross-Contamination in Sample Prep | Retest Samples |
| | | Positive Controls | qPCR Standard Curve: 10, 0.1, 0.01, 0.001 ng/µL (Based on standard pooled RNA). | 1. Ct (Ref) ± 1 each conc. 2. Amplification Efficiency | 1. LLOD Verified 2. Reproducibility Verified 3. Amplification verifies expected qPCR function across linear range. | Flags data-may affect Dose Estimate and Dose Interval Or Require sample retest and Alerts Operator (No operator override) |
| | | | Exogenous Control: Sample RNA Spike-in | Ct (Xeno ™) ± 1 | Inhibitors Sample Integrity | |
| | | | Endogenous Control: Reference Gene(1) | Ct (Ref) ± 1 | 1. Adequate Sample RNA Input. 2. Control for variable RNA input. | |

TABLE 2-continued

Algorithm Function.

| | | | | | | |
|---|---|---|---|---|---|---|
| Step 3 | Biomarker Range Check | Process QC | Biomarker integrity | QC flag | Usability of each Biomarker Value | |
| Step 4 | Apply QC and Biomarker Range Flags | Process QC | Analytical integrity | QC flag | Usability of each Biomarker Value | |
| Step 5 | Calculate Estimated Dose | Quantitative | Endogenous Control | Absorbed dose (Gy) | Estimated absorbed Dose | Checks for intended use dose range |
| | Calculate Dose Interval | Measurement Confidence | Confidence Interval | Dose Range | Dose Interval | Checks for acceptable confidence interval |
| Step 6 | Combine Estimated Dose and Dose Interval | Report | Report | Gy | Dose Estimation Report | Clinic Review/Approval |

In one embodiment, the target mRNAs or cDNAs to which the primers hybridize are those from the following (human) RM genes: CR2, DHRS4L1, HCK, IL1RAP, LYRM4, MYC, TMEM63B, ALOX5, CAMK4, CDKN1A, COCH, DHRS4, MICAL1, MOB3B, NUSAP1, IL27RA, HBA2, PPM1F, PPP2R1A, CFLAR, DHRS13, ACAA1, INPP5J, OAZ1, PNOC, PDE4B, SCARB1, and TMEM9B.

In other embodiments, mRNAs or cDNAs to which primers hybridize may include the following genes: ADAM17, AKT1, ANK1, ANXA3, ARHGAP26, ARID4A, ATG2A, ATIC, BCL11A, BCL6, BID, CFLAR, CIT, CPVL, CYTH4, DDB2, DDX58, DTL, EHBPL1, FCGR2A, FGR, HPRT1, HSP90AB1, HTRA2, IDOL, IL27RA, IRF1, JMJD1C, KIAA0101, LARP4B, LRRC6, LYN, MAP3K11, MAPK3, MDM1, MKNK1, MXD1, NAIP, NFE2L2, NRG1, NUSAP, PCNA, PGK1, PMP22, PPP2RA1, RARA, RNASE6, RPL13A, RPL6, RPS14, SCARB1, SP10, SPOCK2, TAPBP, TBP, TCF3, TNFRSF1A, TNFRSF1B, TNFSF14, USP38, WDR48, XAF1, ZAK, NPM1, ALAS2, ALPK1, CD97, CPSF1, COASY, CXXC5, DNAJC10, DYNLRB1, ELK4, ESD, GPR183, GPRIN, NDE1, PGS1, PPM1K, PTAFR, SLC6A6, SPECC1, and TEX10.

In some embodiments, primers are also included that hybridize to PPP6R3 mRNA or cDNA, where PPP6R3 and its mRNA levels serve as a reference gene for relative quantification of RM gene expression levels in an amplification reaction. In other embodiments primers may be included that hybridize to USP38, WDR48 or LARP4B mRNA or cDNA to serve as the reference gene or some combination thereof.

In some embodiments, the nucleic acid amplification reactions are qPCR reactions. In some embodiments the qPCR reactions are TAQMAN® probe qPCR reactions that include, in addition to the target primer pairs, TAQMAN® probes that hybridize under stringent conditions to the RM gene or reference gene mRNAs or cDNAs. TAQMAN® probe-based qPCR assays are well known in the art as described in, e.g., U.S. Pat. Nos. 5,677,152, 5,773,258 and 5,804,375.

Exemplary RM and reference gene primer and TAQMAN® probe sequences are listed below in Table 3.

TABLE 3

RM and reference gene primer and TAQMAN® probe sequences.

| Gene | Assay ID | Amplicon Sequence | Length (bp) | Tm |
|---|---|---|---|---|
| PPP6R3 | Hs00217759_m1 | TGAGGGAGGAAGACGGCATGGTTAC ATGGGACACCTAACGAGGATAGCTA ACTGTATCGTGCACAGCACTGACAAG (SEQ ID NO: 30) | 76 | 55-65° C. |
| CDKN1A | Hs00217759_m1 | GACAGATTTCTACCACTCCAAACGCC GGCTGATCTTCTCCAAGAGGAAGCCC TAATCCGCCCACAG (SEQ ID NO: 31) | 66 | 55-65° C. |

Typically, stringent hybridization reaction conditions are defined by use of TAQPATH™ qPCR Mastermix chemistry and cycling conditions listed below in Table 4.

TABLE 4

Thermal Cycling Conditions for Target/Primer/Probe Hybridization.

| Step | Incubation Hold | Activation Hold | PCR Cycle (40 cycles) | |
|---|---|---|---|---|
| | | | Denature | Anneal/Extend |
| Temperature | 50° C. | 95° C. | 95° C. | 60° C. |
| Time | 2 min. | 20 sec. | 1 sec. | 20 sec. |
| Volume | | | 10 µL | |

In some embodiments the plurality of nucleic acid amplification reactions are multiplexed such that multiple mRNAs (including a reference mRNA) are assayed in a single qPCR reaction, i.e., nine qPCR reactions would be needed to assay the entire panel of RM gene mRNAs from one sample, where each of the reactions are "tetraplexed," 14 reactions would be needed per sample where each reaction is "triplexed", and 28 reactions would be needed per sample when each qPCR reactions includes primers to a single RM gene mRNA and a reference gene mRNA. In some embodiments, the plurality of qPCR reactions can include different multiplexing, i.e., some reactions may contain primer pairs directed to three RM gene mRNAs and others a primer pair to only two or a single RM gene mRNA. The plurality of reactions can be provided in a number of formats, e.g., 96-, 384-, or even 1536-well formats.

In various embodiments, the mRNA or cDNA in the biodosimetry assay system is from a biological sample from a subject subjected to radiation exposure from about 30 minutes to about seven days prior to the time point at which the biological sample was obtained from the subject, e.g., one hour, three hours, 4 hours, six hours, twelve hours, 1 day, 2 days, 3 days, 4 days, 5 days, 7 days or another time period before biological sample collection from the subject ranging from about 30 minutes to about seven days.

Also contemplated herein is a radiation biomarker assay kit that includes a nucleic acid probe set consisting essentially of nucleic acid probes that hybridize specifically with nucleic acid targets comprising at least one of SEQ ID NOS: 1-29 or the complementary sequences thereof.

In some embodiments the probe set includes no more than about 200 probes, e.g., PCR primers. In other embodiments the probe set includes no more than about 100 probes.

In some embodiments the nucleic acid probe set includes primer pairs and TAQMAN® probes suitable for qPCR analysis of mRNAs or cDNAs comprising at least one of SEQ ID NOS: 1-29.

In some embodiments the kit also includes a thermostable polymerase suitable for qPCR, e.g., Taq polymerase and variants thereof known in the art.

In some embodiments a qPCR probe set in the kit is provided in a multi-well plate format. In some a multi-well plate is provided in which at least two nucleic acid probes that hybridize to at least two different nucleic acid targets are in the same wells, i.e., the probes can be multiplexed, as described above such that up to four different targets can be assayed by qPCR in the same reaction.

In some embodiments the kit also includes radiation exposure positive and negative control mRNA samples, which ensure that a qPCR biodosimetry assay is working properly, i.e., modulation of RM gene expression is detected in the positive control sample and no modulation of RM gene expression is detected in the negative control sample.

EXAMPLES

The invention will be more fully understood upon consideration of the following non-limiting Examples. The invention has been described in connection with what are presently considered to be the most practical and preferred embodiments. However, the present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

Example 1: Description of Test Experiments Used to Develop Biomarkers

Rhesus macaque non-human primate (NHP) in vivo testing was conducted to produce single-dose biodosimetry samples and age/gender confounded samples to calibrate the biodosimeter.

NHP In Vivo Dose Response to Radiation:

The animal test laboratory completed NHP Cobalt-60 irradiations at 0, 2, 4, and 6 (LD30/60), 7 Gy (LD70/60), and 10 Gy with cohorts of 16 (8 male and 8 female), at dose rate of approximately 0.6 Gy/min. Samples of 2.5 ml peripheral blood (PAXGENE™ blood RNA tube) were obtained from each rhesus macaque −2 week and −24 hr. prior to irradiation and 4 hr., 24 hr., 36 hr. post radiation, and on days 2, 3, 5, and 7 for a total of 9 blood draws per animal. Samples (0.5 ml) were also obtained in EDTA tubes to determine WBC differentials. Tests were staged to provide 4 NHP at each condition to determine target genes using discovery techniques (Phase 1), 10 NHP at each condition to determine biomarkers and 2 NHP at each condition to test the biodosimeter (algorithm) accuracy (Phase 2).

NHP Confounder Analysis; Old Age and Juvenile.

The animal test laboratory completed testing of 4 rhesus macaques (2 male and 2 female) exposed to 6 Gy (LD30/60) at a dose rate of approximately 0.6 Gy/min for both geriatric (>15 years) and juvenile (10-14 months) cohorts. Samples of 2.5 ml peripheral blood (PAXGENE™ blood RNA tube) were collected from each NHP −2 week and −24 hr. prior to irradiation and 4 hr., 24 hr., 36 hr. post radiation, and on days 2, 3, 5, and 7 for a total of 9 blood draws per animal. Samples (0.5 ml) were also obtained in EDTA tubes to determine WBC differentials.

NHP Fractionated Dose Testing:

Two NHP models were developed to compare NHP gene response to human gene response for fractionated dose radiotherapy models.

NHP Fractionated Dose Models:

Blood (2.5 ml) was collected from 6 female and 6 male rhesus NHP into PAXGENE™ blood RNA tubes. The NHP were irradiated in vivo to parallel the 4 human in vivo test protocols as described below. For Study 1: Twelve (12) NHPs were exposed to 1.5 Gy twice per day (dose rate 0.6-0.8 Gy/min.) for 4 days at the same time each day. The blood samples were collected within 24 hr. prior to irradiation and 24 hrs. after each daily exposure (6 draws). For Study 2: Twelve (12) NHPs were exposed to 1.2 Gy (dose rate 0.6-0.8 Gy/min.) 3 times per day at the same time each day for 4-days. Blood samples were collected prior to irradiation and 24 hr. following each exposure (prior to the next exposure) for a total of 6 draws. The NHPs were irradiated by LINAC. At the time of sample collection, a complete differential white cell count was conducted.

Human Fractionated Dose Models:

Four human in vivo models were co-developed with Mayo Clinic, City of Hope and Stanford to provide blood samples from humans undergoing whole body and fractional radiation.

Model 1—Bone Marrow Transplant Patients (BMT): Radiation dose is 1.65 to 2 Gy twice daily for 3 to 4 days. Samples are taken prior to and 24 hr. after daily irradiations. The last draw is on Day-7; 7 days after the first dose. (4-6 samples/Series).

Model 2—Bone Marrow Transplant Patients (BMT): Radiation dose is 1.2 Gy three times daily for 4 days. Samples are taken prior to and 24 hr. after irradiation daily irradiations. The last draw is on Day-3 or 4; 3 or 4 days after the first dose. (5-7 samples/Series).

Model 3—Bone Marrow Transplant Patients (BMT): Radiation dose is a single fraction related to models 1 and 2. Samples are taken prior to and every 24 hr. after irradiation. The last draw is on Day-6; 6 days after the first dose. (6-7 samples/Series).

Model 4—X-Ray Therapy (XRT) Patients (>7% bone marrow exposure): Radiation dose is 2-8 Gy each day for multiple days. Samples are taken prior to and 24 hr. after irradiation. The last draw is taken 7 days after the last exposure.

TABLE 5

Nucleotide Sequences of Biodosimetry Biomarker Genes

CR2 (SEQ ID NO: 1; GenBank NM_001006658.2).
ATTTAAGGGCCCGCCTCTCCTGGCTCACAGCTGCTTGCTGCTCCAGCCTTGCCCTCCC
AGAGCTGCCGGACGCTCGCGGGTCTCGGAACGCATCCCGCCGCGGGGCTTCGGCC
GTGGCATGGGCGCCGCGGGCCTGCTCGGGGTTTTCTTGGCTCTCGTCGCACCGGGG
TCCTCGGGATTTCTTGTGGCTCTCCTCCGCCTATCCTAAATGGCCGGATTAGTTATTA
TTCTACCCCCATTGCTGTTGGTACCGTGATAAGGTACAGTTGTTCAGGTACCTTCCGC
CTCATTGGAGAAAAAGTCTATTATGCATAACTAAAGACAAAGTGGATGGAACCTG
GGATAAACCTGCTCCTAAATGTGAATATTTCAATAAATATTCTTCTTGCCCTGAGCCC
ATAGTACCAGGAGGATACAAAATTAGAGGCTCTACACCCTACAGACATGGTGATTC
TGTGACATTTGCCTGTAAAACCAACTTCTCCATGAACGGAAACAAGTCTGTTTGGTG
TCAAGCAAATAATATGTGGGGGCCGACACGACTACCAACCTGTGTAAGTGTTTTCCC
TCTCGAGTGTCCAGCACTTCCTATGATCCACAATGGACATCACACAAGTGAGAATGT
TGGCTCCATTGCTCCAGGATTGTCTGTGACTTACAGCTGTGAATCTGGTTACTTGCTT
GTTGGAGAAAAGATCATTAACTGTTTGTCTTCGGGAAATGGAGTGCTGTCCCCCCC
ACATGTGAAGAGGCACGCTGTAAATCTCTAGGACGATTTCCCAATGGGAAGGTAAA
GGAGCCTCCAATTCTCCGGGTTGGTGTAACTGCAAACTTTTTCTGTGATGAAGGGTA
TCGACTGCAAGGCCCACCTTCAGTCGGTGTGTAATTGCTGGACAGGGAGTTGCTTG
GACCAAAATGCCAGTATGTGAAGAAATTTTTTGCCCATCACCTCCCCCTATTCTCAA
TGGAAGACATATAGGCAACTCACTAGCAAATGTCTCATATGGACATAGTCACTTA
CACTTGTGACCCGGACCCAGAGGAAGGAGTGAACTTCATCCTTATTGGAGAGAGCA
CTCTCCGTTGTACAGTTGATAGTCAGAAGACTGGGACCTGGAGTGGCCCTGCCCCAC
GCTGTGAACTTTCTACTTCTGCGGTTCAGTGTCCACATCCCCAGATCCTAAGAGGCC
GAATGGTATCTGGGCAGAAAGATCGATATACCTATAACGACACTGTGATATTTGCTT
GCATGTTTGGCTTCACCTTGAAGGGCAGCAAGCAAATCCGATGCAATGCCCAAGGC
ACATGGGAGCCATCTGCACCAGTCTGTGAAAAGGAATGCCAGGCCCCTCCTAACAT
CCTCAATGGGCAAAAGGAAGATAGACACATGGTCCGCTTTGACCCTGGAACATCTA
TAAAAATATAGCTGTAACCCTGGCTATGTGCTGGTGGGAGAAGAATCCATACAGTGTA
CCTCTGAGGGGGTGTGGACACCCCCTGTACCCCAATGCAAAGTGGCAGCGTGTGAA
GCTACAGGAAGGCAACTCTTGACAAAACCCCAGCACCAATTTGTTAGACCAGATGT
CAACTCTTCTTGTGGTGAAGGGTACAAGTTAAGTGGGAGTGTTTATCAGGAGTGTCA
AGGCACAATTCCTTGGTTTATGGAGATTCGTCTTTGTAAAGAAATCACCTGCCCACC
ACCCCCTGTTATCTACAATGGGGCACACACCGGGAGTTCCTTAGAAGATTTTCCATA
TGGAACCACGGTCACTTACACATGTAACCCTGGGCCAGAAAGAGGAGTGGAATTCA
GCCTCATTGGAGAGAGCACCATCCGTTGTACAAGCAATGATCAAGAAAGAGGCACC
TGGAGTGGCCCTGCTCCCCTGTGTAAACTTTCCCTCCTTGCTGTCCAGTGCTCACATG
TCCATATTGCAAATGGATACAAGATATCTGGCAAGGAAGCCCCATATTTCTACAATG
ACACTGTGACATTCAAGTGTTATAGTGGATTTACTTTGAAGGGCAGTAGTCAGATTC
GTTGCAAAGCTGATAACACCTGGGATCCTGAAATACCAGTTTGTGAAAAAGGCTGC
CAGTCACCTCCTGGGCTCCACCATGGTCGTCATACAGGTGGAAATACGGTCTTCTTT
GTCTCTGGGATGACTGTAGACTACACTTGTGACCCTGGCTATTTGCTTGTGGGAAAC
AAATCCATTCACTGTATGCCTTCAGGAAATTGGAGTCCTTCTGCCCCACGGTGTGAA
GAAACATGCCAGCATGTGAGACAGAGTCTTCAAGAACTTCCAGCTGGTTCACGTGTG
GAGCTAGTTAATACGTCCTGCCAAGATGGGTACCAGTTGACTGGACATGCTTATCAG
ATGTGTCAAGATGCTGAAAATGGAATTTGGTTCAAAAAGATTCCACTTTGTAAAGTT
ATTCACTGTCACCCTCCACCAGTGATTGTCAATGGGAAGCACACAGGCATGATGGCA
GAAAACTTTCTATATGGAAATGAAGTCTCTTATGAATGTGACCAAGGATTCTATCTC
CTGGGAGAGAAAAAATTGCAGTGCAGAAGTGATTCTAAAGGACATGGATCTTGGAG
CGGGCCTTCCCCACAGTGCTTACGATCTCCTCCTGTGACTCGCTGCCCTAATCCAGA
AGTCAAACATGGGTACAAGCTCAATAAAAACACATTCTGCATATTCCCACAATGACAT
AGTGTATGTTGACTGCAATCCTGGCTTCATCATGAATGGTAGTCGCGTGATTAGGTG
TCATACTGATAACACATGGGTGCCAGGTGTGCCAACTTGTATCAAAAAAGCCTTCAT
AGGGTGTCCACCTCCGCCTAAGACCCCTAACGGGAACCATACTGGTGGAAACATAG
CTCGATTTTCTCCTGGAATGTCAATCCTGTACAGCTGTGACCAAGGCTACCTGCTGGT
GGGAGAGGCACTCCTTCTTTGCACACATGAGGGAACCTGGAGCCAACCTGCCCCTC
ATTGTAAAGAGGTAAACTGTAGCTCACCAGCAGATATGGATGGAATCCAGAAAGGG
CTGGAACCAAGGAAAATGTATCAGTATGGAGCTGTTGTAACTCTGGAGTGTGAAGA
TGGGTATATGCTGGAAGGCAGTCCCCAGAGCCAGTGCCAATCGGATCACCAATGGA
ACCCTCCCCTGGCGGTTTGCAGATCCCGTTCACTTGCTCCTGTCCTTTGTGGTATTGC
TGCAGGTTTGATACTTCTTACCTTCTTGATTGTCATTACCTTATACGTGATATCAAAA
CACAGAGCACGCAATTATTATACAGATACAAGCCAGAAAGAAGCTTTTCATTTAGA
AGCACGAGAAGTATATTCTGTTGATCCATACAACCCAGCCAGCTGATCAGAAGACA
AACTGGTGTGTGCCTCATTGCTTGGAATTCAGCGGAATATTGATTAGAAAGAAACTG
CTCTAATATCAGCAAGTCTCTTTATATGGCCTCAAGATCAATGAAATGATGTCATAA
GCGATCACTTCCTATATGCACTTATTCTCAAGAAGAACATCTTTATGGTAAAGATGG
GAGCCCAGTTTCACTGCCATATACTCTTCAAGGACTTTCTGAAGCCTCACTTATGAG
ATGCCTGAAGCCAGGCCATGGCTATAAACAATTACATGGCTCTAAAAAGTTTTGCCC
TTTTTAAGGAAGGCACTAAAAAGAGCTGTCCTGGTATCTAGACCCCATCTTCTTTTTG
AAATCAGCATACTCAATGTTACTATCTGCTTTTGGTTATAATGTGTTTTTAATTATCT
AAAGTATGAAGCATTTTCTGGGGTTATGATGGCTTTACCTTTATTAGGAAGTATGGT
TTTATTTTGATAGTAGCTTCCTCCTCTGGTGGTGTTAATCATTTCATTTTTACCCTTAC
TTGGTTTGAGTTTCTCTCACATTACTGTATATACTTTGCCTTTCCATAATCACTCAGTG
ATTGCAAATTTGCACAAGTTTTTTTAAATTATGGGAATCAAGATTTAATCCTAGAGATT
TGGTGTACAATTCAGGCTTTGGATGTTTCTTTAGCAGTTTTGTGATAAGTTCAGTTG
CTTGTAAAATTTCACTTAATAATGTGTACATTAGTCATTCAATAAATTGTAATTGTAA
AGAAAACATACAAAAAAAAAAAAAAAA TABLE 5-continued Nucleotide Sequences of Biodosimetry Biomarker Genes DHRS4L1 (SEQ ID NO: 2; GenBank NM_001277864.1).
AGTCGGGCAGCTCTCCGGGCCGGCGTGGGAGCCCGCGCTCCAAAGCCCGGTGGGGG
GAGGGGCGCTCACGCAACCGCCACTGTCTGGAGCGGGCTCGCCTCTGCGGCGGCAC
TCACCGCCCGGGCTTTACTGAAGCGGAGTCTAGCATGTGCGGCTGCTCCACAGCGGT
GTGGGTGGCGGCGGCTCCTCTGCAGCAGCCTCGGCAGTAGGGGTCACGGTGGCCAA
GCCCACCGTGGAGCTCATCTGAGAGTTGTAAGGTACGGGACTGCCTCGGTCTTTGGG
ACGCCCCGTCTGGTAGCATCCCAGATCCAGCACGTTCCTTCCGGCCCTGCACCCCGG
CCCGGTGCCTCACACCCCGCTACCCCATGCATCCAGACTCTAAGGCAGCCCCTGCAT
CTCAGTCCTGACATCGCTGTCCCTGGAGCATCCTCCGCTGGAGCTGGAGCTTGACAG
GATCGGCTTCGCCGTCGCCCAGCGTCTGGCCCAAGACGGGGCCCACGTGGTAGTCA
GCCGCCGGAAGCAGCAGAATGTGGACCAGGCAGTGGCCACGCTGCAGGGGGAGGG
GCTGAGCATGACGGGCACTGTGTGCCATGTGGGGAAGATGAAGGACTGGGAGCGGC
TGGTGGCCACAGTGAGCTGCAGGGAAATGGGCACAGAGCCAGGAGGTGGAAAAGG
GAGCCAGCCTGAGCCTCCTTCCCTGCTTTCCTGGACAGCATTGGGCTTCAGTCCTTAC
AATGTCAGTAAAACAGCCTTGCTGGGCCTCAACAAGACCTTGGCCATAGAGCTGGC
CCCAAGGAACATTAGGGTGAACTGCCTAGCACCTGGACTTATCAAGACTAGCTTCAG
CAGGATGCTCTGGATGGACAAGGAAAAAGAGGAAAGCATGAAAGAAACCCTGCGG
ATAAGAAGGTTAGGCGAGCCAGAGGATTCTCTTGGCATCGTGTCTTTCCTGTGCTCT
GAAGATGCCAGCTACCTCACTGGGGAAACAGTGATGGTGGGTGGAGGAACCCCGTC
CCGCCTCTGAGGACCCGGAGACAGCCCACAGGCCAGAGTTGGGCTCTAGCTCCTGG
TGCTGTTCCTGCATTCACCCACTGGCCTTTCCCACCTCTGCTCACCTTACTGTTCACC
TCATCAAATCAGTTCTGCCCTGTGAAAAGATCCAGCCTTCCCTGCCGTCAAGGTGGT
GTCTTACTCGGGATTCCTGCTGTTGTTGTGGCCTTGGGTAAAGGCCTCCCCTGAGAA
CACAGGACAGGCCTGCTGACAAGGCTGAGTCTACCTTGGCAAAGACCAAGATATTT
TTTGCCCAGGCCACTGGGGAATTTGAGGGGAGATGAGAGAGAAGGAAGCTGGAGTG
GAAGGAGCAGAGTTGCAAATTAACAACTTGCAAATGAGGTGCAAATAAAATGCAGA
TGATTGCGCGGCTTTGAATCGAAAAAAAAAAA HCK (SEQ ID NO: 3; GenBank NM_001172129.1).
GGAGTTAGCCTCGCTCAGGGCGCGGCTAAGGCGCCCAGATGGCCTGCGGGCGCCAC
CACGTCCCTGGTCCCAGCTCGGGAGCACATCAGAGGCTTAGAGGCGAGTGGGAAGG
GACTCAGACAGTGCAGGACGAGAAACGCCCGCGGCACCAAAGCCCCTCAGAGCGTC
GCCCCCGCCTCTAGTTCTAGAAAGTCAGTTTCCCGGCACTGGCACCCCGGAACCTCA
GGGGCTGCCGAGCTGGGGGGGCGCTCAAGCTGCGAGGATCCGGGCTGCCCGCGAGA
CGAGGAGCGGGCGCCCAGGATGGGGTGCATGAAGTCCAAGTTCCTCCAGGTCGGAG
GCAATACATTCTCAAAAACTGAAACCAGCGCCAGCCCACACTGTCCTGTGTACGTGC
CGGATCCCACATCCACCATCAAGCCGGGGCCTAATAGCCACAACAGCAACACACCA
GGAATCAGGGAGGCAGGCTCTGAGGACATCATCGTGGTTGCCCTGTATGATTACGA
GGCCATTCACCACGAAGACCTCAGCTTCCAGAAGGGGGACCAGATGGTGGTCCTAG
AGGAATCCGGGGAGTGGTGGAAGGCTCGATCCCTGGCCACCCGGAAGGAGGGCTAC
ATCCCAAGCAACTATGTCGCCCGCGTTGACTCTCTGGAGACAGAGGAGTGGTTTTTC
AAGGGCATCAGCCGGAAGGACGCAGAGCGCCAACTGCTGGCTCCCGGCAACATGCT
GGGCTCCTTCATGATCCGGGATAGCGAGACCACTAAAGGAAGCTACTCTTTGTCCGT
GCGAGACTACGACCCTCGGCAGGGAGATACCGTGAAACATTACAAGATCCGGACCC
TGGACAACGGGGGCTTCTACATATCCCCCCGAAGCACCTTCAGCACTCTGCAGGAGC
TGGTGGACCACTACAAGAAGGGGAACGACGGGCTCTGCCAGAAACTGTCGGTGCCC
TGCATGTCTTCCAAGCCCCAGAAGCCTTGGGAGAAAGATGCCTGGGAGATCCCTCG
GGAATCCCTCAAGCTGGAGAAGAAACTTGGAGCTGGGCAGTTTGGGGAAGTCTGGA
TGGCCACCTACAACAAGCACACCAAGGTGGCAGTGAAGACGATGAAGCCAGGGAG
CATGTCGGTGGAGGCCTTCCTGGCAGAGGCCAACGTGATGAAAACTCTGCAGCATG
ACAAGCTGGTCAAACTTCATGCGGTGGTCACCAAGGAGCCCATCTACATCATCACG
GAGTTCATGGCCAAAGGAAGCTTGCTGGACTTTCTGAAAAGTGATGAGGGCAGCAA
GCAGCCATTGCCAAAACTCATTGACTTCTCAGCCCAGATTGCAGAAGGCATGGCCTT
CATCGAGCAGAGGAACTACATCCACCGAGACCTCCGAGCTGCCAACATCTTGGTCTC
TGCATCCCTGGTGTGTAAGATTGCTGACTTTGGCCTGGCCCGGGTCATTGAGGACAA
CGAGTACACGGCTCGGGAAGGGGCCAAGTTCCCCATCAAGTGGACAGCTCCTGAAG
CCATCAACTTTGGCTCCTTCACCATCAAGTCAGACGTCTGGTCCTTTGGTATCCTGCT
GATGGAGATCGTCACCTACGGCCGGATCCCTTACCCAGGGATGTCAAACCCTGAAG
TGATCCGAGCTCTGGAGCGTGGATACCGGATGCCTCGCCCAGAGAACTGCCCAGAG
GAGCTCTACAACATCATGATGCGCTGCTGGAAAAACCGTCCGGAGGAGCGGCCGAC
CTTCGAATACATCCAGAGTGTGCTGGATGACTTCTACACAGGCCACAGAGAGCCAGTA
CCAACAGCAGCCATGATAGGGAGGACCAGGGCAGGGCCAGGGGGTGCCCAGGTGG
TGGCTGCAAGGTGGCTCCAGCACCATCCGCCAGGGCCCACACCCCCTTCCTACTCCC
AGACACCCACCCTCGCTTCAGCCACAGTTTCCTCATCTGTCCAGTGGGTAGGTTGGA
CTGGAAAATCTCTTTTTGACTCTTGCAATCCACAATCTGACATTCTCAGGAAGCCCCC
AAGTTGATATTTCTATTTCCTGGAATGGTTGGATTTTAGTTACAGCTGTGATTTGGAA
GGGAAACTTTCAAAATAGTGAAATGAATATTTAAATAAAAGATATAAATGCCAAAG
TCTTTACCAAAAAAAAAAAAAAAAA IL1RAP (SEQ ID NO: 4; GenBank NM_002182.3).
AAAGGGGGAAAAGAAAGTGCGGCGGAAAGTAAGAGGCTCACTGGGGAAGACTGCC
GGGATCCAGGTCTCCGGGGTCCGCTTTGGCCAGAGGCGCGGAAGGAAGCAGTGCCC
GGCGACACTGCACCCATCCCGGCTGCTTTTGCTGCGCCCTCTCAGCTTCCCAAGAAA
GGCATCGTCATGTGATCATCACCTAAGAACTAGAACATCAGCAGGCCCTAGAAGCC
TCACTCTTGCCCCTCCCTTTAATATCTCAAAGGATGACACTTCTGTGGTGTGTAGTGA
GTCTCTACTTTTATGGAATCCTGCAAAGTGATGCCTCAGAACGCTGCGATGACTGGG
GACTAGACACCATGAGGCAAATCCAAGTGTTTGAAGATGAGCCAGCTCGCATCAAG
TGCCCACTCTTTGAACACTTCTTGAAATTCAACTACAGCACAGCCCATTCAGCTGGC TABLE 5-continued Nucleotide Sequences of Biodosimetry Biomarker Genes

```
CTTACTCTGATCTGGTATTGGACTAGGCAGGACCGGGACCTTGAGGAGCCAATTAAC
TTCCGCCTCCCCGAGAACCGCATTAGTAAGGAGAAAGATGTGCTGTGGTTCCGGCCC
ACTCTCCTCAATGACACTGGCAACTATACCTGCATGTTAAGGAACACTACATATTGC
AGCAAAGTTGCATTTCCCTTGGAAGTTGTTCAAAAAGACAGCTGTTTCAATTCCCCC
ATGAAACTCCCAGTGCATAAACTGTATATAGAATATGGCATTCAGAGGATCACTTGT
CCAAATGTAGATGGATATTTTCCTTCCAGTGTCAAACCGACTATCACTTGGTATATG
GGCTGTTATAAAATACAGAATTTTAATAATGTAATACCCGAAGGTATGAACTTGAGT
TTCCTCATTGCCTTAATTTCAAATAATGGAAATTACACATGTGTTGTTACATATCCAG
AAAATGGACGTACGTTTCATCTCACCAGGACTCTGACTGTAAAGGTAGTAGGCTCTC
CAAAAAATGCAGTGCCCCCTGTGATCCATTCACCTAATGATCATGTGGTCTATGAGA
AAGAACCAGGAGAGGAGCTACTCATTCCCTGTACGGTCTATTTTAGTTTTCTGATGG
ATTCTCGCAATGAGGTTTGGTGGACCATTGATGGAAAAAAACCTGATGACATCACTA
TTGATGTCACCATTAACGAAAGTATAAGTCATAGTAGAACAGAAGATGAAACAAGA
ACTCAGATTTTGAGCATCAAGAAAGTTACCTCTGAGGATCTCAAGCGCAGCTATGTC
TGTCATGCTAGAAGTGCCAAAGGCGAAGTTGCCAAAGCAGCCAAGGTGAAGCAGAA
AGTGCCAGCTCCAAGATACACAGTGGAACTGGCTTGTGGTTTTGGAGCCACAGTCCT
GCTAGTGGTGATTCTCATTGTTGTTTACCATGTTTACTGGCTAGAGATGGTCCTATTT
TACCGGGCTCATTTTGGAACAGATGAAACCATTTTAGATGGAAAAGAGTATGATATT
TATGTATCCTATGCAAGGAATGCGGAAGAAGAAGAATTTGTATTACTGACCCTCCGT
GGAGTTTTGGAGAATGAATTTGGATACAAGCTGTGCATCTTTGACCGAGACAGTCTG
CCTGGGGGAATTGTCACAGATGAGCTTTGAGCTTCATTCAGAAAAGCAGACGCCTC
CTGGTTGTTCTAAGCCCCAACTACGTGCTCCAGGGAACCCAAGCCCTCCTGGAGCTC
AAGGCTGGCCTAGAAAATATGGCCTCTCGGGCAACATCAACGTCATTTTAGTACAG
TACAAAGCTGTGAAGGAAACGAAGGTGAAAGAGCTGAAGAGGGCTAAGACGGTGC
TCACGGTCATTAAATGGAAAGGGGAAAAATCCAAGTATCCACAGGGCAGGTTCTGG
AAGCAGCTGCAGGTGGCCATGCCAGTGAAGAAAAGTCCCAGGCGGTCTAGCAGTGA
TGAGCAGGGCCTCTCGTATTCATCTTTGAAAAATGTATGAAAGGAATAATGAAAAG
GGTAAAAAGAACAAGGGGTGCTCCAGGAAGAAAGAGTCCCCCCAGTCTTCATTCGC
AGTTTATGGTTTCATAGGCAAAAATAATGGTCTAAGCCTCCCAATAGGGATAAATTT
AGGGTGACTGTGTGGCTGACTATTCTGCTTCCTCAGGCAACACTAAAGTTTAGAAAG
ATATCATCAACGTTCTGTCACCAGTCTCTGATGCCACTATGTTCTTTGCAGGCAAAG
ACTTGTTCAATGCGAATTTCCCCCTTCTACATTGTCTATCCCTGTTTTTATATGTCTCCA
TTCTTTTTAAAATCTTAACATATGGAGCAGCCTTTCCTATGAATTTAAATATGCCTTT
AAAATAAGTCACTGTTGACAGGGTCATGAGTTTCCGAGTATAGTTTTCTTTTTATCTT
ATTTTTACTCGTCCGTTGAAAAGATAATCAAGGCCTACATTTTAGCTGAGGATAATG
AACTTTTTTCCTCATTCGGCTGTATAATACATAACCACAGCAAGACTGACATCCACTT
AGGATGATACAAAGCAGTGTAACTGAAAATGTTTCTTTTAATTGATTTAAAGGACTT
GTCTTCTATACCACCCTTGTCCTCATCTCAGGTAATTTATGAAATCTATGTAAACTTG
AAAAATATTTCTTAATTTTTGTTTTTGCTCCAGTCAATTCCTGATTATCCACAGGTCA
ACCCACATTTTTTCATTCCTTCTCCCTATCTGCTTATATCGCATTGCTCATTTAGAGTT
TGCAGGAGGCTCCATACTAGGTTCAGTCTGAAAGAAATCTCCTAATGGTGCTATAGA
GAGGGAGGTAACAGAAAGACTCTTTTAGGGCATTTTTCTGACTCATGAAAAGAGCA
CAGAAAAGGATGTTTGGCAATTTGTCTTTTAAGTCTTAACCTTGCTAATGTGAATACT
GGGAAAGTGATTTTTTCTCACTCGTTTTTGTTGCTCCATTGTAAAGGGCGGAGGTCA
GTCTTAGTGGCCTTGAGAGTTGCTTTTGGCATTAATATTCTAAGAGAATTAACTGTAT
TTCCTGTCACCTATTCACTAGTGCAGGAAATACTTGCTCCAAATAAGTCAGTATG
AGAAGTCACTGTCAATGAAAGTTGTTTTGTTTGTTTTCAGTAATATTTTGCTGTTTTT
AAGACTTGGAAAACTAAGTGCAGAGTTTACAGAGTGGTAAATATCTATGTTACATGT
AGATTATACATATATATACACACGTGTATATGAGATATATATCTTATATCTCCACAA
ACACAAATTATATATATACATATCCACACACATACATTACATATATCTGTGTATATA
AATCCACATGCACATGAAATATATATATATATAATTTGTGTGTGTGTATGTGTAT
GTATATGACTTTAAATAGCTATGGGTACAATATTAAAAACCACTGGAACTCTTTGTCC
AGTTTTTAAATTATGTTTTTACTGGAATGTTTTTGTGTCAGTGTTTTCTGTACATATTA
TTTGTTAATTCACAGCTCACAGAGTGATAGTTGTCATAGTTCTTGCCTTCCCTAAGTT
TATATAAATAACTTAAGTATTGCTACAGTTTATCTAGGTTGCAGTGGCATCTGCTGTG
CACAGAGCTTCCATGGTCACTGCTAAGCAGTAGCCAGCCATCGGGCATTAATTGATT
TCCTACTATATTCCCAGCAGACACATTTAGAAACTAAGCTATGTTAACCTCAGTGCT
CAACTATTTGAACTGTTGAGTGATAAAGGAAACAAATATAACTGTAAATGAATCTTG
GTATCCTGTGAAACAGAATAATTCGTAATTTAAGAAAGCCCTTATCCCGGTAACATG
AATGTTGATGAACAAATGTAAAATTATATCCTATATTTAAGTACCCATAATAAATCA
TTTCCCTCTATAAGTGTTATTGATTATTTTAAATTGAAAAAAGTTTCACTTGGATGAA
AAAAGTAGAAAAGTAGGTCATTCTTGGATCTACTTTTTTTTAGCCTTATTAATATTTT
TCCCTATTAGAAACCACAATTACTCCCTCTATTAACCCTTCACTTACTAGACCAGAA
AAGAACTTATTCCAGATAAGCTTTGAATATCAATTCTTACATAAACTTTAGGCAAAC
AGGGAATAGTCTAGTCACCAAAGGACCATTCTCTTGCCAATGCTGCATTCCTTTTGC
ACTTTTGGATTCCATATTTATCCCAAATGCTGTTGGGCACCCCTAGAAATACCTTGAT
GTTTTTTCTATTTATATGCCTGCCTTTGGTACTTAATTTTACAAATGCTGTAATATAA
AGCATATCAAGTTTATGTGATACGTATCATTGCAAGAGAATTTGTTTCAAGATTTTTT
TTTAATGTTCCAGAAGATGGCCAATAGAGAACATTCAAGGGAAATGGGGAAACATA
ATTTAGAGAACAAGAACAAACCATGTCTCAAATTTTTTAAAAAAAATTAATGGTTT
TAAATATATGCTATAGGGACGTTCCATGCCCAGGTTAACAAAGAACTGTGATATATA
GAGTGTCTAATTACAAAATCATATACGATTTATTTAATTCTCTTCTGTATTGTAACTT
AGATGATTCCCAAGGACTCTAATAAAAAATCACTTCATTGTATTTGGAAACAAAAC
ATCATTCATTAATTACTTATTTTCTTTCCATAGGTTTTAATATTTTGAGAGTGTCTTTT
TTATTTCATTCATGAACTTTTGTATTTTTCATTTTTCATTTGATTTGTAAATTTACTTAT
GTTAAAAATAAACCATTTATTTTCAGCTTTGAATTTTAAAAAAAAAAAAAAAAAA
```

TABLE 5-continued

Nucleotide Sequences of Biodosimetry Biomarker Genes

LYRM4 (SEQ ID NO: 5; GenBank NM_020408.5).
GAGCCCTGCCTGCGCCCGCCCCCGAAGCGGCGCGGGACGCCTGGCGCCGTCCGCGA
TCCGCAGGGCTGCCCGCTTAGGCTTAGGCCCGGCCCGCTGGCAAAGCCGAGCCGCA
GCATTTTATTTCGTTCGTGGTTTCCGCACAGGCTGGAGTTTCGTGGGTTGGGTCGTAC
TTGGGACCTCGGCGAAGAGGACCCGTTTATTTTTTTTCTTTCCAAAATGGCAGCCTC
CAGTCGCGCACAAGTGTTATCTCTGTACCGGGCGATGCTGAGAGAGAGCAAGCGTTT
CAGCGCCTACAATTACAGAACATATGCTGTCAGGAGGATAAGAGATGCCTTCAGAG
AAAATAAAAATGTAAAGGATCCTGTAGAAATTCAAACCCTAGTGAATAAAGCCAAG
AGAGACCTTGGAGTAATTCGTCGACAGGTCCACATTGGCCAACTGTATTCAACTGAC
AAGCTGATCATTGAGAATCGAGACATGCCCAGGACCTAGCAAGCCGGGGACCAGCC
ACCAGTGGCGGCCAGGGACCACCTTCAGCATCCACTCTCTGTTTGAGATGGGGGCTC
CCAAAACCAGCTTACAATAGCCTTTTGCGCTGCCTGTCCTGTGGGAGCTGATAAACC
AAGTCACATTTGCATTCTGTTGCAGGCTTAGTGAAAAAGGACTGCTGTCTTTCCTTG
GTTCAAGTGTTAGAATGGAGAGCTGGAGTTCGTTCAGAATAGTGCTGTGTGTTACCA
CGTCTCCCCTGCACCCCATTCCTACCTTGTAGCTCATGACCATTGTGTATAGCATTTC
TACACTTTGTTTCTTGGTCCTTGGCAATAAAAAGAATGATCTCCCTGAGCCTTTGACC
CCAGATAAACCCCTCCCAATTAATGCATTTTCATTTCCTACTGATACAAGGCCTGGA
GAGGGCTGTTGGGGGCCCTCAGGGAGGGTTCAACTCTGAGACGAGAACTGCCTTGG
TGAAGGCAAGTTCAAGCACCACTTGAGACTGGGGGCAGCATGGAGTAGGGCAGGC
TACGGGGATACACGGTGCACCCTGCAACTTATACCTGAGCCCAGTACAACAAAGGT
GACGGGTGTGTAGGTACACACCCAGAGATGGAGCACTGCAGATCAGCAACCTCAGC
CCCACCTGGGAATTTGCTGGAAATGCAGGCTCAAGCCCCTCCCCACACCTGGTGAAT
GAGAGAGCCCCAGCCTGACCCAAGCCCAGGGCGACTCCCATACCCTGAAGCCTGGG
GCATGCTGGGCAGCACCGGTGCCCAAATCTGGCTGGTGGACAGAAGCACCTGGAGA
GTTGGAGAGCTTTTTAAAAAGACATCTCTCAGCACTTCCCTCTCTGCAGATTCTGACT
CAGTAAGTGAGGGGTGAGGCACAGTCATTTTTCTCTATTCTGAAGCTCTCCCACTGT
TTTCAATGTTTAACCAACTGGGGACCCCTGCTCTTTAAGTATATTACAGGTAATAAA
GATATTGTTTGTATGCTTTTAAAAAAAAAAAAAAAAAA MYC (SEQ ID NO: 6; GenBank NM 002467).
GACCCCCGAGCTGTGCTGCTCGCGGCCGCCACCGCCGGGCCCCGGCCGTCCCTGGCT
CCCCTCCTGCCTCGAGAAGGGCAGGGCTTCTCAGAGGCTTGGCGGGAAAAAGAACG
GAGGGAGGGATCGCGCTGAGTATAAAAGCCGGTTTTCGGGGCTTTATCTAACTCGCT
GTAGTAATTCCAGCGAGAGGCAGAGGGAGCGAGCGGGCGGCCGGCTAGGGTGGAA
GAGCCGGGCGAGCAGAGCTGCGCTGCGGGCGTCCTGGGAAGGGAGATCCGGAGCG
AATAGGGGGCTTCGCCTCTGGCCCAGCCCTCCCGCTGATCCCCCAGCCAGCGGTCCG
CAACCCTTGCCGCATCCACGAAACTTTGCCCATAGCAGCGGGCGGGCACTTTGCACT
GGAACTTACAACACCCGAGCAAGGACGCGACTCTCCCGACGCGGGGAGGCTATTCT
GCCCATTTGGGGACACTTCCCCGCCGCTGCCAGGACCCGCTTCTCTGAAAGGCTCTC
CTTGCAGCTGCTTAGACGCTGGATTTTTTTCGGGTAGTGGAAAAACCAGCAGCCTCCC
GCGACGATGCCCCTCAACGTTAGCTTCACCAACAGGAACTATGACCTCGACTACGAC
TCGGTGCAGCCGTATTTCTACTGCGACGAGGAGGAGAACTTCTACCAGCAGCAGCA
GCAGAGCGAGCTGCAGCCCCCGGCGCCCAGCGAGGATATCTGGAAGAAATTCGAGC
TGCTGCCCACCCCGCCCCTGTCCCCTAGCCGCCGCTCCGGCTCTGCTCGCCCCTCCTA
CGTTGCGGTCACACCCTTCTCCCTTCGGGGAGACAACGACGGCGGTGGCGGGAGCTT
CTCCACGGCCGACCAGCTGGAGATGGTGACCGAGCTGCTGGGAGGAGACATGGTGA
ACCAGAGTTTCATCTGCGACCCGGACGACGAGACCTTCATCAAAAACATCATCATCC
AGGACTGTATGTGGAGCGGCTTCTCGGCCGCCGCCAAGCTCGTCTCAGAGAAGCTG
GCCTCCTACCAGGCTGCGCGCAAAGACAGCGGCAGCCCGAACCCCGCCCGCGGCCA
CAGCGTCTGCTCCACCTCCAGCTTGTACCTGCAGGATCTGAGCGCCGCCGCCTCAGA
GTGCATCGACCCCTCGGTGGTCTTCCCCTACCCTCTCAACGACAGCAGCTCGCCCAA
GTCCTGCGCCTCGCAAGACTCCAGCGCCTTCTCTCCGTCCTCGGATTCTCTGCTCTCC
TCGACGGAGTCCTCCCCGCAGGGCAGCCCCGAGCCCCTGGTGCTCCATGAGGAGAC
ACCGCCCACCACCAGCAGCGACTCTGAGGAGGAACAAGAAGATGAGGAAGAAATC
GATGTTGTTTCTGTGGAAAAGAGGCAGGCTCCTGGCAAAAGGTCAGAGTCTGGATC
ACCTTCTGCTGGAGGCCACAGCAAACCTCCTCACAGCCCACTGGTCCTCAAGAGGTG
CCACGTCTCCACACATCAGCACAACTACGCAGCGCCTCCCTCCACTCGGAAGGACTA
TCCTGCTGCCAAGAGGGTCAAGTTGGACAGTGTCAGAGTCCTGAGACAGATCAGCA
ACAACCGAAAATGCACCAGCCCCAGGTCCTCGGACACCGAGGAGAATGTCAAGAGG
CGAACACACAACGTCTTGGAGCGCCAGAGGAGGAACGAGCTAAAACGGAGCTTTTT
TGCCCTGCGTGACCAGATCCCGGAGTTGGAAAACAATGAAAAGGCCCCCAAGGTAG
TTATCCTTAAAAAAGCCACAGCATACATCCTGTCCGTCCAAGCAGAGGAGCAAAAG
CTCATTTCTGAAGAGGACTTGTTGCGGAAACGACGAGAACAGTTGAAACACAAACT
TGAACAGCTACGGAACTCTTGTGCGTAAGGAAAAGTAAGGAAAACGATTCCTTCTA
ACAGAAATGTCCTGAGCAATCACCTATGAACTTGTTTCAAATGCATGATCAAATGCA
ACCTCACAACCTTGGCTGAGTCTTGAGACTGAAAGATTTAGCCATAATGTAAACTGC
CTCAAATTGGACTTTGGGCATAAAAGAACTTTTTTATGCTTACCATCTTTTTTTTTTCT
TTAACAGATTTGTATTTAAGAATTGTTTTTAAAAAATTTTAAGATTTACACAATGTTT
CTCTGTAAATATTGCCATTAAATGTAAATAACTTTAATAAAACGTTTATAGCAGTTA
CACAGAATTTCAATCCTAGTATATAGTACCTAGTATTATAGGTACTATAAACCCTAA
TTTTTTTTATTTAAGTACATTTTGCTTTTTAAAGTTGATTTTTTCTATTGTTTTTAGAA
AAAATAAAATAACTGGCAAATATCATTGAGCCAAATCTTAAAAAAAAAAAAAAA TMEM63B (SEQ ID NO: 7; GenBank NM_018426.1).
AACCCGGGGCTCCGAGCCGGAGCCGAGTCTGCGCCTGGGGGAGGACCATGCGGCAG
TAGCAGCCATGCTGCCCTTTCTGCTGGCCACACTGGGCACCACAGCCCTCAACAACA
GCAACCCCAAGGACTACTGCTACAGCGCCCGCATCCGCAGCACTGTCCTGCAGGGC
CTGCCCTTTGGGGGCGTCCCCACCGTGCTGGCTCTCGACTTCATGTGCTTCCTTGCAC TABLE 5-continued Nucleotide Sequences of Biodosimetry Biomarker Genes

```
TGCTGTTCTTATTCTCTATCCTCCGGAAGGTGGCCTGGGACTATGGGCGGCTGGCCTT
GGTGACAGATGCAGACAGGCTTCGGCGGCAGGAGAGGGACCGAGTGGAACAGGAA
TATGTGGCTTCAGCTATGCACGGGGACAGCCATGACCGGTATGAGCGTCTCACCTCT
GTCTCCAGCTCCGTTGACTTTGACCAAAGGGACAATGGTTTCTGTTCCTGGCTGACA
GCCATCTTCAGGATAAAGGATGATGAGATCCGGGACAAATGTGGGGGCGATGCCGT
GCACTACCTGTCCTTTCAGCGGCACATCATCGGGCTGCTGGTGGTTGTGGGCGTCCT
CTCCGTAGGCATCGTGCTGCCTGTCAACTTCTCAGGGGACCTGCTGGAGAACAATGC
CTACAGCTTTGGGAGAACCACCATTGCCAACTTGAAATCAGGGAACAACCTGCTATG
GCTGCACACCTCCTTCGCCTTCCTGTATCTGCTGCTCACCGTCTACAGCATGCGTAGA
CACACCTCCAAGATGCGCTACAAGGAGGATGATCTGGTGAAGCGGACCCTCTTCAT
CAATGGAATCTCCAAATATGCAGAGTCAGAAAAGATCAAGAAGCATTTTGAGGAAG
CCTACCCCAACTGCACAGTTCTCGAAGCCCGCCCGTGTTACAACGTGGCTCGCCTAA
TGTTCCTCGATGCAGAGAGGAAGAAGGCCGAGCGGGGAAAGCTGTACTTCACAAAC
CTCCAGAGCAAGGAGAACGTGCCTACCATGATCAACCCCAAGCCCTGTGGCCACCT
CTGCTGCTGTGTGGTGCGAGGCTGTGAGCAGGTGGAGGCCATTGAGTACTACACAA
AGCTGGAGCAGAAGCTGAAGGAAGACTACAAGCGGGAGAAGGAGAAGGTGAATGA
GAAGCCTCTTGGCATGGCCTTTGTCACCTTCCACAATGAGACTATCACCGCCATCAT
CCTGAAGGACTTCAACGTGTGTAAATGCCAGGGCTGCACCTGCCGTGGGGAGCCAC
GCCCCTCATCCTGCAGCGAGTCCCTGCACATCTCCAACTGGACCGTGTCCTATGCCC
CTGACCCTCAGAACATCTACTGGGAGCACCTCTCCATCCGAGGCTTCATCTGGTGGC
TGCGCTGCCTGGTCATCAATGTCGTCCTCTTCATCCTCCTCTTCTTCCTCACCACTCC
AGCCATCATCATCACCACCATGGACAAGTTCAACGTCACCAAGCCTGTGGAGTACCT
CAACAACCCCATCATCACCCAGTTCTTCCCCACCCTGCTGCTGTGGTGCTTCTCGGCC
CTCCTTCCCACCATCGTCTACTACTCAGCCTTCTTTGAAGCCCACTGGACACGCTCTG
GGGAGAACAGGACAACCATGCACAAGTGCTACACTTTCCTCATCTTCATGGTGCTGC
TCCTACCCTCGCTGGGACTGAGCAGCCTGGACCTCTTCTTCCGCTGGCTCTTTGATAA
GAAATTCTTGGCTGAGGCAGCTATTCGGTTTGAGTGTGTGTTCCTGCCCGACAACGG
CGCCTTCTTCGTGAACTACGTCATTGCCTCAGCCTTTATCGGCAACGCCATGGACCT
GCTGCGCATCCCAGGCCTGCTCATGTACATGATCCGGCTCTGCCTGGCGCGCTCGGC
CGCCGAGAGGCGCAACGTGAAGCGGCATCAGGCCTACGAGTTCCAGTTTGGCGCAG
CCTACGCTGGATGATGTGCGTCTTCACGGTGGTCATGACCTACAGTATCACCTGCC
CCATCATCGTGCCCTTCGGGCTCATGTACATGCTGCTGAAGCACCTGGTAGACAGGT
ACAATCTCTACTACGCCTACCTGCCGGCCAAGCTGGACAAGAAGATCCACTCGGGG
GCTGTGAACCAGGTGGTGGCCGCGCCCATCCTCTGCCTCTTCTGGCTGCTCTTCTTTT
CCACCATGCGCACGGGGTTCCTAGCTCCCACGTCTATGTTCACATTTGTGGTCCTGGT
CATCACCATCGTCATCTCTCTGCCACGTCTGCTTTGGACACTTCAAATACCTCAGT
GCCCACAACTACAAGATTGAGCACACGGAGACAGATACTGTGGACCCCAGAAGCAA
TGGACGCCCCCCACTGCTGCTGCTGTCCCCAAATCTGCGAAATACATCGCTCAGGT
GCTGCAGGACTCAGAGGTGGACGGGGATGGGGATGGGGCTCCTGGGAGCTCAGGGG
ATGAGCCCCCATCATCCTCATCCCAAGATGAGGAGTTGCTGATGCCACCCGACGCCC
TCACGGACACAGACTTCCAGTCTTGCGAGGACAGCCTCATAGAGAATGAGATTCAC
CAGTAAGGGGAGGGAGGGGCCCTGGAGGCCACATCCTGCCCCACCCCACCCCCACT
CCCACGGACACTAAAACGCTAATAATTTATTAGATCTAAAGCCCCTTCCTCCCCAGC
CCCTGCTTTCATTAAGGTATTTAAACTTGGGGGTTTCACTGCTCTCCCCCATGATGGA
GGGAGGGGAGCCCCCCAACCTCAGTGAGGAGAGCCCCGAGCCGGCCCCGGGGCAAA
GAGGGGTGCAGAGGGAGTTCCCCCAGATCAGTACCCCCCACCCCTCCCCAGCTAGT
AGCATGACCAGGAGAGGGTTAATGAGAGCCAAGAGGAGTACCTGGTGCACCTGGTG
CCGGTGGCTGGAGACCTGGGGGGCAGGTGGATCTGGGGCTGTTCCCCCCCCTCCGTT
TTTTCCACCCCACAGTTCCTCCTGGGATCTGGCCCTCCAGGGAAGTGGAGCCTCCAG
CCCCTAGGGGATGCATGAGGGGGGAGGGGGTGCTGAGTGGGAGGAAGAGTCAGGC
TCACAGCTGGGGTGGCCTGGGGGTGGGGTGGGCAAGGCTGACACTGGAAAATGGG
TTTTTGCACTGTTTTTTTTGGTTTTTTTGTTCTTTTTTGTTTTTTTCCTTTAAAATAA
AAACAAAGAAAAGCTCTGAAAAAAAAAAAAAAAAA
```

ALOX5 (SEQ ID NO: 8; GenBank NM_000698.3).
```
CCGGGGCCAGGGACCAGTGGTGGGAGGAGGCTGCGGCGCTAGATGCGGACACCTG
GACCGCCGCGCCGAGGCTCCCGGCGCTCGCTGCTCCCGCGGCCCGCGCCATGCCCTC
CTACACGGTCACCGTGGCCACTGGCAGCCAGTGGTTCGCCGGCACTGACGACTACAT
CTACCTCAGCCTCGTGGGCTCGGCGGGCTGCAGCGAGAAGCACCTGCTGGACAAGC
CCTTCTACAACGACTTCGAGCGTGGCGCGGTGGATTCATACGACGTGACTGTGGACG
AGGAACTGGGCGAGATCCAGCTGGTCAGAATCGAGAAGCGCAAGTACTGGCTGAAT
GACGACTGGTACCTGAAGTACATCACGCTGAAGACGCCCCACGGGGACTACATCGA
GTTCCCCTGCTACCGCTGGATCACCGGCGATGTCGAGGTTGTCCTGAGGGATGGACG
CGCAAAGTTGGCCCGAGATGACCAAATTCACATTCTCAAGCAACACCGACGTAAAG
AACTGGAAACACGCAAAAACAATATCGATGATGGAGTGGAACCCTGGCTTCCCC
TTGAGCATCGATGCCAAATGCCACAAGGATTTACCCCGTGATATCCAGTTTGATAGT
GAAAAAGGAGTGGACTTTGTTCTGAATTACTCCAAAGCGATGGAGAACCTGTTCATC
AACCGCTTCATGCACATGTTCCAGTCTTCTTGGAATGACTTCGCCGACTTTGAGAAA
ATCTTTGTCAAGATCAGCAACACTATTTCTGAGCGGGTCATGAATCACTGGCAGGAA
GACCTGATGTTTGGCTACCAGTTCCTGAATGGCTGCAACCCTGTGTTGATCGGCGC
TGCACAGAGCTGCCCGAGAAGCTCCCGGTGACCACGGAGATGGTAGAGTGCAGCCT
GGAGCGGCAGCTCAGCTTGGAGCAGGAGGTCCAGCAAGGGAACATTTTCATCGTGG
ACTTTGAGCTGCTGGATGGCATCGATGCCAACAAAACAGACCCCTGCACACTCCAGT
TCCTGGCCGCTCCCATCTGCTTGCTGTATAAGAACCTGGCCAACAAGATTGTCCCCA
TTGCCATCCAGCTCAACCAAATCCGGGAGATGAGAACCCTATTTTCCTCCCCTTCGG
ATGCAAAATACGACTGGCTTTTGGCCAAAATCTGGGTGCGTTCCAGTGACTTCCACG
TCCACCAGACCATCACCCACCTTCTGCGAACACATCTGGTGTCTGAGGTTTTTGGCA
TTGCAATGTACCGCCAGCTGCCTGCTGTGCACCCCATTTTCAAGCTGCTGGTGGCAC
```

TABLE 5-continued

Nucleotide Sequences of Biodosimetry Biomarker Genes

ACGTGAGATTCACCATTGCAATCAACACCAAGGCCCGTGAGCAGCTCATCTGCGAG
TGTGGCCTCTTTGACAAGGCCAACGCCACAGGGGGCGGTGGGCACGTGCAGATGGT
GCAGAGGGCCATGAAGGACCTGACCTATGCCTCCCTGTGCTTTCCCGAGGCCATCAA
GGCCCGGGGCATGGAGAGCAAAGAAGACATCCCCTACTACTTCTACCGGGACGACG
GGCTCCTGGTGTGGGAAGCCATCAGGACGTTCACGGCCGAGGTGGTAGACATCTAC
TACGAGGGCGACCAGGTGGTGGAGGAGGACCCGGAGCTGCAGGACTTCGTGAACGA
TGTCTACGTGTACGGCATGCGGGGCCGCAAGTCCTCAGGCTTCCCCAAGTCGGTCAA
GAGCCGGGAGCAGCTGTCGGAGTACCTGACCGTGGTGATCTTCACCGCCTCCGCCCA
GCACGCCGCGGTCAACTTCGGCCAGTACGACTGGTGCTCCTGGATCCCCAATGCGCC
CCCAACCATGCGAGCCCCGCCACCGACTGCCAAGGGCGTGGTGACCATTGAGCAGA
TCGTGGACACGCTGCCCGACCGCGGCCGCTCCTGCTGGCATCTGGGTGCAGTGTGGG
CGCTGAGCCAGTTCCAGGAAAACGAGCTGTTCCTGGGCATGTACCCAGAAGAGCAT
TTTATCGAGAAGCCTGTGAAGGAAGCCATGGCCCGATTCCGCAAGAACCTCGAGGC
CATTGTCAGCGTGATTGCTGAGCGCAACAAGAAGAAGCAGCTGCCATATTACTACTT
GTCCCCAGACCGGATTCCGAACAGTGTGGCCATCTGAGCACACTGCCAGTCTCACTG
TGGGAAGGCCAGCTGCCCCAGCCAGATGGACTCCAGCCTGCCTGGCAGGCTGTCTG
GCCAGGCCTCTTGGCAGTCACATCTCTTCCTCCGAGGCCAGTACCTTTCCATTTATTC
TTTGATCTTCAGGGAACTGCATAGATTGATCAAAGTGTAAACACCATAGGGACCCAT
TCTACACAGAGCAGGACTGCACAGCGTCCTGTCCACACCCAGCTCAGCATTTCCACA
CCAAGCAGCAACAGCAAATCACGACCACTGATAGATGTCTATTCTTGTTGGAGACAT
GGGATGATTATTTTCTGTTCTATTTGTGCTTAGTCCAATTCCTTGCACATAGTAGGTA
CCCAATTCAATTACTATTGAATGAATTAAGAATTGGTTGCCATAAAAATAAATCAGT
TCATTTAAAATGAAAAAAAAAAAAAAAAAAAAA

CAMK4 (SEQ ID NO: 9; GenBank NM_001744.4).
AGTCTCCCTCCAGCGGGCGGCGACTCCGGGTTCCCCCTCGCGCCCTCTCGCAGAGGC
TCGCCCCCTTCCCCGCCCACCGTCCCTGCGAGCGCGGGCGGCGGCGGTGGGCGTGTG
CGCGCGTGAAGGACGCCGCCTCTCTCGCTCCTGCGTTCGCAGGCGGCGGCTGGCG
GCCGGCTTCTCGCTCGGGCAGCGGCGGCGGCGGCGGCGGCTTCCGGAGTCCCG
CTGCGAAGATGCTCAAAGTCACGGTGCCCTCCTGCTCCGCCTCGTCCTGCTCTTCGG
TCACCGCCAGTGCGGCCCCGGGGACCGCGAGCCTCGTCCCGGATTACTGGATCGAC
GGCTCCAACAGGGATGCGCTGAGCGATTTCTTCGAGGTGGAGTCGGAGCTGGGACG
GGGTGCTACATCCATTGTGTACAGATGCAAACAGAAGGGGACCCAGAAGCCTTATG
CTCTCAAAGTGTTAAAGAAAACAGTGGACAAAAAAATCGTAAGAACTGAGATAGGA
GTTCTTCTTCGCCTCTCACATCCAAACATTATAAAACTTAAAGAGATATTTGAAACC
CCTACAGAAATCAGTCTGGTCCTAGAACTCGTCACAGGAGGAGAACTGTTTGATAG
GATTGTGGAAAAGGGATATTACAGTGAGCGAGATGCTGCAGATGCCGTTAAACAAA
TCCTGGAGGCAGTTGCTTATCTACATGAAAATGGGATTGTCCATCGTGATCTCAAAC
CAGAGAATCTTCTTTATGCAACTCCAGCCCCAGATGCACCACTCAAAATCGCTGATT
TTGGACTCTCTAAAATTGTGGAACATCAAGTGCTCATGAAGACAGTATGTGGAACCC
CAGGGTACTGCGCACCTGAAATTCTTAGAGGTTGTGCCTATGGACCTGAGGTGGACA
TGTGGTCTGTAGGAATAATCACCTACATCTTACTTTGTGGATTTGAACCATTCTATGA
TGAAAGAGGCGATCAGTTCATGTTCAGGAGAATTCTGAATTGTGAATATTACTTTAT
CTCCCCCTGGTGGGATGAAGTATCTCTAAATGCCAAGGACTTGGTCAGAAAATTAAT
TGTTTTGGATCCAAAGAAACGGCTGACTACATTTCAAGCTCTCCAGCATCCGTGGGT
CACAGGTAAAGCAGCCAATTTTGTACACATGGATACCGCTCAAAAGAAGCTCCAAG
AATTCAATGCCCGGCGTAAGCTTAAGGCAGCGGTGAAGGCTGTGGTGGCCTCTTCCC
GCCTGGGAAGTGCCAGCAGCAGCCATGGCAGCATCCAGGAGAGCCACAAGGCTAGC
CGAGACCCTTCTCCAATCCAAGATGGCAACGAGGACATGAAAGCTATTCCAGAAGG
AGAGAAAATTCAAGGCGATGGGGCCCAAGCCGCAGTTAAGGGGGCACAGGCTGAG
CTGATGAAGGTGCAAGCCTTAGAGAAAGTTAAAGGTGCAGATATAAATGCTGAAGA
GGCCCCCAAAATGGTGCCCAAGGCAGTGGAGGATGGGATAAAGGTGGCTGACCTGG
AACTAGAGGAGGGCCTAGCAGAGGAGAAGCTGAAGACTGTGGAGGAGGCAGCAGC
TCCCAGAGAAGGGCAAGGAAGCTCTGCTGTGGGTTTTGAAGTTCCACAGCAAGATG
TGATCCTGCCAGAGTACTAAACAGCTTCCTTCAGATCTGGAAGCCAAACACCGGCAT
TTTATGTACTTTGTCCTTCAGCAAGAAAGGTGTGGAAGCATGATATGTACTATAGTG
ATTCTGTTTTTGAGGTGCAAAAAACATACATATATACCAGTTGGTAATTCTAACTTC
AATGCATGTGACTGCTTTATGAAAATAATAGTGTCTTCTATGGCATGTAATGGATAC
CTAATACCGATGAGTTAAATCTTGCAAGTTAACACAACGTAAACACTTAAAAGCATAC
ATTTTCAGCAACCAGTGGCACATATTTGAAGTGAATAGTAGCAAATTGTTTTTGCTTT
GAAAATCTAGCCATCCTACATCCTTTGGATTTCTTCACAAGGCAGTAATTCCTTTGAA
CTACTGCTTAGCTAATACTAGGTAGTGCTAAAAGACATGTTCCCATAACTTTTACAA
CATTTTACTTTTTATCATTGATGTGTTCAAACTGTTTACAAGGAGATGCTTATAGATG
ATAGTTGTACATATGTGCAAAAAAAAATCCACTTGCAATGGTAAGAAATTGAAGTA
TCCTTAAAGGCCATGAAGCCATATGTCCCTAAAAAAAAAAAAAAAAAAAAAAAA
AAAAAAA CDKN1A (SEQ ID NO: 10; NM_000389.4).
GTTGTATATCAGGGCCGCGCTGAGCTGCGCCAGCTGAGGTGTGAGCAGCTGCCGAA
GTCAGTTCCTTGTGGAGCCGGAGCTGGGCGCGGATTCGCCGAGGCACCGAGGCACT
CAGAGGAGGCGCCATGTCAGAACCGGCTGGGGATGTCCGTCAGAACCCATGCGGCA
GCAAGGCCTGCCGCCGCCTCTTCGGCCCAGTGGACAGCGAGCAGCTGAGCCGCGAC
TGTGATGCGCTAATGGCGGGCTGCATCCAGGAGGCCCGTGAGCGATGGAACTTCGA
CTTTGTCACCGAGACACCACTGGAGGGTGACTTCGCCTGGGAGCGTGTGCGGGGCCT
TGGCCTGCCCAAGCTCTACCTTCCCACGGGGCCCCGGCGAGGCCGGGATGAGTTGG
GAGGAGGCAGGCGGCCTGGCACCTCACCTGCTCTGCTGCAGGGGACAGCAGAGGAA
GACCATGTGGACCTGTCACTGTCTTGTACCCTTGTGCCTCGCTCAGGGGAGCAGGCT
GAAGGGTCCCCAGGTGGACCTGGAGACTCTCAGGGTCGAAAACGGCGGCAGACCAG

TABLE 5-continued

Nucleotide Sequences of Biodosimetry Biomarker Genes

```
CATGACAGATTTCTACCACTCCAAACGCCGGCTGATCTTCTCCAAGAGGAAGCCCTA
ATCCGCCCACAGGAAGCCTGCAGTCCTGGAAGCGCGAGGGCCTCAAAGGCCCGCTC
TACATCTTCTGCCTTAGTCTCAGTTTGTGTGTCTTAATTATTATTTGTGTTTTAATTTA
AACACCTCCTCATGTACATACCCTGGCCGCCCCCTGCCCCCAGCCTCTGGCATTAG
AATTATTTAAACAAAAACTAGGCGGTTGAATGAGAGGTTCCTAAGAGTGCTGGGCA
TTTTTATTTTATGAAATACTATTTAAAGCCTCCTCATCCCGTGTTCTCCTTTTCCTCTC
TCCCGGAGGTTGGGTGGGCCGGCTTCATGCCAGCTACTTCCTCCTCCCCACTTGTCC
GCTGGGTGGTACCCTCTGGAGGGGTGTGGCTCCTTCCCATCGCTGTCACAGGCGGTT
ATGAAATTCACCCCCTTTCCTGGACACTCAGACCTGAATTCTTTTTCATTTGAGAAGT
AAACAGATGGCACTTTGAAGGGGCCTCACCGAGTGGGGGCATCATCAAAAACTTTG
GAGTCCCCTCACCTCCTCTAAGGTTGGGCAGGGTGACCCTGAAGTGAGCACAGCCTA
GGGCTGAGCTGGGGACCTGGTACCCTCCTGGCTCTTGATACCCCCTCTGTCTTGTG
AAGGCAGGGGGAAGGTGGGGTCCTGGAGCAGACCACCCCGCCTGCCCTCATGGCCC
CTCTGACCTGCACTGGGGAGCCCGTCTCAGTGTTGAGCCTTTTCCCTCTTTGGCTCCC
CTGTACCTTTTGAGGAGCCCCAGCTACCCTTCTTCTCCAGCTGGGCTCTGCAATTCCC
CTCTGCTGCTGTCCCTCCCCCTTGTCCTTTCCCTTCAGTACCCTCTCAGCTCCAGGTG
GCTCTGAGGTGCCTGTCCCACCCCCACCCCCAGCTCAATGGACTGGAAGGGGAAGG
GACACACAAGAAGAAGGGCACCCTAGTTCTACCTCAGGCAGCTCAAGCAGCGACCG
CCCCCTCCTCTAGCTGTGGGGGTGAGGGTCCCATGTGGTGGCACAGGCCCCCTTGAG
TGGGGTTATCTCTGTGTTAGGGGTATATGATGGGGGAGTAGATCTTTCTAGGAGGGA
GACACTGGCCCCTCAAATCGTCCAGCGACCTTCCTCATCCACCCCATCCCTCCCCAG
TTCATTGCACTTTGATTAGCAGCGGAACAAGGAGTCAGACATTTTAAGATGGTGGCA
GTAGAGGCTATGGACAGGGCATGCCACGTGGGCTCATATGGGGCTGGGAGTAGTTG
TCTTTCCTGGCACTAACGTTGAGCCCCTGGAGGCACTGAAGTGCTTAGTGTACTTGG
AGTATTGGGGTCTGACCCCAAACACCTTCCAGCTCCTGTAACATACTGGCCTGGACT
GTTTTCTCTCGGCTCCCCATGTGTCCTGGTTCCCGTTTCTCCACCTAGACTGTAAACC
TCTCGAGGGCAGGGACCACACCCTGTACTGTTCTGTGTCTTTCACAGCTCCTCCCAC
AATGCTGAATATACAGCAGGTGCTCAATAAATGATTCTTAGTGACTTTACTTGTAAA
AAAAAAAAAAAAAA

COCH (SEQ ID NO: 11; AY358900.1).
GGGGCCTTGCCTTCCGCACTCGGGCGCAGCCGGGTGGATCTCGAGCAGGTGCGGAG
CCCCGGGCGGCGGGCGCGGGTGCGAGGGATCCCTGACGCCTCTGTCCCTGTTTCTTT
GTCGCTCCCAGCCTGTCTGTCGTCGTTTTGGCGCCCCGCCTCCCCGCGGTGCGGGG
TTGCACACCGATCCTGGGCTTCGCTCGATTTGCCGCCGAGGCGCCTCCCAGACCTAG
AGGGGCGCTGGCCTGGAGCAGCGGGTCGTCTGTGTCCTCTCTCCTCTGCGCCGCGCC
CGGGGATCCGAAGGGTGCGGGGCTCTGAGGAGGTGACGCGCGGGGCCTCCCGCACC
CTGGCCTTGCCCGCATTCTCCCTCTCTCCCAGGTGTGAGCAGCCTATCAGTCACCATG
TCCGCAGCCTGGATCCCGGCTCTCGGCCTCGGTGTGTGTCTGCTGCTGCTGCCGGGG
CCCGCGGGCAGCGAGGGAGCCGCTCCCATTGCTATCACATGTTTTACCAGAGGCTTG
GACATCAGGAAAGAGAAAGCAGATGTCCTCTGCCCAGGGGGCTGCCCTCTTGAGGA
ATTCTCTGTGTATGGGAACATAGTATATGCTTCTGTATCGAGCATATGTGGGGCTGC
TGTCCACAGGGGAGTAATCAGCAACTCAGGGGACCTGTACGAGTCTATAGCCTAC
CTGGTCGAGAAAACTATTCCTCAGTAGATGCCAATGGCATCCAGTCTCAAATGCTTT
CTAGATGGTCTGCTTCTTTCACAGTAACTAAAGGCAAAAGTAGTACACAGGAGGCC
ACAGGACAAGCAGTGTCCACAGCACATCCACCAACAGGTAAACGACTAAAGAAAA
CACCCGAGAAGAAAACTGGCAATAAAGATTGTAAAGCAGACATTGCATTTCTGATT
GATGGAAGCTTTAATATTGGGCAGCGCCGATTTAATTTACAGAAGAATTTTGTTGGA
AAAGTGGCTCTAATGTTGGGAATTGGAACAGAAGGACCACATGTGGGCCTTGTTCA
AGCCAGTGAACATCCCAAAATAGAATTTTACTTGAAAAACTTTACATCAGCCAAAG
ATGTTTTGTTTGCCATAAAGGAAGTAGGTTTCAGAGGGGGTAATTCCAATACAGGAA
AAGCCTTGAAGCATACTGCTCAGAAATTCTTCACGGTAGATGCTGGAGTAAGAAAA
GGGATCCCCAAAGTGGTGGTGGTATTTATTGATGGTTGGCCTTCTGATGACATCGAG
GAAGCAGGCATTGTGGCCAGAGAGTTTGGTGTCAATGTATTTATAGTTTCTGTGGCC
AAGCCTATCCCTGAAGAACTGGGGATGGTTCAGGATGTCACATTTGTTGACAAGGCT
GTCTGTCGGAATAATGGCTTCTTCTCTTACCACATGCCCAACTGGTTTGGCACCACA
AAATACGTAAAGCCTCTGGTACAGAAGCTGTGCACTCATGAACAAATGATGTGCAG
CAAGACCTGTTATAACTCAGTGAACATTGCCTTTCTAATTGATGGCTCCAGCAGTGT
TGGAGATAGCAATTTCCGCCTCATGCTTGAATTTGTTTCCAACATAGCCAAGACTTTT
GAAATCTCGGACATTGGTGCCAAGATAGCTGCTGTACAGTTTACTTATGATCAGCGC
ACGGAGTTCAGTTTCACTGACTATAGCACCAAAGAGAATGTCCTAGCTGTCATCAGA
AACATCCGCTATATGAGTGGTGGAACAGCTACTGGTGATGCCATTTCCTTCACTGTT
AGAAATGTGTTTGGCCCTATAAGGGAGAGCCCCAACAAGAACTTCCTAGTAATTGTC
ACAGATGGGCAGTCCTATGATGATGTCCAAGGCCCTGCAGCTGCTGCACATGATGCA
GGAATCACTATCTTCTCTGTTGGTGTGGCTTGGGCACCTCTGGATGACCTGAAAGAT
ATGGCTTCTAAACCGAAGGAGTCTCACGCTTTCTTCACAAGAGAGTTCACAGGATTA
GAACCAATTGTTTCTGATGTCATCAGAGGCATTTGTAGAGATTTCTTAGAATCCCAG
CAATAATGGTAACATTTTGACAACTGAAAGAAAAAGTACAAGGGGATCCAGTGTGT
AAATTGTATTCTCATAATACTGAAATGCTTTAGCATACTAGAATCAGATACAAAACT
ATTAAGTATGTCAACAGCCATTTAGGCAAATAAGCACTCCTTTAAAGCCGCTGCCTT
CTGGTTACAATTTACAGTGTACTTTGTTAAAAACACTGCTGAGGCTTCATAATCATG
GCTCTTAGAAACTCAGGAAAGAGGAGATAATGTGGATTAAAACCTTAAGAGTTCTA
ACCATGCCTACTAAATGTACAGATATGCAAATTCCATAGCTCAATAAAAGAATCTGA
TACTTAGACCAAAAAAAAAAA

DHRS4 (SEQ ID NO: 12; NM_021004.3).
CTACTCTGTCACCGCCCCTGGGAAGAGTGGAACCCATACTTGCTGGTCTGATCCATG
CACAAGGCGGGGCTGCTAGGCCTCTGTGCCCGGGCTTGGAATTCGGTGCGGATGGC
```

TABLE 5-continued

Nucleotide Sequences of Biodosimetry Biomarker Genes

```
CAGCTCCGGGATGACCCGCCGGGACCCGCTCGCAAATAAGGTGGCCCTGGTAACGG
CCTCCACCGACGGGATCGGCTTCGCCATCGCCCGGCGTTTGGCCCAGGACGGGGCCC
ATGTGGTCGTCAGCAGCCGGAAGCAGCAGAATGTGGACCAGGCGGTGGCCACGCTG
CAGGGGGAGGGGCTGAGCGTGACGGGCACCGTGTGCCATGTGGGGAAGGCGGAGG
ACCGGGAGCGGCTGGTGGCCACGGCTGTGAAGCTTCATGGAGGTATCGATATCCTA
GTCTCCAATGCTGCTGTCAACCCTTTCTTTGGAAGCATAATGGATGTCACTGAGGAG
GTGTGGGACAAGACTCTGGACATTAATGTGAAGGCCCCAGCCCTGATGACAAAGGC
AGTGGTGCCAGAAATGGAGAAACGAGGAGGCGGCTCAGTGGTGATCGTGTCTTCCA
TAGCAGCCTTCAGTCCATCTCCTGGCTTCAGTCCTTACAATGTCAGTAAAACAGCCTT
GCTGGGCCTGACCAAGACCCTGGCCATAGAGCTGGCCCCAAGGAACATTAGGGTGA
ACTGCCTAGCACCTGGACTTATCAAGACTAGCTTCAGCAGGATGCTCTGGATGGACA
AGGAAAAAGAGGAAAGCATGAAAGAAACCCTGCCGGATAAGAAGGTTAGGCGAGCC
AGAGGATTGTGCTGGCATCGTGTCTTTCCTGTGCTCTGAAGATGCCAGCTACATCAC
TGGGGAAACAGTGGTGGTGGGTGGAGGAACCCCGTCCCGCCTCTGAGGACCGGGAG
ACAGCCCACAGGCCAGAGTTGGGCTCTAGCTCCTGGTGCTGTTCCCGCATTCACCCA
CTGGCCTTTCCCCACCTCTGCTCACCTTACTGTTCACCTCATCAAATCAGTTCTGCCCT
GTGAAAAGATCCAGCCTTCCCTGCCGTCAAGGTGGCGTCTTACTCGGGATTTCTGCT
GTTGTTGTGGCCTTGGGTAAAGGCCTCCCCTGAGAACACAGGACAGGCCTGCTGACA
AGGCTGAGTCTACCTTGGCAAAGACCAAGATATTTTTTCCCGGGCCACTGGGGAATC
TGAGGGGTGATGGGAGAGAAGGAACCTGGAGTGGAAGGAGCAGAGTTGCAAATTA
ACAACTTGCAAATGAGGTGCAAATAAAATGCAGATGATTGCGCGGCTTTGAATCCA
AAAAAAAAAAAAAAAA

MICAL1 (SEQ ID NO: 13; NM_022765.3).
CCCAAGACTGTCCCCGCTGGAGGCGGTAGAGGGATCCAGAAGTAATGAGATGCTAA
TGAGTCGCGAATAAAGCCCGGGCGGCGCCCCGCGCCCCTCGCGGAAGCCCACACTC
CGCGCGACTCCAGGCGCACGCCCGGGCGCCCCGCATCCCAGCATCCCCGCCCGA
TCTCGGCGTTTCCGCCCCGCCCCGCCCCGCCCTCCCACCCGCTCAGACCTGGTTG
CCAGCCCAACAGGAAGCGGCCCTCCCGGCTTCGGAGCCGCCGCCACTCATCTCTGC
CCAGCTGCTGCCCTCCCCAGGAGGCCTCCATGGCTTCACCTACCTCCACCAACCCAG
CGCATGCCCACTTTGAGAGCTTCCTGCAGGCCCAGCTGTGCCAGGACGTGCTGAGCA
GCTTCCAGGAGCTGTGTGGGGCCCTGGGGCTGGAACCCGGTGGGGGGCTGCCCCAG
TACCACAAGATCAAGGACCAGCTCAACTACTGGAGCGCCAAGTCACTGTGGACCAA
GCTGGACAAGCGAGCAGGCCAGCCTGTCTACCAGCAGGGCCGGGCCTGCACCAGCA
CCAAGTGCCTGGTGGTGGGTGCTGGACCTTGCGGGCTGCGGGTCGCTGTGGAGCTGG
CGCTGCTGGGGGCCCGAGTGGTGCTGGTGGAAAAGCGCACCAAGTTCTCTCGCCAC
AACGTGCTCCACCTCTGGCCCTTCACCATCCACGACCTGCGGGCACTCGGTGCTAAG
AAGTTCTACGGGCGCTTCTGCACCGGCACCCTGGACCACATCAGCATCAGGCAGCTC
CAGCTGCTTCTGCTGAAGGTAGCATTGCTGCTGGGGGTGGAAATTCACTGGGGTGTC
ACTTTCACTGGCCTCCAGCCCCTCCTAGGAAGGGGAGTGGCTGGCGTGCCCAGCTC
CAACCCAACCCCCCTGCCCAGCTGGCCAACTATGAATTTGACGTCCTTATCTCGGCT
GCAGGAGGTAAATTCGTCCCTGAAGGCTTCAAAGTTCGAGAAATGCGAGGCAAACT
GGCCATTGGCATCACAGCCAACTTTGTGAATGGACGCACCGTGGAGGAGACACAGG
TGCCGGAGATCAGTGGTGTAGCCAGGATCTACAACCAGAGCTTCTTCCAGAGCCTTC
TCAAAGCCACAGGCATTGATCTGGAGAACATTGTGTACTACAAGGACGACACCCAC
TACTTTGTGATGACAGCCAAGAAGCAGTGCCTGCTGCGGCTGGGGGTGCTGCGCCA
GGACTGGCCAGACACCAATCGGCTGCTGGGCAGTGCCAATGTGGTGCCCGAGGCTC
TGCAGCGCTTTACCCGGGCAGCTGCTGACTTTGCCACCCATGGCAAGCTCGGGAAAC
TAGAGTTTGCCCAGGATGCCCATGGGCAGCCTGATGTCTCTGCCTTTGACTTCACGA
GCATGATGCGGGCAGAGAGTTCTGCTCGTGTGCAAGAGAAGCATGGCGCCCGCCTG
CTGCTGGGACTGGTGGGGGACTGCCTGGTGGAGCCCTTCTGGCCCCTGGGCACTGGA
GTGGCACGGGGCTTCCTGGCAGCCTTTGATGCAGCCTGGATGGTGAAGCGGTGGGC
AGAGGGCGCTGAGTCCCTAGAGGTGTTGGCTGAGCGTGAGAGCCTGTACCAGCTTCT
GTCACAGACATCCCCAGAAAACATGCATCGCAATGTGGCCCAGTATGGGCTGGACC
CAGCCACCCGCTACCCCAACCTGAACCTCCGGGCAGTGACCCCCAATCAGGTACGA
GACCTGTATGATGTGCTAGCCAAGGAGCCTGTGCAGAGGAACAACGACAAGACAGA
TACAGGGATGCCAGCCACCGGGTCGGCAGGCACCCAGGAGGAGCTGCTACGCTGGT
GCCAGGAGCAGACAGCTGGGTACCCGGGAGTCCACGTCTCCGATTTGTCTTCCTCCT
GGGCTGATGGGCTAGCTCTGTGTGCCCTGGTGTACCGGCTGCAGCCTGGCCTGCTGG
AACCCTCAGAGCTGCAGGGGCTGGGAGCTCTGGAAGCAACTGCTTGGGCACTAAAG
GTGGCAGAGAATGAGCTGGGCATCACACCGGTGGTGTCTGCACAGGCCGTGGTAGC
AGGGAGTGACCCACTGGGCCTCATTGCCTACCTCAGCCACTTCCACAGTGCCTTCAA
GAGCATGGCCCACAGCCCAGGCCCTGTCAGCCAGGCCTCCCCAGGGACCTCCAGTG
CTGTATTATTCCTTAGTAAACTTCAGAGGACCCTGCAGCGATCCCGGGCAAGGAAA
ATGCAGAGGATGCTGGTGGCAAGAAGCTGCGCTTGGAGATGGAGGCCGAGACCCCA
AGTACTGAGGTGCCACCTGACCCAGAGCCTGGTGTACCCCTGACACCCCATCCCAA
CACCAGGAGGCCGGTGCTGGGGACCTGTGTGCACTTTGTGGGGAACACCTCTATGTC
CTGGAACGCCTCTGTGTCAACGGCCATTTCTTCCACCGGAGCTGCTTCCGCTGCCAT
ACCTGTGAGGCCACACTGTGGCCAGGTGGCTACGAGCAGCACCCAGGAGATGGACA
TTTCTACTGCCTCCAGCACCTGCCCCAGACAGACCACAAAGCGGAAGGCAGCGATA
GAGGCCCTGAGAGTCCGGAGCTCCCCACACCAAGTGAGAATAGCATGCCACCAGGC
CTCTCAACTCCCACAGCCTCGCAGGAGGGGCCGGTCCTGTTCCAGATCCCAGCCAG
CCCACCCGTCGGCAGATCCGCCTCTCCAGCCCGGAGCGCCAGCGGTTGTCCTCCCTT
AACCTTACCCCTGACCCGGAAATGGAGCCTCCACCCAAGCCTCCCCGCAGCTGCTCC
GCCTTGGCCCGCCACGCCCTGGAGAGCAGCTTTGTGGGCTGGGCCTGCCAGTCCAG
AGCCCTCAAGCTCTTGTGGCCATGGAGAAGGAGGAAAAAGAGAGTCCCTTCTCCAG
TGAAGAGGAAGAAGAAGATGTGCCTTTGGACTCAGATGTGGAACAGGCCCTGCAGA
CCTTTGCCAAGACCTCAGGCACCATGAATAACTACCCAACATGGCGTCGGACTCTGC
```

TABLE 5-continued

Nucleotide Sequences of Biodosimetry Biomarker Genes

```
TGCGCCGTGCGAAGGAGGAGGAGATGAAGAGGTTCTGCAAGGCCCAGACCATCCAA
CGGCGACTAAATGAGATTGAGGCTGCCTTGAGGGAGCTAGAGGCCGAGGGCGTGAA
GCTGGAGCTGGCCTTGAGGCGCCAGAGCAGTTCCCCAGAACAGCAAAAGAAACTAT
GGGTAGGACAGCTGCTACAGCTCGTTGACAAGAAAAACAGCCTGGTGGCTGAGGAG
GCCGAGCTCATGATCACGGTGCAGGAATTGAATCTGGAGGAGAAACAGTGGCAGCT
GGACCAGGAGCTACGAGGCTACATGAACCGGGAAGAAAACCTAAAGACAGCTGCT
GATCGGCAGGCTGAGGACCAGGTCCTGAGGAAGCTGGTGGATTTGGTCAACCAGAG
AGATGCCCTCATCCGCTTCCAGGAGGAGCGCAGGCTCAGCGAGCTGGCCTTGGGGA
CAGGGGCCCAGGGCTAGACGAGGGTGGGCCGTCTGCTTTCGTTCCCACAAAGAAAG
CACCTCACCCCAGCACAGTGCCACCCCTGTTCATCTGGGCTGCCTGGCAGAGAGCCT
TGCTGTTTACAATTAAAATGTTTCTGCCACAAAAAAAAAAAAAAAAAAAA

MOB3B (SEQ ID NO: 14; AJ580636.1).
ATGTCCATAGCCCTGAAGCAGGTATTCAACAAGGACAAGACCTTCCGACCCAAGAG
GAAATTTGAACCTGGCACACAGAGGTTTGAGCTGCACAAACGGGCTCAGGCATCCC
TCAACTCGGGTGTGGACCTGAAGGCGGCTGTGCAGTTGCCCAGTGGGGAGGACCAG
AATGACTGGGTGGCAGTACATGTGGTGGACTTCTTCAATCGGATCAACCTCATCTAT
GGCACCATCTGTGAGTTCTGCACCGAGCGGACCTGTCCTGTGATGTCAGGGGGCCCC
AAATATGAGTATCGGTGGCAGGATGATCTCAAGTATAAGAAGCCAACAGCGCTGCC
AGCTCCCCAGTACATGAACCTTCTTATGGATTGGATTGAGGTTCAGATCAACAACGA
GGAAATATTTCCAACATGCGTGGGTGTTCCCTTCCCAAAGAACTTCCTTCAGATCTG
CAAGAAGATCCTGTGCCGCCTTTTCCGGGTCTTTGTCCACGTCTATATCCACCACTTC
GACCGGGTCATTGTGATGGGTGCAGAGGCCCATGTCAACACCTGCTACAAACACTTC
TATTACTTTGTCACAGAGATGAACCTCATAGACCGCAAGGAGCTAGAGCCTTTGAAA
GAAATGACGAGCAGGATGTGTCAC TAA

NUSAP1 (SEQ ID NO: 15; NM_016359.4).
GCGTTACAGGCCCTTTGGCGCCTGCGTATTCGTGAAGTGTGAAAAAGCGCGCCTCT
GTTGGGACGGGAAATCAGCCTTTCTATTGGTCAGGGTTAGAAACCCCGCCTTTGAGG
CATTTTCAACCAATGGAAGCGCGGCATTCTTCATTTAAACTGTCTATAAATTTCTGCC
TAGTCAAAGTTAAGAGTGGCGCCAGGGATTTGAACCGCGCTGACGAAGTTTGGTGA
TCCATCTTCCGAGTATCGCCGGGATTTCGAATCGCGATGATCATCCCCTCTCTAGAG
GAGCTGGACTCCCTCAAGTACAGTGACCTGCAGAACTTAGCCAAGAGTCTGGGTCTC
CGGGCCAACCTGAGGGCAACCAAGTTGTTAAAAGCCTTGAAAGGCTACATTAAACA
TGAGGCAAGAAAAGGAAATGAGAATCAGGATGAAAGTCAAACTTCTGCATCCTCTT
GTGATGAGACTGAGATACAGATCAGCAACCAGGAAGAAGCTGAGAGACAGCCACTT
GGCCATGTCACCAAAACAAGGAGAAGGTGCAAGACTGTCCGTGTGGACCCTGACTC
ACAGCAGAATCATTCAGAGATAAAAATAAGTAATCCCACTGAATTCCAGAATCATG
AAAAGCAGGAAAGCCAGGATCTCAGAGCTACTGCAAAAGTTCCTTCTCCACCAGAC
GAGCACCAAGAAGCTGAGAATGCTGTTTCCTCAGGTAACAGAGATTCAAAGGTACC
TTCAGAAGGAAAGAAATCTCTCTACACAGATGAGTCATCCAAACCTGGAAAAAATA
AAAGAACTGCAATCACTACTCCAAACTTTAAGAAGCTTCATGAAGCTCATTTTAAGG
AAATGGAGTCCATTGATCAATATATTGAGAGAAAAAAGAAACATTTTGAAGAACAC
AATTCCATGAATGAACTGAAGCAGCAGCCCATCAATAAGGAGGGGGTCAGGACTCC
AGTACCTCCAAGAGGAAGACTCTCTGTGGCTTCTACTCCCATCAGCCAACGACGCTC
GCAAGGCCGGTCTTGTGGCCCTGCAAGTCAGAGTACCTTGGGTCTGAAGGGGTCACT
CAAGCGCTCTGCTATCTCTGCAGCTAAAACGGGTGTCAGGTTTTCAGCTGCTACTAA
AGATAATGAGCATAAGCGTTCACTGACCAAGACTCCAGCCAGAAAGTCTGCACATG
TGACCGTGTCTGGGGGCACCCCAAAAGGCGAGGCTGTGCTTGGGACACACAAATTA
AAGACCATCACGGGGAATTCTGCTGCTGTTATTACCCCATTCAAGTTGACAACTGAG
GCAACGCAGACTCCAGTCTCCAATAAGAAACCAGTGTTTGATCTTAAAGCAAGTTTG
TCTCGTCCCCTCAACTATGAACCACACAAAGGAAAGCTAAAACCATGGGGCAATC
TAAAGAAAATAATTATCTAAATCAACATGTCAACAGAATTAACTTCTACAAGAAAA
CTTACAAACAACCCCATCTCCAGACAAAGGAAGAGCAACGGAAGAAACGCGAGCA
AGAACGAAAGGAGAAGAAAGCAAAGGTTTTGGGAATGCGAAGGGGCCTCATTTTGG
CTGAAGATTAATAATTTTTTAACATCTTGTAAATATTCCTGTATTCTCAACTTTTTTCC
TTTTGTAAATTTTTTTTTTTTGCTGTCATCCCCACTTTAGTCACGAGATCTTTTTCTGC
TAACTGTTCATAGTCTGTGTAGTGTCCATGGGTTCTTCATGTGCTATGATCTCTGAAA
AGACGTTATCACCTTAAAGCTCAAATTCTTTGGGATGGTTTTTACTTAAGTCCATTAA
CAATTCAGGTTTCTAACGAGACCCATCCTAAAATTCTGTTTCTAGATTTTTAATGTCA
AGTTCCCAAGTTCCCCCTGCTGGTTCTAATATTAACAGAACTGCAGTCTTCTGCTAGC
CAATAGCATTTACCTGATGGCAGCTAGTTATGCAAGCTTCAGGAGAATTTGAACAAT
AACAAGAATAGGGTAAGCTGGGATAGAAAGGCCACCTCTTCACTCTCTATAGAATA
TAGTAACCTTTATGAAACGGGGCCATATAGTTTGGTTATGACATCAATATTTTACCT
AGGTGAAATTGTTTAGGCTTATGTACCTTCGTTCAAATATCCTCATGTAATTGCCATC
TGTCACTCACTATATTCACAAAAATAAAACTCTACAACTCATTCTAACATTGCTTACT
TAAAAGCTACATAGCCCTATCGAAATGCGAGGATTAATGCTTTAATGCTTTTAGAGA
CAGGGTCTCACTGTGTTGCCCAGGCTGGTCTCAAACTCCACCAAATGTACTTCTTATT
CATTTTATGGAAAAGACTAGGCTTTGCTTAGTATCATGTCCATGTTTCCTTCACCTCA
GTGGAGCTTCTGAGTTTTATACTGCTCAAGATCGTCATAAATAAAATTTTTTCTCATT
GTCATAGAAAAAAAAAAAAAAAAAAAA

IL27RA (SEQ ID NO: 16; NM_004843.3).
GCGGAGGCGGCCTGCCGGGGTGGTTCGGCTTCCCGTTGCCGCCTCGGGCGCTGTACC
CAGAGCTCGAAGAGGAGCAGCGCGGCCGCGCGGACCCGGCAAGGCTGGGCCGGAC
TCGGGGCTCCCGAGGGACGCCATGCGGGGAGGCAGGGGCGCCCCTTTCTGGCTGTG
GCCGCTGCCCAAGCTGGCGCTGCTGCCTCTGTTGTGGGTGCTTTTCCAGCGGACGCG
TCCCCAGGGCAGCGCCGGGCCACTGCAGTGCTACGGAGTTGGACCCTTGGGCGACT
```

TABLE 5-continued

Nucleotide Sequences of Biodosimetry Biomarker Genes

TGAACTGCTCGTGGGAGCCTCTTGGGGACCTGGGAGCCCCCTCCGAGTTACACCTCC
AGAGCCAAAGTACCGTTCCAACAAAACCCAGACTGTGGCAGTGGCAGCCGGACGG
AGCTGGGTGGCCATTCCTCGGGAACAGCTCACCATGTCTGACAAACTCCTTGTCTGG
GGCACTAAGGCAGGCCAGCCTCTCTGGCCCCCGTCTTCGTGAACCTAGAAACCCAA
ATGAAGCCAAACGCCCCCGGCTGGGCCCTGACGTGGACTTTTCCGAGGATGACCC
CCTGGAGGCCACTGTCCATTGGGCCCCACCTACATGGCCATCTCATAAAGTTCTGAT
CTGCCAGTTCCACTACCGAAGATGTCAGGAGGCGGCCTGGACCCTGCTGGAACCGG
AGCTGAAGACCATACCCCTGACCCCTGTTGAGATCCAAGATTTGGAGCTAGCCACTG
GCTACAAAGTGTATGGCCGCTGCCGGATGGAGAAAGAAGAGGATTTGTGGGGCGAG
TGGAGCCCCATTTTGTCCTTCCAGACACCGCCTTCTGCTCCAAAAGATGTGTGGGTA
TCAGGGAACCTCTGTGGGACGCCTGGAGGAGAGGAACCTTTGCTTCTATGGAAGGC
CCCAGGGCCCTGTGTGCAGGTGAGCTACAAAGTCTGGTTCTGGGTTGGAGGTCGTGA
GCTGAGTCCAGAAGGAATTACCTGCTGCTGCTCCCTAATTCCCAGTGGGGCGGAGTG
GGCCAGGGTGTCCGCTGTCAACGCCACAAGCTGGGAGCCTCTCACCAACCTCTCTTT
GGTCTGCTTGGATTCAGCCTCTGCCCCCCGTAGCGTGGCAGTCAGCAGCATCGCTGG
GAGCACGGAGCTACTGGTGACCTGGCAACCGGGGCCTGGGGAACCACTGGAGCATG
TAGTGGACTGGGCTCGAGATGGGGACCCCCTGGAGAAACTCAACTGGGTCCGGCTT
CCCCCTGGGAACCTCAGTGCTCTGTTACCAGGGAATTTCACTGTCGGGGTCCCCTAT
CGAATCACTGTGACCGCAGTCTCTGCTTCAGGCTTGGCCTCTGCATCCTCCGTCTGG
GGGTTCAGGGAGGAATTAGCACCCCTAGTGGGGCCAACGCTTTGGCGACTCCAAGA
TGCCCCTCCAGGGACCCCCGCCATAGCGTGGGGAGAGGTCCCAAGGCACCAGCTTC
GAGGCCACCTCACCCACTACACCTTGTGTGCACAGAGTGGAACCAGCCCCTCCGTCT
GCATGAATGTGAGTGGCAACACACAGAGTGTCACCCTGCCTGACCTTCCTTGGGGTC
CCTGTGAGCTGTGGGTGACAGCATCTACCATCGCTGGACAGGGCCCTCCTGGTCCCA
TCCTCCGGCTTCATCTACCAGATAACACCCTGAGGTGGAAAGTTCTGCCGGGCATCC
TATTCTTGTGGGGCTTGTTCCTGTTGGGGTGTGGCCTGAGCCTGGCCACCTCTGGAA
GGTGCTACCACCTAAGGCACAAAGTGCTGCCCCGCTGGGTCTGGGAGAAAGTTCCT
GATCCTGCCAACAGCAGTTCAGGCCAGCCCCACATGGAGCAAGTACCTGAGGCCCA
GCCCCTTGGGGACTTGCCCATCCTGGAAGTGGAGGAGATGGAGCCCCGCCGGTTA
TGGAGTCCTCCCAGCCCGCCCAGGCCACCGCCCCGCTTGACTCTGGGTATGAGAAGC
ACTTCCTGCCCACACCTGAGGAGCTGGGCCTTCTGGGGCCCCCCAGGCCACAGGTTC
TGGCCTGAACCACACGTCTGGCTGGGGGCTGCCAGCCAGGCTAGAGGGATGCTCAT
GCAGGTTGCACCCCAGTCCTGGATTAGCCCTCTTGATGGATGAAGACACTGAGGACT
CAGAGAGGCTGAGTCACTTACCTGAGGACACCCAGCCAGGCAGAGCTGGGATTGAA
GGACCCCTATAGAGAAGGGCTTGGCCCCCATGGGGAAGACACGGATGGAAGGTGGA
GCAAAGGAAAATACATGAAATTGAGAGTGGCAGCTGCCTGCCAAAATCTGTTCCGC
TGTAACAGAACTGAATTTGGACCCCAGCACAGTGGCTCACGCCTGTAATCCCAGCAC
TTTGGCAGGCCAAGGTGGAAGGATCACTTAGAGCTAGGAGTTTGAGACCAGCCTGG
GCAATATAGCAAGACCCCTCACTACAAAAATAAAACATCAAAAACAAAAACAATTA
GCTGGGCATGATGGCACACACCTGTAGTCCGAGCCACTTGGGAGGCTGAGGTGGGA
GGATCGGTTGAGCCCAGGAGTTCGAAGCTGCAGGGACCTCTGATTGCACCACTGCA
CTCCAGGCTGGGTAACAGAATGAGACCTTATCTCAAAAATAAACAAACTAATAAAA
AGCAAAAAAAAAAAAAAAAAAAAAAAAAA

HBA2 (SEQ ID NO: 17; NM_000517.4).
CATAAACCCTGGCGCGCTCGCGGGCCGGCACTCTTCTGGTCCCCACAGACTCAGAGA
GAACCCACCATGGTGCTGTCTCCTGCCGACAAGACCAACGTCAAGGCCGCCTGGGG
TAAGGTCGGCGCGCACGCTGGCGAGTATGGTGCGGAGGCCCTGGAGAGGATGTTCC
TGTCCTTCCCCACCACCAAGACCTACTTCCCGCACTTCGACCTGAGCCACGGCTCTG
CCCAGGTTAAGGGCCACGGCAAGAAGGTGGCCGACGCGCTGACCAACGCCGTGGCG
CACGTGGACGACATGCCCAACGCGCTGTCCGCCCTGAGCGACCTGCACGCGCACAA
GCTTCGGGTGGACCCGGTCAACTTCAAGCTCCTAAGCCACTGCCTGCTGGTGACCCT
GGCCGCCCACCTCCCCGCCGAGTTCACCCCTGCGGTGCACGCCTCCCTGGACAAGTT
CCTGGCTTCTGTGAGCACCGTGCTGACCTCCAAATACCGTTAAGCTGGAGCCTCGGT
AGCCGTTCCTCCTGCCCGCTGGGCCTCCCAACGGGCCCTCCTCCCCTCCTTGCACCG
GCCCTTCCTGGTCTTTGAATAAAGTCTGAGTGGGCAGCAAAAAAAAAAAAAAAAAAA

PPM1F (SEQ ID NO: 18; NM_014634).
AGGGACGGGAAGTGGGCGGGGCCGGCCGGCAGCAGCTTGCGGGACACGGAGCCGC
GAGGAGACAGCTGAGGCCCGCGGAGACCAGGGGGTGAAGCCTGGAGACCCTCTTGC
CCTGGCCTAGCTGCAGGCCCCCGGGATGCTTTGGGCATGTCCTCTGGAGCCCCACAG
AAGAGCAGCCCAATGGCCAGTGGAGCTGAGGAGACCCCAGGCTTCCTGGACACGCT
CCTGCAAGACTTCCCAGCCCTGCTGAACCCAGAGGACCCTCTGCCATGGAAGGCCCC
AGGGACGGTGCTCAGCCAGGAGGAGGTGGAGGGCGAGCTGGCTGAGCTGGCCATG
GGCTTTCTGGGCAGCAGGAAGGCCCCGCCACCACTTGCTGCTGCTCTGGCCCACGAA
GCAGTTTCACAGCTGCTACAGACAGACCTTTCCGAATTCAGGAAGTTGCCCAGGGAG
GAAGAAGAAGAGGAGGAGGACGATGACGAGGAGGAAAGGCCCCTGTGACCTTGC
TGGATGCCCAAAGCCTGGCACAGAGTTTCTTTAACCGCCTTTGGGAAGTCGCCGGCC
AGTGGCAGAAGCAGGTGCCATTGGCTGCCCGGGCCTCACAGCGGCAGTGGCTGGTC
TCCATCCACGCCATCCGGAACACTCGCCGCAAGATGGAGGACCGGCACGTGTCCCT
CCCTTCCTTCAACCAGCTCTTCGGCTTGTCTGACCCTGTGAACCGCGCCTACTTTGCT
GTGTTTGATGGTCACGGAGGCGTGGATGCTGCGAGGTACGCCGCTGTCCACGTGCAC
ACCAACGCTGCCCGCCAGCCAGAGCTGCCCACAGACCCTGAGGGAGCCCTCAGAGA
AGCCTTCCGGCGCACCGACCAGATGTTTCTCAGGAAAGCCAAGCGAGAGCGGCTGC
AGAGCGGCACCACAGGTGTGTGCGCTCATTGCAGGAGCGACCCTGCACGTCGCC
TGGCTCGGGGATTCCCAGGTCATTTTGGTACAGCAGGGACAGGTGGTGAAGCTGAT
GGAGCCACACAGACCAGAACGCAGGATGAGAAGGCGCGCATTGAAGCATTGGGT
GGCTTTGTGTCTCACATGGACTGCTGGAGAGTCAACGGGACCCTGGCCGTCTCCAGA

TABLE 5-continued

Nucleotide Sequences of Biodosimetry Biomarker Genes

```
GCCATCGGGGATGTCTTCCAGAAGCCCTACGTGTCTGGGGAGGCCGATGCAGCTTCC
CGGGCGCTGACGGGCTCCGAGGACTACCTGCTGCTTGCCTGTGATGGCTTCTTTGAC
GTCGTACCCCACCAGGAAGTTGTTGGCCTGGTCCAGAGCCACCTGACCAGGCAGCA
GGGCAGCGGGCTCCGTGTCGCCGAGGAGCTGGTGGCTGCGGCCCGGGAGCGGGGCT
CCCACGACAACATCACGGTCATGGTGGTCTTCCTCAGGGACCCCCAAGAGCTGCTGG
AGGGCGGGAACCAGGGAGAAGGGGACCCCCAGGCAGAAGGGGAGGAGGCAGGACTT
GCCCTCCAGCCTTCCAGAACCTGAGACCCAGGCTCCACCAAGAAGCTAGGTGGTTTC
CAGGCCCCTGCCCTCCCCTTCCTCCCATCCTTGTCCTTCTCTCCCTCAGAAGCCTCAG
GACCCAACAGGTGGCAGGCAGTGGACAGGGTGCCCGCCCCACAGTGCTTTCCCCAG
CACCCCAGAGCCAGTCGGGACACCCCCCGCAGCCCGTCCTGGTGGCTGTGGAACTG
CACTGGGTGGCGGGCAGATGGTGGAAGGCAGCTTAGGAGACCTCACCAAAGAGAA
GATGGACCGGCTCTTGCTCCCAGCTCCTATTAGGCCCGGGGTGGGACCAGAGGTCAT
AGGTGCCCAACGGCAGCCAAACCAAAGACACTGGTGTGCATGGGGCAGCATGGTTG
TGCACGTGGGACCCTGGGGCGGACCCAGGAGCCAAACTCTTGAAGCACCCCCTGGG
TCAGGCCCAGCAGCGGAGTGGCCAGCCCCAGTTTCCCATTGCTCCTCTCTGCGGCCA
GGGCCAGGTGGGTTCATATTTACAGATATGCCCAGCCAGTCCTGGTCGGCCACACCA
GTGTCCCAAAGAGGAGAGCGCAGCAGAGCCAGGGGTCTGTTCTGTAGCAGCCACCC
CCCTGCCCCCACTCCAGGGCAGCCATGATGTGCTTGGGCCCACCAGGGCCTTCCGGG
CTGCTCTCTTCCCTGAGCCCGGAACCGGCGACGACACATGTGTCTTTTGTTGGTGTT
TGTTTTTTTCCAGGGAGGTCTAATTCCGAAGCAGTATTCCAGGTTTTCTCTTTGTTTT
ATCAGTGCCAAGATGACCTGTTGTGTCATATAATTTAAGCAGAGCTTAGCATTTATT
TTATTCTTTAGAAAACTTAAGTATTTACTTTTTTAAAGCTATTTTTCAAGGAACCTTTT
TTTGCAGTATTATTGAATTTATTTTCTAAATCAGGATTGAAACAGGAACTTTTCCAGG
TGGTGTTAATAAGCCATTCAAGTGCCTTACACAGCTTTGAAGAAACTAGGACTGCAG
TGGGCTCGGATAGGCCCATTGAGGTTTTTAGAAAAGCAGGATTTGTTTTGTTAGGGA
GGCATGATTTTGGTGAGATCTTTCTGGAAGAGTTTTCCGCCTCTTTGTGATGCTGAAC
ACCCCCAAGGTTCTCCCCTCCCCCCGCTGCCCAGGTGACTGGCAGGAGCCTGCGACTG
CCACGTAGTGGTGCCTGGGCCGACAGCGGGGCTCTGGGCATCCCGGGTGACCTTG
GCCCATCTGCCTGCATTCCCACCCCCTTGGGCCTGGCTGGATCCCAGGCAGAGGGAC
CTTGCTGCTGTGTGATTGGAACATTCCCAAATATCTTGTGAATTTGTAATCAAATTGG
TCTCATTGGGAAAGACTCTTAATTAAGAGGCTCAGGCAAGCACAGAGGCAGCCCGT
GGGTCTCTGTCTCAGTCTGGAGGCAGCAGGGATGCTGCTGGGAGTCCATGGCACAG
GCCACAGCCCTCACCTTGCCGCGGTGGCTGGCAGCACGCCTGCCTTGCTCTGCCCC
ATGCCCTGAACAGGCATGAGAGCTCCACGTCCCCTAGTGCACCCTGAGAGGGGCT
CACAAGTGACCGATCCTGGGTGCCTCAGGGAGCTCACTGAGGGCGTGCAAAGTTGA
AAGTGGCAAGGCTGGGGGAGGGTGTCGGGTAGAGGGAAGAGGGCAGGGGGCTAGG
GGAGGACTCAGAGGCCATCTGCAGGGCCAAGCCACAGGAAGGGCTGAGCTGGAGG
TGGGCAGGGCTGCTCCAGGCAGGTCAGAGCAGTGCAGGGGGAGGAGAGGAGAAAG
GGAGGAAGCTGGGCTGTGTGGTCCCCATGAAGGCATTCAGAGTCCACCTGCAGACA
GCGAGAGCCCCAGGAAGGTTTGCACAGCTGTGCCCCAAGCACCTTGGCCTCCTCTCA
GCTCGCCGAGGAGGCACGCTAGAGCCGCCTTCCCGGTGGGAGCCCTCTGTCCCACA
GGGAGCGGGGAGCCAGCTTTGCTGGGGCCCTACCTGCATGCCCAGCCTTACCCCTCA
TTCTCACAGCACAGATGAGGTTGAGACCATGCAGTCAATGCATTGCTTAAGGTCTCT
TATTTACAAAAAAAAACCTTAAACATAGTCGCTGTCATTCAGACATTCAGAGAATG
TTGGCCACAAACAATGACCAAGTATTGCTTGGCTTAACTTGAAGGCCTGCTGTCTCC
TTCTGGGGGTCAGGGACGCAGCTCCACCCTCACCACTAGCCCACCCTGCCCGTGGGC
ATAACCTTGACGAAGAGAGAGAATGATTGGCATCTGCTTTTCTCTTTTCTTTGCTAAT
AATTCTGTTCCTGGCTGCCGAGAGTGAAGTTTCACCATGTGGAGGTTTGGCTCCTAT
CACCTGGTGGTCTGATTCATACCCTAGCCTGAGGCTCCACTGGAAGATCTCGCAGCC
TCAGTGTATGGGAAACCCTTTCCCCAGGCTTGTCCCAGCACTGCCGCTCCCCACCCC
TGAGCCAGGACCCCAGAGGATGGCCATGCCCCGTGCCTGGCAGAGGTCTGGTGCCA
GCACTGGGAGCTGCTCCGCCCTTGCCTTGGGGCCGAGGGAGCCCTCGTCCACCCCTG
CACAGCAGCTGGGCACAGAGGAGCGCTCTTCCATCTTGACCAGGACTGCACCAAGA
AGCACCAGGTGTCTTCAGCCTCCAACCTCCGGGGCGACCTTCTCTTCCAGCCACAGT
CCCATGAGGGCCCCTAGCCAGGGACACTGGTCTGTAAATTGTAATCCTTTCTCCAGC
CCAGCTCTCCACTTGTTCCTTGTGTGAGCTGAGCAGGCAGTGCACCTCTGAGTGTCC
CTTTTGTAAGGCCCAGGGGTTGCACTGAGTCTGCAGAGGCCGCGACCTCCTAGAACG
CTGTGGGTGCAGGTGAGCCGGCGTGTCCTGGGGAGATGCTGCCAGCACACAGGGGC
CCTCCTGCTGCCAGCAGGTTGGGGTGGTTAAGTCTTATTAGTGTCTATTCTTAAAATT
AAGTGGGCTGGAGAAGAATGGAGCTCCACATGCCAGCACCGTATATGGAATACAAA
AGCTGGGGAAGCAGGGCCTGCCTTACAGGTGTGGCTGACTCTGAGCCCAGGCCTGC
AGGGGTGGAGGGCAGTCCCTCAGAATCCCAGAGGCAGTCCCAGCCTCAGAACCCAG
GATAGGAAATGGGTGTGTTTAGTGGGGAAAGGGACGGGGTGCAGACGGCAGGGCC
AGTATGGGGCCCCCTCCCTCTCCTCTCCTCTCCTATGGTGAGCCCAGCGTGGGCACC
GGGCCGTCTCAGCCGTGTTCCCAGGGCTGGGAGGACAGCTCTGGCCCTTCTTAGGCC
TAGCCTCGTCCCAAGCTAAATGTAAGCCAGTTGGGCTGTGTTAAAGGAAGCAGTGTT
TTTGGTTCGATTCTGCCTCTGTAGCTCAAGGGGGGCAGCCCCCAGAGTCCTGTGCAT
TCTGCCAAGGCTCCATAGCTTTGCCAAATGCACGGAGCTCTGCCATTCCGGTGCAGT
GCAGGCCTTGCGAAGGGTTTATCTGCGTTCGTCTCGGTGGGCTTCTCCTGCATGGGA
GTTGTGTTCCTGTGCAAGGGGGAGCTTTGCTCCAGGACAGGATGACTGTCTTCCCTA
TTCTTAGGGACAAGTCCCAAGATGCCAGAAAGGCAGTCTCCCAAGGACCCACCATG
CAGAAGTGTCAATAAACCACAAGTTCTGAACTCTGTAAAAAAAAAAAAAAA
```

PPP2R1A (SEQ ID NO: 19; CR450340.1).
```
ATGGCGGCGGCCGACGGCGACGACTCGCTGTACCCCATCGCGGTGCTCATAGACGA
ACTCCGCAATGAGGACGTTCAGCTTCGCCTCAACAGCATCAAGAAGCTGTCCACCAT
CGCCTTGGCCCTTGGGGTTGAAAGGACCCGAAGTGAGCTTCTGCCTTTCCTTACAGA
TACCATCTATGATGAAGATGAGGTCCTCCTGGCCCTGGCAGAACAGCTGGGAACCTT
```

TABLE 5-continued

Nucleotide Sequences of Biodosimetry Biomarker Genes

CACTACCCTGGTGGGAGGCCCAGAGTACGTGCACTGCCTGCTGCCACCGCTGGAGTC
GCTGGCCACAGTGGAGGAGACAGTGGTGCGGGACAAGGCAGTGGAGTCCTTACGGG
CCATCTCACACGAGCACTCGCCCTCTGACCTGGAGGCGCACTTTGTGCCGCTAGTGA
AGCGGCTGGCGGGCGGCGACTGGTTCACCTCCCGCACCTCGGCCTGCGGCCTCTTCT
CCGTCTGCTACCCCCGAGTGTCCAGTGCTGTGAAGGCGGAACTTCGACAGTACTTCC
GGAACCTGTGCTCAGATGACACCCCCATGGTGCGGCGGGCCGCAGCCTCCAAGCTG
GGGGAGTTTGCCAAGGTGCTGGAGCTGGACAACGTCAAGAGTGAGATCATCCCCAT
GTTCTCCAACCTGGCCTCTGACGAGCAGGACTCGGTGCGGCTGCTGGCGGTGGAGG
CGTGCGTGAACATCGCCCAGCTTCTGCCCCAGGAGGATCTGGAGGCCCTGGTGATGC
CCACTCTGCGCCAGGCCGCTGAAGACAAGTCCTGGCGCGTCCGCTACATGGTGGCTG
ACAAGTTCACAGAGCTCCAGAAAGCAGTGGGGCCTGAGATCACCAAGACAGACCTG
GTCCCTGCCTTCCAGAACCTGATGAAAGACTGTGAGGCCGAGGTGAGGGCCGCAGC
CTCCCACAAGGTCAAAGAGTTCTGTGAAAACCTCTCAGCTGACTGTCGGGAGAATGT
GATCATGTCCCAGATCTTGCCCTGCATCAAGGAGCTGGTGTCCGATGCCAACCAACA
TGTCAAGTCTGCCCTGGCCTCAGTCATCATGGGTCTCTCTCCCATCTTGGGCAAAGA
CAACACCATCGAGCACCTCTTGCCCCTCTTCCTGGCTCAGCTGAAGGATGAGTGCCC
TGAGGTACGGCTGAACATCATCTCTAACCTGGACTGTGTGAACGAGGTGATTGGCAT
CCGGCAGCTGTCCCAGTCCCTGCTCCCTGCCATTGTGGAGCTGGCTGAGGACGCCAA
GTGGCGGGTGCGGCTGGCCATCATTGAGTACATGCCCCTCCTGGCTGGACAGCTGGG
AGTGGAGTTCTTTGATGAGAAACTTAACTCCTTGTGCATGGCCTGGCTTGTGGATCA
TGTATATGCCATCCGCGAGGCAGCCACCAGCAACCTGAAGAAGCTAGTGGAAAAGT
TTGGGAAGGAGTGGGCCCATGCCACAATCATCCCCAAGGTCTTGGCCATGTCCGGA
GACCCCAACTACCTGCACCGCATGACTACGCTCTTCTGCATCAATGTGCTGTCTGAG
GTCTGTGGGCAGGACATCACCACCAAGCACATGCTACCCACGGTTCTGCGCATGGCT
GGGGACCCGGTTGCCAATGTCCGCTTCAATGTGGCCAAGTCTCTGCAGAAGATAGG
GCCCATCCCGGACAACAGCACCTTGCAGAGTGAAGTCAAGCCCATCCTAGAAGC
TGACCCAGGACCAGGATGTGGACGTCAAATACTTTGCCCAGGAGGCTCTGACTGTTC
TGTCTCTCGCC

CFLAR (SEQ ID NO: 20; NM_003879.5).
ATACTCAGTCACACAAGCCATAGCAGGAAACAGCGAGCTTGCAGCCTCACCGACGA
GTCTCAACTAAAAGGGACTCCCGGAGCTAGGGGTGGGGACTCGGCCTCACACAGTG
AGTGCCGGCTATTGGACTTTTGTCCAGTGACAGCTGAGACAACAAGGACCACGGGA
GGAGGTGTAGGAGAGAAGCGCCGCGAACAGCGATCGCCCAGCACCAAGTCCGCTTC
CAGGCTTTCGGTTTCTTTGCCTCCATCTTGGGTGCGCCTTCCCGGCGTCTAGGGGAGC
GAAGGCTGAGGTGGCAGCGGCAGGAGAGTCCGGCCGCGACAGGGACGAACTCCCCC
ACTGGAAAGGATTCTGAAAGAAATGAAGTCAGCCCTCAGAAATGAAGTTGACTGCC
TGCTGGCTTTCTGTTGACTGGCCCGGAGCTGTACTGCAAGACCCTTGTGAGCTTCCCT
AGTCTAAGAGTAGGATGTCTGCTGAAGTCATCCATCAGGTTGAAGAAGCACTTGATA
CAGATGAGAAGGAGATGCTGCTCTTTTTGTGCCGGGATGTTGCTATAGATGTGGTTC
CACCTAATGTCAGGGACCTTCTGGATATTTTACGGGAAAGAGGTAAGCTGTCTGTCG
GGGACTTGGCTGAACTGCTCTACAGAGTGAGGCGATTTGACCTGCTCAAACGTATCT
TGAAGATGGACAGAAAGCTGTGGAGACCCACCTGCTCAGGAACCCTCACCTTGTTT
CGGACTATAGAGTGCTGATGGCAGAGATTGGTGAGGATTTGGATAAATCTGATGTGT
CCTCATTAATTTTCCTCATGAAGGATTACATGGGCCGAGGCAAGATAAGCAAGGAG
AAGAGTTTCTTGGACCTTGTGGTTGAGTTGGAGAAACTAAATCTGGTTGCCCCAGAT
CAACTGGATTTATTAGAAAAATGCCTAAAGAACATCCACAGAATAGACCTGAAGAC
AAAAATCCAGAAGTACAAGCAGTCTGTTCAAGGAGCAGGGACAAGTTACAGGAATG
TTCTCCAAGCAGCAATCCAAAAGAGTCTCAAGGATCCTTCAAATAACTTCAGGCTCC
ATAATGGGAGAAGTAAAGAACAAAGACTTAAGGAACAGCTTGGCGCTCAACAAGA
ACCAGTGAAGAAATCCATTCAGGAATCAGAAGCTTTTTTGCCTCAGAGCATACCTGA
AGAGAGATACAAGATGAAGAGCAAGCCCCTAGGAATCTGCCTGATAATCGATTGCA
TTGGCAATGAGACAGAGCTTCTTCGAGACACCTTCACTTCCCTGGGCTATGAAGTCC
AGAAATTCTTGCATCTCAGTATGCATGGTATATCCCAGATTCTTGGCCAATTTGCCTG
TATGCCCGAGCACCGAGACTACGACAGCTTTGTGTGTGTCCTGGTGAGCCGAGGAG
GCTCCCAGAGTGTGTATGGTGTGGATCAGACTCACTCAGGGCTCCCCCTGCATCACA
TCAGGAGGATGTTCATGGGAGATTCATGCCCTTATCTAGCAGGGAAGCCAAAGATG
TTTTTTATTCAGAACTATGTGGTGTCAGAGGGCCAGCTGGAGGACAGCAGCCTCTTG
GAGGTGGATGGGCCAGCGATGAAGAATGTGGAATTCAAGGCTCAGAAGCGAGGGCT
GTGCACAGTTCACCGAGAAGCTGACTTCTTCTGGAGCCTGTGTACTGCGGACATGTC
CCTGCTGGAGCAGTCTCACAGCTCACCATCCCTGTACCTGCAGTGCCTCTCCCAGAA
ACTGAGACAAGAAAGAAAACGCCCACTCCTGGATCTTCACATTGAACTCAATGGCT
ACATGTATGATTGGAACAGCAGAGTTTCTGCCAAGGAGAAATATTATGTCTGGCTGC
AGCACACTCTGAGAAAGAAACTTATCCTCTCCTACACATAAGAAACCAAAAGGCTG
GGCGTAGTGGCTCACACCTGTAATCCCAGCACTTTGGGAGGCCAAGGAGGGCAGAT
CACTTCAGGTCAGGAGTTCGAGACCAGCCTGGCCAACATGGTAAACGCTGTCCCTA
GTAAAAATACAAAAATTAGCTGGGTGTGGGTGTGGGTACCTGTATTCCCAGTTACTT
GGGAGGCTGAGGTGGGAGGATCTTTTGAACCCAGGAGTTCAGGGTCATAGCATGCT
GTGATTGTGCCTACGAATAGCCACTGCATACCAACCTGGGCAATATAGCAAGATCCC
ATCTCTTTAAAAAAAAAAAAAAAGGACAGGAACTATCTTACTCAATGTATTAGTCAT
GTTTCTCTAGAGGGACAGAACTAATAGGATACATGTATATAAAAAGGGGAGTTTATT
AAGGAGTATTGACTCACATGATCACAGGGTTAGGTCCCACAATAGGTCATCTGCAA
GCAAGGAAGCCAATTCAAGTCCCAAAGCTGAAGAACTTGGAGTCCAATGTTTGAGG
GCAGGAAGCATTCAGCATGAGAGAAAGATGGAGGCCAGAAGACTACACCAGTCTA
GTCTTTTCCATGTTTTGCCTGCTTTTATTCTGGCAGTGCTGGCAGCTGATTAGATGGTG
CCCACCCAGATTGAGGATGGTCTGCCTTTCCCAGTCCACTGACTCAAATGTTAAATC
TCCTTTTGGCAGCACCCTCACAGATGTACCCGGGAACACTTTGCATCCTTCTATTCAAT
CAAGTTGATACTCAGTATTAACCATCACAGTCCATTTGGGCAACTATACCAAATTAC

TABLE 5-continued

Nucleotide Sequences of Biodosimetry Biomarker Genes

```
CATAGACCAGGTGACTTAAACAGCAGTTATTTCTCACAGTTCCGGAGGCTGGGAAAT
CCAACATCTAAGTGGTAGCATATCTGGTGTCTGGTAAGGCATGCTTCCAGATCTTAC
CAGATGTCAGTCTTTTGATGTTCTCACATGGCAGAAAAAGAGGATGCAAACTCTCAA
GTATATCTTTAAGGGCACAAATTCCATTCATGAGGGCTCTACCCTCATCACCTAATT
ACCTCCCAAAGGCCCCACCTTCTGATACTGTCACTTTGGGGATACTGTCTCCCCTTTG
AATTCTGGGGGAATACAAACATTCAGTTTGTAACAATAGCCTTATGATTTAGAGGT
TACTTGTTCATTCACCTAGACCTCAAATTGCATTTTACAGCTAGTCAAGTATATCTTT
CTCTGATTTGATAGTGTGACCTAAAAGGGGACCATTGTTTGAAATATCATTAGAGTT
GCTTATTATTATTATTATTATTATTATTATTATTATTATTATTGAGACAGAGT
TTCATTCTGCTGCCCAGGCTGGAGTGCAGTGGCATCATCTTGGCTCATTGCAACCTCT
GCCTTCTGGGTTCAAGCGATTCTCCTGCCTCAGCCTCCCGAGTAGCTGGGATTACAG
GCTCCTGCCACCACACCCGGCTAATTTTTGTATTTTTAGTGGAGACAGGGTTTCCACC
ATGTTGGCCAGCGTGGTCTTGAACTCCTGACCTCAGGTGATTCACCAGCCTCGGCCT
CCCAAAGTGCTGGGATTACAGGTGTGAGCCACTGCACCTGGCCTATTATTATTTTTA
AATTTTTTTTTTTTAATTGATCATTCTTGGGTGTTTCTCACAGAGGGTGATTTGGCAG
GGTCACAGGACAATAGTGGAGGGAAGGTCAGCAGATAAACAAGTGAACAAAGGTC
TCTGGTTTTCCTAGGCAGAGGACCCTGCGGCCTTCCGCAGTGTTTGTGTCCCTGGGTA
CTTGAGATTAGGGAGTGGTGATGACTCTTAAGGAGCATGCTGCCTTCAAGCATCTGT
TTAACAAAGCACATCTTGCACTGCCCTTAATCCATTTAACCCTGAGTGGACACAGCA
CATGTTTCAGAGAGCACAGGGTTGGGGGTAAGGTCATAGATCAACAGCATCCTAAG
GCAGAAGAATTTTTCTTAGTACAGAACAAAATGAAGTCTCCCATGTCTACTTCTTTCT
ACACAGACACAGCAACAATCTGATTTCTCTATCTTTTCCCCACCTTTCCCCCTTTTCT
ATTCCACAAAACCGCCATCGTCATCATGGCCTGTTCTCAATGAGCTGTTGGGTACAC
CTCCCAGACGGGGTGGCGGCTGGGCAGAGGGGCTCCTCACTTCCCAGATGGGGCGG
CCAGGCGGACGCGCCCCCACCTCCCTCCCGGACGGGATAGCTGGCCGGGCGGGGG
CTGACCCCCCACCTCCCTCCCCGACGGGGCGGCTGGCCGGGCGGGGCTGACCCCC
ACGCCTCCCTCCCGGACGGGGCGGCTGCCAGGCGGAGGGGCTCCTCACTTCTCAGA
CGGGGTGGCTGCTGGGCGGAGACGCTCCTCACTTCCCAGACAGGGTGGCTGTCGGG
CGGAGGGGCTCCTCACTTCTCAGACGGGGCAGCTGCGGGCGGAGGGGCTCCTCACT
TCTCAGACGGGGTGGCCGGGCAGAGAAGCTCCTCACATCCCAGACGGGGGGCGGG
GCAGAGGCGCTCCCCACATCTCAGACGATGGGCGGCCGGGCAGAGACGCTCCTCAC
TTCATCCCAGACGGGGTGGCGGCCGGGCAGAAGCTGTAATCTCGGCACCCTGGGGG
GCCAAGGCAGGCGGCTGGGAGGCGGAGGCCGTAGCCAGCTGAGATCACACCACTGC
ACTCCAGCCTGGGCAACATTGAGCACTGAGTGGACGAGACTCTGCCCGCAATCCCG
GCACCTCGGGAGGCCGAGGCTGGCAGATCACTCGCAGTCAGGAGCTGGAGACCAGC
CCGGCCAACACAGTGAAACCCTGTCTCCACCAAAAAAATACGAAAACCAGTCAGGC
GTGGCGGCGCCCGCAATGGCAGGCACGCGGCAGGCCGAGGCGGGAGAATCAGGCA
GGGAGGCTGCAGTGAGCCGAGATGGCAGCAGTACAGTCCAGCTTCGGCTCGGCATC
AGAGGGAGACCGTGGGAGAGGGAGAAGAGAGGGAGGGGGAGAGGGCTATTTTTA
AAATTTTTTAAAATTGCTGAACAGGGGTACCTCTGGGCAGTGTGTCAGAATACCACT
TTTTTAAATATTTTATGATTTATTTATTTTTCTATTTCTTGAGGTTTTAACTGATGTGTA
TCTGTATGTCTATTTGTGTATATTTTGTCATGATCATGTAACAGAGTCTGAAAAGTGT
CGAAGAGACAGTTTTCAGGAACAACAAGCAATTATTCCTACTTTCCAAGTTATTTTG
ATGCCATGGTGGCTCATACCTATAATCTGAGTACTTTGGGAGGCTGAGGTGGACTGA
TCACTTGAGCCCAGGAGTTTGAGACCAGCCTGGGCAACATAGCAAGACTCCATCTCT
ACAAAAAAAGACAAATTTAGCTGAGCGTGGTGGCGTGTTCCTGTAGTCCCAGCTA
CTTGGGAGGCTGAAGTGAGTGGATCCCCTGAGCCCAGAGAGGTCAAGGTTGTGATG
AGCTGTGATCACACCACTGCACTTCAGCATGGGAGACAGAGTGAGACCCTGTTTCAG
AAAAAAATAAATAAATAAAACCACCAGCACCACAAACAACAACAAAAAGTTATTTTG
TACTTGTTTTGAGCACAGGACTCCTGAGGGTATCTTTGCATTTAATATTACATAGGG
GTGCCAGTGGGAAGTAATGTGTATGCTTGGCCTCATGAGCTAAAACCCTGTGTTAAT
TATGACAGAAGGAAAGTGTGTGAGAGAGATCTTAACTACCTAGCAGCTCTAGCTGC
CATCTTGAACCATGAAGATACGGGCCACACGTAGGGGTAGCTGGGTAGTGAGCAGC
AAGAAGCCTTGTTGGATGAGGGCACGAAGGAGCAGAATCACTGGAATCACTGTGTC
AGCCCTAATTACCTACCTCTGGACTTTTATGTGAGGGGAAAAAAAATTGACAGTTTA
TATTTATCTCAACCTAGTTAACCCAAGTGATGCATTGTTATGAGATTAAAATGTTTGG
AGGCCGGGTGCGGTGGCTCACGCCTATAATCCCAGCCCTTTGGGAGGCCAAGGCGG
GCGGATCACGAGGTCAGGAGATCAAGACCATCCTGGCTAACATGTAAAACCCCGTC
TCTACTAAAAATACAAAAAATTAGCCAGGCGTTGTGGCGGTCGCCTGTAGTCCCTGC
TATTTGGGAGGCCGAGGCAAGAGAACGGCATGAACCTGGGAGGTGGAGCTTGCAGC
GAGCTGAGATCTTGCCACTGCACTCCAGCCTGGGCGACAGTGCGAGACTCTGTCTCA
AAAATAAATAAATAAATAAATAATAAATAAAATGTTTGGAATGTTGGCTTCATCCCT
GGGATGCAAGGCTGGTTCAACATACGCAAATCAAGAAACATAATTCATCACATAAA
CAGAACTAAAGACAAAAACCACATGATTATCTCAATAGATACAGAAAAGGCCTTCA
ATAAAATTCAACGTTGCTTCATGTTAAAAACTCTCAATAAACTAGGTATTGATGGAA
AATATCTCAAAATAATAACCATTTATGACAAACCCACAGCCATTATCATACTGAATG
GGCAAAAGCTGGAAGCATTCCCCTTGAAAACTGGCACAAGACAGGGATGCCGTCTC
ACCACTCCTATTTAACATAGTATTGGAAGTTCTGGCCAAGAAAATCAGGCAAGAGA
AACAAATAAGGGGTATTCAAATAGGAAAAGAGGAAGTAAAACTGTGTTTGCAGATG
ACATGATACTATATCTAGAAAACCCCATTATCTCCACCCAAAAGTTCCTTAAGCTGA
TAAGCAACTTCAGCAAAGTCTCAGGATACAAAATCAATGTGCAGAAATCACAAGCA
TTCTATACACCAACAATACACAAGCAGAGAGCCAAATCATGAATGAACTCCCATTC
ACAGTTGCTAGAAAGAGAATAAAATACCTAGGAATACAGCTAATAAGATGTGAAGG
ATCTCTTCAAGGAGAACTACAAACCACTGCTCAAGGAAATAAGAGAGGACACAAAT
GAAAAAACATTCCATTCTCGTGGATAGGAAGAATCAATATCATGAAAATGGCCATA
CTACCCAAAGTAATTTATAGGTTCATTGCTATTCCCATTAAACTACTATTGACATTCT
TCACAGAATTAGAAAAAACTACTTTAAAATTCAAATGGAACCAAAAAAGAGCCCG
TATAACCAAGACAACAATAAGCAAAAAGAACAAAGCTGGAAGCATCACACTACCC
```

TABLE 5-continued

Nucleotide Sequences of Biodosimetry Biomarker Genes

```
AACTTCAAAGTATACTGCAAGGCTACAGTAGCCAAAATGGCATGGTACTGGTACAA
AAACAGACACATAGACCAATGGAACAGAATAGAGACCAGAGAAAGAAGACCACAC
ATCTACAGCCATCTGATCATCGACAAACCTGACAAAAACAAGCAATGGGGAAAAGA
TTCCCTATTTAATAAATGGTGCTGGGAAAACTGGCTAGCCATATGCAGAAAATTGAA
ACTGACCCCTTCCTTACACCTTATACAAAAATTAACTCAAGATTAAAGACTTAATGT
AAAACCTAAAACTATAAAAACCCTAGAAGAAAATCTATTTAATACCATTCAAGACA
TAGGCACAAGCAAAGGTTTCATGACAAAAACATCAAAAGCAATTGCAACAAAAGCA
AAAATTACAAATGGGATCTAATTAAACTAAAGAGCTCCTGCACAGCAAAAGAAACT
ATCATTAGAGTGAACAGGCAACCTACAGAATGGGAGAACATTTTTGCAATCTATCCA
TCTGACAAAGGTCTAATATCCAGAACCTACAAGGAACTTAAAACAAATTTACAAGG
AAAAAAACAACCCCATCAAAAAGTGGACAAAGGACATGAACAGACACTTCTCAAA
AGAAGACATTTATGTGGCCAACAAACATATAAAAAAAAGCTCAACCTTACTGATCA
TTAGAGAAATGCAAAGGAGAACCACAATGAGATACCATCTCATGCCGGTCAGAATG
GTGATTATTAAAAAGTCAAAAAACAACAGATGCTGGCGAGGCTGTGGAGAAGTAGG
AACACTTTTACATTGTTGGTGGGAATGTAAATTAGTTCAACCGTTGTGGAAGTGTGT
GTGGCTATTCCTCAAAGATCTAGAACTAGAAATACTATTTGTCCCAGCAATCCCATT
ACTGGGTATATACCCAAAGGAATATAAACCATTTTATTATAAAGATACATGCACATT
TTTGTTCATTGCAGCACTCTTCACAATAGCAAAGACACAATAGCAAATGCCCATCAA
AGATAGACTGGATAAAGAAAATGTGGTACATATACACCATGGAATACTGTGCAGTG
CAGCCATTACAGCTTTTGGTGATACAGTGAATCAGATTTTTCATTAATTCTTTTAATT
GGTTATTACTGAACGTGAAAAAGTAATGTTTGTATTGAAATCTTGAGTCTGGCCATG
TTTCTATTTTAAATTCATAAAGAATTCTAACAAGAGGAATTCCAAGAATGTCATAAA
TGGATGTTTCTCCATGGATGAAGGAACTGTTTTATTCACTTGCTGATAATTCAGCCTA
ATCCAGTTTGACATCATATAGATAAGTAGTTGAATTATGGATTTAAAATACATATCA
TTTTCTAACTCCAAAGGTAATACTTATTTAAATGGTTTTGAAAATATAGAAAGGCAC
AATTTCTTTTTAAATCTGTTATTCTCCACCACCACTCAATCTGTCTATCATCTATCTCT
CCATTCATTCTTCCCATTTGTTTATATCTGTTAATCTTTGTATGTGTTCATGTATAGCTT
TTACATGATTGGAATCATAATGCATATTCCATTTTGAAGTCTGCTTTTTTTTACACAA
AAATATGTTGTGAATATTTTCCTATATTATGAAATATCATTAGCTGAGCTTTTAGAAT
TGACTGCATGTTTTGGTACCATTTAGATATAGTTTAAGATACTTAGAAGTTATGTGGC
TTTGCCACTATGGATGAATCTTATTTACTCAATATTAATTACTTACAAATAACCTCAC
CTAAACACTACTCAGCCATAAAAAGGAATGAATTAATGACATTCACAGCAACCTGG
AGACTATTACTCTAAAGGAAGTAACTGAGGAATGGAAAACCAAACATTGTATGTTC
TCACTCATAAGTGGGAGATAAGCTATGAGGATGCAAAGGCATAAGAAGGATACAAT
GGACTTTGGGGACTTAGGGGAAAGGGTGGGAGGGGGGTGAAGGATAAAAGAATAC
AAATTGGGTTCAGTGTATACTGCTCAGGTGATGGGTGCACCGAAATCTCACAAGTAA
CCACTTAATTACTTACGCATGTAACCAGATACCACCTGTTCCCCAAACACCTATGGA
AATAATTTTGTTTTTTTTTTAAAAAAGGAATGAGATCATGTCCTTTGCAGGGACATG
GATGAAGCTGGAAGCCATTATCCTCAGCAAACTAACAGAGGAGCAGGAAACCAAAC
ACCACATGTTCTCACTTGTAAGCGGAAGCTGAACAATGAGAACACACGGACACAGG
GATGAGATCAACACACACTGGGGCCTGATGCAGGGGCCGTAGCGGGGAGAGCATCA
GGATAACTAGCTAATGCATGTGGGCTTAATACCTAGGTGATAGGTTGATAGGTGCA
GCAAACCACCATGGGACACGTTTACCTATGTAACAAACCCGCACATCCTGCACTTGT
ATCCAGAACTTAAAATATTTTAAAAATCTTTAGAGAATACAAAAAAAAAAAAAAAG
ATTCTTCAATGCATACACAATAAAATTGCAGTTCAGTCAAACATTGGAAGTCTTTCT
CTGACTGTCTAGTTGGTATCTTCATTTTCAGCTTCTTCAAGATCCCACTCCAAACACT
GTTAGCTCAGCCAAATTGAACAGCTCATATCTCCTACCTCTGGATCTTTGGTTCTGGT
GATTGTATATTTCTGGACCATCTGGAACCCCAGCATATCACCCTACCCCACATCTCC
ACATCCCCAAAATATAACCATACTTCAAGGGCAGTTCAAATACCATCTCCTTCTATC
CTCCATGAAGTCAGTTATCTCTTCCATTGGAATTATCGCCCCCTCTCCTGAACAGTAC
TATTTCGTGTGAATCTCCTCCAAGCCTTCTTTTCATTTTATATCTCATGCTGTAATTCT
TGGAAAGTATGCTGTAGCTCAAGTGCAGAATTCTCATCAGTTTTATCTTTATATCTCT
CCTAAACACTTTACCTGATGAAGAGCCTGGCATACACATAAATATATATTGAATGAA
TCAGTGATGGATTGAAAAGAGAAATGATGGATCTCCTAAATTTTAACTTTTATAAAA
TATTTTGATACATTCATGACCTTACTTTAGCAAGCAATGAACGTGATGTAAACTATT
GTTGATATAGTTTTTATATTGGAAGTGTAAGTAGTTTGTGGCATGGGATTGTGACAT
ATCCTAGGTTTCCTCATCTTCTTTTTATTGAAATGTAATTCACAAGCCATAAAATTTG
CCCCTTTAAAGTAAATGATGCAGTGGATTTTAGTATATTTACAGAGTTGTGCAATCA
TCACCACTATCTAATTCCAGAACATTTCCATCTACCTAGAAACTCCATACCAGTGAG
CTGCCACTCTAATCCTCCTCTTCCCCCAGCCTCTAGAAACAATAATCCATTTTCTGTC
TCTATGATTTGCCTGTTCTAGATATTTTATAAAAATAAACATGTGGCCTTTCGTGTCT
GACTTCCTTCACTTAAAAAAAAAAAAAAAAAAA

DHRS13 (SEQ ID NO: 21; NM_144683.3).
CGCCTCCGCCTTCGGAGGCTGACGCGCCCGGGCGCCGTTCCAGGCCTGTGCAGGGC
GGATCGGCAGCCGCCTGGCGGCGATCCAGGGCGGTGCGGGGCCTGGGCGGGAGCCG
GGAGGCGCGGCCGGCATGGAGGCGCTGCTGCTGGGCGCGGGGTTGCTGCTGGGCGC
TTACGTGCTTGTCTACTACAACCTGGTGAAGGCCCCGCCGTGCGGCGGCATGGGCAA
CCTGCGGGGCCGCACGGCCGTGGTCACGGGCGCCAACAGCGGCATCGGAAAGATGA
CGGCGCTGGAGCTGGCGCGCCGGGGAGCGCGCGTGGTGCTGGCCTGCCGCAGCCAG
GAGCGCGGGGAGGCGGCTGCCTTCGACCTCCGCAGGAGAGTGGGAACAATGAGGT
CATCTTCATGGCCTTGGACTTGGCCAGTCTGGCCTCGGTGCGGGCCTTTGCCACTGC
CTTTCTGAGCTCTGAGCCACGGTTGGACATCCTCATCCACAATGCGGTGTATCAGTTC
CTGTGGCCGGACCCGTGAGGCGTTTAACCTGCTGCTTCGGGTGAACCATATCGGTCC
CTTTCTGCTGACACATCTGCTGCTGCCTTGCCTGAAGGCATGTGCCCCTAGCCGCGT
GGTGGTGGTAGCCTCAGCTGCCCACTGTCGGGACGTCTTGACTTCAAACGCCTGGA
CCGCCCAGTGGTGGGCTGGCGGCAGGAGCTGCGGGCATATGCTGACACTAAGCTGG
CTAATGTACTGTTTGCCCGGGAGCTCGCCAACCAGCTTGAGGCCACTGGCGTCACCT
```

TABLE 5-continued

Nucleotide Sequences of Biodosimetry Biomarker Genes

```
GCTATGCAGCCCACCCAGGGCCTGTGAACTCGGAGCTGTTCCTGCGCCATGTTCCTG
GATGGCTGCGCCCACTTTTGCGCCCATTGGCTTGGCTGGTGCTCCGGCACCAAGAG
GGGGTGCCCAGACACCCCTGTATTGTGCTCTACAAGAGGGCATCGAGCCCCTCAGTG
GGAGATATTTTGCCAACTGCCATGTGGAAGAGGTGCCTCCAGCTGCCCGAGACGAC
CGGGCAGCCCATCGGCTATGGGAGGCCAGCAAGAGGCTGGCAGGGCTTGGGCCTGG
GGAGGATGCTGAACCCGATGAAGACCCCCAGTCTGAGGACTCAGAGGCCCCATCTT
CTCTAAGCACCCCCACCCTGAGGAGCCCACAGTTTCTCAACCTTACCCCAGCCCTC
AGAGCTCACCAGATTTGTCTAAGATGACGCACCGAATTCAGGCTAAAGTTGAGCCTG
AGATCCAGCTCTCCTAACCCTCAGGCCAGGATGCTTGCCATGGCACTTCATGGTCCT
TGAAAACCTCGGATGTGTGCGAGGCCATGCCCTGGACACTGACGGGTTTGTGATCTT
GACCTCCGTGGTTACTTTCTGGGGCCCCAAGCTGTGCCCTGGACATCTCTTTTCCTGG
TTGAAGGAATAATGGGTGATTATTTCTTCCTGAGAGTGACAGTAACCCCAGATGGAG
AGATAGGGGTATGCTAGACACTGTGCTTCTCGGAAATTTGGATGTAGTATTTTCAGG
CCCCACCCTTATTGATTCTGATCAGCTCTGGAGCAGAGGCAGGGAGTTTGCAATGTG
ATGCACTGCCAACATTGAGAATTAGTGAACTGATCCCTTTGCAACCGTCTAGCTAGG
TAGTTAAATTACCCCCATGTTAATGAAGCGGAATTAGGCTCCCGAGCTAAGGGACTC
GCCTAGGGTCTCACAGTGAGTAGGAGGAGGGCCTGGGATCTGAACCCAAGGGTCTG
AGGCCAGGGCCGACTGCCGTAAGATGGGTGCTGAGAAGTGAGTCAGGGCAGGGCA
GCTGGTATCGAGGTGCCCCATGGGAGTAAGGGGACGCCTTCCGGGCGGATGCAGGG
CTGGGGTCATCTGTATCTGAAGCCCCTCGGAATAAAGCGCGTTGACCGCCGAAAAA
AAAAAAAAAAAAAAA

ACAA1 (SEQ ID NO: 22; NM_001607.3).
GGGTTCCCAGGCCGACTCTCCTTGTGGTTGGCTGAGGCTGGAGGTGGACGGGACTTT
TGGAGGGTCGCTCGCGTCTGTTCGCAGAGCTGTGGGCGGAGTTGAGGCCTTGGAGG
CTGAGATGTGGTTCTGCGCGTGTGCGGACGGCTGTCTGTTAACTCCGCGGTCAGTTC
CCGGACTGGTGGCTGGTCTGCAGGGTTGACCTGCGCAATGCAGAGGCTGCAGGTAG
TGCTGGGCCACCTGAGGGGTCCGGCCGATTCCGCTGGATGCCGCAGGCCGCGCCTT
GCCTGAGCGGTGCCCCGCAGGCCTCGGCCGCGGACGTGGTGGTGGTGCACGGGCGG
CGCACGGCCATCTGCCGGGCGGGCCGCGGCGGCTTCAAGGACACCACCCCCGACGA
GCTTCTCTCGGCAGTCATGACCGCGGTTCTCAAGGACGTGAATCTGAGGCCGGAACA
GCTGGGGACATCTGTGTCGGAAATGTGCTGCAGCCTGGGGCCGGGGCAATCATGG
CCCGAATCGCCCAGTTTCTGAGTGACATCCCGGAGACTGTGCCTTTGTCCACTGTCA
ATAGACAGTGTTCGTCGGGGCTACAGGCAGTGGCCAGCATAGCAGGTGGCATCAGA
AATGGGTCTTATGACATTGGCATGGCCTGTGGGGTGGAGTCCATGTCCCTGGCTGAC
AGAGGGAACCCTGGAAATATTACTTCGCGCTTGATGGAGAAGGAGAAGGCCAGAGA
TTGCCTGATTCCTATGGGGATAACCTCTGAGAATGTGGCTGAGCGGTTTGGCATTTC
ACGGGAGAAGCAGGATACCTTTGCCCTGGCTTCCCAGCAGAAGGCAGCAAGAGCCC
AGAGCAAGGGCTGTTTCCAAGCTGAGATTGTGCCTGTGACCACCACGGTCCATGATG
ACAAGGGCACCAAGAGGAGCATCACTGTGACCCAGGATGAGGGTATCCGCCCCAGC
ACCACCATGGAGGGCCTGGCCAAACTGAAGCCTGCCTTCAAGAAAGATGGTTCTAC
CACAGCTGGAAACTCTAGCCAGGTGAGTGATGGGCAGCTGCCATCCTGCTGGCCC
GGAGGTCCAAGGCAGAAGAGTTGGGCCTTCCCATCCTTGGGGTCCTGAGGTCTTATG
CAGTGGTTGGGGTCCCACCTGACATCATGGGCATTGGACCTGCCTATGCCATCCCAG
TAGCTTTGCAAAAAGCAGGGCTGACAGTGAGTGACGTGGACATCTTCGAGATCAAT
GAGGCCTTTGCAAGCCAGGCTGCCTACTGTGTGGAGAAGCTACGACTCCCCCCTGAG
AAGGTGAACCCCCTGGGGGGTGCAGTGGCCTTAGGGCACCCACTGGGCTGCACTGG
GGCACGACAGGTGTCATCACGCTGCTCAATGAGCTGAAGCGCCGTGGGAAGAGGGCAT
ACGGAGTGGTGTCCATGTGCATCGGGACTGGAATGGGAGCCGCTGCCGTCTTTGAAT
ACCCTGGGAACTGAGTGAGGTCCCAGGCTGGAGGCGCTACGCAGACAGTCCTGCTG
CTCTAGCAGCAAGGCAGTAACACCACAAAAGCAAAACCACATGGGAAAACTCAGC
ACTGGTGGTGGTGGCAGTGGACAGATCAAGGCACTTCAACTCATTTGGAAAATGTG
AACACTGATGACATGGTATAGGAGTGGGTGGGGTGTTGAGCCACCCATCAGACCCT
CTTTAGCTGTGCAAGATAAAAGCAGCCTGGGTCACCCAGGCCACAAGGCCATGGTT
AATTCTTAAGGCAAGGCAAATCCATGGATGAGAAGTGCAATGGGCATAGTAAAAGT
GCATGAATTTATCTTAAAAAAAAAAAAAAAAAAAAAA

INPP5J (SEQ ID NO: 23; NM_001284285.1).
CAGGTTGAAATGGCTGATGACATCACTGGTTCCCGGGAGCGGTAGAGCTGGAGCCG
GAGCCAAGGGAGTCCAGGCTGCCGGGGGCTGCAGACATGGAGGGCCAGAGCAGCA
GGGGCAGCAGGAGGCCAGGGACCCGGGCTGGCCTGGGTTCCTGCCCATGCCCCAG
GGTGTTGCCCAAACTGGGGCACCCTCCAAGGTGGACTCAAGTTTTCAGCTCCCAGCA
AAGAAGAACGCAGCCCTAGGACCCTCGGAACCAAGGTTGGCTCTGGCACCTGTAGG
GCCACGGGCAGCTATGTCAGCTTCCTCGGAAGGACCGAGGCTGGCTCTGGCATCTCC
CCGACCAATCCTGGCTCCACTGTGTACCCCTGAAGGGCAGAAAACAGCTACTGCCC
ACCGCAGCTCCAGCCTGGCCCCAACATCGTGGGCCAGCTGGTGATGTCTGCCTCAG
CTGGACCAAAGCCTCCCCAGCGACCACAGGTCAGTTCTGGCTCCGACGTCCCTGG
GGCTGGTGATGCCTGCCTCAGCAGGGCCAAGATCTCCCCAGTCACCCTGGGGCCCA
ATCTGGCCCAACCTCCAGAGACCAGAAGCAGGAGCCACCTGCCTCCGTGGGACCC
AAGCCAACACTGGCAGCCTCTGGCCTGAGCCTGGCCCTGGCTTCTGAGGAGCAGCC
CCCAGAACTCCCCTCCACCCCTTCCCCGGTGCCCAGTCCAGTTCTGTCTCCAACTCAG
GAACAGGCCCTGGCTCCAGCATCCACGGCATCAGGCGCAGCCTCTGTGGGACAGAC
ATCAGCTAGAAAGAGGGATGCCCCAGCCCCTAGACCTCTCCCTGCTTCTGAGGGGC
ATCTCCAGCCTCCAGCTCAGACATCTGGTCCTACAGGCTCCCCACCCTGCATCCAAA
CCTCCCCAGACCCTCGGCTCTCCCCTCCTTCCGAGCCCGGCCTGAGGCCCTCCACA
GCAGCCCTGAGGATCCTGTTTTGCCACGGCCACCCCAGACCTTGCCCTTGGATGTGG
GCCAGGGTCCTTCAGAGCCTGGCACTCACTCCCCTGGACTTCTGTCCCCCACCTTCC
GGCCTGGGGCCCCCTCAGGCCAGACTGTGCCCCCACCTCTGCCCAAGCCACCCCGAT
```

TABLE 5-continued

Nucleotide Sequences of Biodosimetry Biomarker Genes

```
CACCCAGCCGTTCCCCAAGCCACTCCCCGAATCGCTCTCCCTGTGTTCCCCCAGCCC
CTGACATGGCCCTCCCCAAGGCTTGGCACACAGAGTACAGGGCCTGGCAGGTGCCTG
AGCCCCAACCTTCAGGCCCAAGAAGCCCCAGCCCCAGTCACCACCTCCTCTTCTACA
TCCACCCTGTCATCCTCCCCTTGGTCAGCTCAGCCTACCTGGAAGAGCGACCCCGGC
TTCCGGATCACTGTGGTCACATGGAACGTGGGCACTGCCATGCCCCCAGACGATGTC
ACATCCCTCCTCCACCTGGGCGGTGGTGACGACAGCGACGGCGCAGACATGATCGC
CATAGGGTTGCAGGAAGTGAACTCCATGCTCAACAAGCGACTCAAGGACGCCCTCT
TCACGGACCAGTGGAGTGAGCTGTTCATGGATGCGCTAGGGCCCTTCAACTTCGTGC
TGGTGAGTTCGGTGAGGATGCAGGGTGTCATCCTGCTGCTGTTCGCCAAGTACTACC
ACCTGCCCTTCCTGCGAGACGTGCAGACCGACTGCACGCGCACTGGCCTGGGCGGCT
ACTGGGGTAACAAGGGTGGCGTGAGCGTGCGCCTGGCGGCCTTCGGGCACATGCTC
TGCTTCCTGAACTGCCACTTGCCTGCGCATATGGACAAGGCGGAGCAGCGCAAAGA
CAACTTCCAGACCATCCTCAGCCTCCAGCAGTTCCAAGGGCGGGCGCACAGGGCA
TCCTGGATCATGACCTCGTGTTCTGGTTCGGGGACCTGAACTTCCGCATTGAGAGCT
ATGACCTGCACTTTGTCAAGTTTGCCATCGACAGTGACCAGCTCCATCAGCTCTGGG
AGAAGGACCAGCTCAACATGGCCAAGAACACCTGGCCCATTCTGAAGGGCTTTCAG
GAGGGGCCCCTCAACTTCGCTCCCACCTTCAAGTTTGATGTGGGTACCAACAAATAC
GATACCAGTGCCAAGAAACGGAAGCCAGCTTGGACAGACCGTATCCTATGGAAGGT
CAAGGCTCCAGGTGGGGGTCCCAGCCCCTCAGGACGGAAGAGCCACCGACTCCAGG
TGACGCAGCACAGCTACCGCAGCCACATGGAATACACAGTCAGCGACCACAAGCCT
GTGGCTGCCCAGTTCCTCCTGCAGTTTGCCTTCAGGGACGACATGCCACTGGTGCGG
CTGGAGGTGGCAGATGAGTGGGTGCGGCCCGAGCAGGCGGTGGTGAGGTACCGCAT
GGAAACAGTGTTCGCCCGCAGCTCCTGGGACTGGATCGGCTTATACCGGGTGGGTTT
CCGCCATTGCAAGGACTATGTGGCTTATGTCTGGGCCAAACATGAAGATGTGGATGG
GAATACCTACCAGGTAACATTCAGTGAGGAATCACTGCCCAAGGGCCATGGAGACT
TCATCCTGGGCTACTATAGTCACAACCACAGCATCCTCATCGGCATCACTGAACCCT
TCCAGATCTCGCTGCCTTCCTCGGAGTTGGCCAGCAGCAGCAGACAGCTCAGGCA
CCAGCTCAGAGGGAGAGGATGACAGCACACTGGAGCTCCTTGCACCCAAGTCCCGC
AGCCCCAGTCCTGGCAAGTCCAAGCGACACCGCAGCCGCAGCCCGGGACTGGCCAG
GTTCCCTGGGCTTGCCCTACGGCCCTCATCCCGTGAACGCCGTGGTGCCAGCCGTAG
CCCCTCACCCCAGAGCCGCCGCCTGTCCCGAGTGGCTCCTGACAGGAGCAGTAATG
GCAGCAGCCGGGGCAGTAGTGAAGAGGGGCCCTCTGGGTTGCCTGGCCCCTGGGCC
TTCCCACCAGCTGTGCCTCGAAGCCTGGGCCTGTTGCCCGCCTTGCGCCTAGAGACT
GTAGACCCTGGTGGTGGTGGCTCCTGGGGACCTGATCGGGAGGCCCTGGCGCCCAA
CAGCCTGTCTCCTAGTCCCCAGGGCCATCGGGGGCTGGAGGAAGGGGGCCTGGGGC
CCTGAGGGTGGGGTAGGCAGATGGGCCAAGGTGACCACCATTCTGCCTCAATCTTTT
GCAAGCCCACCTGCCTCTCTCCTGCTGCTCCTCCAGCTGTATCTGCACCTGCCTCTCT
GTCCTGGCCAGGGGTGGACAACTGGGGTCCCCCAAAACTCAGTCCTGGCACCTCAA
CTGTGACAATCAGCAAAGCCCCACCCAGGCCCCCATCTGGGATGATGGGAGAGCTC
TGGCAGATGTCCCAATCCTGGAGGTCATCCATTAGGAATTAAATTCTCCAGCCTCAA
AAAAAAAAAAAAAAAA

OAZ1 (SEQ ID NO: 24; NM_004152.2).
TTTTGCGAACGGCGAGCAGCGGCGGCGGCGCGGAGAGACGCAGCGGAGGTTTTCCT
GGTTTCGGACCCCAGCGGCCGGATGGTGAAATCCTCCCTGCAGCGGATCCTCAATAG
CCACTGCTTCGCCAGAGAGAAGGAAGGGGATAAACCCAGCGCCACCATCCACGCCA
GCCGCACCATGCCGCTCCTAAGCCTGCACAGCCGCGGCGGCAGCAGCAGTGAGAGT
TCCAGGGTCTCCCTCCACTGCTGTAGTAACCCGGGTCCGGGGCCTCGGTGGTGCTCC
TGATGCCCCTCACCCACCCCTGAAGATCCCAGGTGGGCGAGGGAATAGTCAGAGGG
ATCACAATCTTTCAGCTAACTTATTCTACTCCGATGATCGGCTGAATGTAACAGAGG
AACTAACGTCCAACGACAAGACGAGGATTCTCAACGTCCAGTCCAGGCTCACAGAC
GCCAAACGCATTAACTGGCGAACAGTGCTGAGTGGCGGCAGCCTCTACATCGAGAT
CCCGGGCGGCGCGCTGCCCGAGGGGAGCAAGGACAGCTTTCAGTTCTCCTGGAGT
TCGCTGAGGAGCAGCTGCGAGCCGACCATGTCTTCATTTGCTTCCACAAGAACCGCG
AGGACAGAGCCGCCTTGCTCCGAACCTTCAGCTTTTTGGGCTTTGAGATTGTGAGAC
CGGGGCATCCCCTTGTCCCCAAGAGACCCGACGCTTGCTTCATGGCCTACACGTTCG
AGAGAGAGTCTTCGGGAGAGGAGGAGGAGTAGGGCCGCCTCGGGGCTGGGCATCC
GGCCCCTGGGGCCACCCCTTGTCAGCCGGGTGGGTAGGAACCGTAGACTCGCTCATC
TCGCCTGGGTTTGTCCGCATGTTGTAATCGTGCAAATAAACGCTCACTCCGAATTAG
CGGTGTATTTCTTGAAGTTTAATATTGTGTTTGTGATACTGAAGTATTTGCTTTAATT
CTAAATAAAAATTTATATTTTACTTTTTTATTGCTGGTTTAAGATGATTCAGATTATC
CTTGTACTTTGAGGAGAAGTTTCTTATTTGGAGTCTTTTGGAAACAGTCTTAGTCTTT
TAACTTGGAAAGATGAGGTATTAATCCCCTCCATTGCTCTCCAAAAGCCAATAAAGT
GATTACACCCGA

PNOC (SEQ ID NO: 25; NM_006228).
GCCAGGAAGGCTTGCAGGTTCTGCTGTTTGGTTGCTGAAGGGGGTCAGTGTGTGTAT
GTGTCATGGAGGTGGGCAGGGAAGGGGAGGGCTGTGCGTGGGGGAGAGGATATAT
ATGCTGGTGTGGCTGAGAAAGCGGAACCGAGCCTCGCATCCATCGGAGGGAGCCGG
GGACTGACAGCTCTCAGCACCTGCTTCCTGCTCCTGCACCATGAAAGTCCTGCTTTG
TGACCTGCTGCTGCTCAGTCTCTTCTCCAGTGTGTTCAGCAGTTGTCAGAGGGACTGT
CTCACATGCCAGGAGAAGCTCCACCCAGCCCTGGACAGCTTCGACCTGGAGGTGTG
CATCCTCGAGTGTGAAGAGAAGGTCTTCCCCAGCCCCCTCTGGACTCCATGCACCAA
GGTCATGGCCAGGAGCTCTTGGCAGCTCAGCCCTGCCGCCCAGAGCATGTGGCGG
CTGCTCTCTACCAGCCGAGAGCTTCGGAGATGCAGCATCTGCGGCGAATGCCCCGA
GTCCGGAGCTTGTTCCAGGAGCAGGAAGAGCCCGAGCCTGGCATGGAGGAGGCTGG
TGAGATGGAGCAGAAGCAGCTGCAGAAGAGATTTGGGGGCTTCACCGGGGCCCGGA
AGTCGGCCAGGAAGTTGGCCAATCAGAAGCGGTTCAGTGAGTTTATGAGGCAATAC
```

TABLE 5-continued

Nucleotide Sequences of Biodosimetry Biomarker Genes

TTGGTCCTGAGCATGCAGTCCAGCCAGCGCCGGCGCACCCTGCACCAGAATGGTAA
TGTGTAGCCGGAAGGGCGCTCCTCCCAGCTGTACCGGCCACTGCAACCCATGAGC
GTCCAGGTGATCCCCCAAACAGCATGTGCTCAGCCCCAGACCTGCCGCCTGGGAATC
AGGATTCCTTCTTCCCCAAGGCACTGAGCGCCTGCAGATCCCGCAGGCTTCGTTTGC
CTCCAGAACCTTCCCGTCTGATTGTTCCTCCCCAGCCCCTGGCATGTTTCACCACAA
CCCTGTTGCTACATCAGAGTGTATTTTTGTAATTCCTCTAGCTACCATTTCAATAGCC
CCATCTCTCCTGCTCACCCGCCTCTTGCCCCTTCTAGGGGCAGGTGAAAGGAATAGG
AAATTGAACCTGGGGTTTTGACTTGCCACTGCCATAACTTGTTTGTAAAAGAGCTGT
TCTTTTTGACTGATTGTTTTAAACAACGATTTCTCCATTAAACTTCTACTGAGCAAAT
GGTTAATAAAAAAAAAAAAAAAAAA

PDE4B (SEQ ID NO: 26; NM_002600).
AGAGCGCTGCGGCCGCGGCGGTGCAGCAGAGGCGCCTCGGGCAGGAGGAGGGCGG
CTTCTGCGAGGGCAGCCTGAGGTATTAAAAAGTGTCAGCAAACTGCATTGAATAAC
AGACATCCTAAGAGGGGATATTTTCCACCTCTATAATGAAGAAAAGCAGGAGTGTG
ATGACGGTGATGGCTGATGATAATGTTAAAGATTATTTTGAATGTAGCTTGAGTAAA
TCCTACAGTTCTTCCAGTAACACACTTGGGATCGACCTCTGGAGAGGGAGAAGGTGT
TGCTCAGGAAACTTACAGTTACCACCACTGTCTCAAAGACAGAGTGAAAGGGCAAG
GACTCCTGAGGGAGATGGTATTTCCAGGCCGACCACACTGCCTTTGCAACGCTTCC
AAGCATTGCTATTACAACTGTAAGCCAGGAGTGCTTTGATGTGGAAAATGGCCCTTC
CCCAGGTCGGAGTCCACTGGATCCCCAGGCCAGCTCTTCCGCTGGGCTGGTACTTCA
CGCCACCTTTCCTGGGCACAGCCAGCGCAGAGAGTCATTTCTCTACAGATCAGACAG
CGACTATGACTTGTCACCAAAGGCGATGTCGAGAAACTCTTCTCTTCCAAGCGAGCA
ACACGGCGATGACTTGATTGTAACTCCTTTTGCCCAGGTCCTTGCCAGCTTGCGAAG
TGTGAGAACAACTTCACTATACTGACAAACCTTCATGGTACATCTAACAAGAGGTC
CCCAGCTGCTAGTCAGCCTCCTGTCTCCAGAGTCAACCCACAAGAAGAATCTTATCA
AAAATTAGCAATGGAAACGCTGGAGGAATTAGACTGGTGTTTAGACCAGCTAGAGA
CCATACAGACCTACCGGTCTGTCAGTGAGATGGCTTCTAACAAGTTCAAAAGAATGC
TGAACCGGGAGCTGACACACCTCTCAGAGATGAGCCGATCAGGGAACCAGGTGTCT
GAATACATTTCAAATACTTTCTTAGACAAGCAGAATGATGTGGAGATCCCATCTCCT
ACCCAGAAAGACAGGGAGAAAAAGAAAAAGCAGCAGCTCATGACCCAGATAAGTG
GAGTGAAGAAATTAATGCATAGTTCAAGCCTAAACAATACAAGCATCTCACGCTTTG
GAGTCAACACTGAAAATGAAGATCACCTGGCCAAGGAGCTGGAAGACCTGAACAAA
TGGGGTCTTAACATCTTTAATGTGGCTGGATATTCTCACAATAGACCCCTAACATGC
ATCATGTATGCTATATTCCAGGAAAGAGACCTCCTAAAGACATTCAGAATCTCATCT
GACACATTTATAACCTACATGATGACTTTAGAAGACCATTACCATTCTGACGTGGCA
TATCACAACAGCCTGCACGCTGCTGATGTAGCCCAGTCGACCCATGTTCTCCTTTCT
ACACCAGCATTAGACGCTGTCTTCACAGATTTGGAGATCCTGGCTGCCATTTTTGCA
GCTGCCATCCATGACGTTGATCATCCTGGAGTCTCCAATCAGTTTCTCATCAACACA
AATTCAGAACTTGCTTTGATGTATAATGATGAATCTGTGTTGGAAAATCATCACCTT
GCTGTGGGTTTCAAACTGCTGCAAGAAGAACACTGTGACATCTTCATGAATCTCACC
AAGAAGCAGCGTCAGACACTCAGGAAGATGGTTATTGACATGGTGTTAGCAACTGA
TATGTCTAAACATATGAGCCTGCTGGCAGACCTGAAGACAATGGTAGAAACGAAGA
AAGTTACAAGTTCAGGCGTTCTTCTCCTAGACAACTATACCGATCGCATTCAGGTCC
TTCGCAACATGGTACACTGTGCAGACCTGAGCAACCCCACCAAGTCCTTGGAATTGT
ATCGGCAATGGACAGACCGCATCATGGAGGAATTTTTCCAGCAGGGAGACAAAGAG
CGGGAGAGGGGAATGGAAATTAGCCCAATGTGTGATAAACACACAGCTTCTGTGGA
AAAATCCCAGGTTGGTTTCATCGACTACATTGTCCATCCATTGTGGGAGACATGGGC
AGATTTGGTACAGCCTGATGCTCAGGACATTCTCGATACCTTAGAAGATAACAGGAA
CTGGTATCAGAGCATGATACCTCAAAGTCCCTCACCACCACTGGACGAGCAGAACA
GGGACTGCCAGGGTCTGATGGAGAAGTTTCAGTTTGAACTGACTCTCGATGAGGAA
GATTCTGAAGGACCTGAGAAGGAGGGAGAGGGACACAGCTATTTCAGCAGCACAAA
GACGCTTTGTGTGATTGATCCAGAAAACAGAGATTCCCTGGGAGAGACTGACATAG
ACATTGCAACAGAAGACAAGTCCCCCGTGGATACATAATCCCCCTCTCCCTGTGGAG
ATGAACATTCTATCCTTGATGAGCATGCCAGCTATGTGGTAGGGCCAGCCCACCATG
GGGGCCAAGACCTGCACGGACAAGGGCCACCTGGCCTTTCAGTTACTTGAGTTTGG
AGTCAGAAAGCAAGACCAGGAAGCAAATAGCAGCTCAGGAAATCCCACGGTTGACT
TGCCTTGATGGCAAGCTTGGTGGAGAGGGCTGAAGCTGTTGCTGGGGGCCGATTCTG
ATCAAGACACATGGCTTGAAAATGGAAGACACAAAACTGAGAGATCATTCTGCACT
AAGTTTCGGGAACTTATCCCCGACAGTGACTGAACTCACTGACTAATAACTTCATTT
ATGAATCTTCTCACTTGTCCCTTTGTCTGCCAACCTGTGTGCCTTTTTTGTAAAACATT
TTCATGTCTTTAAAATGCCTGTTGAATACCTGGAGTTTAGTATCAACTTCTACACAGA
TAAGCTTTCAAAGTTGACAAACTTTTTTGACTCTTTCTGAAAAGGGAAAGAAAATA
GTCTTCCTTCTTCTTGGGCAATATCCTTCACTTTACTACAGTTACTTTTGCAAACAG
ACAGAAAGGATACACTTCTAACCACATTTTACTTCCTTCCCCTGTTGTCCAGTCCAAC
TCCACAGTCACTCTTAAAACTTCTCTCTGTTTGCCTGCCTCCAACAGTACTTTTAACT
TTTTGCTGTAAACAGAATAAAATTGAACAAATTAGGGGGTAGAAAGGAGCAGTGGT
GTCGTTCACCGTGAGAGTCTGCATAGAACTCAGCAGTGTGCCCTGCTGTGTCTTGGA
CCCTGCCCCCACAGGAGTTGTACAGTCCCTGGCCCTGTTCCCTACCTCCTCTCTTCA
CCCCGTTAGGCTGTTTTCAATGTAATGCTGCCGTCCTTCTCTTGCACTGCCTTCTGCG
CTAACACCTCCATTCCTGTTTATAACCGTGTATTTATTACTTAATGTATATAATGTAA
TGTTTTGTAAGTTATTAATTTATATATCTAACATTGCCTGCCAATGGTGGTGTTAAAT
TTGTGTAGAAAACTCTGCCTAAGAGTTACGACTTTTTCTTGTAATGTTTTGTATTGTG
TATTATATAACCCAAACGTCACTTAGTAGAGACATATGGCCCCCTTGGCAGAGAGGA
CAGGGGTGGGCTTTTGTTCAAAGGGTCTGCCCTTTCCCTGCCTGAGTTGCTACTTCTG
CACAACCCCTTTATGAACCAGTTTTGGAAACAATATTCTCACATTAGATACTAAATG
GTTTATACTGAGCTTTTACTTTTGTATAGCTTGATAGGGCAGGGGGCAATGGGATG
TAGTTTTTACCCAGGTTCTATCCAAATCTATGTGGGCATGAGTTGGGTTATAACTGG

TABLE 5-continued

Nucleotide Sequences of Biodosimetry Biomarker Genes

ATCCTACTATCATTGTGGCTTTGGTTCAAAAGGAAACACTACATTTGCTCACAGATG
ATTCTTCTGAATGCTCCCGAACTACTGACTTTGAAGAGGTAGCCTCCTGCCTGCCATT
AAGCAGGAATGTCATGTTCCAGTTCATTACAAAAGAAAACAATAAAACAATGTGAA
TTTTTATAATAAAATGTGAACTGATGTAGCAAATTACGCAAATGTGAAGCCTCTTCT
GATAACACTTGTTAGGCCTCTTACTGATGTCAGTTTCAGTTTGTAAAATATGTTTCAT
GCTTTCAGTTCAGCATTGTGACTCAGTAATTACAGAAAATGGCACAAATGTGCATGA
CCAATGTATGTCTATGAACACTGCATTGTTTCAGGTGGACATTTTATCATTTTCAAAT
GTTTCTCACAATGTATGTTATAGTATTATTATTATATATTGTGTTCAAATGCATTCTA
AAGAGACTTTTATATGAGGTGAATAAAGAAAAGCATGATTAGATTAAAAAAA

SCARB1 (SEQ ID NO: 27; NM_005505.4).
GCTCAGGCCCCGCCCCTGCCGCCGGAATCCTGAAGCCCAAGGCTGCCCGGGGGCGG
TCCGGCGGCGCCGGCGATGGGGCATAAAACCACTGGCCACCTGCCGGGCTGCTCCT
GCGTGCGCTGCCGTCCCGGATCCACCGTGCCTCTGCGGCCTGCGTGCCCGGAGTCCC
CGCCTGTGTCGTCTCTGTCGCCGTCCCCGTCTCCTGCCAGGCGCGGAGCCCTGCGAG
CCGCGGGTGGGCCCCAGGCGCGCAGACATGGGCTGCTCCGCCAAAGCGCGCTGGGC
TGCCGGGGCGCTGGGCGTCGCGGGGCTACTGTGCGCTGTGCTGGGCGCTGTCATGAT
CGTGATGGTGCCGTCGCTCATCAAGCAGCAGGTCCTTAAGAACGTGCGCATCGACCC
CAGTAGCCTGTCCTTCAACATGTGGAAGGAGATCCCTATCCCCTTCTATCTCTCCGTC
TACTTCTTTGACGTCATGAACCCCAGCGAGATCCTGAAGGGCGAGAAGCCGCAGGT
GCGGGAGCGCGGGCCCTACGTGTACAGGGAGTTCAGGCACAAAAGCAACATCACCT
TCAACAACAACGACACCGTGTCCTTCCTCGAGTACCGCACCTTCCAGTTCCAGCCCT
CCAAGTCCCACGGCTCGGAGAGCGACTACATCGTCATGCCCAACATCCTGGTCTTGG
GTGCGGCGGTGATGATGGAGAATAAGCCCATGACCCTGAAGCTCATCATGACCTTG
GCATTCACCACCCTCGGCAACGTGCCTTCATGAACCGCACTGTGGGTGAGATCATG
TGGGGCTACAAGGACCCCCTTGTGAATCTCATCAACAAGTACTTTCCAGGCATGTTC
CCCTTCAAGGACAAGTTCGGATTATTTGCTGAGCTCAACAACTCCGACTCTGGGCTC
TTCACGGTGTTCACGGGGGTCCAGAACATCAGCAGGATCCACCTCGTGGACAAGTG
GAACGGGCTGAGCAAGGTTGACTTCTGGCATTCCGATCAGTGCAACATGATCAATG
GAACTTCTGGGCAAATGTGGCCGCCCTTCATGACTCCTGAGTCCTCGCTGGAGTTCT
ACAGCCCGGAGGCCTGCCGATCCATGAAGCTAATGTACAAGGAGTCAGGGGTGTTT
GAAGGCATCCCCACCTATCGCTTCGTGGCTCCCAAAACCCTGTTTGCCAACGGGTCC
ATCTACCCACCCAACGAAGGCTTCTGCCCGTGCCTGGAGTCTGGAATTCAGAACGTC
AGCACCTGCAGGTTCAGTGCCCCCTTGTTTCTCTCCCATCCTCACTTCCTCAACGCTG
ACCCGGTTCTGGCAGAAGCGGTGACTGGCCTGCACCCTAACCAGGAGGCACACTCC
TTGTTCCTGGACATCCACCCGGTCACGGGAATCCCCATGAACTGCTCTGTGAAACTG
CAGCTGAGCCTCTACATGAAATCTGTCGCAGGCATTGGACAAACTGGGAAGATTGA
GCCTGTGGTCCTGCCGCTGCTCTGGTTTGCAGAGAGCGGGGCCATGGAGGGGGAGA
CTCTTCACACATTCTACACTCAGCTGGTGTTGATGCCCAAGGTGATGCACTATGCCC
AGTACGTCCTCCTGGCGCTGGGCTGCGTCCTGCTGCTGGTCCCTGTCATCTGCCAAA
TCCGGAGCCAAGAGAAATGCTATTTATTTTGGAGTAGTAGTAAAAAGGGCTCAAAG
GATAAGGAGGCCATTCAGGCCTATTCTGAATCCCTGATGACATCAGCTCCCAAGGGC
TCTGTGCTGCAGGAAGCAAAACTGTAGGGTCCTGAGGACACCGTGAGCCAGCCAGG
CCTGGCCGCTGGGCCTGACCGGCCCCCAGCCCCTACACCCCGCCTTCTCCCGGACTC
TCCCAGCGGACAGCCCCCAGCCCCACAGCCTGAGCCTCCCAGCTGCCATGTGCCTG
TTGCACACCTGCACACACGCCCTGGCACACATACACACATGCGTGCAGGCTTGTGCA
GACACTCAGGGATGGAGCTGCTGCTGAAGGGACTTGTAGGGAGAGGCTCGTCAACA
AGCACTGTTCTGGAACCTTCTCTCCACGTGGCCCACAGGCCTGACCACAGGGGCTGT
GGGTCCTGCGTCCCCTTCCTGGGTGAGCCTGGCCTGTCCCGTTCAGCCGTTGGGCC
CAGGCTTCCTCCCCTCCAAGGTGAAACACTGCAGTCCCGGTGTGGTGGCTCCCCATG
CAGGACGGGCCAGGCTGGGAGTGCCGCCTTCCTGTGCCAAATTCAGTGGGGACTCA
GTGCCCAGGCCCTGGCCACGAGCTTTGGCCTTGGTCTACCTGCCAGGCCAGGCAAAG
CGCCTTTACACAGGCCTCGGAAAACAATGGAGTGAGCACAAGATGCCCTGTGCAGC
TGCCCGAGGGTCTCCGCCCACCCCGGCCGGACTTTGATCCCCCGAAGTCTTCACAG
GCACTGCATCGGGTTGTCTGGCGCCCTTTTCCTCCAGCCTAAACTGACATCATCCTAT
GGACTGAGCCGGCCACTCTCTGGCCGAAGTGGCCGCAGGCTGTGCCCCCGAGCTGC
CCCCACCCCCTCACAGGGTCCCTCAGATTATAGGTGCCCAGGCTGAGGTGAAGAGG
CCTGGGGGCCCTGCCTTCCGGGCGCTCCTGGACCCTGGGGCAAACCTGTGACCCTTT
TCTACTGGAATAGAAATGAGTTTTATCATCTTTGAAAAATAATTCACTCTTGAAGTA
ATAAACGTTTAAAAAAATGGGAAAAAAAAAAAAAAAAA

TMEM9B (SEQ ID NO: 28; NM_020644.2).
GTGCGCGAACGGCTCCGGCCCGCACGGGTCGCCAGAGGCGACTGTGTGACACTCGG
AGTTTGCTGGGGTCTCCGTGGGCGGGAGGACTTTCCAGCGCAATGGCGACTCCCTAA
GCCCCGCAGCTTCTGCGCCCGGGAAAGATATCCAAGAGATGCAAAGCTCTACTGGG
CCCAGGCTGCCACCCCAGAGGCCCCCTTCCGTCCCGGGGCCGGGGCTAGGCCAAGG
CGGGCACCAGGACTGCCCAGCCTCCCGGCCCTTCGCACTGGTAACCGGTTCCGGGGC
GGATGCTTTTTGCATCTGACCCGGCGCGCCCGGTGACGCCTTCGCGTCCAGACGGAA
GTGCGGGCGGAGGATCCCCAGCCGGGTCCCAAGCCTGTGCCTGAGCCTGAGCCTGA
GCCTGAGCCCGAGCCGGGAGCCGGTCGCGGGGGCTCCGGGCTGTGGGACCGCTGGG
CCCCCAGCGATGGCGACCCTGTGGGGAGGCCTTCTTCGGCTTGGCTCCTTGCTCAGC
CTGTCGTGCCTGGCGCTTTCCGTGCTGCTGCTGGCGCAGCTGTCAGACGCCGCCAAG
AATTTCGAGGATGTCAGATGTAAATGTATCTGCCCTCCCTATAAAGAAATTCTGGG
CATATTTATAATAAGAACATATCTCAGAAAGATTGTGATTGCCTTCATGTTGTGGAG
CCCATGCCTGTGCGGGGCCTGATGTAGAAGCATACTGTCTACGCTGTGAATGCAAA
TATGAAGAAAGAAGCTCTGTCACAATCAAGGTTACCATTATAATTTATCTCTCCATT
TTGGGCCTTCTACTTCTGTACATGGTATATCTTACTCTGGTTGAGCCCATACTGAAGA
GGCGCCTCTTTGGACATGCACAGTTGATACAGAGTGATGATGATATTGGGGATCACC

TABLE 5-continued

Nucleotide Sequences of Biodosimetry Biomarker Genes

AGCCTTTTGCAAATGCACACGATGTGCTAGCCCGCTCCCGCAGTCGAGCCAACGTGC
TGAACAAGGTAGAATATGCACAGCAGCGCTGGAAGCTTCAAGTCCAAGAGCAGCGA
AAGTCTGTCTTTGACCGGCATGTTGTCCTCAGCTAATTGGGAATTGAATTCAAGGTG
ACTAGAAAGAAACAGGCAGACAACTGGAAAGAACTGACTGGGTTTTGCTGGGTTTC
ATTTTAATACCTTGTTGATTTCACCAACTGTTGCTGGAAGATTCAAAACTGGAAGCA
AAAACTTGCTTGATTTTTTTTTCTTGTTAACGTAATAATAGAGACATTTTTAAAAGCA
CACAGCTCAAAGTCAGCCAATAAGTCTTTTCCTATTTGTGACTTTTACTAATAAAAAT
AAATCTGCCTGTAAATTATCTTGAAGTCCTTTACCTGGAACAAGCACTCTCTTTTTCA
CCACATAGTTTTAACTTGACTTTCAAGATAATTTTCAGGGTTTTTGTTGTTGTTGTTTT
TTGTTTGTTTGTTTTGGTGGGAGAGGGGAGGGATGCCTGGGAAGTGGTTAACAACTT
TTTTCAAGTCACTTTACTAAACAAACTTTTGTAAATAGACCTTACCTTCTATTTTCGA
GTTTCATTTATATTTTGCAGTGTAGCCAGCCTCATCAAAGAGCTGACTTACTCATTTG
ACTTTTGCACTGACTGTATTATCTGGGTATCTGCTGTGTCTGCACTTCATGGTAAACG
GGATCTAAAATGCCTGGTGGCTTTTCACAAAAAGCAGATTTTCTTCATGTACTGTGA
TGTCTGATGCAATGCATCCTAGAACAAACTGGCCATTTGCTAGTTTACTCTAAAGAC
TAAACATAGTCTTGGTGTGTGTGGTCTTACTCATCTTCTAGTACCTTTAAGGACAAAT
CCTAAGGACTTGGACACTTGCAATAAAGAAATTTTATTTTAAACCCAAGCCTCCCTG
GATTGATAATATATACACATTTGTCAGCATTTCCGGTCGTGGTGAGAGGCAGCTGTT
TGAGCTCCAATGTGTGCAGCTTTGAACTAGGGCTGGGGTTGTGGGTGCCTCTTCTGA
AAGGTCTAACCATTATTGGATAACTGGCTTTTTTCTTCCTATGTCCTCTTTGGAATGT
AACAATAAAAATAATTTTTGAAACATCCATCAGTGTATCTATCTATGTCTCCTAGTTT
TTTCCTCCTCCCTCTTTTGCTGTATAATGAGATTGAAGTATAAAGACATTTTGTACC
CTGTAAAAAAAA

PPP6R3 (SEQ ID NO: 29; XM_005274081).
AACTCAAGGCCTGCTTGATACGTCCGCCATTTTGGGCGCTTCGCTGATGGTGTCGGT
GAGCGCGTTTCCCGCCTGAGCGCAACTAGCGGCGGGTCGTGGGCACCTCCAGGAGA
GCTTGTTTCATATCCATATCCCACTGTATTCCTGCTAATCTGCTAATGCAGTAAATTG
GAGGGAAAACTGTTACCAGGATAACCTGTAATGGGCAAGGAGCCACAAAGAAGAAA
ACATTTCTTTTAATTTTTAAACTTGGTTTGAAAGACCAGCATGTTTTGGAAATTTGAT
CTTCACTCATCATCCCACATAGACACACTTCTAGAAAGAGAAGATGTAACACTGAAG
GAGTTAATGGATGAGGAAGATGTTTTACAGGAATGTAAAGCTCAGAACCGCAAACT
TATAGAGTTTCTGTTAAAAGCAGAATGTCTCGAAGATTTAGTCTCATTCATTATAGA
AGAACCACCTCAAGACATGGATGAAAAGATCAGATACAAGTATCCAAATATATCTT
GTGAGTTGCTCACTTCTGATGTCTCCCAGATGAATGATAGACTGGGAGAAGATGAAT
CCTTGCTAATGAAATTATATAGCTTCCTCCTAAACGATTCCCCTTTGAATCCACTACT
TGCCAGTTTCTTCAGCAAGGTGCTAAGTATTCTTATCAGCAGAAAACCAGAACAGAT
TGTGGATTTCTTAAAGAAGAAGCATGATTTTGTAGACCTTATTATAAAGCACATAGG
AACTTCTGCTATCATGGATTTGTTGCTCAGGCTCCTGACGTGTATCGAACCTCCACAG
CCCAGGCAAGATGTGCTGAATTGGTTAAATGAGGAGAAAATTATCGAAGGCTTGT
GGAAATAGTTCATCCATCGCAAGAAGAAGATCGACATTCAAATGCATCACAATCAC
TTTGTGAAATTGTTCGCCTGAGCAGAGACCAGATGTTACAAATTCAGAACAGTACAG
AGCCCGACCCCCTGCTTGCCACTCTAGAAAAGCAAGAAATTATAGAGCAGCTTCTAT
CAAATATTTTCCACAAGGAGAAAATGAGTCAGCCATAGTCAGTGCAATCCAGATA
TTGCTGACTTTACTTGAGACACGACGACCAACATTTGAAGGCCATATAGAGATCTGC
CCACCAGGCATGAGCCATTCAGCTTGTTCAGTAAACAAGAGTGTTCTAGAAGCCATC
AGAGGAAGACTTGGATCTTTTCATGAACTCCTGCTGGAGCCACCCAAGAAAAGTGT
GATGAAGACCACATGGGGTGTGCTGGATCCTCCTGTGGGGAATACCCGGTTGAATGT
CATTAGGTTGATATCCAGCCTGCTTCAAACCAATACCAGCAGTATAAATGGGGACCT
TATGGAGCTGAATAGCATTGGAGTCATATTGAACATGTTCTTCAAGTATACATGGAA
TAACTTTTTGCATACACAAGTGGAAATTTGTATTGCACTGATTCTTGCAAGTCCTTTT
GAAAACACAGAAAATGCCACAATTACCGATCAAGACTCCACTGGTGATAATTTGTT
ATTAAAACATCTTTTCCAAAAATGTCAATTAATAGAACGAATACTTGAAGCCTGGGA
AATGAATGAGAAGAAACAGGCTGAGGGAGGAAGACGGCATGTTACATGGGACAC
CTAACGAGGATAGCTAACTGTATCGTGCACAGCACTGACAAGGGCCCCAACAGTGC
ATTAGTGCAGCAGCTTATCAAAGATCTTCCCGACGAAGTCAGGGAACGATGGGAGA
CGTTCTGCACAAGCTCCTTAGGAGAAACTAACAAGAGGAACACGGTAGATCTAGTT
ACAACCTGCCATATTCATTCATCCAGTGATGATGAAATTGACTTTAAAGAAACGGGT
TTCTCACAGGATTCTTCTTTGCAGCAAGCCTTTTCTGATTATCAGATGCAACAAATGA
CGTCCAATTTTATTGACCAGTTTGGCTTCAACGATGAGAAGTTTGCAGATCAAGATG
ACATTGGCAATGTTTCTTTTGATCGAGTATCAGACATCAACTTTACTCTCAATACAAA
TGAAAGTGGAAATATTGCCTTGTTTGAAGCATGTGTAAGGAAAGAATACAACAGTT
TGATGATGGTGGCTCTGATGAGGAAGATATATGGGAGGAAAAGCACATCGCATTCA
CACCAGAATCCCAAAGACGATCCAGCTCGGGGAGTACAGACAGTGAGGAAAGTAC
AGACTCTGAAGAAGAAGATGGAGCAAAGCAAGACTTGTTTGAACCCAGCAGTGCCA
ACACGGAGGATAAAATGGAGGTGGACCTGAGTGAACCACCCAACTGGTCAGCTAAC
TTTGATGTCCCAATGGAAACAACCCACGGTGCTCCATTGGATTCTGTGGGATCTGAT
GTCTGGAGCACAGAGGAGCCGATGCCAACTAAAGAGACGGGCTGGGCTTCTTTTTC
AGAGTTCACGTCTTCCCTGAGCACAAAAGATTCTTTAAGGAGTAATTCTCCAGTGGA
AATGGAAACCAGCACTGAACCCATGGACCCTCTGACTCCCAGTGCGGCTGCCCTGG
CAGTGCAGCCAGAAGCGGCAGGCAGTGTGGCCATGGAAGCCAGCTCTGACGGAGA
GGAGGATGCAGAAAGTACAGACAAGGTAACTGAGACAGTGATGAATGGCGGCATG
AAGGAAAACGCTCAGCCTCACTGTAGATGCCAAGACAGAGACTGCGGTCTTCAAAG
TGAGGAAGGGAAACTGTCTACCTCTCAAGATGCTGCTTGTAAAGACGCAGAGGAGT
GTCCCGAGACTGCAGAGGCGAAGTGCGCGGCGCCCAGGCCTCCCAGCAGCAGTCCC
GAGCAGAGTGCCTCCGATGCCTGTCTGTTGCTCCTTAGGACTGGCCAACCAAGCGCA
CCAGGTGACACTTCAGTGAATGGCCCTGTATGACGGGTGACGTCTGCTGCTGCTGAC
TGAGGACTGCAGACCGCCACCACTCAGGGGCTCTGGAGGGGTCAGCTGGAGCCCAC

TABLE 5-continued

Nucleotide Sequences of Biodosimetry Biomarker Genes

```
CAAGCTGTCACTGCTGCACTCACTCTGCAAGGGATCAGGACCAGCAACCTTTATATT
CTAGATTCTAAGACATTGTACAGAGAAATTCAGAAGTGTAAAAATATTGCACATTGA
CAAATACCAAGAATTTTTGCGTATGTTTATATTGTATTGTTCTAAATAATGGGTAGCC
TGTGAAATAAGATCTTGCCACCCATGTAATAATAGTAGTAATACTATAGTTAAAATG
GCTGTAAGAATAGTTTTATAAAAGTGAATACACAGATCTATTGTATTTGAAACATAA
CTTTGACAATTATTAGTGTGACCAAAGTATTAGGCGGTTTTCATACATTTTTCACCTT
GTACAAAATTATGAATTCATTTTTCCTCCAGGCCGACAAGGAGTTGTAGAATGAAAA
TGCCCTCTAAGTGTTATTTTGGTTGTTCTAACTTACAAAAGTGATTTTGAATAAGAAA
TATTTGGTGTTCTTTTTATAACCAGTTTTTGATTGGTAATTGTTTTCTGTATTGTTTAA
AACGGATCAAAAATGTAAGTCTATTGGTAGAGATTAAGTAAAGTATTTATTGCTACA
TCATAGTTGATAAATTGATGTTATCGTAAAGCCATATGTTCTGTTCAAGTCTTGTTTG
CTTGAAATGATTATTCCTACAAGTGAAACACTAGACTATTTGGAGTGTATATGGCTT
GTGTTTTGGGATTTTTTTTTTTTTTTTGGCTTTTGTTTTTGTTGTTTTTTTGTTTCAT
TTGGTAGTTCATCTGCCTTTTAACCCATTCACCAAAATTTACCTTGTTAACAAGCATC
ACCAATGAACATTTCAGAGCAATCTGCATATTTAACAGACCTAAAATAAATCCTATT
AGGCAAGTCAGTTGAAAATGCTCGTGCTGCTAATGGAATTAGAGTGCGTTCATTTTA
CAGGCTAGTATTTTAAAAGTAGAAATCAAAATCTGGCACCGAAGCATGCTAATTGTT
TACTGTACCTTGTGAGGTTTTCACTCATAAATTTAAACCAGTGTATTTTTTTAGAACT
GGTTTGTGTATATATAGTGATTATGGATACTAATTCAATGTAATTTATAATTTTCT
ATGTCAATACAAAAATACATCACAGCCTTCTCAAACAGCTCAAGCAATATATTGTAT
ATTGCCATATCGTCTGGTGAAAGGGTTAAATTACTTCACCTCTTGCACTTTTAGATGC
AAATCAGTTTTTCATTTCTGTAATAGAAAATTATTCACGTATTTTTACATCATTTGTTT
TTCCTGACCAGTATTTAAAACCAAAAGGATATTCTGAAAAATGGCCAACAATTTTTT
TAGAAGTAGCATCCCAAGCAGCGTGCCTAAACATTACATTGCATATGGAAATAAAA
GAATCAAACGTCTAATGCCTTATTATTCTGATTTCCTTTTTCATTTTAAGTGGTGTG
GAGATTCCAGCACTCCCAGGACAGTGGAGTCAGCAGTAAGCCCTGGGACAGGTGGC
AAGGGTGGGTCCCTTGACCTTTGCACGCCTCCTCAGGAACCCCCTTTCCCGGGTGAG
CCCCTCTCTGAAGAGACTGTCCTTGGGCCTCCTCTGGAAGCAGCACCCCCAGAGGAC
AGGGCTCCTCCTGCTTGCCTCAGGGCTGCCTGACTTGAATGGCGTTGGACCTCGGGG
ATTACTGGTAGATAATATGCTCTGGTCTCGCCTGGTGGTGAGTTTTGCCAGCCATGG
CCAGGGTTTGGCTCCACTGGTGGCACACGTGGCCTCCGTGGTATGGACCTGGTGGCT
TCTCCATCCCACTGTGGCCTCTGTGGTATGGACCTGGTGGCTTCTCCATCCTACCCAA
GGTAACAGTGTCTTGCTTCATCCCACTGACTGCTGGGAGGAGCCTCTGGGACTTTT
CTTTGGGGCATCATTTTGTTTTGTCTTTCGTAGCAGGGAAAGGATATGACAATGGGG
AGGACAGTTCTTTTGGAGGTTGGAGGGGCCAAGCCAAGGACAGGAGCAAGTGTGCC
CTCATTTTGTTTCTACTTTTAATTTCTGTGTGTTGGCCATACTGAATTATGAGACTAA
CAGATGTCTACAATACAATACCTGTATTCAAAATAACAAAAATAAAGCCTGATTCTT
TGTTTCTAGAAA
```

We claim:

1. A method for estimating absorbed dose of ionizing radiation exposure received by a subject, comprising (i) determining the mRNA expression levels of mRNAs comprising at least three of SEQ ID NOs: 6, 8, 9, 10 or 14 in a stabilized blood sample comprising mRNA from the subject by contacting the mRNA or cDNA derived therefrom with a plurality of primer pairs, each pair comprising primers of at least 10 nucleotides, that are directed to at least three of SEQ ID NOs: 6, 8, 9, 10, or 14 or the complementary sequences thereof under conditions suitable for amplification to obtain an expression profile; and (ii) transforming the gene expression profile into an estimate of absorbed radiation dose for the subject based on a mathematical algorithm.

2. The method of claim 1, further comprising treating the subject based on the absorbed dose of radiation determined in step (ii).

3. The method of claim 1, wherein the absorbed dose of ionizing radiation is determined within about seven days of subject exposure to ionizing radiation.

4. The method of claim 1, further comprising obtaining the blood sample from the subject prior to step (i).

5. The method of claim 1, wherein transforming in step (ii) comprises calculating an estimate of absorbed radiation dose from a fluorescence value obtained by contacting in vitro an mRNA sample from a human subject suspected of suffering from radiation exposure or a cDNA derived therefrom to a nucleic acid probe set and a thermostable polymerase under PCR conditions suitable for amplification of the mRNA or cDNA.

6. The method of claim 5, wherein the nucleic acid probe set comprises a plurality of nucleic acid probes of at least 10 nucleotides each that are directed to at least three of SEQ ID NOs: 6, 8, 9, 10, or 14 or the complementary sequences thereof, the nucleic acid probe set further comprising a probe detectably labeled with a fluorescent dye and a quencher and configured for PCR amplification.

* * * * *

UNITED STATES PATENT AND TRADEMARK OFFICE
CERTIFICATE OF CORRECTION

| | | |
|---|---|---|
| PATENT NO. | : 10,787,710 B2 | Page 1 of 1 |
| APPLICATION NO. | : 16/532138 | |
| DATED | : September 29, 2020 | |
| INVENTOR(S) | : Joshua LaBaer et al. | |

It is certified that error appears in the above-identified patent and that said Letters Patent is hereby corrected as shown below:

In the Specification

Column 6, Line 10, "PPP2RIA" should be --PPP2R1A--.

Column 6, Line 30, "XAFJ" should be --XAF1--.

Column 6, Line 45, "1-2949" should be --1-29--.

Column 13, Line 23, "PPP2RIA" should be --PPP2R1A--.

Column 13, Line 51, "SP10" should be --SP110--.

Signed and Sealed this
Twenty-sixth Day of July, 2022

Katherine Kelly Vidal
*Director of the United States Patent and Trademark Office*

SEQUENCE LISTING

<160> NUMBER OF SEQ ID NOS: 31

<210> SEQ ID NO 1
<211> LENGTH: 4184
<212> TYPE: DNA
<213> ORGANISM: Homo sapiens

<400> SEQUENCE: 1

```
atttaagggc cgcctctcc tggctcacag ctgcttgctg ctccagcctt gccctccag      60 agctgccgga cgctcgcggg tctcggaacg catcccgccg cggggcttc ggccgtggca     120 tgggcgccgc gggcctgctc gggtttttct tggctctcgt cgcaccgggg gtcctcggga    180
tttcttgtgg ctctcctccg cctatcctaa atggccggat tagttattat tctaccccca    240
ttgctgttgg taccgtgata aggtacagtt gttcaggtac cttccgcctc attggagaaa    300
aaagtctatt atgcataact aaagacaaag tggatggaac ctgggataaa cctgctccta    360
aatgtgaata tttcaataaa tattcttctt gccctgagcc catagtacca ggaggataca    420
aaattagagg ctctacaccc tacagacatg gtgattctgt gacatttgcc tgtaaaacca    480
acttctccat gaacggaaac aagtctgttt ggtgtcaagc aaataatatg tggggccga    540 cacgactacc aacctgtgta agtgttttcc ctctcgagtg tccagcactt cctatgatcc    600
acaatggaca tcacacaagt gagaatgttg gctccattgc tccaggattg tctgtgactt    660
acagctgtga atctggttac ttgcttgttg gagaaaagat cattaactgt ttgtcttcgg    720
```

```
gaaaatggag tgctgtcccc cccacatgtg aagaggcacg ctgtaaatct ctaggacgat    780
ttcccaatgg gaaggtaaag gagcctccaa ttctccgggt tggtgtaact gcaaactttt    840
tctgtgatga agggtatcga ctgcaaggcc caccttctag tcggtgtgta attgctggac    900
agggagttgc ttggaccaaa atgccagtat gtgaagaaat tttttgccca tcacctcccc    960
ctattctcaa tggaagacat ataggcaact cactagcaaa tgtctcatat ggaagcatag   1020
tcacttacac ttgtgacccg gacccagagg aaggagtgaa cttcatcctt attggagaga   1080
gcactctccg ttgtacagtt gatagtcaga agactgggac ctggagtggc cctgccccac   1140
gctgtgaact ttctacttct gcggttcagt gtccacatcc ccagatccta agaggccgaa   1200
tggtatctgg gcagaaagat cgatatacct ataacgacac tgtgatattt gcttgcatgt   1260
ttggcttcac cttgaagggc agcaagcaaa tccgatgcaa tgcccaaggc acatgggagc   1320
catctgcacc agtctgtgaa aaggaatgcc aggcccctcc taacatcctc aatgggcaaa   1380
aggaagatag acacatggtc cgctttgacc ctggaacatc tataaaatat agctgtaacc   1440
ctggctatgt gctggtggga aagaatccta cagtgtac ctctgagggg gtgtggacac   1500
cccctgtacc ccaatgcaaa gtggcagcgt gtgaagctac aggaaggcaa ctcttgacaa   1560
aaccccagca ccaatttgtt agaccagatg tcaactcttc ttgtggtgaa gggtacaagt   1620
taagtgggag tgtttatcag gagtgtcaag gcacaattcc ttggtttatg agattcgtc    1680 tttgtaaaga aatcacctgc ccaccacccc ctgttatcta caatgggca cacaccggga    1740 gttccttaga agattttcca tatggaacca cggtcactta cacatgtaac cctgggccag   1800
aaagaggagt ggaattcagc ctcattggag agagcaccat ccgttgtaca agcaatgatc   1860
aagaaagagg cacctggagt ggccctgctc ccctgtgtaa actttccctc cttgctgtcc   1920
agtgctcaca tgtccatatt gcaaatggat acaagatatc tggcaaggaa gccccatatt   1980
tctacaatga cactgtgaca ttcaagtgtt atagtggatt tactttgaag ggcagtagtc   2040
agattcgttg caaagctgat aacacctggg atcctgaaat accagtttgt gaaaaaggct   2100
gccagtcacc tcctgggctc caccatggtc gtcatacagg tggaaatacg gtcttctttg   2160
tctctgggat gactgtagac tacacttgtg accctggcta tttgcttgtg ggaaacaaat   2220
ccattcactg tatgccttca ggaaattgga gtccttctgc cccacggtgt gaagaaacat   2280
gccagcatgt gagacagagt cttcaagaac ttccagctgg ttcacgtgtg gagctagtta   2340
atacgtcctg ccaagatggg taccagttga ctggacatgc ttatcagatg tgtcaagatg   2400
ctgaaaatgg aatttggttc aaaaagattc cactttgtaa agttattcac tgtcaccctc   2460
caccagtgat tgtcaatggg aagcacacag gcatgatggc agaaaacttt ctatatggaa   2520
atgaagtctc ttatgaatgt gaccaaggat tctatctcct gggagagaaa aaattgcagt   2580
gcagaagtga ttctaaagga catggatctt ggagcgggcc ttccccacag tgcttacgat   2640
ctcctcctgt gactcgctgc cctaatccag aagtcaaaca tgggtacaag ctcaataaaa   2700
cacattctgc atattcccac aatgacatag tgtatgttga ctgcaatcct ggcttcatca   2760
tgaatggtag tcgcgtgatt aggtgtcata ctgataacac atgggtgcca ggtgtgccaa   2820
cttgtatcaa aaaagccttc ataggggtgtc cacctccgcc taagacccct aacgggaacc   2880
atactggtgg aaacatagct cgattttctc ctggaatgtc aatcctgtac agctgtgacc   2940
aaggctacct gctggtggga gaggcactcc ttctttgcac acatgaggga acctggagcc   3000
aacctgcccc tcattgtaaa gaggtaaact gtagctcacc agcagatatg gatggaatcc   3060
```

-continued

| | |
|---|---|
| agaaagggct ggaaccaagg aaaatgtatc agtatggagc tgttgtaact ctggagtgtg | 3120 |
| aagatgggta tatgctggaa ggcagtcccc agagccagtg ccaatcggat caccaatgga | 3180 |
| accctcccct ggcggtttgc agatcccgtt cacttgctcc tgtcctttgt ggtattgctg | 3240 |
| caggtttgat acttcttacc ttcttgattg tcattacctt atacgtgata tcaaaacaca | 3300 |
| gagcacgcaa ttattataca gatacaagcc agaagaagc ttttcattta gaagcacgag | 3360 |
| aagtatattc tgttgatcca tacaacccag ccagctgatc agaagacaaa ctggtgtgtg | 3420 |
| cctcattgct tggaattcag cggaatattg attagaaaga aactgctcta atatcagcaa | 3480 |
| gtctctttat atggcctcaa gatcaatgaa atgatgtcat aagcgatcac ttcctatatg | 3540 |
| cacttattct caagaagaac atctttatgg taaagatggg agcccagttt cactgccata | 3600 |
| tactcttcaa ggactttctg aagcctcact tatgagatgc ctgaagccag gccatggcta | 3660 |
| taaacaatta catggctcta aaagttttg ccctttttaa ggaaggcact aaaaagagct | 3720 |
| gtcctggtat ctagacccat cttctttttg aaatcagcat actcaatgtt actatctgct | 3780 |
| tttggttata atgtgttttt aattatctaa agtatgaagc attttctggg gttatgatgg | 3840 |
| ctttaccttt attaggaagt atggttttat tttgatagta gcttcctcct ctggtggtgt | 3900 |
| taatcatttc attttaccc ttacttggtt tgagtttctc tcacattact gtatatactt | 3960 |
| tgcctttcca taatcactca gtgattgcaa tttgcacaag ttttttttaaa ttatgggaat | 4020 |
| caagatttaa tcctagagat ttggtgtaca attcaggctt tggatgtttc tttagcagtt | 4080 |
| ttgtgataag ttctagttgc ttgtaaaatt tcacttaata atgtgtacat tagtcattca | 4140 |
| ataaattgta attgtaaaga aaacatacaa aaaaaaaaa aaaa | 4184 |

<210> SEQ ID NO 2
<211> LENGTH: 1442
<212> TYPE: DNA
<213> ORGANISM: Homo sapiens

<400> SEQUENCE: 2

| | |
|---|---|
| agtcgggcag ctctccgggc cggcgtggga gcccgcgctc caaagcccgg tgggggagg | 60 |
| ggcgctcacg caaccgccac tgtctggagc gggctcgcct ctgcggcggc actcaccgcc | 120 |
| cgggctttac tgaagcggag tctagcatgt gcggctgctc cacagcggtg tgggtggcgg | 180 |
| cggctcctct gcagcagcct cggcagtagg ggtcacggtg gccaagccca ccgtggagct | 240 |
| catctgagag ttgtaaggta cgggactgcc tcggtctttg ggacgccccg tctggtagca | 300 |
| tcccagatcc agcacgttcc ttccggcccc gcaccccggc ccgtgcctc acaccccgct | 360 |
| accccatgca tccagactct aaggcagccc ctgcatctca gtcctgacat cgctgtccct | 420 |
| ggagcatcct ccgctggagc tggagcttga caggatcggc ttcgccgtcg cccagcgtct | 480 |
| ggcccaagac ggggcccacg tggtagtcag ccgccggaag cagcagaatg tggaccaggc | 540 |
| agtggccacg ctgcaggggg aggggctgag catgacgggc actgtgtgcc atgtggggaa | 600 |
| gatgaaggac tgggagcggc tggtggccac agtgagctgc agggaaatgg gcacagagcc | 660 |
| aggaggtgga aaagggagcc agcctgagcc tccttccctg cttttcctgga cagcattggg | 720 |
| cttcagtcct tacaatgtca gtaaaacagc cttgctgggc tcaacaaga ccttggccat | 780 |
| agagctggcc ccaaggaaca ttagggtgaa ctgcctagca cctggactta tcaagactag | 840 |
| cttcagcagg atgctctgga tggacaagga aaagaggaa agcatgaaag aaaccctgcg | 900 |
| gataagaagg ttaggcgagc cagaggattc tcttggcatc gtgtctttcc tgtgctctga | 960 |
| agatgccagc tacctcactg gggaaacagt gatggtgggt ggaggaaccc cgtcccgcct | 1020 |

```
ctgaggaccc ggagacagcc cacaggccag agttgggctc tagctcctgg tgctgttcct   1080
gcattcaccc actggccttt cccacctctg ctcaccttac tgttcacctc atcaaatcag   1140
ttctgccctg tgaaaagatc cagccttccc tgccgtcaag gtggtgtctt actcgggatt   1200
cctgctgttg ttgtggcctt gggtaaaggc ctcccctgag aacacaggac aggcctgctg   1260
acaaggctga gtctaccttg gcaaagacca agatattttt tgcccaggcc actggggaat   1320
ttgaggggag atgagagaga aggaagctgg agtggaagga gcagagttgc aaattaacaa   1380
cttgcaaatg aggtgcaaat aaaatgcaga tgattgcgcg gctttgaatc gaaaaaaaaa   1440
aa                                                                 1442

<210> SEQ ID NO 3
<211> LENGTH: 2168
<212> TYPE: DNA
<213> ORGANISM: Homo sapiens

<400> SEQUENCE: 3
ggagttagcc tcgctcaggg cgcggctaag gcgcccagat ggcctgcggg cgccaccacg     60
tccctggtcc cagctcggga gcacatcaga ggcttagagg cgagtgggaa gggactcaga    120
cagtgcagga cgagaaacgc ccgcggcacc aaagcccctc agagcgtcgc cccgcctct    180 agttctagaa agtcagtttc ccggcactgg caccccggaa cctcaggggc tgccgagctg    240 gggggcgct caagctgcga ggatccgggc tgcccgcgag acgaggagcg ggcgcccagg     300
atggggtgca tgaagtccaa gttcctccag gtcggaggca atacattctc aaaaactgaa    360
accagcgcca gcccacactg tcctgtgtac gtgccggatc ccacatccac catcaagccg    420
gggcctaata gccacaacag caacacacca ggaatcaggg aggcaggctc tgaggacatc    480
atcgtggttg ccctgtatga ttacgaggcc attcaccacg aagacctcag cttccagaag    540
ggggaccaga tggtggtcct agaggaatcc ggggagtggt ggaaggctcg atccctggcc    600
acccggaagg agggctacat cccaagcaac tatgtcgccc gcgttgactc tctggagaca    660
gaggagtggt ttttcaaggg catcagccgg aaggacgcag agcgccaact gctggctccc    720
ggcaacatgc tgggctcctt catgatccgg gatagcgaga ccactaaagg aagctactct    780
ttgtccgtgc gagactacga ccctcggcag ggagataccg tgaaacatta caagatccgg    840
accctggaca cgggggcttt ctacatatcc ccccgaagca ccttcagcac tctgcaggag    900
ctggtggacc actacaagaa ggggaacgac gggctctgcc agaaactgtc ggtgccctgc    960
atgtcttcca gccccagaa gccttgggag aaagatgcct gggagatccc tcgggaatcc    1020
ctcaagctgg agaagaaact tggagctggg cagtttgggg aagtctggat ggccacctac    1080
aacaagcaca ccaaggtggc agtgaagacg atgaagccag ggagcatgtc ggtggaggcc    1140
ttcctggcag aggccaacgt gatgaaaact ctgcagcatg acaagctggt caaacttcat    1200
gcggtggtca ccaaggagcc catctacatc atcacggagt tcatggccaa ggaagcttg    1260 ctggactttc tgaaaagtga tgagggcagc aagcagccat gccaaaact cattgacttc    1320 tcagcccaga ttgcagaagg catggccttc atcgagcaga ggaactacat ccaccgagac    1380
ctccgagctg ccaacatctt ggtctctgca tcccctggtgt gtaagattgc tgactttggc    1440
ctggcccggg tcattgagga caacgagtac acggctcggg aaggggccaa gttccccatc    1500
aagtggacag ctcctgaagc catcaacttt ggctccttca ccatcaagtc agacgtctgg    1560
tcctttggta tcctgctgat ggagatcgtc acctacggcc ggatcccttg cccagggatg    1620
```

```
tcaaaccctg aagtgatccg agctctggag cgtggatacc ggatgcctcg cccagagaac    1680
tgcccagagg agctctacaa catcatgatg cgctgctgga aaaaccgtcc ggaggagcgg    1740
ccgaccttcg aatacatcca gagtgtgctg gatgacttct acacggccac agagagccag    1800
taccaacagc agccatgata gggaggacca gggcagggcc aggggtgcc caggtggtgg     1860 ctgcaaggtg gctccagcac catccgccag ggcccacacc cccttcctac tcccagacac    1920
ccaccctcgc ttcagccaca gtttcctcat ctgtccagtg ggtaggttgg actgaaaaat    1980 ctcttttga ctcttgcaat ccacaatctg acattctcag gaagccccca agttgatatt     2040
tctatttcct ggaatggttg gatttttagtt acagctgtga tttggaaggg aaactttcaa   2100
aatagtgaaa tgaatattta aataaaagat ataaatgcca aagtctttac caaaaaaaaa   2160
aaaaaaaa                                                             2168

<210> SEQ ID NO 4
<211> LENGTH: 4801
<212> TYPE: DNA
<213> ORGANISM: Homo sapiens

<400> SEQUENCE: 4 aaaggggaa aagaaagtgc ggcggaaagt aagaggctca ctggggaaga ctgccgggat       60
ccaggtctcc ggggtccgct ttggccagag gcgcggaagg aagcagtgcc cggcgacact     120
gcacccatcc cggctgcttt tgctgcgccc tctcagcttc ccaagaaagg catcgtcatg     180
tgatcatcac ctaagaacta gaacatcagc aggccctaga agcctcactc ttgcccctcc     240
ctttaatatc tcaaaggatg acacttctgt ggtgtgtagt gagtctctac ttttatggaa     300
tcctgcaaag tgatgcctca gaacgctgcg atgactgggg actagacacc atgaggcaaa    360
tccaagtgtt tgaagatgag ccagctcgca tcaagtgccc actctttgaa cacttcttga    420
aattcaacta cagcacagcc cattcagctg gccttactct gatctggtat tggactaggc    480
aggaccggga ccttgaggag ccaattaact tccgcctccc cgagaaccgc attagtaagg    540
agaaagatgt gctgtggttc cggcccactc tcctcaatga cactggcaac tatacctgca    600
tgttaaggaa cactacatat tgcagcaaag ttgcatttcc cttggaagtt gttcaaaaag    660
acagctgttt caattccccc atgaaactcc cagtgcataa actgtatata gaatatggca    720
ttcagaggat cacttgtcca aatgtagatg atattttcc ttccagtgtc aaaccgacta     780
tcacttggta tatgggctgt tataaaatac agaatttaa taatgtaata cccgaaggta     840
tgaacttgag tttcctcatt gccttaattt caaataatgg aaattacaca tgtgttgtta   900
catatccaga aaatggacgt acgtttcatc tcaccaggac tctgactgta aaggtagtag   960
gctctccaaa aaatgcagtg ccccctgtga tccattcacc taatgatcat gtggtctatg   1020
agaaagaacc aggagaggag ctactcattc cctgtacggt ctattttagt tttctgatgg   1080
attctcgcaa tgaggtttgg tggaccattg atggaaaaaa acctgatgac atcactattg   1140
atgtcaccat taacgaaagt ataagtcata gtagaacaga agatgaaaca gaaactcaga   1200
ttttgagcat caagaaagtt acctctgagg atctcaagcg cagctatgtc tgtcatgcta   1260
gaagtgccaa aggcgaagtt gccaaagcag ccaaggtgaa gcagaaagtg ccagctccaa   1320
gatacacagt ggaactggct tgtggttttg agccacagt cctgctagtg gtgattctca   1380
ttgttgttta ccatgtttac tggctagaga tggtcctatt ttaccgggct cattttggaa   1440
cagatgaaac cattttagat ggaaaagagt atgatattta tgtatcctat gcaaggaatg   1500
cggaagaaga agaatttgta ttactgaccc tccgtggagt tttggagaat gaatttggat   1560
```

```
acaagctgtg catctttgac cgagacagtc tgcctggggg aattgtcaca gatgagactt   1620
tgagcttcat tcagaaaagc agacgcctcc tggttgttct aagccccaac tacgtgctcc   1680
agggaaccca agccctcctg gagctcaagg ctggcctaga aaatatggcc tctcggggca   1740
acatcaacgt cattttagta cagtacaaag ctgtgaagga aacgaaggtg aaagagctga   1800
agagggctaa gacggtgctc acggtcatta aatggaaagg ggaaaaatcc aagtatccac   1860
agggcaggtt ctggaagcag ctgcaggtgg ccatgccagt gaagaaaagt cccaggcggt   1920
ctagcagtga tgagcagggc ctctcgtatt catctttgaa aaatgtatga aggaataat    1980 gaaaagggta aaaagaacaa ggggtgctcc aggaagaaag agtcccccca gtcttcattc   2040
gcagtttatg gtttcatagg caaaaataat ggtctaagcc tcccaatagg gataaattta   2100
gggtgactgt gtggctgact attctgcttc ctcaggcaac actaaagttt agaaagatat   2160
catcaacgtt ctgtcaccag tctctgatgc cactatgttc tttgcaggca aagacttgtt   2220
caatgcgaat ttccccttct acattgtcta tccctgtttt tatatgtctc cattctttt    2280 aaaatcttaa catatggagc agcctttcct atgaatttaa atatgccttt aaaataagtc   2340
actgttgaca gggtcatgag tttccgagta tagttttctt tttatcttat ttttactcgt   2400
ccgttgaaaa gataatcaag gcctacattt tagctgagga taatgaactt ttttcctcat   2460
tcggctgtat aatacataac cacagcaaga ctgacatcca cttaggatga tacaaagcag   2520
tgtaactgaa aatgtttctt ttaattgatt taaaggactt gtcttctata ccaccttgt    2580 cctcatctca ggtaattat gaatctatg taaacttgaa aaatatttct taatttttgt     2640
ttttgctcca gtcaattcct gattatccac aggtcaaccc acattttttc attccttctc   2700
cctatctgct tatatcgcat tgctcattta gagtttgcag gaggctccat actaggttca   2760
gtctgaaaga aatctcctaa tggtgctata gagagggagg taacagaaag actcttttag   2820 ggcattttc tgactcatga aaagagcaca gaaaaggatg tttggcaatt tgtcttttaa    2880
gtcttaacct tgctaatgtg aatactggga aagtgatttt ttctcactcg ttttgttgc    2940 tccattgtaa agggcggagg tcagtcttag tggccttgag agttgctttt ggcattaata   3000
ttctaagaga attaactgta tttcctgtca cctattcact agtgcaggaa atatacttgc   3060
tccaaataag tcagtatgag aagtcactgt caatgaaagt tgttttgttt gttttcagta   3120
atattttgct gttttaaga cttggaaaac taagtgcaga gttacagag tggtaaatat     3180 ctatgttaca tgtagattat acatatatat acacacgtgt atatgagata tatatcttat   3240
atctccacaa acacaaatta tatatataca tatccacaca catacattac atatatctgt   3300
gtatataaat ccacatgcac atgaaatata tatatatata aatttgtgt gtgtgtatgt    3360 gtatgtatat gactttaaat agctatgggt acaatattaa aaaccactgg aactcttgtc   3420
cagtttttaa attatgtttt tactggaatg ttttttgtgtc agtgttttct gtacatatta   3480
tttgttaatt cacagctcac agagtgatag ttgtcatagt tcttgccttc cctaagttta   3540
tataaataac ttaagtattg ctacagttta tctaggttgc agtggcatct gctgtgcaca   3600
gagcttccat ggtcactgct aagcagtagc cagccatcgg gcattaattg atttcctact   3660
atattcccag cagacacatt tagaaactaa gctatgttaa cctcagtgct caactatttg   3720
aactgttgag tgataaagga acaaatata actgtaaatg aatcttggta tcctgtgaaa    3780
cagaataatt cgtaatttaa gaaagccctt atcccggtaa catgaatgtt gatgaacaaa   3840
tgtaaaatta tatcctatat ttaagtaccc ataataaatc atttccctct ataagtgtta   3900
```

| | |
|---|---|
| ttgattattt taaattgaaa aaagtttcac ttggatgaaa aaagtagaaa agtaggtcat | 3960 |
| tcttggatct acttttttt agccttatta atatttttcc ctattagaaa ccacaattac | 4020 |
| tccctctatt aacccttcac ttactagacc agaaaagaac ttattccaga taagctttga | 4080 |
| atatcaattc ttacataaac tttaggcaaa cagggaatag tctagtcacc aaaggaccat | 4140 |
| tctcttgcca atgctgcatt cctttttgcac ttttggattc catatttatc ccaaatgctg | 4200 |
| ttgggcaccc ctagaaatac cttgatgttt tttctattta tatgcctgcc tttggtactt | 4260 |
| aattttacaa atgctgtaat ataaagcata tcaagtttat gtgatacgta tcattgcaag | 4320 |
| agaatttgtt tcaagatttt tttttaatgt tccagaagat ggccaataga gaacattcaa | 4380 |
| gggaaatggg gaaacataat ttagagaaca agaacaaacc atgtctcaaa ttttttttaaa | 4440 |
| aaaaattaat ggttttaaat atatgctata gggacgttcc atgcccaggt taacaaagaa | 4500 |
| ctgtgatata tagagtgtct aattacaaaa tcatatacga tttatttaat tctcttctgt | 4560 |
| attgtaactt agatgattcc caaggactct aataaaaaat cacttcattg tatttggaaa | 4620 |
| caaaaacatc attcattaat tacttatttt cttcccatag gttttaatat tttgagagtg | 4680 |
| tcttttttat ttcattcatg aacttttgta tttttcattt ttcatttgat ttgtaaattt | 4740 |
| acttatgtta aaataaaacc atttattttc agctttgaat tttaaaaaaa aaaaaaaaa | 4800 |
| a | 4801 |

<210> SEQ ID NO 5
<211> LENGTH: 1514
<212> TYPE: DNA
<213> ORGANISM: Homo sapiens

<400> SEQUENCE: 5

| | |
|---|---|
| gagccctgcc tgcgcccgcc cccgaagcgg cgcgggacgc ctggcgccgt ccgcgatccg | 60 |
| cagggctgcc cgcttaggct taggcccggc ccgctggcaa agccgagccg cagcattta | 120 |
| tttcgttcgt ggtttccgca caggctgag tttcgtgggt tgggtcgtac ttgggacctc | 180 |
| ggcgaagagg acccgtttat tttttttct ttccaaaatg gcagcctcca gtcgcgcaca | 240 |
| agtgttatct ctgtaccggg cgatgctgag agagagcaag cgtttcagcg cctacaatta | 300 |
| cagaacatat gctgtcagga ggataagaga tgccttcaga gaaaataaaa atgtaaagga | 360 |
| tcctgtagaa attcaaaccc tagtgaataa agccaagaga gaccttggag taattcgtcg | 420 |
| acaggtccac attggccaac tgtattcaac tgacaagctg atcattgaga atcgagacat | 480 |
| gcccaggacc tagcaagccg gggaccagcc accagtggcg gccagggacc accttcagca | 540 |
| tccactctct gtttgagatg ggggctccca aaaccagctt acaatagcct tttgcgctgc | 600 |
| ctgtcctgtg ggagctgata aaccaagtca catttgcatt ctgttgcagg cttagtgaaa | 660 |
| aaggactgct gtcttttcctt ggttcaagtg ttagaatgga gagctggagt tcgttcagaa | 720 |
| tagtgctgtg tgttaccacg tctccccctgc acccattcc tacccttgtag ctcatgacca | 780 |
| ttgtgtatag catttctaca ctttgttttct tggtccttgg caataaaaag aatgatctcc | 840 |
| ctgagccttt gaccccagat aaaccctcc caattaatgc attttcattt cctactgata | 900 |
| caaggcctgg agagggctgt tgggggcct caggagggt tcaactctga gacgagaact | 960 |
| gccttggtga aggcaagttc aagcaccact tgagactggg ggcagcatgg agtagggcag | 1020 |
| ggctacgggg atacacggtg caccctgcaa cttatacctg agcccagtac aacaaaggtg | 1080 |
| acgggtgtga aggtacacac ccagagatgg agcactgcag atcagcaacc tcagccccac | 1140 |
| ctgggaattt gctggaaatg caggctcaag cccctcccca cacctggtga atgagagagc | 1200 |

```
cccagcctga cccaagccca gggcgactcc catacccTga agcctggggc atgctgggca    1260
gcaccggtgc ccaaatctgg ctggtggaca aagcacctg agagttgga gagctttta      1320 aaaagacatc tctcagcact tccctctctg cagattctga ctcagtaagt gagggggtgag   1380 gcacagtcat ttttctctat tctgaagctc tcccactgtt ttcaatgttt aaccaactgg   1440 ggaccctgc tctttaagta tattacaggt aataaagata ttgtttgtat gcttttaaaa    1500
aaaaaaaaaa aaaa                                                      1514

<210> SEQ ID NO 6
<211> LENGTH: 2379
<212> TYPE: DNA
<213> ORGANISM: Homo sapiens

<400> SEQUENCE: 6
gacccccgag ctgtgctgct cgcggccgcc accgccgggc cccggccgtc cctggctccc     60
ctcctgcctc gagaagggca gggcttctca gaggcttggc gggaaaaaga acggagggag    120
ggatcgcgct gagtataaaa gccggttttc ggggctttat ctaactcgct gtagtaattc    180
cagcgagagg cagagggagc gagcgggcgg ccggctaggg tggaagagcc gggcgagcag    240
agctgcgctg cgggcgtcct gggaagggag atccggagcg aatagggggc ttcgcctctg    300
gcccagccct cccgctgatc cccagccag cggtccgcaa cccttgccgc atccacgaaa     360
cttTgcccat agcagcgggc gggcactttg cactggaact acaacaccc gagcaaggac     420 gcgactctcc cgacgcgggg aggctattct gcccatttgg ggacacttcc ccgccgctgc    480
caggacccgc ttctctgaaa ggctctcctt gcagctgctt agacgctgga ttttttcgg    540 gtagtggaaa accagcagcc tcccgcgacg atgcccctca acgttagctt caccaacagg    600
aactatgacc tcgactacga ctcggtgcag ccgtatttct actgcgacga ggaggagaac    660
ttctaccagc agcagcagca gagcgagctg cagccccccgg cgcccagcga ggatatctgg    720
aagaaattcg agctgctgcc caccccgccc ctgtccccta gccgccgctc cgggctctgc    780
tcgccctcct acgttgcggt cacacccctt cccttcgggg agacaacga cggcggtggc    840 gggagcttct ccacggccga ccagctggag atggtgaccg agctgctggg aggagacatg    900
gtgaaccaga gttTcatctg cgacccggac gacgagacct tcatcaaaaa catcatcatc    960
caggactgta tgtggagcgg cttctcggcc gccgccaagc tcgtctcaga aagctggcc    1020 tcctaccagg ctgcgcgcaa agacagcggc agcccgaacc ccgccgcgg ccacagcgtc   1080 tgctccacct ccagcttgta cctgcaggat ctgagcgccg ccgcctcaga gtgcatcgac   1140
ccctcggtgg tcttcccta ccctctcaac gacagcagct cgcccaagtc ctgcgcctcg    1200
caagactcca gcgccttctc tccgtcctcg gattctctgc tctcctcgac ggagtcctcc    1260
ccgcagggca gccccgagcc cctggtgctc catgaggaga caccgccac caccagcagc   1320 gactctgagg aggaacaaga agatgaggaa gaaatcgatg ttgtttctgt ggaaaagagg    1380
caggctcctg gcaaaaggtc agagtctgga tcaccttctg ctggaggcca cagcaaacct   1440
cctcacagcc cactggtcct caaggaggtgc cacgtctcca cacatcagca caactacgca    1500
gcgcctccct ccactcggaa ggactatcct gctgccaaga gggtcaagtt ggacagtgtc    1560
agagtcctga cagatcag caacaaccga aaatgcacca gccccaggtc ctcggacacc    1620
gaggagaatg tcaagaggcg aacacacaac gtcttggagc gccagaggag gaacgagcta    1680
aaacggagct ttttTgccct gcgtgaccag atcccggagt tggaaaacaa tgaaaaggcc    1740
```

| | |
|---|---:|
| cccaaggtag ttatccttaa aaaagccaca gcatacatcc tgtccgtcca agcagaggag | 1800 |
| caaaagctca tttctgaaga ggacttgttg cggaaacgac gagaacagtt gaaacacaaa | 1860 |
| cttgaacagc tacggaactc ttgtgcgtaa ggaaaagtaa ggaaaacgat tccttctaac | 1920 |
| agaaatgtcc tgagcaatca cctatgaact tgtttcaaat gcatgatcaa atgcaacctc | 1980 |
| acaaccttgg ctgagtcttg agactgaaag atttagccat aatgtaaact gcctcaaatt | 2040 |
| ggactttggg cataaaagaa cttttttatg cttaccatct ttttttttc tttaacagat | 2100 |
| ttgtatttaa gaattgtttt taaaaaattt taagatttac acaatgtttc tctgtaaata | 2160 |
| ttgccattaa atgtaaataa ctttaataaa acgtttatag cagttacaca gaatttcaat | 2220 |
| cctagtatat agtacctagt attataggta ctataaaccc taattttttt tatttaagta | 2280 |
| cattttgctt tttaaagttg attttttttct attgttttta gaaaaaataa aataactggc | 2340 |
| aaatatatca ttgagccaaa tcttaaaaaa aaaaaaaaa | 2379 |

<210> SEQ ID NO 7
<211> LENGTH: 3215
<212> TYPE: DNA
<213> ORGANISM: Homo sapiens

<400> SEQUENCE: 7

| | |
|---|---:|
| aacccggggc tccgagccgg agccgagtct gcgcctgggg gaggaccatg cggcagtagc | 60 |
| agccatgctg ccctttctgc tggccacact gggcaccaca gccctcaaca acagcaaccc | 120 |
| caaggactac tgctacagcg cccgcatccg cagcactgtc ctgcagggcc tgccctttgg | 180 |
| gggcgtcccc accgtgctgg ctctcgactt catgtgcttc cttgcactgc tgttcttatt | 240 |
| ctctatcctc cggaaggtgg cctgggacta tgggcggctg gccttggtga cagatgcaga | 300 |
| caggcttcgg cggcaggaga gggaccgagt ggaacaggaa tatgtggctt cagctatgca | 360 |
| cggggacagc catgaccggt atgagcgtct cacctctgtc tccagctccg ttgactttga | 420 |
| ccaaagggac aatggtttct gttcctggct gacagccatc ttcaggataa aggatgatga | 480 |
| gatccgggac aaatgtgggg gcgatgccgt gcactacctg tcctttcagc ggcacatcat | 540 |
| cgggctgctg gtggttgtgg gcgtcctctc cgtaggcatc gtgctgcctg tcaacttctc | 600 |
| aggggacctg ctgagaacaa tgcctacag ctttgggaga ccaccattg ccaacttgaa | 660 |
| atcagggaac aacctgctat ggctgcacac ctccttcgcc ttcctgtatc tgctgctcac | 720 |
| cgtctacagc atgcgtagac acacctccaa gatgcgctac aaggaggatg atctggtgaa | 780 |
| gcggaccctc ttcatcaatg gaatctccaa atatgcagag tcagaaaaga tcaagaagca | 840 |
| ttttgaggaa gcctaccca actgcacagt tctcgaagcc cgcccgtgtt acaacgtggc | 900 |
| tcgcctaatg ttcctcgatg cagagaggaa gaaggccgag cggggaaagc tgtacttcac | 960 |
| aaacctccag agcaaggaga cgtgcctac catgatcaac cccaagccct gtggccacct | 1020 |
| ctgctgctgt gtggtgcgag gctgtgagca ggtggaggcc attgagtact acacaaagct | 1080 |
| ggagcagaag ctgaaggaag actacaagcg ggagaaggag aaggtgaatg agaagcctct | 1140 |
| tggcatggcc tttgtcacct tccacaatga ctatcacc gccatcatcc tgaaggactt | 1200 |
| caacgtgtgt aaatgccagg gctgcacctg ccgtggggag ccacgcccct catcctgcag | 1260 |
| cgagtccctg cacatctcca actggaccgt gtcctatgcc cctgaccctc agaacatcta | 1320 |
| ctgggagcac ctctccatcc gaggcttcat ctggtggctg cgctgcctgg tcatcaatgt | 1380 |
| cgtcctcttc atcctcctct tcttcctcac cactccagcc atcatcatca ccaccatgga | 1440 |
| caagttcaac gtcaccaagc ctgtggagta cctcaacaac cccatcatca cccagttctt | 1500 |

```
cccacccctg ctgctgtggt gcttctcggc cctccttccc accatcgtct actactcagc    1560
cttctttgaa gcccactgga cacgctctgg ggagaacagg acaaccatgc acaagtgcta    1620
cactttcctc atcttcatgg tgctgctcct accctcgctg ggactgagca gcctggacct    1680
cttcttccgc tggctctttg ataagaaatt cttggctgag gcagctattc ggtttgagtg    1740
tgtgttcctg cccgacaacg gcgccttctt cgtgaactac gtcattgcct cagcctttat    1800
cggcaacgcc atggacctgc tgcgcatccc aggcctgctc atgtacatga tccggctctg    1860
cctggcgcgc tcggccgccg agaggcgcaa cgtgaagcgg catcaggcct acgagttcca    1920
gtttggcgca gcctacgcct ggatgatgtg cgtcttcacg gtggtcatga cctacagtat    1980
cacctgcccc atcatcgtgc ccttcgggct catgtacatg ctgctgaagc acctggtaga    2040
caggtacaat ctctactacg cctacctgcc ggccaagctg acaagaaga tccactcggg    2100 ggctgtgaac caggtggtgg ccgcgcccat cctctgcctc ttctggctgc tcttcttttc    2160
caccatgcgc acggggttcc tagctcccac gtctatgttc acatttgtgg tcctggtcat    2220
caccatcgtc atctgtctct gccacgtctg ctttggacac ttcaaatacc tcagtgccca    2280
caactacaag attgagcaca cggagacaga tactgtggac cccagaagca atggacggcc    2340
ccccactgct gctgctgtcc ccaaatctgc gaaatacatc gctcaggtgc tgcaggactc    2400
agaggtggac ggggatgggg atggggctcc tgggagctca ggggatgagc cccatcatc    2460 ctcatcccaa gatgaggagt tgctgatgcc acccgacgcc ctcacggaca cagacttcca    2520
gtcttgcgag gacagcctca tagagaatga gattcaccag taaggggagg aggggccct    2580 ggaggccaca tcctgcccca ccccaccccc actcccacgg acactaaaac gctaataatt    2640
tattagatct aaagccccctt cctcccccagc ccctgctttc attaaggtat ttaaacttgg    2700
gggtttcact gctctccccc atgatggagg gagggagccc cccaacctca gtgaggagag    2760
ccccgagccg gccccggggc aaagaggggg gcagagggag ttcccccaga tcagtaccc    2820 ccaccccctcc ccagctagta gcatgaccag gagagggtta atgagagcca agaggagtac    2880
ctggtgcacc tggtgccggt ggctggagac ctgggggggca ggtggatctg ggctgttcc    2940 ccccctccg ttttttccac cccacagttc ctcctgggat ctggccctcc agggaagtgg    3000
agcctccagc ccctagggga tgcatgaggg gggaggggt gctgagtggg aggaagagtc    3060
aggctcacag ctggggtggc ctggggtgg gggtgggcaa ggctgacact ggaaaatggg    3120
tttttgcact gtttttttt tggttttttt gttctttttt gtttttttcc tttaaaataa    3180
aaacaaagaa aagctctgaa aaaaaaaaaa aaaaa                              3215
```

<210> SEQ ID NO 8
<211> LENGTH: 2581
<212> TYPE: DNA
<213> ORGANISM: Homo sapiens

<400> SEQUENCE: 8

```
ccggggccag ggaccagtgg tgggaggagg ctgcggcgct agatgcggac acctggaccg      60
ccgcgccgag gctcccggcg ctcgctgctc ccgcggcccg cgccatgccc tcctacacgg     120
tcaccgtggc cactggcagc cagtggttcg ccggcactga cgactacatc tacctcagcc     180
tcgtgggctc ggcgggctgc agcgagaagc acctgctgga caagcccttc tacaacgact     240
tcgagcgtgg cgcggtggat tcatacgacg tgactgtgga cgaggaactg ggcgagatcc     300
agctggtcag aatcgagaag cgcaagtact ggctgaatga cgactggtac ctgaagtaca     360
```

```
tcacgctgaa gacgccccac ggggactaca tcgagttccc ctgctaccgc tggatcaccg    420
gcgatgtcga ggttgtcctg agggatggac gcgcaaagtt ggcccgagat gaccaaattc    480
acattctcaa gcaacaccga cgtaaagaac tggaaacacg gcaaaaacaa tatcgatgga    540
tggagtggaa ccctggcttc cccttgagca tcgatgccaa atgccacaag gatttacccc    600
gtgatatcca gtttgatagt gaaaaaggag tggactttgt tctgaattac tccaaagcga    660
tggagaacct gttcatcaac cgcttcatgc acatgttcca gtcttcttgg aatgacttcg    720
ccgactttga gaaaatcttt gtcaagatca gcaacactat ttctgagcgg tcatgaatc    780
actggcagga agacctgatg tttggctacc agttcctgaa tggctgcaac cctgtgttga    840
tccggcgctg cacagagctg cccgagaagc tcccggtgac cacggagatg gtagagtgca    900
gcctggagcg gcagctcagc ttggagcagg aggtccagca agggaacatt ttcatcgtgg    960
actttgagct gctggatggc atcgatgcca acaaaacaga cccctgcaca ctccagttcc   1020
tggccgctcc catctgcttg ctgtataaga acctggccaa caagattgtc cccattgcca   1080
tccagctcaa ccaaatcccg ggagatgaga accctatttt cctcccttcg gatgcaaaat   1140
acgactggct tttggccaaa atctgggtgc gttccagtga cttccacgtc caccagacca   1200
tcacccacct tctgcgaaca catctggtgt ctgaggtttt tggcattgca atgtaccgcc   1260
agctgcctgc tgtgcacccc attttcaagc tgctggtggc acacgtgaga ttcaccattg   1320
caatcaacac caaggcccgt gagcagctca tctgcgagtg tggcctcttt gacaaggcca   1380
acgccacagg gggcggtggg cacgtgcaga tggtgcagag ggccatgaag gacctgacct   1440
atgcctccct gtgctttccc gaggccatca aggcccgggg catggagagc aaagaagaca   1500
tcccctacta cttctaccgg gacgacgggc tcctggtgtg ggaagccatc aggacgttca   1560
cggccgaggt ggtagacatc tactacgagg gcgaccaggt ggtggaggag gacccggagc   1620
tgcaggactt cgtgaacgat gtctacgtgt acggcatgcg gggccgcaag tcctcaggct   1680
tccccaagtc ggtcaagagc cgggagcagc tgtcggagta cctgaccgtg gtgatcttca   1740
ccgcctccgc ccagcacgcc gcggtcaact tcggccagta cgactggtgc tcctggatcc   1800
ccaatgcgcc cccaaccatg cgagcccgc caccgactgc caagggcgtg gtgaccattg   1860
agcagatcgt ggacacgctg cccgaccgcg gccgctcctg ctggcatctg ggtgcagtgt   1920
gggcgctgag ccagttccag gaaaacgagc tgttcctggg catgtaccca gaagagcatt   1980
ttatcgagaa gcctgtgaag gaagccatgg cccgattccg caagaacctc gaggccattg   2040
tcagcgtgat tgctgagcgc aacaagaaga gcagctgcc atattactac ttgtccccag   2100
accggattcc gaacagtgtg gccatctgag cacactgcca gtctcactgt gggaaggcca   2160
gctgccccag ccagatggac tccagcctgc ctggcaggct gtctggccag gcctcttggc   2220
agtcacatct cttcctccga ggccagtacc tttccattta ttctttgatc ttcagggaac   2280
tgcatagatt gatcaaagtg taaacaccat agggacccat tctacacaga gcaggactgc   2340
acagcgtcct gtccacaccc agctcagcat ttccacacca agcagcaaca gcaaatcacg   2400
accactgata gatgtctatt cttgttggag acatgggatg attattttct gttctatttg   2460
tgcttagtcc aattccttgc acatagtagg tacccaattc aattactatt gaatgaatta   2520
agaattggtt gccataaaaa taaatcagtt catttaaaat gaaaaaaaaa aaaaaaaaa    2580
a                                                                  2581
```

<210> SEQ ID NO 9
<211> LENGTH: 2272

<212> TYPE: DNA
<213> ORGANISM: Homo sapiens

<400> SEQUENCE: 9

```
agtctccctc cagcgggcgg cgactccggg ttcccnctcg cgccctctcg cagaggctcg      60
ccccttccc cgcccaccgt ccctgcgagc gcgggcggcg gcgtgggcg tgtgcgcgcg       120
tgaaggacgc cgcctctctc tcgctcctgc gttcgcaggc ggcggctggc ggccggcttc     180
tcgctcgggc agcggcggcg gcggcggcgg cggcttccgg agtcccgctg cgaagatgct     240
caaagtcacg gtgccctcct gctccgcctc gtcctgctct tcggtcaccg ccagtgcggc     300
cccgggacc gcgagcctcg tcccggatta ctggatcgac ggctccaaca gggatgcgct      360
gagcgatttc ttcgaggtgg agtcggagct gggacggggt gctacatcca ttgtgtacag    420
atgcaaacag aaggggaccc agaagcctta tgctctcaaa gtgttaaaga aaacagtgga    480
caaaaaaatc gtaagaactg atataggagt tcttcttcgc ctctcacatc caaacattat    540
aaaacttaaa gagatatttg aaccccctac agaaatcagt ctggtcctag aactcgtcac    600
aggaggagaa ctgtttgata ggattgtgga aaagggatat tacagtgagc gagatgctgc    660
agatgccgtt aaacaaatcc tggaggcagt tgcttatcta catgaaaatg ggattgtcca    720
tcgtgatctc aaaccagaga atcttcttta tgcaactcca gccccagatg caccactcaa    780
aatcgctgat tttggactct ctaaaattgt ggaacatcaa gtgctcatga agacagtatg    840
tggaaccca gggtactgcg cacctgaaat tcttagaggt tgtgcctatg acctgaggt      900
ggacatgtgg tctgtaggaa taatcaccta catcttactt tgtggatttg aaccattcta   960
tgatgaaaga ggcgatcagt tcatgttcag gagaattctg aattgtgaat attactttat  1020
ctccccctgg tgggatgaag tatctctaaa tgccaaggac ttggtcagaa aattaattgt  1080
tttggatcca agaaacggc tgactacatt tcaagctctc cagcatccgt gggtcacagg   1140
taaagcagcc aattttgtac acatggatac cgctcaaaag aagctccaag aattcaatgc  1200
ccggcgtaag cttaaggcag cggtgaaggc tgtggtggcc tcttcccgcc tgggaagtgc  1260
cagcagcagc catggcagca tccaggagag ccacaaggct agccgagacc cttctccaat  1320
ccaagatggc aacgaggaca tgaaagctat tccagaagga gagaaaattc aaggcgatgg  1380
ggcccaagcc gcagttaagg gggcacaggc tgagctgatg aaggtgcaag ccttagagaa  1440
agttaaaggt gcagatataa atgctgaaga ggccccaaa atggtgccca aggcagtgga   1500
ggatgggata aaggtggctg acctggaact agaggagggc ctagcagagg agaagctgaa  1560
gactgtggag gaggcagcag ctcccagaga agggcaagga agctctgctg tgggttttga  1620
agttccacag caagatgtga tcctgccaga gtactaaaca gcttccttca gatctggaag  1680
ccaaacaccg gcatttatg tactttgtcc ttcagcaaga aaggtgtgga agcatgatat   1740
gtactatagt gattctgttt tgaggtgca aaaaacatac atatatacca gttggtaatt   1800
ctaacttcaa tgcatgtgac tgctttatga aaataatagt gtcttctatg gcatgtaatg  1860
gataccctaat accgatgagt aaatcttgc aagttaacac aacgtaacac ttaaaagcat   1920
acattttcag caaccagtgg cacatatttg aagtgaatag tagcaaattg ttttgctt     1980
gaaaatctag ccatcctaca tcctttggat ttcttcacaa ggcagtaatt cctttgaact   2040
actgcttagc taatactagg tagtgctaaa agacatgttc ccataacttt tacaacattt   2100
tactttttat cattgatgtg ttcaaactgt ttacaaggag atgcttatag atgatagttg  2160
tacatatgtg caaaaaaaaa tccacttgca atggtaagaa attgaagtat ccttaaaggc  2220
```

| | |
|---|---:|
| catgaagcca tatgtccta aaaaaaaaaa aaaaaaaaaa aaaaaaaaaa aa | 2272 |

<210> SEQ ID NO 10
<211> LENGTH: 2175
<212> TYPE: DNA
<213> ORGANISM: Homo sapiens

<400> SEQUENCE: 10

| | |
|---|---:|
| gttgtatatc agggccgcgc tgagctgcgc cagctgaggt gtgagcagct gccgaagtca | 60 |
| gttccttgtg gagccggagc tgggcgcgga ttcgccgagg caccgaggca ctcagaggag | 120 |
| gcgccatgtc agaaccggct ggggatgtcc gtcagaaccc atgcggcagc aaggcctgcc | 180 |
| gccgcctctt cggcccagtg gacagcgagc agctgagccg cgactgtgat gcgctaatgg | 240 |
| cgggctgcat ccaggaggcc cgtgagcgat ggaacttcga ctttgtcacc gagacaccac | 300 |
| tggagggtga cttcgcctgg gagcgtgtgc ggggccttgg cctgcccaag ctctaccttc | 360 |
| ccacggggcc ccggcgaggc cgggatgagt tgggaggagg caggcggcct ggcacctcac | 420 |
| ctgctctgct gcaggggaca gcagaggaag accatgtgga cctgtcactg tcttgtaccc | 480 |
| ttgtgcctcg ctcaggggag caggctgaag ggtccccagg tggacctgga gactctcagg | 540 |
| gtcgaaaacg gcggcagacc agcatgacag atttctacca ctccaaacgc cggctgatct | 600 |
| tctccaagag gaagccctaa tccgcccaca ggaagcctgc agtcctggaa gcgcgagggc | 660 |
| ctcaaaggcc cgctctacat cttctgcctt agtctcagtt tgtgtgtctt aattattatt | 720 |
| tgtgttttaa tttaaacacc tcctcatgta catacctgg ccgccccctg cccccagcc | 780 |
| tctggcatta gaattattta aacaaaaact aggcggttga atgagaggtt cctaagagtg | 840 |
| ctgggcatt ttattttatg aaatactatt taaagcctcc tcatcccgtg ttctcctttt | 900 |
| cctctctccc ggaggttggg tgggccggct tcatgccagc tacttcctcc tccccacttg | 960 |
| tccgctgggt ggtaccctct ggaggggtgt ggctccttcc catcgctgtc acaggcggtt | 1020 |
| atgaaattca ccccctttcc tggacactca gacctgaatt ctttttcatt tgagaagtaa | 1080 |
| acagatggca ctttgaaggg gcctcaccga gtgggggcat catcaaaaac tttggagtcc | 1140 |
| cctcacctcc tctaaggttg gcagggtga ccctgaagtg agcacagcct agggctgagc | 1200 |
| tggggacctg gtaccctcct ggctcttgat accccctct gtcttgtgaa ggcaggggga | 1260 |
| aggtggggtc ctggagcaga ccaccccgcc tgccctcatg gccctctga cctgcactgg | 1320 |
| ggagcccgtc tcagtgttga gccttttccc tctttggctc cctgtacct tttgaggagc | 1380 |
| cccagctacc cttcttctcc agctgggctc tgcaattccc ctctgctgct gtccctcccc | 1440 |
| cttgtccttt cccttcagta ccctctcagc tccaggtggc tctgaggtgc ctgtcccacc | 1500 |
| cccacccccca gctcaatgga ctggaagggg aagggacaca caagaagaag ggcaccctag | 1560 |
| ttctacctca ggcagctcaa gcagcgaccg ccccctcctc tagctgtggg ggtgagggtc | 1620 |
| ccatgtggtg gcacaggccc ccttgagtgg ggttatctct gtgttagggg tatatgatgg | 1680 |
| gggagtagat ctttctagga gggagacact ggcccctcaa atcgtccagc gaccttcctc | 1740 |
| atccacccca tccctcccca gttcattgca cttttgattag cagcggaaca aggagtcaga | 1800 |
| cattttaaga tggtggcagt agaggctatg gacagggcat gccacgtggg ctcatatggg | 1860 |
| gctgggagta gttgtctttc ctggcactaa cgttgagccc ctggaggcac tgaagtgctt | 1920 |
| agtgtacttg gagtattggg gtctgacccc aaacaccttc cagctcctgt aacatactgg | 1980 |
| cctgactgt tttctctcgg ctccccatgt gtcctggttc ccgttctcc acctagactg | 2040 |
| taaacctctc gagggcaggg accacaccct gtactgttct gtgtctttca cagctcctcc | 2100 |

| | | | | |
|---|---|---|---|---|
| cacaatgctg | aatatacagc | aggtgctcaa | taaatgattc | ttagtgactt | tacttgtaaa | 2160 |
| aaaaaaaaaa | aaaaa | | | | | 2175 |

<210> SEQ ID NO 11
<211> LENGTH: 2403
<212> TYPE: DNA
<213> ORGANISM: Homo sapiens

<400> SEQUENCE: 11

| | | | | | | |
|---|---|---|---|---|---|---|
| ggggccttgc | cttccgcact | cgggcgcagc | cgggtggatc | tcgagcaggt | gcggagcccc | 60 |
| gggcggcggg | cgcgggtgcg | agggatccct | gacgcctctg | tccctgtttc | tttgtcgctc | 120 |
| ccagcctgtc | tgtcgtcgtt | ttggcgcccc | cgcctccccg | cggtgcgggg | ttgcacaccg | 180 |
| atcctgggct | tcgctcgatt | tgccgccgag | gcgcctccca | gacctagagg | ggcgctggcc | 240 |
| tggagcagcg | ggtcgtctgt | gtcctctctc | ctctgcgccg | cgcccgggga | tccgaagggt | 300 |
| gcggggctct | gaggaggtga | cgcgcggggc | ctcccgcacc | ctggccttgc | ccgcattctc | 360 |
| cctctctccc | aggtgtgagc | agcctatcag | tcaccatgtc | cgcagcctgg | atcccggctc | 420 |
| tcggcctcgg | tgtgtgtctg | ctgctgctgc | cggggcccgc | gggcagcgag | ggagccgctc | 480 |
| ccattgctat | cacatgtttt | accagaggct | tggacatcag | gaaagagaaa | gcagatgtcc | 540 |
| tctgcccagg | gggctgccct | cttgaggaat | tctctgtgta | tgggaacata | gtatatgctt | 600 |
| ctgtatcgag | catatgtggg | gctgctgtcc | acaggggagt | aatcagcaac | tcaggggggac | 660 |
| ctgtacgagt | ctatagccta | cctggtcgag | aaaactattc | ctcagtagat | gccaatggca | 720 |
| tccagtctca | aatgctttct | agatggtctg | cttctttcac | agtaactaaa | ggcaaaagta | 780 |
| gtacacagga | ggcccacagga | caagcagtgt | ccacagcaca | tccaccaaca | ggtaaacgac | 840 |
| taaagaaaac | acccgagaag | aaaactggca | ataaagattg | taaagcagac | attgcatttc | 900 |
| tgattgatgg | aagctttaat | attgggcagc | gccgatttaa | tttacagaag | aattttgttg | 960 |
| gaaaagtggc | tctaatgttg | ggaattggaa | cagaaggacc | acatgtgggc | cttgttcaag | 1020 |
| ccagtgaaca | tcccaaaata | gaattttact | tgaaaaactt | tacatcagcc | aaagatgttt | 1080 |
| tgtttgccat | aaaggaagta | ggtttcagag | ggggtaattc | caatacagga | aaagccttga | 1140 |
| agcatactgc | tcagaaattc | ttcacggtag | atgctggagt | aagaaaaggg | atccccaaag | 1200 |
| tggtggtggt | atttattgat | ggttggccttt | ctgatgacat | cgaggaagca | ggcattgtgg | 1260 |
| ccagagagtt | tggtgtcaat | gtatttatag | tttctgtggc | caagcctatc | cctgaagaac | 1320 |
| tggggatggt | tcaggatgtc | acatttgttg | acaaggctgt | ctgtcggaat | aatggcttct | 1380 |
| tctcttacca | catgcccaac | tggtttggca | ccacaaaata | cgtaaagcct | ctggtacaga | 1440 |
| agctgtgcac | tcatgaacaa | atgatgtgca | gcaagacctg | ttataactca | gtgaacattg | 1500 |
| cctttctaat | tgatggctcc | agcagtgttg | gagatagcaa | tttccgcctc | atgcttgaat | 1560 |
| ttgtttccaa | catagccaag | acttttgaaa | tctcggacat | tggtgccaag | atagctgctg | 1620 |
| tacagtttac | ttatgatcag | cgcacggagt | tcagtttcac | tgactatagc | accaaagaga | 1680 |
| atgtcctagc | tgtcatcaga | aacatccgct | atatgagtgg | tggaacagct | actggtgatg | 1740 |
| ccatttcctt | cactgttaga | aatgtgtttg | gccctataag | ggagagcccc | aacaagaact | 1800 |
| tcctagtaat | tgtcacagat | gggcagtcct | atgatgatgt | ccaaggccct | gcagctgctg | 1860 |
| cacatgatgc | aggaatcact | atcttctctg | tggtgtggc | ttgggcacct | ctggatgacc | 1920 |
| tgaaagatat | ggcttctaaa | ccgaaggagt | ctcacgcttt | cttcacaaga | gagttcacag | 1980 |

```
gattagaacc aattgtttct gatgtcatca gaggcatttg tagagatttc ttagaatccc    2040
agcaataatg gtaacatttt gacaactgaa agaaaaagta caaggggatc cagtgtgtaa    2100
attgtattct cataatactg aaatgctttt gcatactaga atcagataca aaactattaa    2160
gtatgtcaac agccatttag gcaaataagc actcctttaa agccgctgcc ttctggttac    2220
aatttacagt gtactttgtt aaaaacactg ctgaggcttc ataatcatgg ctcttagaaa    2280
ctcaggaaag aggagataat gtggattaaa accttaagag ttctaaccat gcctactaaa    2340
tgtacagata tgcaaattcc atagctcaat aaaagaatct gatacttaga ccaaaaaaaa    2400
aaa                                                                  2403

<210> SEQ ID NO 12
<211> LENGTH: 1315
<212> TYPE: DNA
<213> ORGANISM: Homo sapiens

<400> SEQUENCE: 12
ctactctgtc accgcccctg ggaagagtgg aacccatact tgctggtctg atccatgcac     60
aaggcggggc tgctaggcct ctgtgcccgg gcttggaatt cggtgcggat ggccagctcc    120
gggatgaccc gccgggaccc gctcgcaaat aaggtggccc tggtaacggc ctccaccgac    180
gggatcggct cgccatcgc ccggcgtttg gcccaggacg gggcccatgt ggtcgtcagc    240
agccggaagc agcagaatgt ggaccaggcg gtggccacgc tgcaggggga ggggctgagc    300
gtgacgggca ccgtgtgcca tgtggggaag gcggaggacc gggagcggct ggtggccacg    360
gctgtgaagc ttcatggagg tatcgatatc ctagtctcca atgctgctgt caacccttc    420 tttggaagca taatggatgt cactgaggag gtgtgggaca agactctgga cattaatgtg    480
aaggccccag ccctgatgac aaaggcagtg gtgccagaaa tggagaaacg aggaggcggc    540
tcagtggtga tcgtgtcttc catagcagcc ttcagtccat ctcctggctt cagtccttac    600
aatgtcagta aaacagcctt gctgggcctg accaagaccc tggccataga gctggcccca    660
aggaacatta gggtgaactg cctagcacct ggacttatca agactagctt cagcaggatg    720
ctctggatgg acaaggaaaa agaggaaagc atgaaagaaa ccctgcggat aagaaggtta    780
ggcgagccag aggattgtgc tggcatcgtg tctttcctgt gctctgaaga tgccagctac    840
atcactgggg aaacagtggt ggtgggtgga ggaaccccgt cccgcctctg aggaccggga    900
gacagcccac aggccagagt gggctctag ctcctggtgc tgttcccgca ttcacccact    960
ggcctttccc acctctgctc accttactgt tcacctcatc aaatcagttc tgccctgtga   1020
aaagatccag ccttccctgc cgtcaaggtg gcgtcttact cgggatttct gctgttgttg   1080
tggccttggg taaaggcctc ccctgagaac acaggacagg cctgctgaca aggctgagtc   1140
taccttggca agaccaaga tattttttcc cgggccactg gggaatctga ggggtgatgg    1200
gagagaagga acctggagtg gaaggagcag agttgcaaat taacaacttg caaatgaggt   1260
gcaaataaaa tgcagatgat tgcgcggctt tgaatccaaa aaaaaaaaaa aaaaa         1315

<210> SEQ ID NO 13
<211> LENGTH: 3661
<212> TYPE: DNA
<213> ORGANISM: Homo sapiens

<400> SEQUENCE: 13
cccaagactg tccccgctgg aggcggtaga gggatccaga agtaatgaga tgctaatgag     60
tcgcgaataa agcccgggcg gcgccccgcg ccctcgcgg aagcccacac tccgcgcgac    120
```

```
tccaggcgca cgccccgggc cgccccgcat cccagcatcc ccgcccgatc tcggcgtttc    180
cgcccccgcc cccgccccg ccctcccacc cgctcagacc tggttgccag cccaacagga    240
agcggcccct cccggcttcg gagccgccgc cactcatctc tgcccagctg ctgccctccc    300
caggaggcct ccatggcttc acctacctcc accaacccag cgcatgccca ctttgagagc    360
ttcctgcagg cccagctgtg ccaggacgtg ctgagcagct tccaggagct gtgtggggcc    420
ctggggctgg aacccggtgg ggggctgccc cagtaccaca agatcaagga ccagctcaac    480
tactggagcg ccaagtcact gtggaccaag ctggacaagc gagcaggcca gcctgtctac    540
cagcagggcc gggcctgcac cagcaccaag tgcctggtgg tgggtgctgg accttgcggg    600
ctgcgggtcg ctgtggagct ggcgctgctg ggggcccgag tggtgctggt ggaaaagcgc    660
accaagttct ctcgccacaa cgtgctccac ctctggccct tcaccatcca cgacctgcgg    720
gcactcggtg ctaagaagtt ctacgggcgc ttctgcaccg gcaccctgga ccacatcagc    780
atcaggcagc tccagctgct tctgctgaag gtagcattgc tgctggggt ggaaattcac    840 tggggtgtca cttttcactgg cctccagccc cctcctagga aggggagtgg ctggcgtgcc    900
cagctccaac ccaacccccc tgcccagctg gccaactatg aatttgacgt ccttatctcg    960
gctgcaggag gtaaattcgt ccctgaaggc ttcaaagttc gagaaatgcg aggcaaactg   1020
gccattggca tcacagccaa cttttgtgaat ggacgcaccg tggaggagac acaggtgccg   1080
gagatcagtg gtgtagccag gatctacaac cagagcttct tccagagcct tctcaaagcc   1140
acaggcattg atctggagaa cattgtgtac tacaaggacg acaccccacta ctttgtgatg   1200 acagccaaga agcagtgcct gctgcggctg ggggtgctgc ccaggactg gccagacacc   1260 aatcggctgc tgggcagtgc caatgtggtg ccgaggctc tgcagcgctt taccgggca   1320 gctgctgact ttgccacca tggcaagctc gggaaactag agtttgccca ggatgcccat   1380
gggcagcctg atgtctctgc cttttgactt cacgagcatga tgcgggcaga gagttctgct   1440
cgtgtgcaag agaagcatgg cgcccgcctg ctgctgggac tggtggggga ctgcctggtg   1500
gagcccttct ggcccctggg cactggagtg gcacggggct tcctggcagc ctttgatgca   1560
gcctggatgg tgaagcggtg ggcagagggc gctgagtccc tagaggtgtt ggctgagcgt   1620
gagagcctgt accagcttct gtcacagaca tccccagaaa acatgcatcg caatgtggcc   1680
cagtatgggc tggaccccagc cacccgctac cccaacctga acctccgggc agtgaccccc   1740
aatcaggtac gagacctgta tgatgtgcta gccaaggagc ctgtgcagag gaacaacgac   1800
aagacagata cagggatgcc agccaccggg tcggcaggca cccaggagga gctgctacgc   1860
tggtgccagg agcagacagc tgggtacccg ggagtccacg tctccgattt gtcttcctcc   1920
tgggctgatg ggctagctct gtgtgccctg tgtaccggc tgcagcctgg cctgctggaa   1980
ccctcagagc tgcaggggct gggagctctg gaagcaactg cttgggcact aaaggtggca   2040
gagaatgagc tgggcatcac accggtggtg tctgcacagg ccgtggtagc agggagtgac   2100
ccactgggcc tcattgccta cctcagccac ttccacagtg ccttcaagag catggcccac   2160
agcccaggcc ctgtcagcca ggcctcccca gggacctcca gtgctgtatt attccttagt   2220
aaacttcaga ggaccctgca cgatcccgg gccaaggaaa atgcagagga tgctggtggc   2280
aagaagctgc gcttggagat ggaggccgag accccaagta ctgaggtgcc acctgaccca   2340
gagcctggtg taccctgac accccatcc caacaccagg aggccggtgc tggggacctg   2400
tgtgcacttt gtggggaaca cctctatgtc ctggaacgcc tctgtgtcaa cggccatttc   2460
```

| | | | | |
|---|---|---|---|---|
| ttccaccgga | gctgcttccg | ctgccatacc | tgtgaggcca | cactgtggcc aggtggctac | 2520 |
| gagcagcacc | caggagatgg | acatttctac | tgcctccagc | acctgcccca gacagaccac | 2580 |
| aaagcggaag | gcagcgatag | aggccctgag | agtccggagc | tccccacacc aagtgagaat | 2640 |
| agcatgccac | caggcctctc | aactcccaca | gcctcgcagg | aggggggccgg tcctgttcca | 2700 |
| gatcccagcc | agcccacccg | tcggcagatc | cgcctctcca | gcccggagcg ccagcggttg | 2760 |
| tcctccctta | accttacccc | tgacccgaaa | atggagcctc | acccaagcc tccccgcagc | 2820 |
| tgctccgcct | tggcccgcca | cgccctggag | agcagctttg | tgggctgggg cctgccagtc | 2880 |
| cagagccctc | aagctcttgt | ggccatggag | aaggaggaaa | aagagagtcc cttctccagt | 2940 |
| gaagaggaag | aagaagatgt | gcctttggac | tcagatgtgg | aacaggccct gcagaccttt | 3000 |
| gccaagacct | caggcaccat | gaataactac | ccaacatggc | gtcggactct gctgcgccgt | 3060 |
| gcgaaggagg | aggagatgaa | gaggttctgc | aaggcccaga | ccatccaacg gcgactaaat | 3120 |
| gagattgagg | ctgccttgag | ggagctagag | gccgagggcg | tgaagctgga gctggccttg | 3180 |
| aggcgccaga | gcagttcccc | agaacagcaa | agaaactat | gggtaggaca gctgctacag | 3240 |
| ctcgttgaca | agaaaaacag | cctggtggct | gaggaggccg | agctcatgat cacggtgcag | 3300 |
| gaattgaatc | tggaggagaa | acagtggcag | ctggaccagg | agctacgagg ctacatgaac | 3360 |
| cgggaagaaa | acctaaagac | agctgctgat | cggcaggctg | aggaccaggt cctgaggaag | 3420 |
| ctggtggatt | tggtcaacca | gagagatgcc | ctcatccgct | tccaggagga gcgcaggctc | 3480 |
| agcgagctgg | ccttggggac | aggggcccag | ggctagacga | gggtggggccg tctgctttcg | 3540 |
| ttcccacaaa | gaaagcacct | cacccccagca | cagtgccacc | cctgttcatc tgggctgcct | 3600 |
| ggcagagagc | cttgctgttt | acaattaaaa | tgtttctgcc | acaaaaaaaa aaaaaaaaa | 3660 |
| a | | | | | 3661 |

<210> SEQ ID NO 14
<211> LENGTH: 651
<212> TYPE: DNA
<213> ORGANISM: Homo sapiens

<400> SEQUENCE: 14

| | | | | |
|---|---|---|---|---|
| atgtccatag | ccctgaagca | ggtattcaac | aaggacaaga | ccttccgacc caagaggaaa | 60 |
| tttgaacctg | gcacacagag | gtttgagctg | cacaaacggg | ctcaggcatc cctcaactcg | 120 |
| ggtgtggacc | tgaaggcggc | tgtgcagttg | cccagtgggg | aggaccagaa tgactgggtg | 180 |
| gcagtacatg | tggtggactt | cttcaatcgg | atcaacctca | tctatggcac catctgtgag | 240 |
| ttctgcaccg | agcggacctg | tcctgtgatg | tcaggggggcc | ccaaatatga gtatcggtgg | 300 |
| caggatgatc | tcaagtataa | gaagccaaca | gcgctgccag | ctccccagta catgaacctt | 360 |
| cttatggatt | ggattgaggt | tcagatcaac | aacgaggaaa | tatttccaac atgcgtgggt | 420 |
| gttcccttcc | caaagaactt | ccttcagatc | tgcaagaaga | tcctgtgccg ccttttccgg | 480 |
| gtctttgtcc | acgtctatat | ccaccacttc | gacccgggtca | ttgtgatggg tgcagaggcc | 540 |
| catgtcaaca | cctgctacaa | acacttctat | tactttgtca | cagagatgaa cctcatagac | 600 |
| cgcaaggagc | tagagccttt | gaaagaaatg | acgagcagga | tgtgtcacta a | 651 |

<210> SEQ ID NO 15
<211> LENGTH: 2471
<212> TYPE: DNA
<213> ORGANISM: Homo sapiens

<400> SEQUENCE: 15

```
gcgttacagg ccctttggcg cctgcgtatt cgtgaagtgt gaaaaaagcg cgcctctgtt    60
gggacgggaa atcagccttt ctattggtca gggttagaaa ccccgccttt gaggcatttt   120
caaccaatgg aagcgcggca ttcttcattt aaactgtcta taaatttctg cctagtcaaa   180
gttaagagtg cgccaggga tttgaaccgc gctgacgaag tttggtgatc catcttccga   240
gtatcgccgg gatttcgaat cgcgatgatc atccctctc tagaggagct ggactccctc   300
aagtacagtg acctgcagaa cttagccaag agtctgggtc tccgggccaa cctgagggca   360
accaagttgt taaaagcctt gaaaggctac attaaacatg aggcaagaaa aggaaatgag   420
aatcaggatg aaagtcaaac ttctgcatcc tcttgtgatg agactgagat acagatcagc   480
aaccaggaag aagctgagag acagccactt ggccatgtca ccaaaacaag gagaaggtgc   540
aagactgtcc gtgtggaccc tgactcacag cagaatcatt cagagataaa aataagtaat   600
cccactgaat tccagaatca tgaaaagcag gaaagccagg atctcagagc tactgcaaaa   660
gttccttctc caccagacga gcaccaagaa gctgagaatg ctgtttcctc aggtaacaga   720
gattcaaagg taccttcaga aggaaagaaa tctctctaca cagatgagtc atccaaacct   780
ggaaaaaata aaagaactgc aatcactact ccaaacttta agaagcttca tgaagctcat   840
tttaaggaaa tggagtccat tgatcaatat attgagagaa aaagaaaca ttttgaagaa   900 cacaattcca tgaatgaact gaagcagcag cccatcaata agggagggt caggactcca   960 gtacctccaa gaggaagact ctctgtggct tctactccca tcagccaacg acgctcgcaa  1020
ggccggtctt gtggccctgc aagtcagagt accttgggtc tgaaggggtc actcaagcgc  1080
tctgctatct ctgcagctaa acgggtgtc aggttttcag ctgctactaa agataatgag  1140
cataagcgtt cactgaccaa gactccagcc agaaagtctg cacatgtgac cgtgtctggg  1200
ggcaccccaa aaggcgaggc tgtgcttggg acacacaaat taaagaccat cacggggaat  1260
tctgctgctg ttattacccc attcaagttg acaactgagg caacgcagac tccagtctcc  1320
aataagaaac cagtgtttga tcttaaagca gtttgtctc gtcccctcaa ctatgaacca  1380
cacaaaggaa agctaaaacc atgggggcaa tctaaagaaa ataattatct aaatcaacat  1440
gtcaacagaa ttaacttcta caagaaaact tacaaacaac cccatctcca gacaaaggaa  1500
gagcaacgga agaaacgcga gcaagaacga aaggagaaga agcaaaaggt tttgggaatg  1560
cgaaggggcc tcattttggc tgaagattaa taatttttta acatcttgta atattcctg   1620 tattctcaac tttttttcctt ttgtaaattt ttttttttg ctgtcatccc cactttagtc  1680
acgagatctt tttctgctaa ctgttcatag tctgtgtagt gtccatgggt tcttcatgtg  1740
ctatgatctc tgaaaagacg ttatcacctt aaagctcaaa ttctttggga tggtttttac  1800
ttaagtccat taacaattca ggtttctaac gagacccatc ctaaaattct gtttctagat  1860
ttttaatgtc aagttcccaa gttcccctg ctggttctaa tattaacaga actgcagtct  1920
tctgctagcc aatagcattt acctgatggc agctagttat gcaagcttca ggagaatttg  1980
aacaataaca agaatagggt aagctggat agaaaggcca cctcttcact ctctatagaa  2040
tatagtaacc tttatgaaac ggggccatat agtttggtta tgacatcaat attttaccta  2100
ggtgaaattg tttaggctta tgtaccttcg ttcaaatatc ctcatgtaat tgccatctgt  2160
cactcactat attcacaaaa ataaaactct acaactcatt ctaacattgc ttacttaaaa  2220
gctacatagc cctatcgaaa tgcgaggatt aatgctttaa tgcttttaga gacagggtct  2280
cactgtgttg cccaggctgg tctcaaactc caccaaatgt acttcttatt cattttatgg  2340
```

```
aaaagactag gctttgctta gtatcatgtc catgtttcct tcacctcagt ggagcttctg    2400
agttttatac tgctcaagat cgtcataaat aaaattttt ctcattgtca tagaaaaaaa    2460
aaaaaaaaaa a                                                         2471

<210> SEQ ID NO 16
<211> LENGTH: 2685
<212> TYPE: DNA
<213> ORGANISM: Homo sapiens

<400> SEQUENCE: 16
gcggaggcgg cctgccgggg tggttcggct tcccgttgcc gcctcgggcg ctgtacccag      60
agctcgaaga ggagcagcgc ggccgcgcgg accggcaag gctgggccgg actcggggct     120
cccgagggac gccatgcggg gaggcagggg cgccccttc tggctgtggc cgctgcccaa     180
gctggcgctg ctgcctctgt tgtgggtgct tttccagcgg acgcgtcccc agggcagcgc     240
cgggccactg cagtgctacg gagttggacc cttgggcgac ttgaactgct cgtgggagcc     300
tcttggggac ctgggagccc cctccgagtt acacctccag agccaaaagt accgttccaa     360
caaaacccag actgtggcag tggcagccgg acggagctgg gtggccattc ctcgggaaca     420
gctcaccatg tctgacaaac tccttgtctg ggcactaag gcaggccagc ctctctggcc     480
ccccgtcttc gtgaacctag aaacccaaat gaagccaaac gccccccggc tgggccctga     540
cgtggacttt tccgaggatg acccctgga ggccactgtc cattgggccc acctacatg      600 gccatctcat aaagttctga tctgccagtt ccactaccga agatgtcagg aggcggcctg     660
gaccctgctg gaaccggagc tgaagaccat accctgacc cctgttgaga tccaagattt     720
ggagctagcc actggctaca agtgtatgg ccgctgccgg atggagaaag aagaggattt     780
gtggggcgag tggagcccca ttttgtcctt ccagacaccg ccttctgctc caaaagatgt     840
gtgggtatca gggaacctct gtgggacgcc tggaggagag gaacctttgc ttctatggaa     900
ggccccaggg ccctgtgtgc aggtgagcta caaagtctgg ttctggggttg gaggtcgtga     960 gctgagtcca gaaggaatta cctgctgctg ctccctaatt cccagtgggg cggagtgggc    1020
cagggtgtcc gctgtcaacg ccacaagctg ggagcctctc accaacctct ctttggtctg    1080
cttggattca gcctctgccc cccgtagcgt ggcagtcagc agcatcgctg ggagcacgga    1140
gctactggtg acctggcaac cggggcctgg gaaccactg gagcatgtag tggactgggc    1200
tcgagatggg gaccccctgg agaaactcaa ctgggtccgg cttccccctg ggaacctcag    1260
tgctctgtta ccagggaatt tcactgtcgg ggtcccctat cgaatcactg tgaccgcagt    1320
ctctgcttca ggcttggcct ctgcatcctc cgtctggggg ttcagggagg aattagcacc    1380
cctagtgggg ccaacgcttt ggcgactcca agatgcccct ccaggacccc cgccatagc     1440 gtggggagag gtcccaaggc accagcttcg aggccacctc acccactaca ccttgtgtgc    1500
acagagtgga accagccct ccgtctgcat gaatgtgagt ggcaacacac agagtgtcac    1560
cctgcctgac cttccttggg gtccctgtga gctgtgggtg acagcatcta ccatcgctgg    1620
acagggccct cctggtccca tcctccggct tcatctacca gataacaccc tgaggtggaa    1680
agttctgccg gcatcctat tcttgtgggg cttgttcctg ttggggtgtg gcctgagcct    1740
ggccacctct ggaaggtgct accacctaag gcacaaagtg ctgccccgct gggtctggga    1800
gaaagttcct gatcctgcca acagcagttc aggccagccc cacatggagc aagtacctga    1860
ggcccagccc cttggggact tgcccatcct ggaagtggag gagatggagc cccgccggt     1920 tatggagtcc tcccagcccg cccaggccac cgccccgctt gactctgggt atgagaagca    1980
```

```
cttcctgccc acacctgagg agctgggcct tctggggccc ccaggccac aggttctggc    2040 ctgaaccaca cgtctggctg ggggctgcca gccaggctag agggatgctc atgcaggttg    2100
caccccagtc ctggattagc cctcttgatg gatgaagaca ctgaggactc agagaggctg    2160
agtcacttac ctgaggacac ccagccaggc agagctggga ttgaaggacc cctatagaga    2220
agggcttggc ccccatgggg aagacacgga tggaaggtgg agcaaaggaa aatacatgaa    2280
attgagagtg gcagctgcct gccaaaatct gttccgctgt aacagaactg aatttggacc    2340
ccagcacagt ggctcacgcc tgtaatccca gcactttggc aggccaaggt ggaaggatca    2400
cttagagcta ggagtttgag accagcctgg gcaatatagc aagacccctc actacaaaaa    2460
taaaacatca aaaacaaaaa caattagctg ggcatgatgg cacacacctg tagtccgagc    2520
cacttgggag gctgaggtgg gaggatcggt tgagcccagg agttcgaagc tgcagggacc    2580
tctgattgca ccactgcact ccaggctggg taacagaatg agaccttatc tcaaaaataa    2640
acaaactaat aaaagcaaa aaaaaaaaaa aaaaaaaaa aaaaa                     2685

<210> SEQ ID NO 17
<211> LENGTH: 622
<212> TYPE: DNA
<213> ORGANISM: Homo sapiens

<400> SEQUENCE: 17
cataaaccct ggcgcgctcg cgggccggca ctcttctggt ccccacagac tcagagagaa     60
cccaccatgg tgctgtctcc tgccgacaag accaacgtca aggccgcctg ggtaaggtc    120 ggcgcgcacg ctggcgagta tggtgcggag gccctggaga ggatgttcct gtccttcccc    180
accaccaaga cctacttccc gcacttcgac ctgagccacg gctctgccca ggttaagggc    240
cacggcaaga aggtggccga cgcgctgacc aacgccgtgg cgcacgtgga cgacatgccc    300
aacgcgctgt ccgccctgag cgacctgcac gcgcacaagc ttcgggtgga cccggtcaac    360
ttcaagctcc taagccactg cctgctggtg accctggccg ccaccctccc cgccgagttc    420
accccctgcg gtgcacgcct cctggacaag ttcctggctt ctgtgagcac cgtgctgacc    480
tccaaatacc gttaagctgg agcctcggta gccgttcctc ctgcccgctg ggcctcccaa    540
cgggccctcc tcccctcctt gcaccggccc ttcctggtct ttgaataaag tctgagtggg    600
cagcaaaaaa aaaaaaaaaa aa                                           622

<210> SEQ ID NO 18
<211> LENGTH: 5199
<212> TYPE: DNA
<213> ORGANISM: Homo sapiens

<400> SEQUENCE: 18
agggacggga agtgggcggg gccggccggc agcagcttgc gggacacgga gccgcgagga     60
gacagctgag gcccgcggag accaggggt gaagcctgga gaccctcttg ccctggccta    120
gctgcaggcc cccgggatgc tttgggcatg tcctctggag ccccacagaa gagcagccca    180
atggccagtg gagctgagga gaccccaggc ttcctggaca cgctcctgca agacttccca    240
gccctgctga acccagagga ccctctgcca tggaaggccc cagggacggt gctcagccag    300
gaggaggtgg agggcgagct ggctgagctg gccatgggct ttctgggcag caggaaggcc    360
ccgccaccac ttgctgctgc tctggcccac gaagcagttt cacagctgct acagacagac    420
ctttccgaat tcaggaagtt gcccagggag gaagaagaag aggaggagga cgatgacgag    480
```

| | |
|---|---|
| gaggaaaagg cccctgtgac cttgctggat gcccaaagcc tggcacagag tttctttaac | 540 |
| cgcctttggg aagtcgccgg ccagtggcag aagcaggtgc cattggctgc ccgggcctca | 600 |
| cagcggcagt ggctggtctc catccacgcc atccggaaca ctcgccgcaa gatggaggac | 660 |
| cggcacgtgt ccctcccttc cttcaaccag ctcttcggct tgtctgaccc tgtgaaccgc | 720 |
| gcctactttg ctgtgtttga tggtcacgga ggcgtggatg ctgcgaggta cgccgctgtc | 780 |
| cacgtgcaca ccaacgctgc ccgccagcca gagctgccca cagaccctga gggagccctc | 840 |
| agagaagcct tccggcgcac cgaccagatg tttctcagga aagccaagcg agagcggctg | 900 |
| cagagcggca ccacaggtgt gtgtgcgctc attgcaggag cgaccctgca cgtcgcctgg | 960 |
| ctcggggatt cccaggtcat tttggtacag cagggacagg tggtgaagct gatggagcca | 1020 |
| cacagaccag aacggcagga tgagaaggcg cgcattgaag cattgggtgg ctttgtgtct | 1080 |
| cacatggact gctggagagt caacgggacc ctggccgtct ccagagccat cggggatgtc | 1140 |
| ttccagaagc cctacgtgtc tggggaggcc gatgcagctt cccgggcgct gacgggctcc | 1200 |
| gaggactacc tgctgcttgc ctgtgatggc ttctttgacg tcgtaccccca ccaggaagtt | 1260 |
| gttggcctgg tccagagcca cctgaccagg cagcagggca gcgggctccg tgtcgccgag | 1320 |
| gagctggtgg ctgcggcccg ggagcggggc tcccacgaca acatcacggt catggtggtc | 1380 |
| ttcctcaggg accccaaga gctgctggag ggcgggaacc agggagaagg ggaccccccag | 1440 |
| gcagaaggga ggaggcagga cttgcccctcc agccttccag aacctgagac ccaggctcca | 1500 |
| ccaagaagct aggtggtttc caggcccctg ccctcccctt cctcccatcc ttgtccttct | 1560 |
| ctccctcaga agcctcagga cccaacaggt ggcaggcagt ggacagggtg cccgccccac | 1620 |
| agtgctttcc ccagcacccc agagccagtc gggacacccc ccgcagcccg tcctggtggc | 1680 |
| tgtggaactg cactgggtgg cgggcagatg gtggaaggca gcttaggaga cctcaccaaa | 1740 |
| gagaagatgg accggctctt gctcccagct cctattaggc ccggggtggg accagaggtc | 1800 |
| ataggtgccc aacggcagcc aaaccaaaga cactggtgtg catggggcag catggttgtg | 1860 |
| cacgtgggac cctggggcgg acccaggagc caaactcttg aagcaccccc tgggtcaggc | 1920 |
| ccagcagcgg agtggccagc cccagttccc cattgctcct ctctgcggcc agggccaggt | 1980 |
| gggttcatat ttacagatat gcccagccag tcctggtcgg ccacaccagt gtcccaaaga | 2040 |
| ggagagcgca gcagagccag gggtctgttc tgtagcagcc accccctgc ccccactcca | 2100 |
| gggcagccat gatgtgcttg gcccaccag ggccttccgg gctgctctct tccctgagcc | 2160 |
| cggaaccggc gacgcacatg tgtctttgt tggtgtgttt gttttttcc agggaggtct | 2220 |
| aattccgaag cagtattcca ggttttctct tgtttttatc agtgccaaga tgacctgttg | 2280 |
| tgtcatataa tttaagcaga gcttagcatt tattttattc tttagaaaac ttaagtattt | 2340 |
| acttttttaa agctattttt caaggaacct ttttttgcag tattattgaa tttatttct | 2400 |
| aaatcaggat tgaaacagga acttttccag gtggtgttaa taagccattc aagtgcctta | 2460 |
| cacagctttg aagaaactag gactgcagtg ggctcggata ggcccattga ggttttaga | 2520 |
| aaagcaggat ttgttttgtt agggaggcat gattttggtg agatctttct ggaagagttt | 2580 |
| tccgcctctt tgtgatgctg aacaccccca aggttctccc ctcccccgc tgcccaggtg | 2640 |
| actggcagga gctgcgactg ccacgtagtg gtgcctgggc ccgacagcgg ggctctgggc | 2700 |
| atcccggggtg accttggccc atctgcctgc attcccaccc ccttgggcct ggctggatcc | 2760 |
| caggcagagg gaccttgctg ctgtgtgatt ggaacattcc caaatatctt gtgaatttgt | 2820 |
| aatcaaattg gtctcattgg gaaagactct taattaagag gctcaggcaa gcacagaggc | 2880 |

```
agcccgtggg tctctgtctc agtctggagg cagcagggat gctgctggga gtccatggca    2940
caggccacag cccctcacct tgccgcggtg gctggcagca cgcctgcctt gctctgcccc    3000
atgccctgaa caggcatgag agctccacgt ccctagtgc accctgagag ggggctcaca     3060
agtgaccgat cctgggtgcc tcagggagct cactgagggc gtgcaaagtt gaaagtggca    3120 aggctgggg agggtgtcgg gtagagggaa gagggcaggg ggctagggga ggactcagag     3180
gccatctgca gggccaagcc acaggaaggg ctgagctgga ggtgggcagg gctgctccag    3240
gcaggtcaga gcagtgcagg gggaggagag gagaaaggga ggaagctggg ctgtgtggtc    3300
cccatgaagg cattcagagt ccacctgcag acagcgagag ccccaggaag gtttgcacag    3360
ctgtgcccca agcaccttgg cctcctctca gctcgccgag gaggcacgct agagccgcct    3420
tcccggtggg agccctctgt cccacaggga gcggggagcc agctttgctg gggccctacc    3480
tgcatgccca gccttacccc tcattctcac agcacagatg aggttgagac catgcagtca    3540
atgcattgct taaggtctct tatttacaaa aaaaaaccttt aaacatagtc gctgtcattc    3600
agacattcag agaatggttg gccacaaaca atgaccaagt attgcttggc ttaacttgaa    3660
ggcctgctgt ctccttctgg gggtcaggga cgcagctcca ccctcaccac tagcccaccc    3720
tgcccgtggg cataaccttg acgaagagag agaatgattg gcatctgctt ttctcttttc    3780
tttgctaata attctgttcc tggctgccga gagtgaagtt tcaccatgtg gaggtttggc    3840
tcctatcacc tggtggtctg attcataccc tagcctgagg ctccactgga agatctcgca    3900
gcctcagtgt atgggaaacc cttttcccag gcttgtccca gcactgccgc tccccacccc    3960
tgagccagga ccccagagga tggccatgcc ccgtgcctgg cagaggtctg gtgccagcac    4020
tgggagctgc tccgcccttg ccttggggcc gagggagccc tcgtccaccc ctgcacagca    4080
gctgggcaca gaggagcgct cttccatctt gaccaggact gcaccaagaa gcaccaggtg    4140
tcttcagcct ccaacctccg gggcgacctt ctcttccagc cacagtccca tgagggcccc    4200
tagccaggga cactggtctg taaattgtaa tcctttctcc agcccagctc tccacttgtt    4260
ccttgtgtga gctgagcagg cagtgcacct ctgagtgtcc cttttgtaag gcccaggggt    4320
tgcactgagt ctgcagaggc cgcgacctcc tagaacgctg tgggtgcagg tgagccggcg    4380
tgtcctgggg agatgctgcc agcacacagg ggccctcctg ctgccagcag gttggggtgg    4440
ttaagtctta ttagtgtcta ttcttaaaat taagtgggct ggagaagaat ggagctccac    4500
atgccagcac cgtatatgga atacaaaagc tggggaagca gggcctgcct tacaggtgtg    4560
gctgactctg agcccaggcc tgcaggggtg gagggcagtc cctcagaatc ccagaggcag    4620
tcccagcctc agaacccagg ataggaaatg ggtgtgttta gtggggaaag ggacggggtg    4680
cagacggcag ggccagtatg gggcccctc cctctcctct cctctcctat ggtgagccca     4740
gcgtgggcac cgggccgtct cagccgtgtt cccagggctg ggaggacagc tctggccctt    4800
cttaggccta gcctcgtccc aagctaaatg taagccagtt gggctgtgtt aaaggaagca    4860 gtgttttttgg ttcgattctg cctctgtagc tcaagggggg cagccccag agtcctgtgc    4920 attctgccaa ggctccatag ctttgccaaa tgcacggagc tctgccattc cggtgcagtg    4980
caggccttgc gaagggttta tctgcgttcg tctcggtggg cttctcctgc atgggagttg    5040
tgttcctgtg caaggggag ctttgctcca ggacaggatg actgtcttcc ctattcttag     5100
ggacaagtcc caagatgcca gaaaggcagt ctcccaagga cccaccatgc agaagtgtca    5160
ataaaccaca agttctgaac tctgtaaaaa aaaaaaaaa                            5199
```

<210> SEQ ID NO 19
<211> LENGTH: 1767
<212> TYPE: DNA
<213> ORGANISM: Homo sapiens

<400> SEQUENCE: 19

| | | | | | | |
|---|---|---|---|---|---|---|
| atggcggcgg | ccgacggcga | cgactcgctg | tacccatcg | cggtgctcat | agacgaactc | 60 |
| cgcaatgagg | acgttcagct | tcgcctcaac | agcatcaaga | agctgtccac | catcgccttg | 120 |
| gcccttgggg | ttgaaaggac | ccgaagtgag | cttctgcctt | tccttacaga | taccatctat | 180 |
| gatgaagatg | aggtcctcct | ggccctggca | gaacagctgg | gaaccttcac | taccctggtg | 240 |
| ggaggcccag | agtacgtgca | ctgcctgctg | ccaccgctgg | agtcgctggc | cacagtggag | 300 |
| gagacagtgg | tgcgggacaa | ggcagtggag | tccttacggg | ccatctcaca | cgagcactcg | 360 |
| ccctctgacc | tggaggcgca | ctttgtgccg | ctagtgaagc | ggctggcggg | cggcgactgg | 420 |
| ttcacctccc | gcacctcggc | ctgcggcctc | ttctccgtct | gctaccccg | agtgtccagt | 480 |
| gctgtgaagg | cggaacttcg | acagtacttc | cggaacctgt | gctcagatga | caccccatg | 540 |
| gtgcggcggg | ccgcagcctc | caagctgggg | gagtttgcca | aggtgctgga | gctggacaac | 600 |
| gtcaagagtg | agatcatccc | catgttctcc | aacctggcct | ctgacgagca | ggactcggtg | 660 |
| cggctgctgg | cggtggaggc | gtgcgtgaac | atcgcccagc | ttctgcccca | ggaggatctg | 720 |
| gaggccctgg | tgatgcccac | tctgcgccag | gccgctgaag | acaagtcctg | gcgcgtccgc | 780 |
| tacatggtgg | ctgacaagtt | cacagagctc | cagaaagcag | tggggcctga | gatcaccaag | 840 |
| acagacctgg | tccctgcctt | ccagaacctg | atgaaagact | gtgaggccga | ggtgagggcc | 900 |
| gcagcctccc | acaaggtcaa | agagttctgt | gaaaacctct | cagctgactg | tcgggagaat | 960 |
| gtgatcatgt | cccagatctt | gccctgcatc | aaggagctgg | tgtccgatgc | caaccaacat | 1020 |
| gtcaagtctg | ccctggcctc | agtcatcatg | ggtctctctc | ccatcttggg | caaagacaac | 1080 |
| accatcgagc | cctccttgcc | cctcttcctg | gctcagctga | aggatgagtg | ccctgaggta | 1140 |
| cggctgaaca | tcatctctaa | cctggactgt | gtgaacgagg | tgattggcat | ccggcagctg | 1200 |
| tcccagtccc | tgctccctgc | cattgtggag | ctggctgagg | acgccaagtg | gcgggtgcgg | 1260 |
| ctggccatca | ttgagtacat | gcccctcctg | gctggacagc | tgggagtgga | gttctttgat | 1320 |
| gagaaactta | actccttgtg | catggcctgg | cttgtggatc | atgtatatgc | catccgcgag | 1380 |
| gcagccacca | gcaacctgaa | gaagctagtg | aaaagtttg | ggaaggagtg | ggcccatgcc | 1440 |
| acaatcatcc | ccaaggtctt | ggccatgtcc | ggagaccca | actacctgca | ccgcatgact | 1500 |
| acgtctcttct | gcatcaatgt | gctgtctgag | gtctgtgggc | aggacatcac | caccaagcac | 1560 |
| atgctaccca | cggttctgcg | catggctggg | gacccggttg | ccaatgtccg | cttcaatgtg | 1620 |
| gccaagtctc | tgcagaagat | agggcccatc | ccggacaaca | gcaccttgca | gagtgaagtc | 1680 |
| aagcccatcc | tagagaagct | gacccaggac | caggatgtgg | acgtcaaata | ctttgcccag | 1740 |
| gaggctctga | ctgttctgtc | tctcgcc | | | | 1767 |

<210> SEQ ID NO 20
<211> LENGTH: 10640
<212> TYPE: DNA
<213> ORGANISM: Homo sapiens

<400> SEQUENCE: 20

| | | | | | | |
|---|---|---|---|---|---|---|
| atactcagtc | acacaagcca | tagcaggaaa | cagcgagctt | gcagcctcac | cgacgagtct | 60 |
| caactaaaag | ggactcccgg | agctaggggt | ggggactcgg | cctcacacag | tgagtgccgg | 120 |

```
ctattggact tttgtccagt gacagctgag acaacaagga ccacgggagg aggtgtagga    180
gagaagcgcc gcgaacagcg atcgcccagc accaagtccg cttccaggct ttcggtttct    240
ttgcctccat cttgggtgcg ccttcccggc gtctagggga gcgaaggctg aggtggcagc    300
ggcaggagag tccggccgcg acaggacgaa ctcccccact ggaaaggatt ctgaaagaaa    360
tgaagtcagc cctcagaaat gaagttgact gcctgctggc tttctgttga ctggcccgga    420
gctgtactgc aagacccttg tgagcttccc tagtctaaga gtaggatgtc tgctgaagtc    480
atccatcagg ttgaagaagc acttgataca gatgagaagg agatgctgct cttttgtgc     540
cgggatgttg ctatagatgt ggttccacct aatgtcaggg accttctgga tattttacgg    600
gaaagaggta agctgtctgt cggggacttg gctgaactgc tctacagagt gaggcgattt    660
gacctgctca acgtatcttg aagatggacg agaaaagctg tggagaccca cctgctcagg    720
aaccctcacc ttgtttcgga ctatagagtg ctgatggcag agattggtga ggatttggat    780
aaatctgatg tgtcctcatt aattttcctc atgaaggatt acatgggccg aggcaagata    840
agcaaggaga gagtttctt ggaccttgtg gttgagttgg agaaactaaa tctggttgcc     900
ccagatcaac tggatttatt agaaaaatgc taaagaaca tccacagaat agacctgaag     960
acaaaaatcc agaagtacaa gcagtctgtt caaggagcag ggacaagtta caggaatgtt   1020
ctccaagcag caatccaaaa gagtctcaag gatccttcaa ataacttcag gctccataat   1080
gggagaagta agaacaaag acttaaggaa cagcttggcg ctcaacaaga accagtgaag    1140
aaatccattc aggaatcaga agcttttttg cctcagagca tacctgaaga gagatacaag   1200
atgaagagca agcccctagg aatctgcctg ataatcgatt gcattggcaa tgagacagag   1260
cttcttcgag acaccttcac ttccctgggc tatgaagtcc agaaattctt gcatctcagt   1320
atgcatggta tatcccagat tcttggccaa tttgcctgta tgcccgagca ccgagactac   1380
gacagctttg tgtgtgtcct ggtgagccga ggaggctccc agagtgtgta tggtgtggat   1440
cagactcact cagggctccc cctgcatcac atcaggagga tgttcatggg agattcatgc   1500
ccttatctag cagggaagcc aaagatgttt tttattcaga actatgtggt gtcagagggc   1560
cagctggagg acagcagcct cttggaggtg atgggccag cgatgaagaa tgtggaattc     1620
aaggctcaga gcgagggct gtgcacagtt caccgagaag ctgacttctt ctggagcctg    1680
tgtactgcgg acatgtccct gctggagcag tctcacagct caccatccct gtacctgcag   1740
tgcctctccc agaaactgag acaagaaaga aaacgcccac tcctggatct tcacattgaa   1800
ctcaatggct acatgtatga ttggaacagc agagtttctg ccaaggagaa atattatgtc   1860
tggctgcagc acactctgag aaagaaactt atcctctcct acacataaga aaccaaaagg   1920
ctgggcgtag tggctcacac ctgtaatccc agcactttgg gaggccaagg agggcagatc   1980
acttcaggtc aggagttcga gaccagcctg ccaacatgg taaacgctgt ccctagtaaa    2040
aatacaaaaa ttagctgggt gtgggtgtgg gtacctgtat tcccagttac ttgggaggct   2100
gaggtgggag gatcttttga acccaggagt tcagggtcat agcatgctgt gattgtgcct   2160
acgaatagcc actgcatacc aacctgggca atatagcaag atcccatctc tttaaaaaaa   2220
aaaaaaaagg acaggaacta tcttactcaa tgtattagtc atgtttctct agagggacag   2280
aactaatagg atacatgtat ataaaaaggg gagtttatta aggagtattg actcacatga   2340
tcacagggtt aggtcccaca ataggtcatc tgcaagcaag gaagccaatt caagtcccaa   2400
agctgaagaa cttggagtcc aatgtttgag ggcaggaagc attcagcatg agagaaagat   2460
```

```
ggaggccaga agactacacc agtctagtct ttccatgttt tgcctgcttt tattctggca    2520
gtgctggcag ctgattagat ggtgcccacc cagattgagg atggtctgcc tttcccagtc    2580
cactgactca aatgttaaat ctcctttggc agcaccctca cagatgtacc cgggaacact    2640
ttgcatcctt ctattcaatc aagttgatac tcagtattaa ccatcacagt ccatttgggc    2700
aactatacca aattaccata gaccaggtga cttaaacagc agttatttct cacagttccg    2760
gaggctggga atccaacat ctaagtggta gcatatctgg tgtctggtaa ggcatgcttc     2820
cagatcttac cagatgtcag tcttttgatg ttctcacatg gcagaaaaag aggatgcaaa    2880
ctctcaagta tatctttaag ggcacaaatt ccattcatga gggctctacc ctcatcacct    2940
aattacctcc caaaggcccc accttctgat actgtcactt tggggatact gtctcccctt    3000
tgaattctgg ggggaataca aacattcagt ttgtaacaat agccttatga tttagaggtt    3060
acttgttcat tcacctagac ctcaaattgc attttacagc tagtcaagta tatctttctc    3120
tgatttgata gtgtgaccta aaaggggacc attgtttgaa atatcattag agttgcttat    3180
tattattatt attattatta ttattattat tattattatt attgagacag agtttcattc    3240
tgctgcccag gctggagtgc agtggcatca tcttggctca ttgcaacctc tgccttctgg    3300
gttcaagcga ttctcctgcc tcagcctccc gagtagctgg gattacaggc cctgccacc     3360 acacccggct aatttttgta ttttagtgg agacagggtt tccaccatgt tggccagcgt     3420
ggtcttgaac tcctgacctc aggtgattca ccagcctcgg cctcccaaag tgctgggatt    3480
acaggtgtga gccactgcac ctggcctatt attatttta aatttttttt ttttaattga     3540
tcattcttgg gtgtttctca cagagggtga tttggcaggg tcacaggaca atagtggagg    3600
gaaggtcagc agataaacaa gtgaacaaag gtctctggtt ttcctaggca gaggaccctg    3660
cggccttccg cagtgtttgt gtccctgggt acttgagatt agggagtggt gatgactctt    3720
aaggagcatg ctgccttcaa gcatctgttt aacaaagcac atcttgcact gcccttaatc    3780
catttaaccc tgagtggaca cagcacatgt ttcagagagc acagggttgg gggtaaggtc    3840
atagatcaac agcatcctaa ggcagaagaa ttttttcttag tacagaacaa aatgaagtct    3900
cccatgtcta cttcttttcta cacagacaca gcaacaatct gatttctcta tcttttcccc    3960
acctttcccc cttttctatt ccacaaaacc gccatcgtca tcatggcctg ttctcaatga    4020
gctgttgggt acacctccca gacggggtgg cggctgggca gaggggctcc tcacttccca    4080
gatggggcgg ccaggcggac gcgcccccca cctccctccc ggacgggata gctggccggg    4140 cggggggctga cccccacct ccctcccga cgggcggct ggcgggcgg gggctgaccc       4200 ccacgcctcc ctcccggacg gggcggctgc caggcggagg ggctcctcac ttctcagacg    4260
gggtggctgc tggcggaga cgctcctcac ttcccagaca gggtggctgt cgggcggagg    4320
ggctcctcac ttctcagacg gggcagctgc gggcggaggg gctcctcact tctcagacgg    4380
ggtggccggg cagagaagct cctcacatcc cagacggggg ggcggggcag aggcgctccc    4440
cacatctcag acgatgggcg gccgggcaga gacgctcctc acttcatccc agacggggtg    4500
gcggccgggc agaagctgta atctcggcac cctgggggc caaggcaggc ggctgggagg    4560
cggaggccgt agccagctga gatcacacca ctgcactcca gcctgggcaa cattgagcac    4620
tgagtggacg agactctgcc cgcaatcccg gcacctcggg aggccgaggc tggcagatca    4680
ctcgcagtca ggagctggag accagccccgg ccaacacagt gaaaccctgt ctccaccaaa    4740
aaaatacgaa aaccagtcag gcgtggcggc gcccgcaatg gcaggcacgc ggcaggccga    4800
ggcgggagaa tcaggcaggg aggctgcagt gagccgagat ggcagcagta cagtccagct    4860
```

```
tcggctcggc atcagaggga gaccgtgggg agagggagaa gagagggagg gggagagggc   4920 tattttaaa  attttttaaa  attgctgaac  aggggtacct  ctgggcagtg  tgtcagaata   4980 ccactttta  aatattttat  gatttattta  tttttctatt  tcttgaggtt  ttaactgatg   5040
tgtatctgta tgtctatttg tgtatatttt gtcatgatca tgtaacagag tctgaaaagt   5100
gtcgaagaga cagttttcag gaacaacaag caattattcc tactttccaa gttattttga   5160
tgccatggtg gctcatacct ataatctgag tactttggga ggctgaggtg gactgatcac   5220
ttgagcccag gagtttgaga ccagcctggg caacatagca agactccatc tctacaaaaa   5280
aagacaaaat ttagctgagc gtggtggcgt gttcctgtag tcccagctac ttgggaggct   5340
gaagtgagtg gatcccctga gcccagagag gtcaaggttg tgatgagctg tgatcacacc   5400
actgcacttc agcatgggag acagagtgag accctgtttc agaaaaaata aataaataaa   5460
accaccagca ccacaaacaa caacaaaaag ttattttgta cttgttttga gcacaggact   5520
cctgagggta tctttgcatt taatattaca taggggtgcc agtgggaagt aatgtgtatg   5580
cttggcctca tgagctaaaa ccctgtgtta attatgacag aaggaaagtg tgtgagagag   5640
atcttaacta cctagcagct ctagctgcca tcttgaacca tgaagatacg ggccacacgt   5700
aggggtagct gggtagtgag cagcaagaag ccttgttgga tgagggcacg aaggagcaga   5760
atcactggaa tcactgtgtc agccctaatt acctacctct ggacttttat gtgaggggaa   5820
aaaaaattga cagtttatat ttatctcaac ctagttaacc caagtgatgc attgttatga   5880
gattaaaatg tttggaggcc gggtgcggtg gctcacgcct ataatcccag ccctttggga   5940
ggccaaggcg ggcggatcac gaggtcagga gatcaagacc atcctggcta acatgtaaaa   6000
ccccgtctct actaaaaata caaaaaatta gccaggcgtt gtggcggtcg cctgtagtcc   6060
ctgctatttg ggaggccgag gcaagagaac ggcatgaacc tgggaggtgg agcttgcagc   6120
gagctgagat cttgccactg cactccagcc tgggcgacag tgcgagactc tgtctcaaaa   6180
ataaataaat aaataaataa taaataaaat gtttggaatg ttggcttcat ccctgggatg   6240
caaggctggt tcaacatacg caaatcaaga aacataattc atcacataaa cagaactaaa   6300
gacaaaaacc acatgattat ctcaatagat acagaaaagg ccttcaataa aattcaacgt   6360
tgcttcatgt taaaaactct caataaacta ggtattgatg gaaatatct  caaaataata   6420 accatttatg caaacccac  agccattatc atactgaatg ggcaaaagct ggaagcattc   6480
cccttgaaaa ctggcacaag acagggatgc cgtctcacca ctcctattta acatagtatt   6540
ggaagttctg gccaagaaaa tcaggcaaga gaaacaaata aggggtattc aaataggaaa   6600
agaggaagta aaactgtgtt tgcagatgac atgatactat atctagaaaa ccccattatc   6660
tccacccaaa agttccttaa gctgataagc aacttcagca aagtctcagg atacaaaatc   6720
aatgtgcaga aatcacaagc attctataca ccaacaatac acaagcagag agccaaatca   6780
tgaatgaact cccattcaca gttgctagaa agagaataaa ataactagga atacagctaa   6840
taagatgtga aggatctctt caaggagaac tacaaaccac tgctcaagga ataagagag   6900 gacacaaatg aaaaaacatt ccattctcgt ggataggaag aatcaatatc atgaaaatgg   6960
ccatactacc caaagtaatt tataggttca ttgctattcc cattaaacta ctattgacat   7020
tcttcacaga attagaaaaa aactactttta aaattcaaat ggaaccaaaa aagagcccgt   7080
ataaccaaga caacaataag caaaagaac  aaagctggaa gcatcacact acccaacttc   7140
aaagtatact gcaaggctac agtagccaaa atggcatggt actggtacaa aaacagacac   7200
```

```
atagaccaat ggaacagaat agagaccaga gaaagaagac cacacatcta cagccatctg   7260
atcatcgaca aacctgacaa aaacaagcaa tggggaaaag attccctatt taataaatgg   7320
tgctgggaaa actggctagc catatgcaga aaattgaaac tgaccccttc cttacacctt   7380
atacaaaaat taactcaaga ttaaagactt aatgtaaaac ctaaaactat aaaaacccta   7440
gaagaaaatc tatttaatac cattcaagac ataggcacaa gcaaaggttt catgacaaaa   7500
acatcaaaag caattgcaac aaaagcaaaa attacaaatg ggatctaatt aaactaaaga   7560
gctcctgcac agcaaaagaa actatcatta gagtgaacag gcaacctaca gaatgggaga   7620
acatttttgc aatctatcca tctgacaaag gtctaatatc cagaacctac aaggaactta   7680
aaacaaattt acaaggaaaa aaacaacccc atcaaaaagt ggacaaagga catgaacaga   7740
cacttctcaa aagaagacat ttatgtggcc aacaaacata aaaaaaaag ctcaaccttta  7800 ctgatcatta gagaaatgca aaggagaacc acaatgagat accatctcat gccggtcaga   7860
atggtgatta ttaaaaagtc aaaaaacaac agatgctggc gaggctgtgg agaagtagga   7920 acactttttac attgttggtg ggaatgtaaa ttagttcaac cgttgtggaa gtgtgtgtgg   7980
ctattcctca aagatctaga actagaaata ctatttgtcc cagcaatccc attactgggt   8040
atatacccaa aggaatataa accattttat tataaagata catgcacatt tttgttcatt   8100
gcagcactct tcacaatagc aaagacacaa tagcaaatgc ccatcaaaga tagactggat   8160
aaagaaaatg tggtacatat acaccatgga atactgtgca gtgcagccat tacagctttt   8220
ggtgatacag tgaatcagat ttttcattaa ttctttttaat tggttattac tgaacgtgaa   8280
aaagtaatgt ttgtattgaa atcttgagtc tggccatgtt tctatttaa attcataaag   8340 aattctaaca agaggaattc caagaatgtc ataaatggat gtttctccat ggatgaagga   8400
actgttttat tcacttgctg ataattcagc ctaatccagt ttgacatcat atagataagt   8460
agttgaatta tggatttaaa atacatatca ttttctaact ccaaaggtaa tacttattta   8520
aatggttttg aaaatataga aaggcacaat ttccttttaa atctgttatt ctccaccacc   8580
actcaatctg tctatcatct atctctccat tcattcttcc atttgtttat atctgttaat   8640
ctttgtatgt gttcatgtat agcttttaca tgattggaat cataatgcat attccatttt   8700
gaagtctgct ttttttaca caaaaatatg ttgtgaatat tttcctatat tatgaaatat   8760
cattagctga gcttttagaa ttgactgcat gttttggtac catttagata tagtttaaga   8820
tacttagaag ttatgtggct ttgccactat ggatgaatct tatttactca atattaatta   8880
cttacaaata acctcaccta aacactactc agccataaaa aggaatgaat taatgacatt   8940
cacagcaacc tggagactat tactctaaag gaagtaactg aggaatggaa aaccaaacat   9000
tgtatgttct cactcataag tgggagataa gctatgagga tgcaaaggca taagaaggat   9060
acaatggact ttggggactt aggggaaagg gtgggagggg ggtgaaggat aaaagaatac   9120
aaattgggtt cagtgtatac tgctcaggtg atgggtgcac cagaatctca caagtaacca   9180
cttaattact tacgcatgta accagatacc acctgttccc caaacaccta tggaaataat   9240
tttgtttttt ttttttaaaaa aggaatgaga tcatgtcctt tgcagggaca tggatgaagc   9300
tggaagccat tatcctcagc aaactaacag aggagcagga aaccaaacac cacatgttct   9360
cacttgtaag cggaagctga acaatgagaa cacacggaca cagggatgag atcaacacac   9420
actggggcct gatgcagggg ccgtagcggg gagagcatca ggataactag ctaatgcatg   9480
tggggcttaa tacctaggtg ataggttgat aggtgcagca aaccaccatg ggacacgttt   9540
acctatgtaa caaacccgca catcctgcac ttgtatccag aacttaaaat atttttaaaaa  9600
```

```
tctttagaga atacaaaaaa aaaaaaaaag attcttcaat gcatacacaa taaaattgca    9660
gttcagtcaa acattggaag tctttctctg actgtctagt tggtatcttc attttcagct    9720
tcttcaagat cccactccaa acactgttag ctcagccaaa ttgaacagct catatctcct    9780
acctctggat ctttggttct ggtgattgta tatttctgga ccatctggaa ccccagcata    9840
tcaccctacc ccacatctcc acatcccaa aatataacca tacttcaagg gcagttcaaa    9900
taccatctcc ttctatcctc catgaagtca gttatctctt ccattggaat tatcgccccc    9960
tctcctgaac agtactattt cgtgtgaatc tcctccaagc cttcttttca ttttatatct   10020
catgctgtaa ttcttggaaa gtatgctgta gctcaagtgc agaattctca tcagttttat   10080
ctttatatct ctcctaaaca ctttacctga tgaagagcct ggcatacaca taaatatata   10140
ttgaatgaat cagtgatgga ttgaaaagag aaatgatgga tctcctaaat tttaactttt   10200
ataaaatatt ttgatacatt catgaccttta ctttagcaag caatgaacgt gatgtaaact   10260
attgttgata tagtttttat attggaagtg taagtagttt gtggcatggg attgtgacat   10320
atcctaggtt tcctcatctt cttttttattg aaatgtaatt cacaagccat aaaatttgcc   10380
cctttaaagt aaatgatgca gtggatttta gtatatttac agagttgtgc aatcatcacc   10440
actatctaat tccagaacat ttccatctac ctagaaactc cataccagtg agctgccact   10500
ctaatcctcc tcttccccca gcctctagaa acaataatcc attttctgtc tctatgattt   10560
gcctgttcta gatattttat aaaaataaac atgtggcctt tcgtgtctga cttccttcac   10620
ttaaaaaaaa aaaaaaaaaa                                                10640

<210> SEQ ID NO 21
<211> LENGTH: 1939
<212> TYPE: DNA
<213> ORGANISM: Homo sapiens

<400> SEQUENCE: 21
cgcctccgcc ttcggaggct gacgcgcccg ggcgccgttc caggcctgtg cagggcggat      60
cggcagccgc ctggcggcga tccagggcgg tgcggggcct gggcgggagc cgggaggcgc     120
ggccggcatg gaggcgctgc tgctgggcgc ggggttgctg ctgggcgctt acgtgcttgt     180
ctactacaac ctggtgaagg ccccgccgtg cggcggcatg ggcaacctgc ggggccgcac     240
ggccgtggtc acgggcgcca acagcggcat cggaaagatg acggcgctgg agctggcgcg     300
ccggggagcg cgcgtggtgc tggcctgccg cagccaggag gcgcggggagg cggctgcctt     360
cgacctccgc caggagagtg ggaacaatga ggtcatcttc atggccttgg acttggccag     420
tctggcctcg gtgcgggcct ttgccactgc ctttctgagc tctgagccac ggttggacat     480
cctcatccaa aatgccggta tcagttcctg tggccggacc cgtgaggcgt ttaacctgct     540
gcttcgggtg aaccatatcg gtcccttctt gctgacacat ctgctgctgc cttgcctgaa     600
ggcatgtgcc cctagccgcg tggtggtggt agcctcagct gcccactgtc ggggacgtct     660
tgacttcaaa cgcctggacc gcccagtggt gggctggcgg caggagctgc gggcatatgc     720
tgacactaag ctggctaatg tactgtttgc ccggggagctc gccaaccagc ttgaggccac     780
tggcgtcacc tgctatgcag cccacccagg gcctgtgaac tcggagctgt tcctgcgcca     840
tgttcctgga tggctgcgcc cactttgcg cccattggct tggctggtgc tccgggcacc     900
aagaggggg tgccagacac ccctgtattg tgctctacaa gagggcatcg agccctcag     960
tgggagatat tttgccaact gccatgtgga agaggtgcct ccagctgccc gagacgaccg    1020
```

| | |
|---|---:|
| ggcagcccat cggctatggg aggccagcaa gaggctggca gggcttgggc ctggggagga | 1080 |
| tgctgaaccc gatgaagacc cccagtctga ggactcagag gccccatctt ctctaagcac | 1140 |
| cccccaccct gaggagccca cagtttctca accttacccc agccctcaga gctcaccaga | 1200 |
| tttgtctaag atgacgcacc gaattcaggc taaagttgag cctgagatcc agctctccta | 1260 |
| accctcaggc caggatgctt gccatggcac ttcatggtcc ttgaaaacct cggatgtgtg | 1320 |
| cgaggccatg ccctggacac tgacgggttt gtgatcttga cctccgtggt tactttctgg | 1380 |
| ggccccaagc tgtgccctgg acatctcttt tcctggttga aggaataatg ggtgattatt | 1440 |
| tcttcctgag agtgacagta accccagatg gagagatagg ggtatgctag acactgtgct | 1500 |
| tctcggaaat ttggatgtag tattttcagg ccccacccct attgattctg atcagctctg | 1560 |
| gagcagaggc agggagtttg caatgtgatg cactgccaac attgagaatt agtgaactga | 1620 |
| tcccttttgca accgtctagc taggtagtta aattaccccc atgttaatga agcggaatta | 1680 |
| ggctcccgag ctaagggact cgcctagggt ctcacagtga gtaggaggag ggcctgggat | 1740 |
| ctgaacccaa gggtctgagg ccaggccga ctgccgtaag atgggtgctg agaagtgagt | 1800 |
| cagggcaggg cagctggtat cgaggtgccc catgggagta aggggacgcc ttccgggcgg | 1860 |
| atgcagggct ggggtcatct gtatctgaag cccctcggaa taaagcgcgt tgaccgccga | 1920 |
| aaaaaaaaaa aaaaaaaa | 1939 |

<210> SEQ ID NO 22
<211> LENGTH: 1840
<212> TYPE: DNA
<213> ORGANISM: Homo sapiens

<400> SEQUENCE: 22

| | |
|---|---:|
| gggttcccag gccgactctc cttgtggttg gctgaggctg gaggtggacg ggacttttgg | 60 |
| agggtcgctc gcgtctgttc gcagagctgt gggcggagtt gaggccttgg aggctgagat | 120 |
| gtggttctgc gcgtgtgcgg acggctgtct gttaactccg cggtcagttc ccggactggt | 180 |
| ggctggtctg cagggttgac ctgcgcaatg cagaggctgc aggtagtgct gggccacctg | 240 |
| aggggtccgg ccgattccgg ctggatgccg caggccgcgc cttgcctgag cggtgccccg | 300 |
| caggcctcgg ccgcggacgt ggtggtggtg cacgggcggc gcacggccat ctgccgggcg | 360 |
| ggccgcggcg gcttcaagga caccaccccc gacgagcttc tctcggcagt catgaccgcg | 420 |
| gttctcaagg acgtgaatct gaggccggaa cagctggggg acatctgtgt cggaaatgtg | 480 |
| ctgcagcctg ggccgggc aatcatggcc cgaatcgccc agtttctgag tgacatcccg | 540 |
| gagactgtgc ctttgtccac tgtcaataga cagtgttcgt cggggctaca ggcagtggcc | 600 |
| agcatagcag gtggcatcag aaatgggtct tatgacattg gcatggcctg tggggtggag | 660 |
| tccatgtccc tggctgacag agggaaccct ggaaatatta cttcgcgctt gatggagaag | 720 |
| gagaaggcca gagattgcct gattcctatg gggataacct ctgagaatgt ggctgagcgg | 780 |
| tttggcattt cacgggagaa gcaggatacc tttgccctgg cttcccagca gaaggcagca | 840 |
| agagcccaga gcaagggctg tttccaagct gagattgtgc ctgtgaccac cacggtccat | 900 |
| gatgacaagg gcaccaagag gagcatcact gtgacccagg atgagggtat ccgccccagc | 960 |
| accaccatgg agggcctggc caaactgaag cctgccttca gaaagatgg ttctaccaca | 1020 |
| gctggaaact ctagccaggt gagtgatggg gcagctgcca tcctgctggc ccggaggtcc | 1080 |
| aaggcagaag agttgggcct tcccatcctt ggggtcctga ggtcttatgc agtggttggg | 1140 |
| gtcccacctg acatcatggg cattggacct gcctatgcca tcccagtagc tttgcaaaaa | 1200 |

```
gcagggctga cagtgagtga cgtggacatc ttcgagatca atgaggcctt tgcaagccag   1260
gctgcctact gtgtggagaa gctacgactc ccccctgaga aggtgaaccc cctgggggt   1320 gcagtggcct tagggcaccc actgggctgc actgggcac acaggtcat cacgctgctc   1380 aatgagctga agcgccgtgg gaagagggca tacgagtgg tgtccatgtg catcgggact   1440
ggaatgggag ccgctgccgt ctttgaatac cctgggaact gagtgaggtc ccaggctgga   1500
ggcgctacgc agacagtcct gctgctctag cagcaaggca gtaacaccac aaaagcaaaa   1560
ccacatggga aaactcagca ctggtggtgg tggcagtgga cagatcaagg cacttcaact   1620
catttggaaa atgtgaacac tgatgacatg gtataggagt gggtgggtg ttgagccacc   1680 catcagaccc tctttagctg tgcaagataa aagcagcctg ggtcacccag gccacaaggc   1740
catggttaat tcttaaggca aggcaaatcc atggatgaga agtgcaatgg gcatagtaaa   1800
agtgcatgaa tttatcttaa aaaaaaaaaa aaaaaaaaa                         1840

<210> SEQ ID NO 23
<211> LENGTH: 3407
<212> TYPE: DNA
<213> ORGANISM: Homo sapiens

<400> SEQUENCE: 23
caggttgaaa tggctgatga catcactggt tcccgggagc ggtagagctg gagccggagc     60
caagggagtc caggctgccg ggggctgcag acatggaggg ccagagcagc aggggcagca    120
ggaggccagg gacccgggct ggcctgggtt ccctgcccat gccccaggt gttgcccaaa    180 ctggggcacc ctccaaggtg gactcaagtt ttcagctccc agcaaagaag aacgcagccc    240
taggaccctc ggaaccaagg ttggctctgg cacctgtagg gccacgggca gctatgtcag    300
cttcctcgga aggaccgagg ctggctctgg catctccccg accaatcctg gctccactgt    360 gtaccctga agggcagaaa acagctactg cccaccgcag ctccagcctg ccccaacat    420 ctgtgggcca gctggtgatg tctgcctcag ctggaccaaa gcctccccca gcgaccacag    480
gctcagttct ggctccgacg tccctggggc tggtgatgcc tgcctcagca gggccaagat    540
ctcccccagt caccctgggg cccaatctgg ccccaacctc cagagaccag aagcaggagc    600
cacctgcctc cgtgggaccc aagccaacac tggcagcctc tggcctgagc ctggccctgg    660
cttctgagga gcagccccca gaactcccct ccacccttc cccggtgccc agtccagttc    720
tgtctccaac tcaggaacag gccctggctc cagcatccac ggcatcaggc gcagcctctg    780
tgggacagac atcagctaga aagagggatg ccccagcccc tagacctctc cctgcttctg    840 agggcatct ccagcctcca gctcagacat ctggtcctac aggctcccca ccctgcatcc    900
aaacctcccc agaccctcgg ctctcccct ccttccgagc ccggcctgag gcctccaca    960 gcagccctga ggatcctgtt ttgccacggc caccccagac cttgcccttg gatgtgggcc   1020
agggtccttc agagcctggc actcactccc ctggacttct gtccccacc ttccggcctg   1080 gggcccctc aggccagact gtgcccccac ctctgcccaa gccacccccga tcacccagcc   1140 gttccccaag ccactccccg aatcgctctc cctgtgttcc cccagcccct gacatggccc   1200
tcccaaggct tggcacacag agtacagggc ctggcaggtg cctgagcccc aaccttcagg   1260
cccaagaagc cccagcccca gtcaccacct cctcttctac atccaccctg tcatcctccc   1320
cttggtcagc tcagcctacc tggaagagcg acccggctt ccggatcact gtggtcacat   1380
ggaacgtggg cactgccatg ccccagacg atgtcacatc cctcctccac ctgggcggtg   1440
```

| | |
|---|---|
| gtgacgacag cgacggcgca gacatgatcg ccatagggtt gcaggaagtg aactccatgc | 1500 |
| tcaacaagcg actcaaggac gccctcttca cggaccagtg gagtgagctg ttcatggatg | 1560 |
| cgctagggcc cttcaacttc gtgctggtga gttcggtgag gatgcagggt gtcatcctgc | 1620 |
| tgctgttcgc caagtactac cacctgcccc tcctgcgaga cgtgcagacc gactgcacgc | 1680 |
| gcactggcct gggcggctac tggggtaaca agggtggcgt gagcgtgcgc ctggcggcct | 1740 |
| tcgggcacat gctctgcttc ctgaactgcc acttgcctgc gcatatggac aaggcggagc | 1800 |
| agcgcaaaga caacttccag accatcctca gcctccagca gttccaaggg ccgggcgcac | 1860 |
| agggcatcct ggatcatgac ctcgtgttct ggttcgggga cctgaacttc cgcattgaga | 1920 |
| gctatgacct gcactttgtc aagtttgcca tcgacagtga ccagctccat cagctctggg | 1980 |
| agaaggacca gctcaacatg gccaagaaca cctggcccat tctgaagggc tttcaggagg | 2040 |
| ggcccctcaa cttcgctccc accttcaagt ttgatgtggg taccaacaaa tacgatacca | 2100 |
| gtgccaagaa acggaagcca gcttggacag accgtatcct atggaaggtc aaggctccag | 2160 |
| gtgggggtcc cagcccctca ggacggaaga gccaccgact ccaggtgacg cagcacagct | 2220 |
| accgcagcca catggaatac acagtcagcg accacaagcc tgtggctgcc cagttcctcc | 2280 |
| tgcagtttgc cttcagggac gacatgccac tggtgcggct ggaggtggca gatgagtggg | 2340 |
| tgcggcccga gcaggcggtg gtgaggtacc gcatggaaac agtgttcgcc cgcagctcct | 2400 |
| gggactggat cggcttatac cgggtggggtt ccgccattg caaggactat gtggcttatg | 2460 |
| tctgggccaa acatgaagat gtggatggga atacctacca ggtaacattc agtgaggaat | 2520 |
| cactgcccaa gggccatgga gacttcatcc tgggctacta tagtcacaac cacagcatcc | 2580 |
| tcatcggcat cactgaaccc ttccagatct cgctgccttc ctcggagttg ccagcagca | 2640 |
| gcacagacag ctcaggcacc agctcagagg gagaggatga cagcacactg gagctccttg | 2700 |
| cacccaagtc ccgcagcccc agtcctggca agtccaagcg acaccgcagc cgcagcccgg | 2760 |
| gactggccag gttccctggg cttgccctac ggccctcatc ccgtgaacgc cgtggtgcca | 2820 |
| gccgtagccc ctcaccccag agccgccgcc tgtcccgagt ggctcctgac aggagcagta | 2880 |
| atggcagcag ccggggcagt agtgaagagg ggccctctgg gttgcctggc ccctgggcct | 2940 |
| tcccaccagc tgtgcctcga agcctgggcc tgttgcccgc cttgcgccta gagactgtag | 3000 |
| accctggtgg tggtggctcc tggggacctg atcgggaggc cctggcgccc aacagcctgt | 3060 |
| ctcctagtcc ccagggccat cggggggctgg aggaagggg cctggggccc tgagggtggg | 3120 |
| gtaggcagat gggccaaggt gaccaccatt ctgcctcaat cttttgcaag cccacctgcc | 3180 |
| tctctcctgc tgctcctcca gctgtatctg cacctgcctc tctgtcctgg ccaggggtgg | 3240 |
| acaactgggg tcccccaaaa ctcagtcctg gcacctcaac tgtgacaatc agcaaagccc | 3300 |
| cacccaggcc cccatctggg atgatgggag agctctggca gatgtcccaa tcctggaggt | 3360 |
| catccattag gaattaaatt ctccagcctc aaaaaaaaaa aaaaaaa | 3407 |

<210> SEQ ID NO 24
<211> LENGTH: 1146
<212> TYPE: DNA
<213> ORGANISM: Homo sapiens

<400> SEQUENCE: 24

| | |
|---|---|
| ttttgcgaac ggcgagcagc ggcggcggcg cggagagacg cagcggaggt tttcctggtt | 60 |
| tcggacccca gcggccggat ggtgaaatcc tccctgcagc ggatcctcaa tagccactgc | 120 |
| ttcgccagag agaaggaagg ggataaaccc agcgccacca tccacgccag ccgcaccatg | 180 |

```
ccgctcctaa gcctgcacag ccgcggcggc agcagcagtg agagttccag ggtctccctc    240
cactgctgta gtaacccggg tccggggcct cggtggtgct cctgatgccc ctcacccacc    300
cctgaagatc ccaggtgggc gagggaatag tcagagggat cacaatcttt cagctaactt    360
attctactcc gatgatcggc tgaatgtaac agaggaacta acgtccaacg acaagacgag    420
gattctcaac gtccagtcca ggctcacaga cgccaaacgc attaactggc gaacagtgct    480
gagtggcggc agcctctaca tcgagatccc gggcggcgcg ctgcccgagg ggagcaagga    540
cagctttgca gttctcctgg agttcgctga ggagcagctg cgagccgacc atgtcttcat    600
ttgcttccac aagaaccgcg aggacagagc cgccttgctc cgaaccttca gcttttttggg    660 ctttgagatt gtgagaccgg ggcatcccct tgtccccaag agacccgacg cttgcttcat    720
ggcctacacg ttcgagagag agtcttcggg agaggaggag gagtagggcc gcctcggggc    780
tgggcatccg gcccctgggg ccaccccttg tcagccgggt gggtaggaac cgtagactcg    840
ctcatctcgc ctgggtttgt ccgcatgttg taatcgtgca aataaacgct cactccgaat    900
tagcggtgta tttcttgaag tttaatattg tgtttgtgat actgaagtat ttgctttaat    960
tctaaataaa aatttatatt ttacttttt attgctggtt taagatgatt cagattatcc   1020
ttgtactttg aggagaagtt tcttatttgg agtcttttgg aaacagtctt agtcttttaa   1080
cttggaaaga tgaggtatta atcccctcca ttgctctcca aaagccaata aagtgattac   1140
acccga                                                              1146

<210> SEQ ID NO 25
<211> LENGTH: 1215
<212> TYPE: DNA
<213> ORGANISM: Homo sapiens

<400> SEQUENCE: 25
gccaggaagg cttgcaggtt ctgctgtttg gttgctgaag ggggtcagtg tgtgtatgtg     60
tcatggaggt gggcagggaa ggggagggct gtgcgtgggg gagaggatat atatgctggt    120
gtggctgaga aagcggaacc gagcctcgca tccatcggag ggagccgggg actgacagct    180
ctcagcacct gcttcctgct cctgcaccat gaaagtcctg ctttgtgacc tgctgctgct    240
cagtctcttc tccagtgtgt tcagcagttg tcagagggac tgtctcacat gccaggagaa    300
gctccaccca gccctggaca gcttcgacct ggaggtgtgc atcctcgagt gtgaagagaa    360
ggtcttcccc agccccctct ggactccatg caccaaggtc atggccagga gctcttggca    420
gctcagccct gccgccccag agcatgtggc ggctgctctc taccagccga gagcttcgga    480
gatgcagcat ctgcggcgaa tgccccgagt ccggagcttg ttccaggagc aggaagagcc    540
cgagcctggc atggaggagg ctggtgagat ggagcagaag cagctgcaga agagatttgg    600
gggcttcacc ggggcccgga agtcggccag gaagttggcc aatcagaagc ggttcagtga    660
gtttatgagg caatacttgg tcctgagcat gcagtccagc cagcgccggc gcaccctgca    720
ccagaatggt aatgtgtagc cggaaggggc gctcctccca gctgtaccgg ccactgcaac    780
ccatgagcgt ccaggtgatc ccccaaacag catgtgctca gccccagacc tgccgcctgg    840
gaatcaggat tccttcttcc ccaaggcact gagcgcctgc agatcccgca ggcttcgttt    900
gcctccagaa ccttcccgtc tgattgttcc tccccagccc ctggcatgtt tcaccacaa    960 ccctgttgct acatcagagt gtattttgt aattcctcta gctaccattt caatagcccc   1020
atctctcctg ctcacccgcc tcttgcccct tctagggca ggtgaaagga ataggaaatt   1080
```

-continued

| | |
|---|---|
| gaacctgggg ttttgacttg ccactgccat aacttgtttg taaaagagct gttcttttg | 1140 |
| actgattgtt ttaaacaacg atttctccat taaacttcta ctgagcaaat ggttaataaa | 1200 |
| aaaaaaaaaa aaaaa | 1215 |

<210> SEQ ID NO 26
<211> LENGTH: 4264
<212> TYPE: DNA
<213> ORGANISM: Homo sapiens

<400> SEQUENCE: 26

| | |
|---|---|
| agagcgctgc ggccgcggcg gtgcagcaga ggcgcctcgg gcaggaggag ggcggcttct | 60 |
| gcgagggcag cctgaggtat taaaaagtgt cagcaaactg cattgaataa cagacatcct | 120 |
| aagagggat attttccacc tctataatga agaaaagcag gagtgtgatg acggtgatgg | 180 |
| ctgatgataa tgttaaagat tattttgaat gtagcttgag taaatcctac agttcttcca | 240 |
| gtaacacact tgggatcgac ctctggagag ggagaaggtg ttgctcagga aacttacagt | 300 |
| taccaccact gtctcaaaga cagagtgaaa gggcaaggac tcctgaggga gatggtattt | 360 |
| ccaggccgac cacactgcct ttgacaacgc ttccaagcat tgctattaca actgtaagcc | 420 |
| aggagtgctt tgatgtggaa aatggcccctt ccccaggtcg gagtccactg gatccccagg | 480 |
| ccagctcttc cgctgggctg gtacttcacg ccacctttcc tgggcacagc cagcgcagag | 540 |
| agtcatttct ctacagatca gacagcgact atgacttgtc accaaaggcg atgtcgagaa | 600 |
| actcttctct tccaagcgag caacacggcg atgacttgat tgtaactcct tttgcccagg | 660 |
| tccttgccag cttgcgaagt gtgagaaaca acttcactat actgacaaac cttcatggta | 720 |
| catctaacaa gaggtcccca gctgctagtc agcctcctgt ctccagagtc aacccacaag | 780 |
| aagaatctta tcaaaaatta gcaatggaaa cgctggagga attagactgg tgtttagacc | 840 |
| agctagagac catacagacc taccggtctg tcagtgagat ggcttctaac aagttcaaaa | 900 |
| gaatgctgaa ccgggagctg acacacctct cagagatgag ccgatcaggg aaccaggtgt | 960 |
| ctgaatacat ttcaaatact ttcttagaca agcagaatga tgtggagatc ccatctccta | 1020 |
| cccagaaaga cagggagaaa aagaaaaagc agcagctcat gacccagata agtggagtga | 1080 |
| agaaattaat gcatagttca agcctaaaca atacaagcat ctcacgcttt ggagtcaaca | 1140 |
| ctgaaaatga agatcacctg gccaaggagc tggaagacct gaacaaatgg ggtcttaaca | 1200 |
| tctttaatgt ggctggatat tctcacaata gaccccctaac atgcatcatg tatgctatat | 1260 |
| tccaggaaag agacctccta aagacattca gaatctcatc tgacacattt ataacctaca | 1320 |
| tgatgacttt agaagaccat taccattctg acgtggcata tcacaacagc ctgcacgctg | 1380 |
| ctgatgtagc ccagtcgacc catgttctcc tttctacacc agcattagac gctgtcttca | 1440 |
| cagatttgga gatcctggct gccattttg cagctgccat ccatgacgtt gatcatcctg | 1500 |
| gagtctccaa tcagtttctc atcaacacaa attcagaact tgctttgatg tataatgatg | 1560 |
| aatctgtgtt ggaaaatcat caccttgctg tgggtttcaa actgctgcaa gaagaacact | 1620 |
| gtgacatctt catgaatctc accaagaagc agcgtcagac actcaggaag atggttattg | 1680 |
| acatggtgtt agcaactgat atgtctaaac atatgagcct gctggcagac ctgaagacaa | 1740 |
| tggtagaaac gaagaaagtt acaagttcag gcgttcttct cctagacaac tataccgatc | 1800 |
| gcattcaggt ccttcgcaac atggtacact gtgcagacct gagcaacccc accaagtcct | 1860 |
| tggaattgta tcggcaatgg acagaccgca tcatggagga attttccag cagggagaca | 1920 |
| aagagcggga gagggaatg gaaattagcc caatgtgtga taaacacaca gcttctgtgg | 1980 |

```
aaaaatccca ggttggtttc atcgactaca ttgtccatcc attgtgggag acatgggcag    2040
atttggtaca gcctgatgct caggacattc tcgatacctt agaagataac aggaactggt    2100
atcagagcat gatacctcaa agtccctcac caccactgga cgagcagaac agggactgcc    2160
agggtctgat ggagaagttt cagtttgaac tgactctcga tgaggaagat tctgaaggac    2220
ctgagaagga gggagaggga cacagctatt tcagcagcac aaagacgctt tgtgtgattg    2280
atccagaaaa cagagattcc ctgggagaga ctgacataga cattgcaaca gaagacaagt    2340
cccccgtgga tacataatcc ccctctccct gtggagatga acattctatc cttgatgagc    2400
atgccagcta tgtggtaggg ccagcccacc atggggccca agacctgcac aggacaaggg    2460
ccacctggcc tttcagttac ttgagtttgg agtcagaaag caagaccagg aagcaaatag    2520
cagctcagga aatcccacgg ttgacttgcc ttgatggcaa gcttggtgga gagggctgaa    2580
gctgttgctg ggggccgatt ctgatcaaga cacatggctt gaaaatggaa gacacaaaac    2640
tgagagatca ttctgcacta agtttcggga acttatcccc gacagtgact gaactcactg    2700
actaataact tcatttatga atcttctcac ttgtcccttt gtctgccaac ctgtgtgcct    2760
tttttgtaaa acattttcat gtctttaaaa tgcctgttga atacctggag tttagtatca    2820
acttctacac agataagctt tcaaagttga caaactttt tgactctttc tggaaaaggg    2880
aaagaaaata gtcttccttc tttcttgggc aatatccttc actttactac agttactttt    2940
gcaaacagac agaaaggata cacttctaac cacattttac ttccttcccc tgttgtccag    3000
tccaactcca cagtcactct taaaacttct ctctgtttgc ctgcctccaa cagtactttt    3060
aacttttgc tgtaaacaga ataaaattga acaaattagg gggtagaaag gagcagtggt    3120
gtcgttcacc gtgagagtct gcatagaact cagcagtgtg ccctgctgtg tcttggaccc    3180
tgccccccac aggagttgta cagtccctgg ccctgttccc tacctcctct cttcaccccg    3240
ttaggctgtt ttcaatgtaa tgctgccgtc cttctcttgc actgccttct gcgctaacac    3300
ctccattcct gtttataacc gtgtatttat tacttaatgt atataatgta atgttttgta    3360
agttattaat ttatatatct aacattgcct gccaatggtg gtgttaaatt tgtgtagaaa    3420
actctgccta agagttacga cttttttcttg taatgttttg tattgtgtat tatataaccc    3480
aaacgtcact tagtagagac atatggcccc cttggcagag aggacagggg tgggcttttg    3540
ttcaaagggt ctgccctttc cctgcctgag ttgctacttc tgcacaaccc ctttatgaac    3600
cagttttgga aacaatattc tcacattaga tactaaatgg tttatactga gcttttactt    3660
ttgtatagct tgataggggc aggggcaat gggatgtagt ttttacccag gttctatcca    3720
aatctatgtg ggcatgagtt gggttataac tggatcctac tatcattgtg gctttggttc    3780
aaaaggaaac actacatttg ctcacagatg attcttctga atgctcccga actactgact    3840
ttgaagaggt agcctcctgc ctgccattaa gcaggaatgt catgttccag ttcattacaa    3900
aagaaaacaa taaacaatg tgaatttta taataaaatg tgaactgatg tagcaaatta    3960
cgcaaatgtg aagcctcttc tgataacact tgttaggcct cttactgatg tcagtttcag    4020
tttgtaaaat atgtttcatg ctttcagttc agcattgtga ctcagtaatt acagaaaatg    4080
gcacaaatgt gcatgaccaa tgtatgtcta tgaacactgc attgtttcag gtggacattt    4140
tatcattttc aaatgtttct cacaatgtat gttatagtat tattattata tattgtgttc    4200
aaatgcattc taaagagact tttatatgag gtgaataaag aaaagcatga ttagattaaa    4260
aaaa                                                                 4264
```

<210> SEQ ID NO 27
<211> LENGTH: 2759
<212> TYPE: DNA
<213> ORGANISM: Homo sapiens

<400> SEQUENCE: 27

```
gctcaggccc cgcccctgcc gccggaatcc tgaagcccaa ggctgcccgg gggcggtccg      60
gcggcgccgg cgatggggca taaaaccact ggccacctgc cgggctgctc ctgcgtgcgc     120
tgccgtcccg gatccaccgt gcctctgcgg cctgcgtgcc cggagtcccc gcctgtgtcg     180
tctctgtcgc cgtccccgtc tcctgccagg cgcggagccc tgcgagccgc gggtgggccc     240
caggcgcgca gacatgggct gctccgccaa agcgcgctgg gctgccgggg cgctgggcgt     300
cgcggggcta ctgtgcgctg tgctgggcgc tgtcatgatc gtgatggtgc cgtcgctcat     360
caagcagcag gtccttaaga acgtgcgcat cgacccagt agcctgtcct tcaacatgtg     420
gaaggagatc cctatcccct tctatctctc cgtctacttc tttgacgtca tgaaccccag     480
cgagatcctg aagggcgaga agccgcaggt gcggagcgc gggccctacg tgtacaggga     540
gttcaggcac aaaagcaaca tcaccttcaa caacaacgac accgtgtcct tcctcgagta     600
ccgcaccttc cagttccagc cctccaagtc ccacggctcg gagagcgact acatcgtcat     660
gcccaacatc ctggtcttgg gtgcggcggt gatgatggag aataagccca tgaccctgaa     720
gctcatcatg accttggcat tcaccaccct cggcgaacgt gccttcatga accgcactgt     780
gggtgagatc atgtggggct acaaggaccc ccttgtgaat ctcatcaaca agtactttcc     840
aggcatgttc cccttcaagg acaagttcgg attatttgct gagctcaaca actccgactc     900
tgggctcttc acggtgttca cggggggtcca gaacatcagc aggatccacc tcgtggacaa     960
gtggaacggg ctgagcaagg ttgacttctg gcattccgat cagtgcaaca tgatcaatgg    1020
aacttctggg caaatgtggc cgcccttcat gactcctgag tcctcgctgg agttctacag    1080
cccggaggcc tgccgatcca tgaagctaat gtacaaggag tcaggggtgt ttgaaggcat    1140
ccccacctat cgcttcgtgg ctcccaaaac cctgtttgcc aacgggtcca tctacccacc    1200
caacgaaggc ttctgcccgt gcctggagtc tggaattcag aacgtcagca cctgcaggtt    1260
cagtgccccc ttgtttctct cccatcctca cttcctcaac gctgaccgg ttctggcaga    1320
agcggtgact ggcctgcacc ctaaccagga ggcacactcc ttgttcctgg acatccaccc    1380
ggtcacggga atccccatga actgctctgt gaaactgcag ctgagcctct acatgaaatc    1440
tgtcgcaggc attggacaaa ctgggaagat tgagcctgtg gtcctgccgc tgctctggtt    1500
tgcagagagc ggggccatgg aggggagac tcttcacaca ttctacactc agctggtgtt    1560
gatgcccaag gtgatgcact atgcccagta cgtcctcctg gcgctgggct gcgtcctgct    1620
gctggtccct gtcatctgcc aaatccggag ccaagagaaa tgctatttat tttggagtag    1680
tagtaaaaag ggctcaaagg ataaggaggc cattcaggcc tattctgaat ccctgatgac    1740
atcagctccc aagggctctg tgctgcagga agcaaaactg tagggtcctg aggacaccgt    1800
gagccagcca ggcctggccg ctgggcctga ccggcccccc agcccctaca ccccgcttct    1860
cccggactct cccagcggac agccccccag cccacagcc tgagcctccc agctgccatg    1920
tgcctgttgc acacctgcac acacgccctg gcacacatac acacatgcgt gcaggcttgt    1980
gcagacactc agggatggag ctgctgctga agggacttgt agggagaggc tcgtcaacaa    2040
gcactgttct ggaaccttct ctccacgtgg cccacaggcc tgaccacagg ggctgtgggt    2100
cctgcgtccc cttcctcggg tgagcctggc ctgtcccgtt cagccgttgg gcccaggctt    2160
```

```
cctcccctcc aaggtgaaac actgcagtcc cggtgtggtg gctccccatg caggacgggc    2220
caggctggga gtgccgcctt cctgtgccaa attcagtggg gactcagtgc ccaggccctg    2280
gccacgagct ttggccttgg tctacctgcc aggccaggca aagcgccttt acacaggcct    2340
cggaaaacaa tggagtgagc acaagatgcc ctgtgcagct gcccgagggt ctccgcccac    2400
cccggccgga ctttgatccc cccgaagtct tcacaggcac tgcatcgggt tgtctggcgc    2460
ccttttcctc cagcctaaac tgacatcatc ctatggactg agccggccac tctctggccg    2520
aagtggccgc aggctgtgcc ccgagctgc ccccaccccc tcacagggtc cctcagatta    2580
taggtgccca ggctgaggtg aagaggcctg ggggccctgc cttccgggcg ctcctggacc    2640
ctggggcaaa cctgtgaccc ttttctactg aatagaaat gagttttatc atctttgaaa    2700
aataattcac tcttgaagta ataaacgttt aaaaaatgg gaaaaaaaaa aaaaaaaa      2759
```

<210> SEQ ID NO 28
<211> LENGTH: 2184
<212> TYPE: DNA
<213> ORGANISM: Homo sapiens

<400> SEQUENCE: 28

```
gtgcgcgaac ggctccggcc cgcacgggtc gccagaggcg actgtgtgac actcggagtt      60
tgctggggtc tccgtgggcg ggaggacttt ccagcgcaat ggcgactccc taagccccgc    120
agcttctgcg cccgggaaag atatccaaga gatgcaaagc tctactgggc ccaggctgcc    180
accccagagg cccccttccg tcccgggggcc ggggctaggc caaggcgggc accaggactg    240
cccagcctcc cggcccttcg cactggtaac cggttccggg gcggatgctt tttgcatctg    300
acccggcgcg cccggtgacg ccttcgcgtc cagacggaag tgcgggcgga ggatccccag    360
ccgggtccca agcctgtgcc tgagcctgag cctgagcctg agcccgagcc gggagccggt    420
cgcgggggct ccgggctgtg gaccgctgg gcccccagcg atggcgaccc tgtggggagg    480
ccttcttcgg cttggctcct tgctcagcct gtcgtgcctg gcgctttccg tgctgctgct    540
ggcgcagctg tcagacgccg ccaagaattt cgaggatgtc agatgtaaat gtatctgccc    600
tccctataaa gaaaattctg gcatatttta taatgagaac atatctcaga aagattgtga    660
ttgccttcat gttgtggagc ccatgcctgt gcggggcct gatgtagaag catactgtct    720
acgctgtgaa tgcaaatatg aagaagaag ctctgtcaca atcaaggtta ccattataat    780
ttatctctcc attttgggcc ttctacttct gtacatggta tatcttactc tggttgagcc    840
catactgaag aggcgcctct ttggacatgc acagttgata cagagtgatg atgatattgg    900
ggatcaccag ccttttgcaa atgcacacga tgtgctagcc cgctcccgca gtcgagccaa    960
cgtgctgaac aaggtagaat atgcacagca gcgctggaag cttcaagtcc aagagcagcg   1020
aaagtctgtc tttgaccggc atgttgtcct cagctaattg ggaattgaat tcaaggtgac   1080
tagaaagaaa caggcagaca actggaaaga actgactggg ttttgctggg ttcattttta   1140
ataccttgtt gatttcacca actgttgctg gaagattcaa aactggaagc aaaaacttgc   1200 ttgattttt tttcttgtta acgtaataat agagacattt ttaaaagcac acagctcaaa   1260
gtcagccaat aagtctttttc ctatttgtga cttttactaa taaaaataaa tctgcctgta   1320
aattatcttg aagtccttta cctggaacaa gcactctctt tttcaccaca tagttttaac   1380
ttgactttca agtaattttt cagggttttt gttgttgttg tttttttgttt gtttgttttg   1440 gtgggagagg ggagggatgc ctgggaagtg gttaacaact ttttcaagt cactttacta   1500
```

```
aacaaactttt tgtaaataga ccttaccttc tattttcgag tttcatttat attttgcagt    1560
gtagccagcc tcatcaaaga gctgacttac tcatttgact tttgcactga ctgtattatc    1620
tgggtatctg ctgtgtctgc acttcatggt aaacgggatc taaaatgcct ggtggctttt    1680
cacaaaaagc agattttctt catgtactgt gatgtctgat gcaatgcatc ctagaacaaa    1740
ctggccattt gctagtttac tctaaagact aaacatagtc ttggtgtgtg tggtcttact    1800
catcttctag tacctttaag gacaaatcct aaggacttgg acacttgcaa taagaaaatt    1860 ttatttttaaa cccaagcctc cctggattga taatatatac acatttgtca gcatttccgg    1920
tcgtggtgag aggcagctgt ttgagctcca atgtgtgcag cttttgaacta gggctggggt    1980 tgtgggtgcc tcttctgaaa ggtctaacca ttattggata actggctttt ttcttcctat    2040
gtcctctttg gaatgtaaca ataaaaataa ttttttgaaac atccatcagt gtatctatct    2100
atgtctccta gttttttcct cctccctctt ttgctgtata atgagattga agatataaag    2160
acattttgta ccctgtaaaa aaaa                                           2184

<210> SEQ ID NO 29
<211> LENGTH: 5135
<212> TYPE: DNA
<213> ORGANISM: Homo sapiens

<400> SEQUENCE: 29
aactcaaggc ctgcttgata cgtccgccat tttgggcgct tcgctgatgg tgtcggtgag     60
cgcgtttccc gcctgagcgc aactagcggc gggtcgtggg cacctccagg agagcttgtt    120
tcatatccat atcccactgt attcctgcta atctgctaat gcagtaaatt ggaggaaaac    180
tgttaccagg ataacctgta atgggcaagg agccacaaag aagaaaacat ttcttttaat    240
ttttaaactt ggtttgaaag accagcatgt tttggaaatt tgatcttcac tcatcatccc    300
acatagacac acttctagaa agagaagatg taacactgaa ggagttaatg gatgaggaag    360
atgttttaca ggaatgtaaa gctcagaacc gcaaacttat agagtttctg ttaaaagcag    420
aatgtctcga gatttagtc tcattcatta tagaagaacc acctcaagac atggatgaaa    480
agatcagata caagtatcca aatatatctt gtgagttgct cacttctgat gtctcccaga    540
tgaatgatag actgggagaa gatgaatcct tgctaatgaa attatatagc ttcctcctaa    600
acgattcccc tttgaatcca ctacttgcca gtttcttcag caaggtgcta agtattctta    660
tcagcagaaa accagaacag attgtggatt tcttaaagaa gaagcatgat tttgtagacc    720
ttattataaa gcacatagga acttctgcta tcatggattt gttgctcagg ctcctgacgt    780
gtatcgaacc tccacagccc aggcaagatg tgctgaattg gttaaatgag gagaaaatta    840
tccagaggct tgtggaaata gttcatccat cgcaagaaga agatcgacat tcaaatgcat    900
cacaatcact ttgtgaaatt gttcgcctga gcagagacca gatgttacaa attcagaaca    960
gtacagagcc cgaccccctg cttgccactc tagaaaagca agaaattata gagcagcttc   1020
tatcaaatat tttccacaag gagaaaaatg agtcagccat agtcagtgca atccagatat   1080
tgctgacttt acttgagaca cgacgaccaa catttgaagg ccatatagag atctgcccac   1140
caggcatgag ccattcagct tgttcagtaa acaagagtgt tctagaagcc atcagaggaa   1200
gacttggatc ttttcatgaa ctcctgctgg agccacccaa gaaaagtgtg atgaagacca   1260
catggggtgt gctggatcct cctgtgggga atacccggtt gaatgtcatt aggttgatat   1320
ccagcctgct tcaaaccaat accagcagta taaatgggga ccttatggag ctgaatagca   1380
ttggagtcat attgaacatg ttcttcaagt atacatggaa taacttttg catacacaag   1440
```

```
tggaaatttg tattgcactg attcttgcaa gtccttttga aaacacagaa aatgccacaa    1500
ttaccgatca agactccact ggtgataatt tgttattaaa acatcttttc caaaaatgtc    1560
aattaataga acgaatactt gaagcctggg aaatgaatga aagaaacag gctgagggag     1620 gaagacggca tggttacatg ggacacctaa cgaggatagc taactgtatc gtgcacagca    1680
ctgacaaggg ccccaacagt gcattagtgc agcagcttat caaagatctt cccgacgaag    1740
tcagggaacg atgggagacg ttctgcacaa gctccttagg agaaactaac aagaggaaca    1800
cggtagatct agttacaacc tgccatattc attcatccag tgatgatgaa attgacttta    1860
aagaaacggg tttctcacag gattcttctt tgcagcaagc cttttctgat tatcagatgc    1920
aacaaatgac gtccaatttt attgaccagt ttggcttcaa cgatgagaag tttgcagatc    1980
aagatgacat tggcaatgtt tcttttgatc gagtatcaga catcaacttt actctcaata    2040
caaatgaaag tggaaatatt gccttgtttg aagcatgttg taaggaaaga atacaacagt    2100
ttgatgatgg tggctctgat gaggaagata tatgggagga aaagcacatc gcattcacac    2160
cagaatccca aagacgatcc agctcgggga gtacagacag tgaggaaagt acagactctg    2220
aagaagaaga tggagcaaag caagacttgt ttgaacccag cagtgccaac acggaggata    2280
aaatggaggt ggacctgagt gaaccaccca actggtcagc taactttgat gtcccaatgg    2340
aaacaaccca cggtgctcca ttggattctg tgggatctga tgtctggagc acagaggagc    2400
cgatgccaac taaagagacg ggctgggctt cttttttcaga gttcacgtct tccctgagca    2460
caaaagattc tttaaggagt aattctccag tggaaatgga aaccagcact gaacccatgg    2520
accctctgac tcccagtgcg gctgccctgg cagtgcagcc agaagcggca ggcagtgtgg    2580
ccatggaagc cagctctgac ggagaggagg atgcagaaag tacagacaag gtaactgaga    2640
cagtgatgaa tggcggcatg aaggaaacgc tcagcctcac tgtagatgcc aagacagaga    2700
ctgcggtctt caaaagtgag gaagggaaac tgtctacctc tcaagatgct gcttgtaaag    2760
acgcagagga gtgtccgag actgcagagg cgaagtgcgc ggcgcccagg cctcccagca    2820
gcagtcccga gcagagtgcc tccgatgcct gtctgttgct ccttaggact ggccaaccaa    2880
gcgcaccagg tgacacttca gtgaatggcc ctgtatgacg ggtgacgtct gctgctgctg    2940
actgaggact gcagaccgcc accactcagg ggctctggag gggtcagctg agcccacca    3000 agctgtcact gctgcactca ctctgcaagg gatcaggacc agcaaccttt atattctaga    3060
ttctaagaca ttgtacagag aaattcagaa gtgtaaaaat attgcacatt gacaaatacc    3120 aagaatttt gcgtatgttt atattgtatt gttctaaata atgggtagcc tgtgaaataa    3180
gatcttgcca cccatgtaat aatagtagta atactatagt taaaatggct gtaagaatag    3240
ttttataaaa gtgaatacac agatctattg tatttgaaac ataactttga caattattag    3300
tgtgaccaaa gtattaggcg gttttcatac attttttcacc ttgtacaaaa ttatgaattc    3360 attttttcctc caggccgaca aggagttgta gaatgaaaat gccctctaag tgttatttg    3420 gttgttctaa cttacaaaag tgattttgaa taagaaatat ttggtgttct ttttataacc    3480
agtttttgat tggtaattgt tttctgtatt gtttaaaacg gatcaaaaat gtaagtctat    3540
tggtagagat taagtaaagt atttattgct acatcatagt tgataaattg atgttatcgt    3600
aaagccatat gttctgttca agtcttgttt gcttgaaatg attattccta caagtgaaac    3660
actagactat ttggagtgta tatggcttgt gttttgggat tttttttttt tttttttggc    3720
ttttgttttt gtttgttttt ttgtttcatt tggtagttca tctgccttt aacccattca    3780
```

```
ccaaaattta ccttgttaac aagcatcacc aatgaacatt tcagagcaat ctgcatattt    3840
aacagaccta aaataaatcc tattaggcaa gtcagttgaa aatgctcgtg ctgctaatgg    3900
aattagagtg cgttcatttt acaggctagt attttaaaag tagaaatcaa atctggcac    3960 cgaagcatgc taattgttta ctgtaccttg tgaggttttc actcataaat ttaaaccagt    4020 gtatttttt agaactggtt tgtgtatata tatagtgatt atggatacta attcaatgta    4080
atttataatt ttctatgtca atacaaaaat acatcacagc cttctcaaac agctcaagca    4140
atatattgta tattgccata tcgtctggtg aaagggttaa attacttcac ctcttgcact    4200
tttagatgca aatcagtttt tcatttctgt aatagaaaat tattcacgta ttttttacatc    4260 atttgttttt cctgaccagt atttaaaacc aaaaggatat tctgaaaaat ggccaacaat    4320 tttttagaa gtagcatccc aagcagcgtg cctaaacatt acattgcata tggaaataaa    4380
agaatcaaac gtctaatgcc ttattatttc tgatttcctt tttcatttta agtggtgtgg    4440
agattccagc actcccagga cagtggagtc agcagtaagc cctgggacag gtggcaaggg    4500
tgggtccctt gacctttgca cgcctcctca ggaaccccct ttcccgggtg agccctctc    4560 tgaagagact gtccttgggc ctcctctgga agcagcaccc cagaggaca gggctcctcc    4620 tgcttgcctc agggctgcct gacttgaatg gcgttggacc tcggggatta ctggtagata    4680
atatgctctg gtctcgcctg gtggtgagtt ttgccagcca tggccagggt ttggctccac    4740
tggtggcaca cgtggcctcc gtggtatgga cctggtggct tctccatccc actgtggcct    4800
ctgtggtatg gacctggtgg cttctccatc ctacccaagg taacagtgtc ttgcttcatc    4860
ccactgactg ctgggagaga gcctctggga cttttctttg gggcatcatt ttgttttgtc    4920
tttcgtagca gggaaaggat atgacaatgg ggaggacagt tcttttggag gttggagggg    4980
ccaagccaag gacaggagca agtgtgccct cattttgttt ctacttttaa tttctgtgtg    5040
ttggccatac tgaattatga gactaacaga tgtctacaat acaatacctg tattcaaaat    5100
aacaaaaata aagcctgatt ctttgtttct agaaa    5135
```

<210> SEQ ID NO 30
<211> LENGTH: 76
<212> TYPE: DNA
<213> ORGANISM: Homo sapiens

<400> SEQUENCE: 30

```
tgagggagga agacggcatg gttacatggg acacctaacg aggatagcta actgtatcgt    60
gcacagcact gacaag                                                    76
```

<210> SEQ ID NO 31
<211> LENGTH: 66
<212> TYPE: DNA
<213> ORGANISM: Homo sapiens

<400> SEQUENCE: 31

```
gacagatttc taccactcca aacgccggct gatcttctcc aagaggaagc cctaatccgc    60
ccacag                                                                66
```